US009290530B2

(12) United States Patent
Chen et al.

(10) Patent No.: US 9,290,530 B2
(45) Date of Patent: Mar. 22, 2016

(54) CHEMOENZYMATIC SYNTHESIS OF HEPARIN AND HEPARAN SULFATE ANALOGS

(71) Applicant: THE REGENTS OF THE UNIVERSITY OF CALIFORNIA, Oakland, CA (US)

(72) Inventors: Xi Chen, Davis, CA (US); Hai Yu, Woodland, CA (US); Kam Lau, Parkwood (AU); Lars Bode, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/160,451

(22) Filed: Jan. 21, 2014

(65) Prior Publication Data
US 2014/0235575 A1   Aug. 21, 2014

Related U.S. Application Data

(63) Continuation-in-part of application No. PCT/US2012/047875, filed on Jul. 23, 2012, and application No. 14/160,451.

(60) Provisional application No. 61/510,125, filed on Jul. 21, 2011, provisional application No. 61/926,088, filed on Jan. 10, 2014, provisional application No. 61/836,067, filed on Jun. 17, 2013, provisional application No. 61/815,050, filed on Apr. 23, 2013.

(51) Int. Cl.
C07H 5/06 (2006.01)
C12P 19/26 (2006.01)
C07H 1/00 (2006.01)
C07H 3/04 (2006.01)
C07H 3/06 (2006.01)
C07H 3/08 (2006.01)
C07H 13/04 (2006.01)
C07H 19/10 (2006.01)
C08B 37/00 (2006.01)
C12P 19/00 (2006.01)
C12P 19/04 (2006.01)
C12P 19/12 (2006.01)
C12P 19/18 (2006.01)

(52) U.S. Cl.
CPC .. C07H 5/06 (2013.01); C07H 1/00 (2013.01); C07H 3/04 (2013.01); C07H 3/06 (2013.01); C07H 3/08 (2013.01); C07H 13/04 (2013.01); C07H 19/10 (2013.01); C08B 37/0075 (2013.01); C12P 19/00 (2013.01); C12P 19/04 (2013.01); C12P 19/12 (2013.01); C12P 19/18 (2013.01); C12P 19/26 (2013.01)

(58) Field of Classification Search
CPC .......................................................... C07H 1/00
USPC ....................................................... 536/123.1
See application file for complete search history.

(56) References Cited

U.S. PATENT DOCUMENTS 5,824,472 A    10/1998  Betlach et al.
6,040,158 A     3/2000  Takenouchi et al.
2005/0070464 A1* 3/2005  Stahl et al. ........................ 514/8

FOREIGN PATENT DOCUMENTS

WO    2006/043525 A1    4/2006

OTHER PUBLICATIONS

Ohman "Thin layer chromatography of sialyloigosaccharides", Acta Chem. Scand., 1967, 21(6):1670-1672.*
Drzeniek et al. "Differences in substrate specificity of myxovirus neuraminidases", Biochem. And Biophy. Research Communication, 1970, 38(4):651-656.*
Kleczkowski, et al., "UDP-Sugar Pyrophosphorylase: A New Old Mechanism for Sugar Activation," Plant Physiology, vol. 156, pp. 3-10 (2011).
Nycholat, et al, "Synthesis of Biologically Active N- and O-Linked Glycans with Multisialylated Poly-N-acetyllactosamine Extensions Using P. damsela α2-6 Sialyltransferase," J. Am. Chem. Soc., 2013, vol. 135, pp. 18280-18283.
Yu, et al., "Aldolase-Catalyzed Synthesis of β-D-Galp-(1→9)-D-KDN: A Novel Acceptor for Sialyltransferases," Organic Letters, 2006, vol. 8(11), pp. 2393-2396.
Yu, et al., "Highly Efficient Chemoenzymatic Synthesis of Naturally Occurring and Non-Natural α-2,6- Linked Sialosides: A P. damsela α-2,6- Sialyltransferase with Extremely Flexible Donor-Substrate Specificity," Angew. Chem. Int. Ed., 2006, vol. 45, pp. 3938-3944.
International Search Report and Written Opinion for PCT/US2012/047875, mailed Mar. 4, 2013.

* cited by examiner

Primary Examiner — Bin Shen
(74) Attorney, Agent, or Firm — Kilpatrick Townsend and Stockton LLP

(57) ABSTRACT

The present invention provides a one-pot multi-enzyme method for preparing UDP-sugars from simple sugar starting materials. The invention also provides a one-pot multi-enzyme method for preparing oligosaccharides from simple sugar starting materials.

4 Claims, 43 Drawing Sheets

| | | |
|---|---|---|
| NahK_JMC1217 | : MTESNEVLFGIASHFALEGAVTGIEPYGDGHINTTYLVTTDGPRYILQMNTSIFPDTVN | 60 |
| NahK_ATCC55813 | : MTESNEVLFGIASHFALEGAVTGIEPYGDGHINTTYLVTTDGPRYILQMNTSIFPDTVN | 60 |
| NahK_ATCC15697 | : MNNTNEALFDVASHFALEGTVDSIEPYGDGHINTTYLVTTDGPRYILQRMNTGIFPDTVN | 60 |
| NahK_JMC1217 | : LMRNVELVTSTLKAQGKETLDIVPTTSGATWAEIDGGAWRVYKFIEHTMSYNLVPNPDVF | 120 |
| NahK_ATCC55813 | : LMRNVELVTSTLKAQGKETLDIVPTTSGATWAEIDGGAWRVYKFIEHTMSYNLVPNPDVF | 120 |
| NahK_ATCC15697 | : LMRNVELVTSTLKAQGKETLDIVRTTSGDTWAEIDGGAWRVYKFIEHTMSYNLVPNPDVF | 120 |
| NahK_JMC1217 | : REAGSAFGDFQNFLSEFDASQLTETIAHFHDTPHRFEDEKALAADKLGRAACGPEIDF | 180 |
| NahK_ATCC55813 | : REAGSAFGDFQNFLSEFDASQLTETIAHFHDTPHRFEDFKALAADKLGRAACGPEIDF | 180 |
| NahK_ATCC15697 | : REAGRAFGDFQNFLSGFDANQLTETIAHFHDTPHRFEDEKKALAADELGRAAGGPEIEF | 180 |
| NahK_JMC1217 | : YLSHADQYAVVMDGLRDGSIPLRVTHNDTKLNNILMDATTGKARAIIDLDTIMPGSMLFD | 240 |
| NahK_ATCC55813 | : YLSHADQYAVVMDGLRDGSIPLRVTHNDTKLNNILMDATTGKARAIIDLDTIMPGSMLFD | 240 |
| NahK_ATCC15697 | : YLSHADQYAVVMDGLRDGSIPLRVTHNDTKLNNILMDATTGKARAIIDLDTIMPGSMLFD | 240 |
| NahK_JMC1217 | : FGDSIRFGASTALEDERDLSKVHFSTELFRAYTEGFVGELRGSITAREAELLPFSGNLLT | 300 |
| NahK_ATCC55813 | : FGDSIRFGASTALEDERDLSKVHFSTELFRAYTEGFVGELRGSITAREAELLPFSGNLLT | 300 |
| NahK_ATCC15697 | : FGDSIRFGASTALEDERDLDKVHFSTELFRAYTEGFVGELRDSITAREAELLPFSGNLLT | 300 |
| NahK_JMC1217 | : MECGMRFLADYLEGDIYFATKYPEHNLVRTRTQIKLVQEMEQKASETRAIVADIMEAAR | 359 |
| NahK_ATCC55813 | : MECGMRFLADYLEGDIYFATKYPEHNLVRTRTQIKLVQEMEQKASETHAIVADIMEAAR | 359 |
| NahK_ATCC15697 | : MECGMRFLADVLEGDVYFATKYPEHNLVRSRTQIKLVREMEQRADETRAIVADVMETTK | 359 |

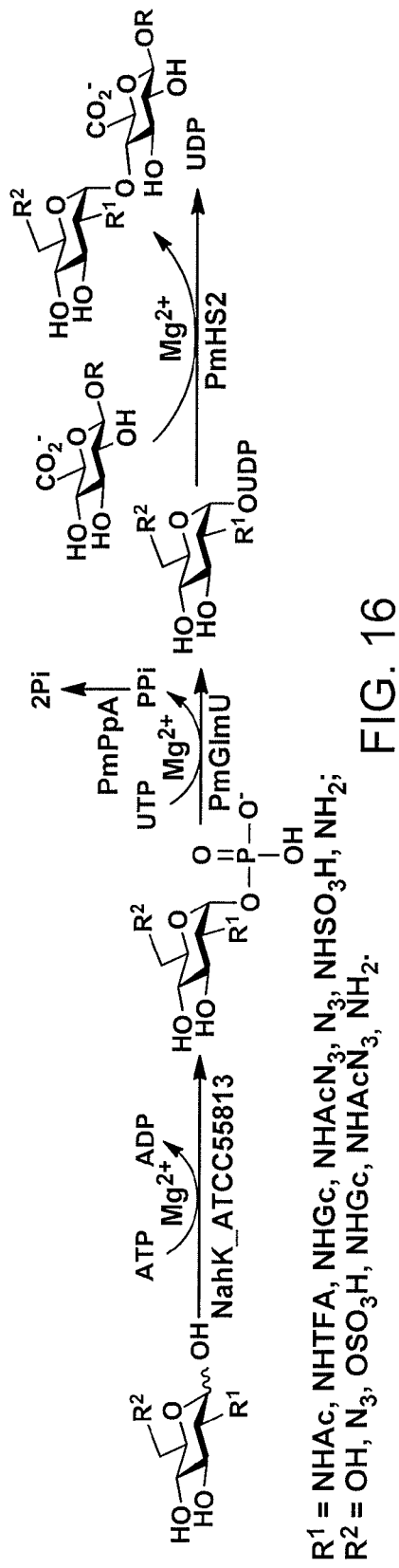

FIG. 16

$R^1$ = NHAc, NHTFA, NHGc, NHAcN$_3$, N$_3$, NHSO$_3$H, NH$_2$;
$R^2$ = OH, N$_3$, OSO$_3$H, NHGc, NHAcN$_3$, NH$_2$.

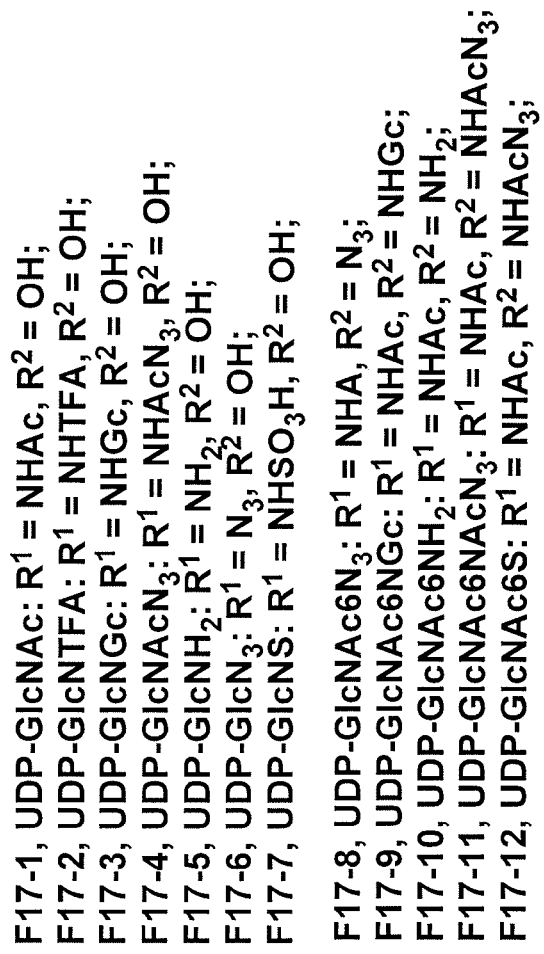

F17-1, UDP-GlcNAc: $R^1$ = NHAc, $R^2$ = OH;
F17-2, UDP-GlcNTFA: $R^1$ = NHTFA, $R^2$ = OH;
F17-3, UDP-GlcNGc: $R^1$ = NHGc, $R^2$ = OH;
F17-4, UDP-GlcNAcN$_3$: $R^1$ = NHAcN$_3$, $R^2$ = OH;
F17-5, UDP-GlcNH$_2$: $R^1$ = NH$_2$, $R^2$ = OH;
F17-6, UDP-GlcN$_3$: $R^1$ = N$_3$, $R^2$ = OH;
F17-7, UDP-GlcNS: $R^1$ = NHSO$_3$H, $R^2$ = OH;
F17-8, UDP-GlcNAc6N$_3$: $R^1$ = NHA, $R^2$ = N$_3$;
F17-9, UDP-GlcNAc6NGc: $R^1$ = NHAc, $R^2$ = NHGc;
F17-10, UDP-GlcNAc6NH$_2$: $R^1$ = NHAc, $R^2$ = NH$_2$;
F17-11, UDP-GlcNAc6NAcN$_3$: $R^1$ = NHAc, $R^2$ = NHAcN$_3$;
F17-12, UDP-GlcNAc6S: $R^1$ = NHAc, $R^2$ = NHAcN$_3$;

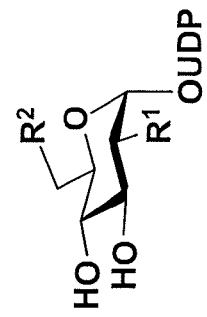

FIG. 17

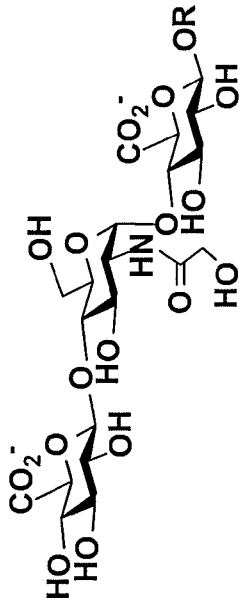
F18-4, GlcNGcα1-4GlcAβ2AAMe
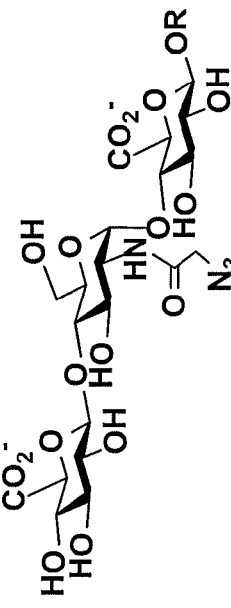
F18-5, GlcNAcN₃α1-4GlcAβ2AAMe
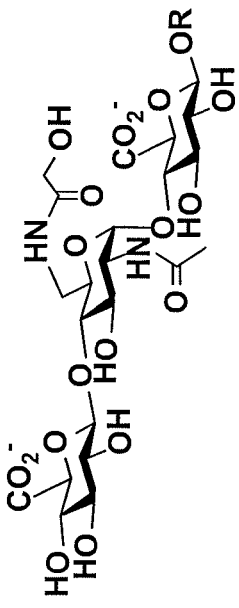
F18-6, GlcNAc6NGcα1-4GlcAβ2AAMe
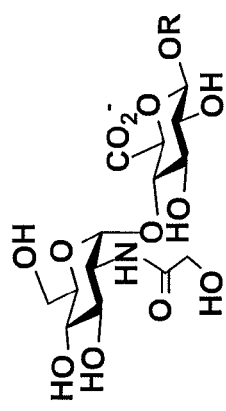
F20-4, GlcAβ1-4GlcNGcα1-4GlcAβ2AAMe
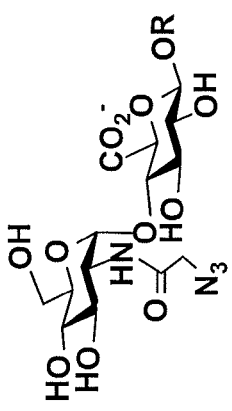
F20-5, GlcAβ1-4GlcNAcN₃α1-4GlcAβ2AAMe
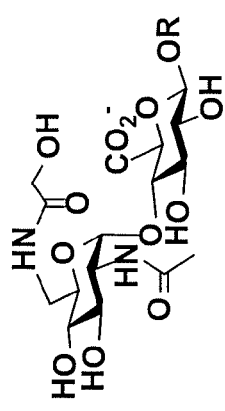
F20-6, GlcAβ1-4GlcNAc6NGcα1-4GlcAβ2AAMe
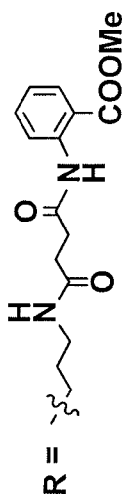
FIG. 20 (Cont.)

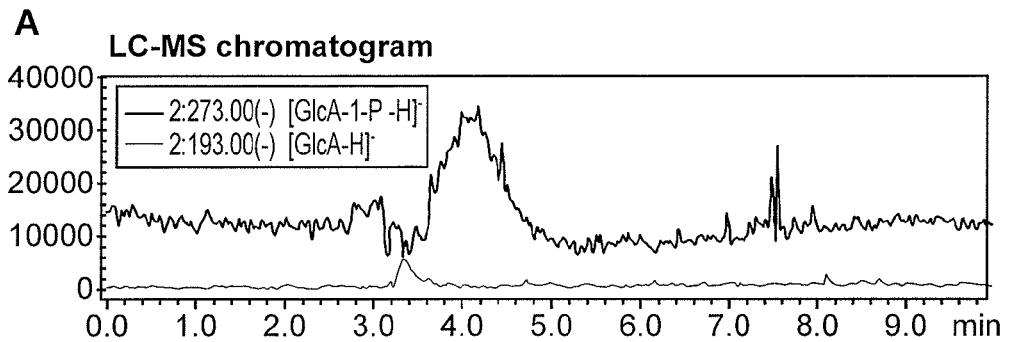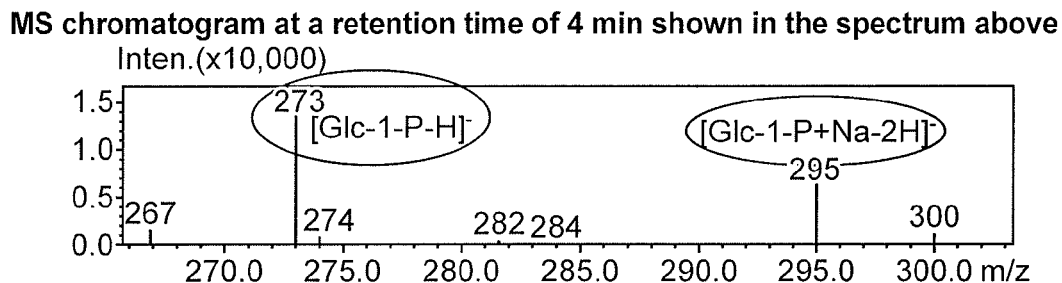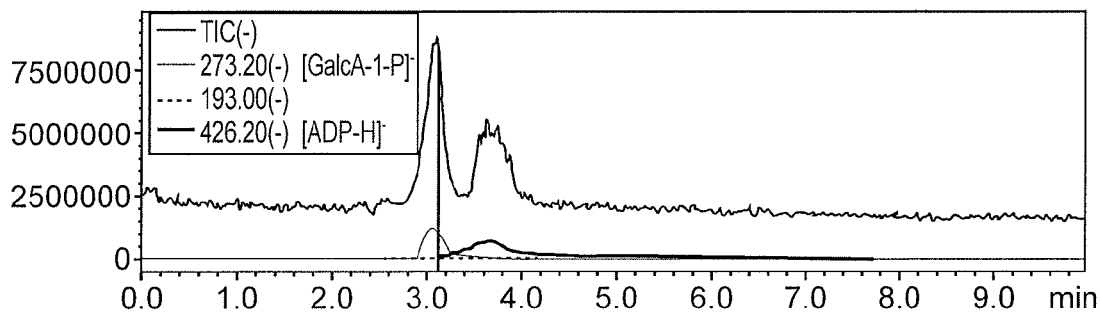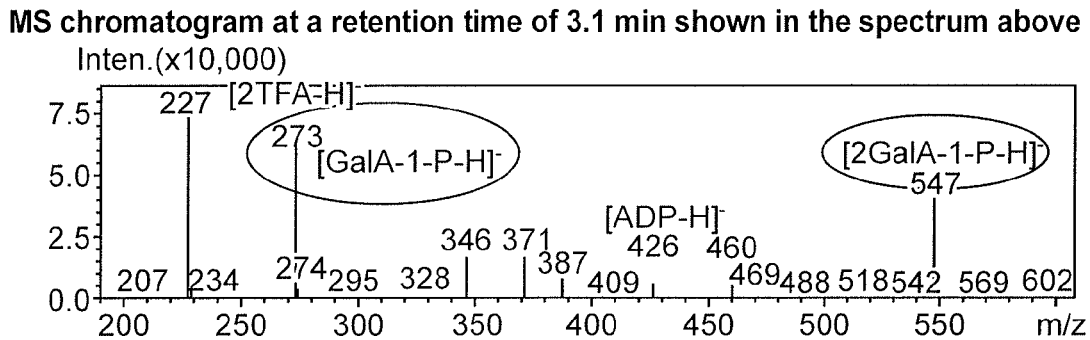
FIG. 26

C
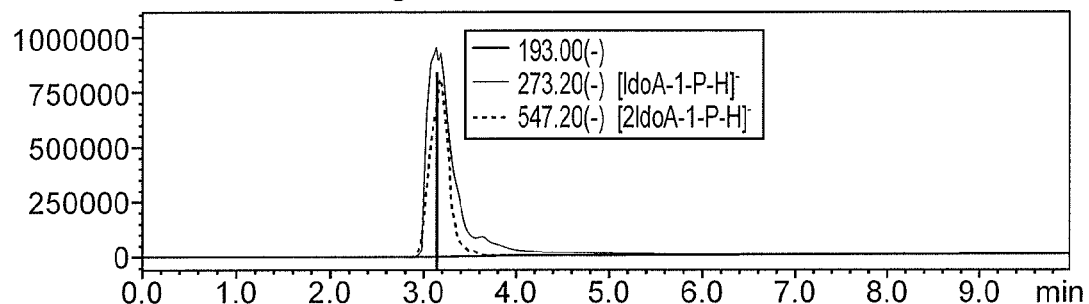
MS chromatogram at a retention time of 3.1 min shown in the spectrum above
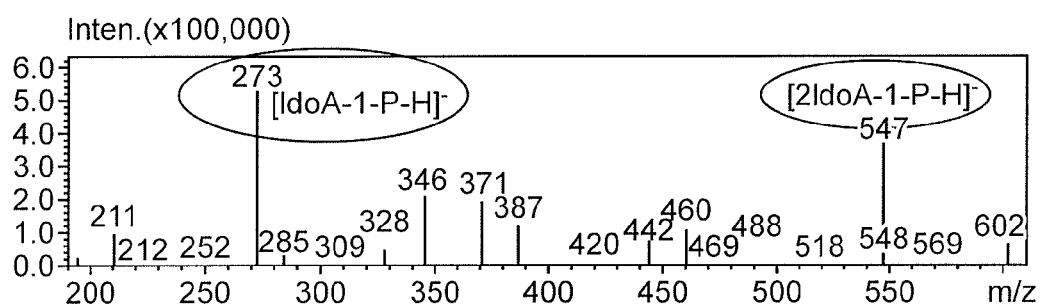
FIG. 26 (Cont.)

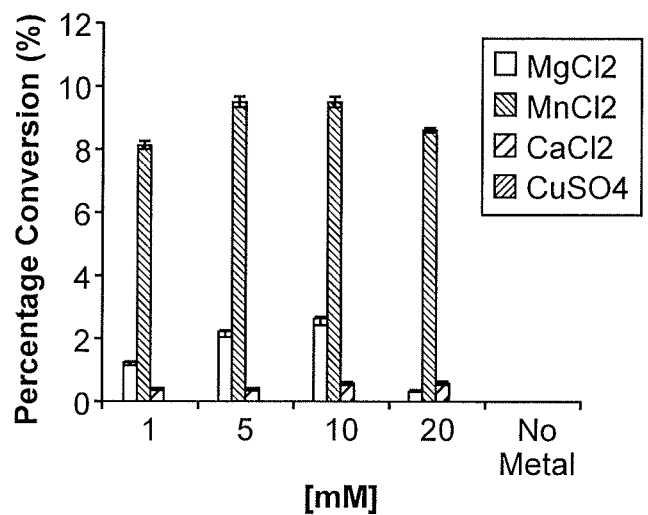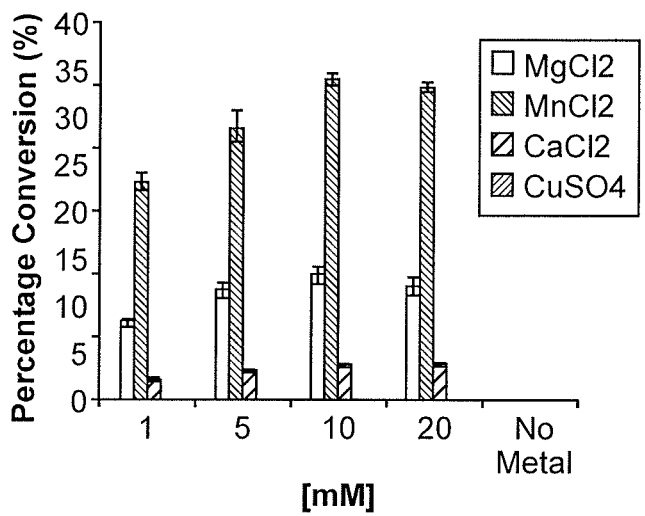
FIG. 28

A
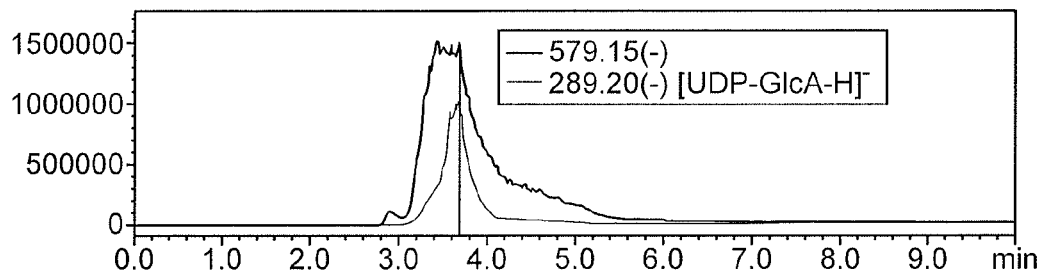
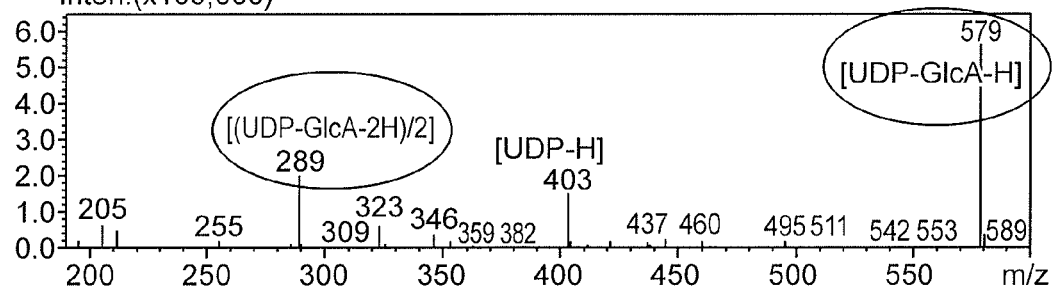
B
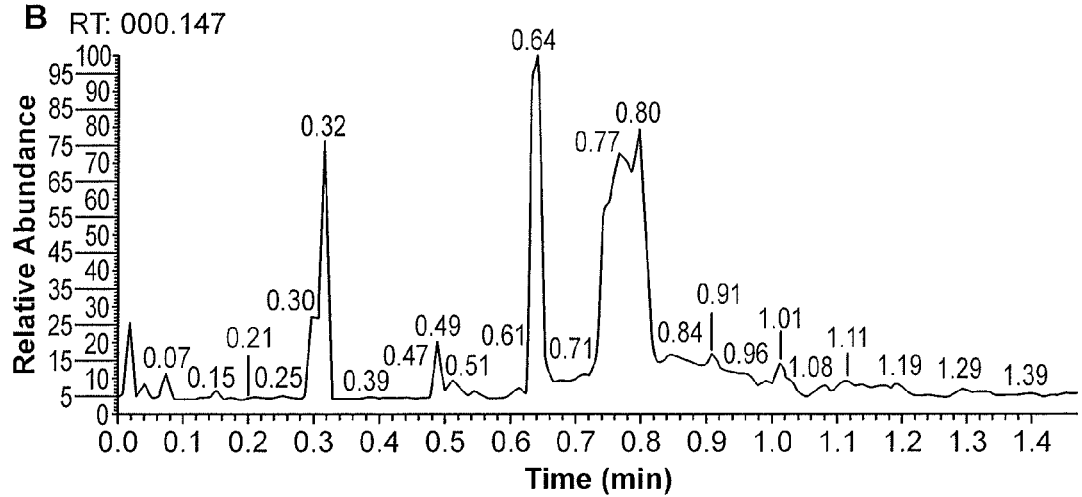
FIG. 30

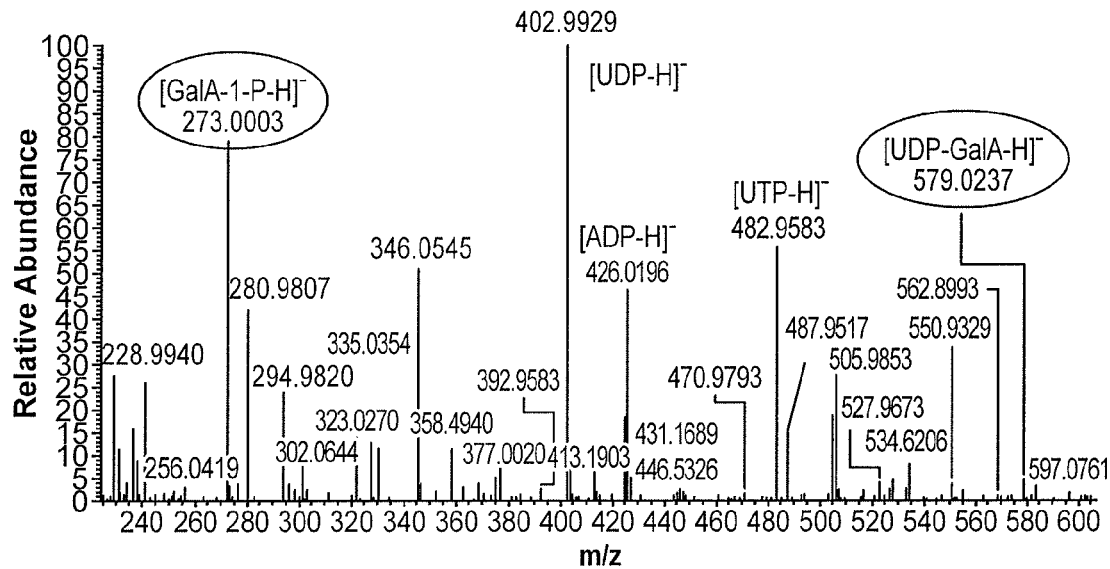
GalA-1-P, HRMS (ESI) m/z calcd for $C_6H_{10}O_{10}P$ (M-H) 273.0012, found 273.0003.
UDP-GalA, HRMS (ESI) m/z calcd for $C_{15}H_{21}N_2O_{18}P_2$ (M-H) 579.0219, found 579.0237.
UTP m/z calcd for $C_9H_{14}N_2O_{15}P_2$ (M-H) 482.9613, found 482.9683
UTP m/z calcd for $C_9H_{14}N_2O_{15}P_2$ (M-H) 402.9949, found 402.9929
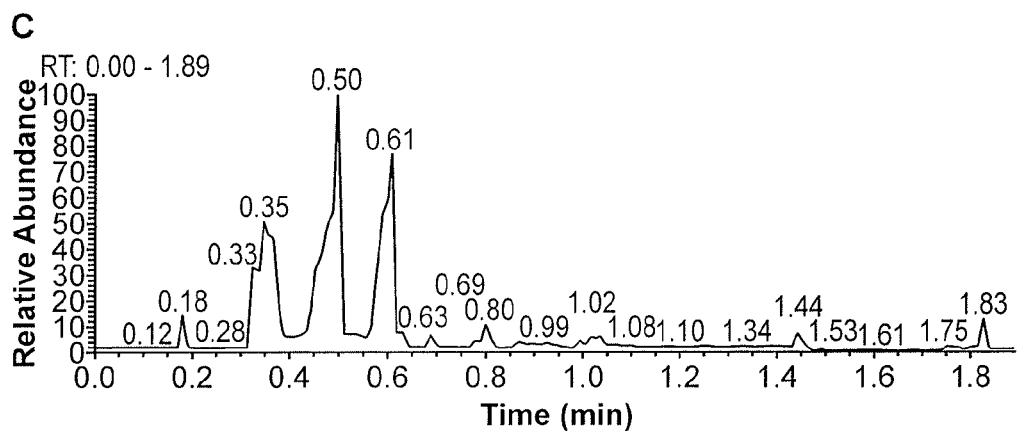
FIG. 30 (Cont. 1)

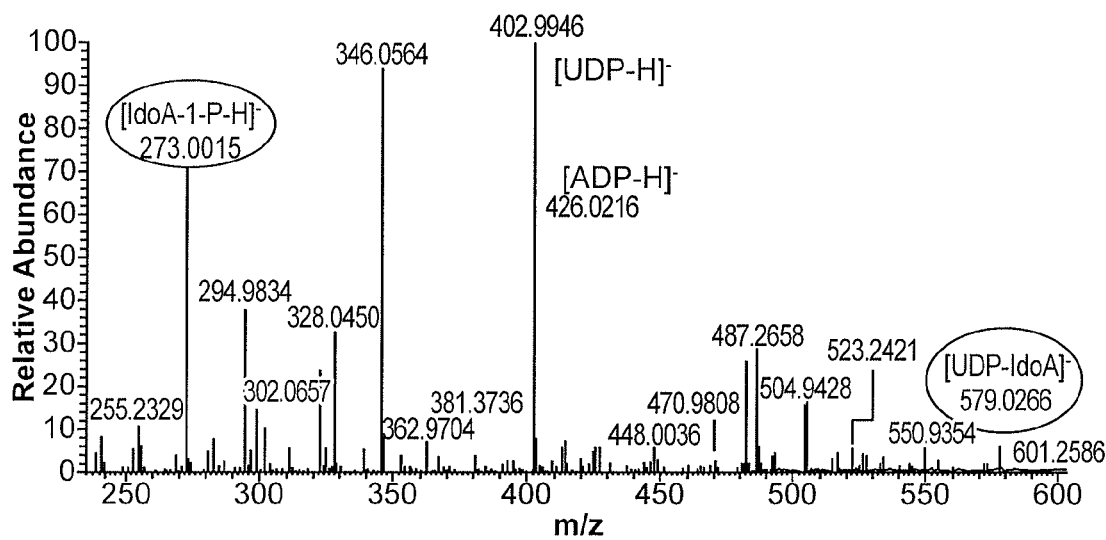
IdoA-1-P, HRMS (ESI) m/z calcd for $C_6H_{10}O_{10}P$ (M-H) 273.0012, found 273.0015.
UDP-IdoA, HRMS (ESI) m/z calcd for $C_{15}H_{21}N_2O_{18}P_2$ (M-H) 579.0219, found 579.0266.
UDP m/z calcd for $C_9H_{13}N_2O_{12}P_2$ (M-H) 402.9949, found 402.9929.
FIG. 30 (Cont. 2)

Developing solvent:
    EtOAc:H₂O:MeHO = 8:2:1 (by volume)

1. Reaction mixture with GlcNAcβMU
2. GlcNAcβMU standard
3. Reaction mixture with GlcNAcα2AA
4. GlcNAcα2AA standard
5. Reaction mixture with GlcNAcβProN₃
6. GlcNAcβProN₃ standard
5. Reaction mixture with GlcNAcαProN₃
6. GlcNAcαProN₃ standard 1  2  3  4  5  6  7  8

A
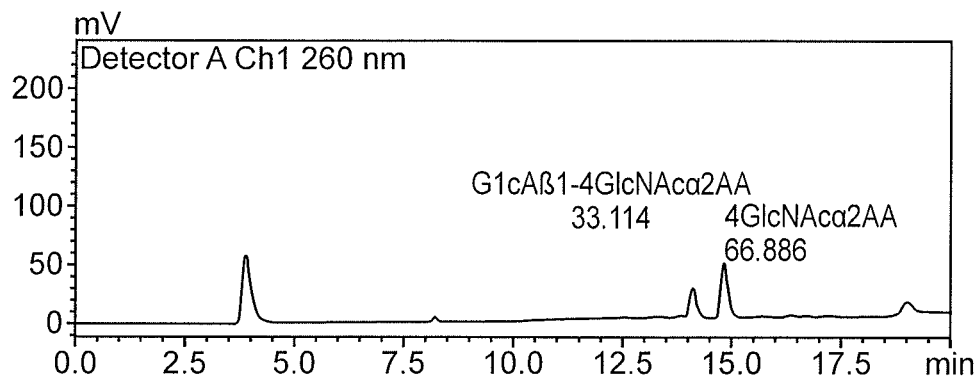
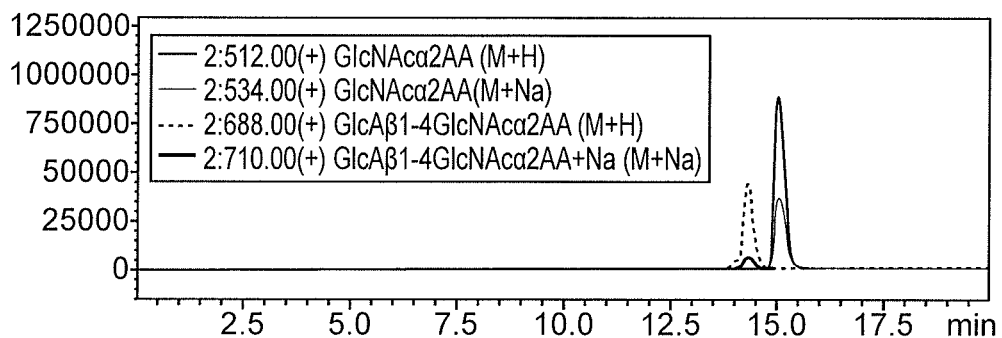
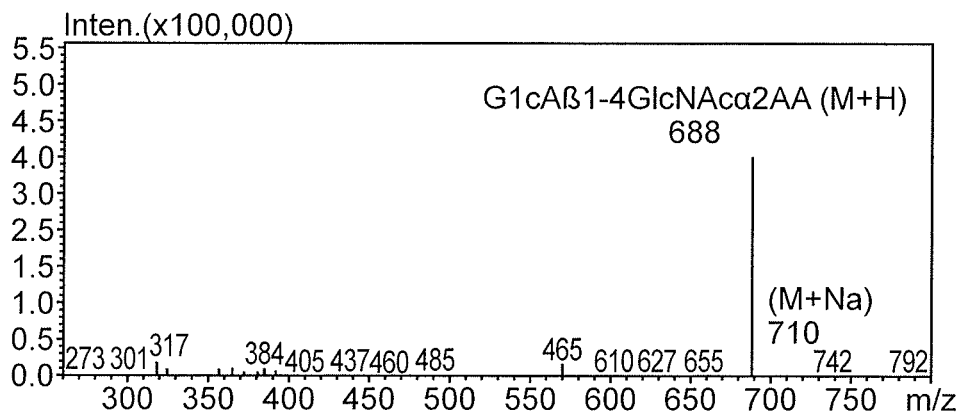
FIG. 32

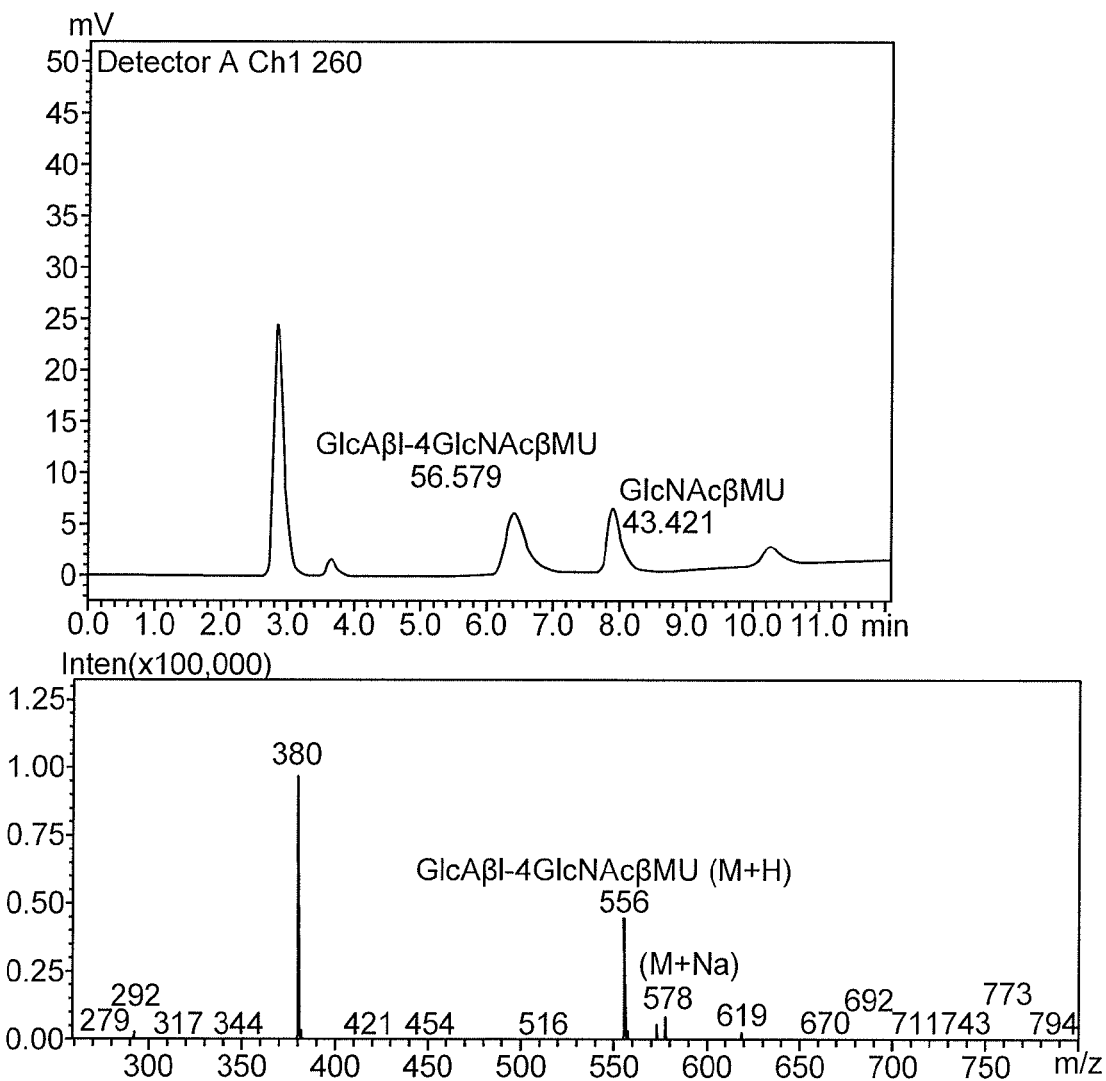
FIG. 32 (Cont. 1)

C   LCMS Chromatogram
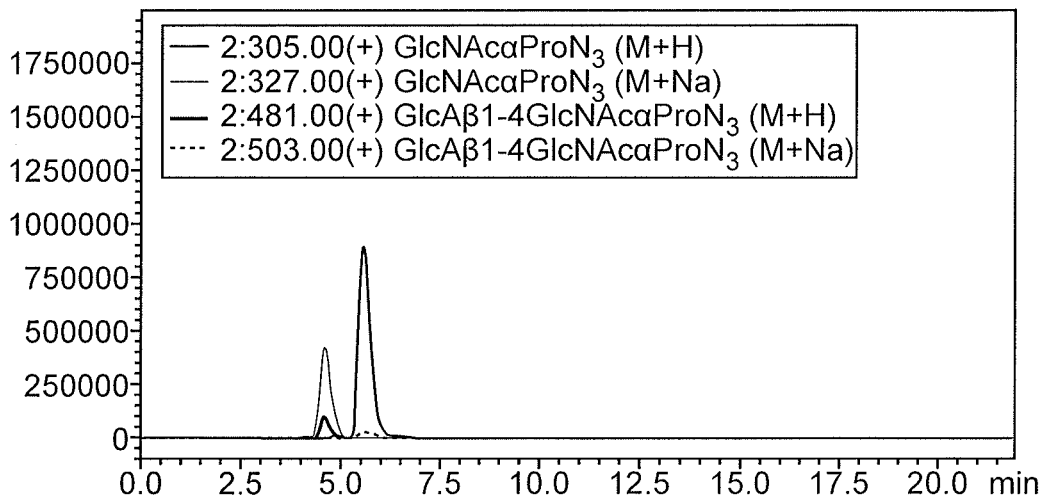
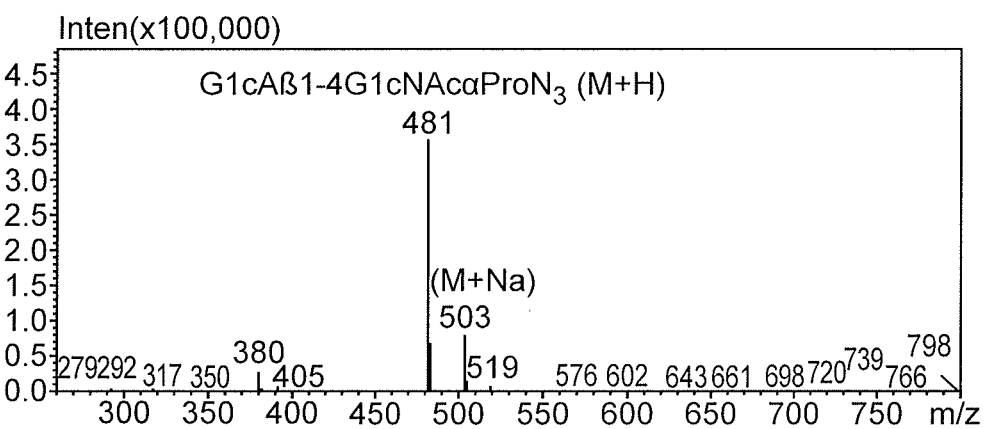
D
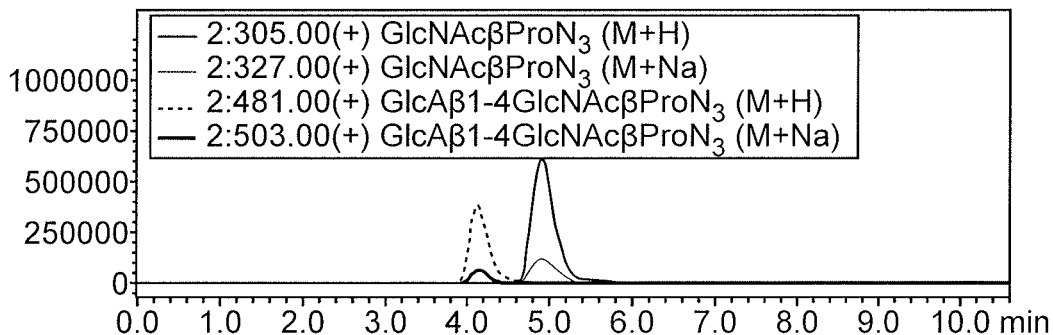
FIG. 32 (Cont. 2)

CHEMOENZYMATIC SYNTHESIS OF HEPARIN AND HEPARAN SULFATE ANALOGS

CROSS-REFERENCES TO RELATED APPLICATIONS

The present application is a continuation-in-part of International Patent Application No. PCT/US12/47875, filed Jul. 23, 2012, which claims priority to U.S. Provisional Patent Application No. 61/510,125, filed Jul. 21, 2011, and further claims priority to U.S. Provisional Patent Application No. 61/926,088, filed Jan. 10, 2014, U.S. Provisional Patent Application No. 61/836,067, filed Jun. 17, 2013, and U.S. Provisional Patent Application No. 61/815,050, filed Apr. 23, 2013, each of which is incorporated herein by reference in its entirety.

STATEMENT AS TO RIGHTS TO INVENTIONS MADE UNDER FEDERALLY SPONSORED RESEARCH AND DEVELOPMENT

This work was supported by NIH grants R01HD065122 and R00DK078668, and NSF grants CHE-1012511 and CHE-0548235. The United States government may have certain rights to the invention disclosed herein.

BACKGROUND OF THE INVENTION

Reference to a "Sequence Listing," a Table, or a Computer Program Listing Appendix Submitted as an ASCII Text File The Sequence Listing written in file -2050-1-1.TXT, created on Feb. 27, 2014, 69,632 bytes, machine format IBM-PC, MS-Windows operating system, is hereby incorporated by reference in its entirety for all purposes.

Heparin and heparan sulfate (HS) are sulfated linear polysaccharides composed of alternating α1-4-linked D-glucosamine ($GlcNH_2$) residues and 1-4 linked uronic acid α-linkage for L-iduronic acid, IdoA, and β-linkage for D-glucuronic acid, GlcA). Possible modifications are 2-O-sulfation on the uronic acid residues and one or more modifications on the glucosamine residues including N-sulfation, N-acetylation, 6-O-sulfation, and 3-O-sulfation. Heparin is a mixture of polysaccharides that can be considered as special forms of HS with higher levels of sulfation and iduronic acid content per disaccharide repeat unit. Heparin is mostly produced by mast cells and heparan sulfates are produced by different cell types in animals. They are attractive synthetic targets due to their structural complexity which possesses great synthetic challenges and their important roles in regulating cancer growth, blood coagulation, inflammation, assisting viral and bacterial infections, signal transduction, lipid metabolism, and cell differentiation.

Currently, more than a hundred heparan sulfate binding proteins have been identified, and the structure-activity relationship studies (SAS) have revealed the interaction pattern between heparan sulfate and protein, and further directed toward discovering and designing HS mimics. Heparin pentasaccharide sequence $H_5$ (also call DEFGH) GlcNS6S-GlcA-GlcNS3S6S-IdoA2S-GlcNS6S is essential for antithrombin III binding and thrombin inhibition activities. Based on the DEFGH structure, a new potential antithrombotic, idraparinux, was synthesized by replacing N-sulfate groups in all three glucosamine residues of heparin pentasaccharide DEFGH with O-sulfates and introducing methyl ethers at the available free hydroxyl groups and showed better anticoagulation activity and longer duration of action than DEFGH. Another pentasaccharide sequence HexA-GlcNS-HexA-GlcNS-IdoA2S has high affinity selectively for FGF-2 (fibroblast grow factor 2), while trisaccharide motif IdoA2S-GlcNS6S-IdoA2S is specific for FGF-1. N-, 2-O- and 6-O-sulfations of the glucosamine residues in HS have been shown to be required for FGF4 binding. Additionally, it has been suggested that the N-acetylated glucosamine region rich in GlcA residues displays structural plasticity and hence could mediate protein interactions. However, the detailed information about sequence requirement of HS that interact with many other proteins is currently unclear due to the lack of the technology of preparing a wide range of structurally defined HS.

Current chemical and enzymatic synthetic methods do not provide convenient access to all possible heparin and HS oligosaccharide sequences. Chemical synthetic approaches are time-consuming and tedious. The production yields decrease dramatically with the increase of the length of the target molecules. Obtaining defined structures longer than octasaccharides remains as a major challenge for chemical synthesis. HS-modifying enzymes have been used with other enzymes to prepare heparin polysaccharides and oligosaccharides with a limited range of sulfation patterns. Due to the complex nature of HS-modifying enzymes, these types of methods do not allow the synthesis of a wide range of HS structures.

Sialic acid-containing oligo- and poly-saccharides belong to another group of sugars implicated in various biological and pathological processes. Sialyltransferases are the key enzymes that catalyze the transfer of a sialic acid residue from cytidine 5'-monophosphate-sialic acid (CMP-sialic acid) to an acceptor to form sialic acid-containing products. They function in processes including cell-cell recognition, cell growth and differentiation, cancer metastasis, immunological regulation, as well as bacterial and viral infection. Besides being prevalent in mammals, sialyltransferases have been found in some pathogenic bacteria. They are mainly involved in the formation of sialic acid-containing capsular polysaccharides (CPS) and lipooligo(poly)saccharides (LOS/LPS), serving as virulence factors, preventing recognition by host's immune system, and modulating interactions with the environment.

Cloning of sialyltransferases from various sources, including mammalian tissues, bacteria, and viruses has been reported. However, most mammalian glycosyltransferases—including sialyltransferases—suffer from restricted substrate specificity and no or low expression in laboratory *E. coli* systems. In comparison, bacterial glycosyltransferases have more promiscuous substrate flexibility and are generally easier to access using *E. coli* expression systems.

What is needed is a convenient route to form complex oligosaccharide products from simple starting materials. Methods for conversion of monosaccharides and monosaccharide derivatives to chemically and biologically important products, including those containing post-glycosylational modifications and sialic acid moieties, are needed. Importantly, the intermediates and products should be formed in a highly regio- and stereo-selective manner. The one-pot enzymatic methods of the present invention meet this and other needs.

BRIEF SUMMARY OF THE INVENTION

In a first embodiment, the invention provides a method of synthesizing a UDP-sugar. The method includes forming a reaction mixture comprising a first sugar, a nucleotide-sugar pyrophosphorylase, and a first enzyme selected from a kinase and a dehydrogenase under conditions sufficient to form the UDP-sugar.

In a second embodiment, the invention provides a method of preparing an oligosaccharide. The method includes forming a first reaction mixture containing a first sugar, an acceptor sugar, a glycosyltransferase, a nucleotide-sugar pyrophosphorylase, and an enzyme selected from a kinase and a dehydrogenase. The first sugar is selected from a substituted or unsubstituted N-acetylglucosamine (2-acetamido-2-deoxy glucose, GlcNAc), a substituted or unsubstituted glucosamine (GlcNH$_2$), a substituted or unsubstituted glucuronic acid (GlcA), a substituted or unsubstituted iduronic acid (IdoA), and a substituted or unsubstituted glucose-1-phosphate (Glc-1-P), and the acceptor sugar includes at least one member selected from a substituted or unsubstituted N-acetylglucosamine (GlcNAc), a substituted or unsubstituted glucosamine (GlcNH$_2$), a substituted or unsubstituted glucuronic acid (GlcA), and a substituted or unsubstituted iduronic acid (IdoA). The reaction mixture is formed under conditions sufficient to convert the first sugar to a UDP-sugar, and sufficient to couple the sugar in the UDP-sugar to the acceptor sugar. When the first sugar is substituted or unsubstituted GlcNAc or GlcNH$_2$, the sugar in the UDP-sugar is coupled to a substituted or unsubstituted GlcA or a substituted or unsubstituted IdoA of the acceptor sugar. When the first sugar is substituted or unsubstituted Glc-1-P, substituted or unsubstituted GlcA, or substituted or unsubstituted IdoA, the sugar in the UDP-sugar is coupled to a substituted or unsubstituted GlcNH$_2$ or a substituted or unsubstituted GlcNAc of the acceptor sugar.

In a third embodiment, the invention provides a method of preparing a sialylated oligosaccharide having at least two sialic acid moieties. The method includes forming a reaction mixture containing: a substrate sugar; cytidine-5'-monophospho-sialic acid (CMP-sialic acid or CMP-Sia) or derivatives; and *Photobacterium damselae* α2-6-sialyltransferase (Pd2,6ST) under conditions sufficient to form the sialylated oligosaccharide. The substrate sugar can be prepared using the one-pot multi-enzyme methods of the invention.

BRIEF DESCRIPTION OF THE DRAWINGS

FIG. 1 shows a sequence alignment of NahK_JCM1217 (GenBank accession no. BAF73925) (SEQ ID NO:19), NahK_ATCC55813 (SEQ ID NO:20), and NahK_ATCC15697 (SEQ ID NO:21).

FIG. 16 shows the one-pot four-enzyme synthesis of dissacharides with different modification on C2 and C6. Enzymes used: NahK_ATCC55813, N-acetylhexosamine 1-kinase cloned from *Bifidobacterium longum* ATCC55813; PmGlmU, *Pasteurella multocida* N-acetylglucosamine-1-phosphate uri-dylyltransferase; PmPpA, *Pasteurella multocida* inorganic pyrophosphatase; PmHS2, *Pasteurella multocida* heparosan synthase 2.

FIG. 17 shows the structures of UDP-GlcNAc derivatives F17-1-F17-12 including UDP-GlcNAc (F17-1), UDP-GlcNTFA (F17-2), UDP-GlcNAc (F17-3), UDP-GlcNAcN$_3$ (F17-4), UDP-GlcNH$_2$ (F17-5), UDP-GlcN$_3$ (F17-6), UDP-GlcNS (F17-7), UDP-GlcNAc6N$_3$ (F17-8), UDP-GlcNAc6NGc (F17-9), UDP-GlcNAc6NH$_2$ (F17-10j), UDP-GlcNAc6NAcN$_3$ (F17-11), and UDP-GlcNAc6S (F17-12).

FIG. 18A shows the one-pot four-enzyme system of the disaccharides GlcNAcα1-4GlcAβ2AAMe (F18-1), GlcNTFAα1-4GlcAβ2AAMe (F18-2), GlcNAc6N$_3$α1-4GlcAβ2AAMe (F18-3). FIG. 18B shows the PmHS2-catalyzed synthesis of the disaccharides GlcNGcα1-4GlcAβ2AAMe (F18-4), GlcNAcN$_3$α1-4GlcAβ2AAMe (F18-5), GlcNAc6NGcα1-4GlcAβ2AAMe (F18-6).

FIG. 26 shows LC-MS assay data for AtGlcAK-catalyzed synthesis of sugar-1-phosphate from sugar and ATP. FIG. 26A, AtGlcAK kinase reaction using GlcA as the starting sugar; FIG. 26B, AtGlcAK kinase reaction using GalA as the starting sugar; FIG. 26C, AtGlcAK kinase reaction using IdoA as the starting sugar.

FIG. 28 shows metal effects on the heparosan synthase activity of KfiA (FIG. 28A) and PmHS2 (FIG. 28B).

FIG. 30 shows LC-MS or high resolution mass spectrometry (Orbitrap HRMS) assay for the synthesis of UDP-sugars from sugar, ATP, and UTP using one-pot three-enzyme reactions containing AtGlcAK, BLUSP, and PmPpA. FIG. 30A, LC-MS assay and GlcA was used as the starting sugar; FIG. 30B, FIRMS assay and GalA was used as the starting sugar; FIG. 30C, HRMS assay and IdoA was used as the starting sugar.

FIG. 32 shows LC-MS analysis of PmHS2-catalyzed reaction for the formation of GlcA-GlcNAc disaccharide derivatives. FIG. 32A, GlcNAcα2AA was used as the acceptor; FIG. 32B, GlcNAcβMU was used as the acceptor; FIG. 32C, GlcNAcαProN$_3$ was used as the acceptor; FIG. 32D, GlcNAcβProN$_3$ was used as the acceptor.

DETAILED DESCRIPTION OF THE INVENTION

I. General

Figure 2:
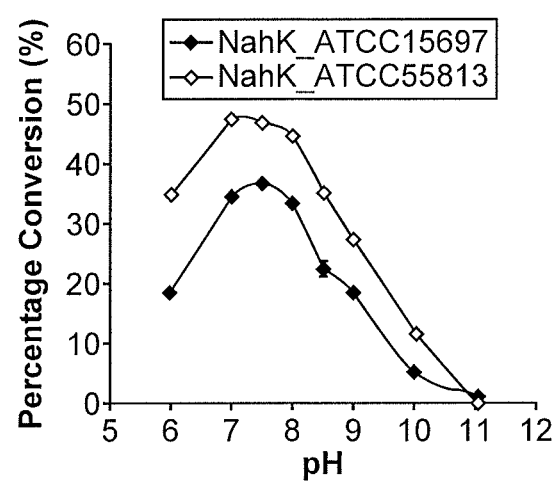
FIG. 2 shows the pH profiles of NahK_ATCC15697 (♦, filled diamond) and NahK_ATCC55813 (◊, open diamond). Buffers used: MES, pH 6.0; Tris-HCl, pH 7.0-9.0; CAPS, pH 10.0-11.0.

The present invention provides a convenient and highly efficient one-pot multienzyme system for the synthesis of UDP-sugars and oligosaccharides including heparin and heparosan sulfate (HS) analogs as well as human milk oligosaccharides (HMOs). Kinases or dehydrogenases, nucleotide-sugar pyrophosphorylases, and/or glycosyltransferases are used in one-pot reactions to convert monosaccharide precursors to UDP-sugars and/or oligosaccharides. Chemical diversification of the enzymatically formed UDP-sugars and oligosaccharides can be conducted to produce more structural variations. In particular, non-sulfated oligosaccharides can be selectively modified to prepare structurally defined products with desired sulfation patterns. A diverse set of enzymatic substrates can be used in the methods of the invention to prepare a wide range of useful UDP-sugars and oligosaccharides.

II. Definitions

As used herein, the term "first sugar" refers to a monosaccharide starting material used in the methods of the invention. The monosaccharide can be a hexose or a pentose. Hexoses include, but are not limited to, glucose (Glc), glucosamine (2-amino-2-deoxy-glucose; GlcNH$_2$), N-acetylglucosamine (2-acetamido-2-deoxy-glucose; GlcNAc), galactose (Gal), galactosamine (2-amino-2-deoxy-galactose; GalNH$_2$), N-acetylgalactosamine (2-acetamido-2-deoxy-galactose; GalNAc), mannose (Man), mannosamine (2-amino-2-deoxy-mannose; ManNH$_2$), N-acetylmannosamine (2-acetamido-2-deoxy-mannose; ManNAc), glucuronic acid (GlcA), iduronic acid (IdoA), and galacturonic acid (GalA). Pentoses include, but are not limited to, ribose (Rib), xylose (Xyl), and arabinose (Arb). The sugar can be a D sugar or an L sugar. The sugar can be unsubstituted or substituted with moieties including, but not limited to, amino groups, azido groups, amido groups, acylamido groups, N-sulfate groups (sulfamate), and O-sulfate groups. A "second sugar" and subsequent sugars are generally defined as for the first sugar, except that they are used after the first sugar in a multi-step synthesis.

As used herein, the term "UDP-sugar" refers to a sugar containing a uridine diphosphate moiety. The sugar portion of the UDP-sugar is defined as for the "first sugar" described above. UDP-sugars include, but are not limited to UDP-Glc, UDP-GlcNAc, UDP-GlcNH$_2$, UDP-GlcA, UDP-IdoA, UDP-GalA, UDP-Gal, UDP-GalNAc, UDP-GalNH$_2$, UDP-Man, UDP-ManNAc, and UDP-ManNH$_2$. The UDP-sugar can be unsubstituted or substituted as described above.

As used herein, the term "CMP-sialic acid" refers to a sialic acid having a cytidine-5'-monophosphate moiety. The sialic acid moiety can include N- and O-substituted derivatives of neuraminic acid (i.e., 5-acetamido-3,5-dideoxy-D-glycero-D-galacto-non-2-ulosonic acid, or (4S,5R,6R,7S,8R)-5-amino-4,6,7,8,9-pentahydroxy-2-oxo-nonanoic acid). CMP-sialic acids include, but are not limited to, cytidine 5'-monophosphate N-acetylneuraminic acid (CMP-Neu5Ac).

As used herein, the term "oligosaccharide" refers to a compound containing at least two monosaccharides covalently linked together. Oligosaccharides include disaccharides, trisaccharides, tetrasachharides, pentasaccharides, hexasaccharides, heptasaccharides, octasaccharides, and the like. Covalent linkages generally consist of glycosidic linkages (i.e., C—O—C bonds) formed from the hydroxyl groups of adjacent sugars. Linkages can occur between the 1-carbon and the 4-carbon of adjacent sugars (i.e., a 1-4 linkage), the 1-carbon and the 3-carbon of adjacent sugars (i.e., a 1-3 linkage), the 1-carbon and the 6-carbon of adjacent sugars (i.e., a 1-6 linkage), or the 1-carbon and the 2-carbon of adjacent sugars (i.e., a 1-2 linkage). Linkages can occur between the 2-carbon and the 3-carbon of adjacent sugars (i.e., a 2-3 linkage), the 2-carbon and the 6-carbon of adjacent sugars (i.e., a 2-6 linkage), the 2-carbon and the 8-carbon of adjacent sugars (i.e., a 2-8 linkage), or the 2-carbon and the 9-carbon of adjacent sugars (i.e., a 2-9 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons or the 2-, 3-, 6-, 8-, and 9-carbons.

As used herein, the term "sialylated oligosaccharide" refers to an oligosaccharide as described above having at least one sialic acid moiety covalently linked to the oligosaccharide. The sialic acid moiety is a monosaccharide subunit and can include N- and O-substituted derivatives of neuraminic acid (i.e., (4S,5R,6R,7S,8R)-5-amino-4,6,7,8,9-pentahydroxy-2-oxo-nonanoic acid).

As used herein, the term "enzyme" refers to a polypeptide that catalyzes the transformation of a starting material, such as a sugar, to an intermediate or product of the one-pot reactions of the invention. Examples of enzymes include, but are not limited to, kinases, dehydrogenases, nucleotide-sugar pyrophosphorylases, pyrophosphatases, and glycosyltransferases. Other enzymes may be useful in the methods of the invention.

As used herein, the term "kinase" refers to a polypeptide that catalyzes the covalent addition of a phosphate group to a substrate. The substrate for a kinase used in the methods of the invention is generally a sugar as defined above, and a phosphate group is added to the anomeric carbon (i.e. the "1" position) of the sugar. The product of the reaction is a sugar-1-phosphate. Kinases include, but are not limited to, N-acetylhexosamine 1-kinases (NahKs), glucuronokinases (GlcAKs), glucokinases (GlcKs), galactokinases (GalKs), monosaccharide-1-kinases, and xylulokinases. Certain kinases utilize nucleotide triphosphates, including adenosine-5'-triphosphate (ATP) as substrates.

As used herein, the term "dehydrogenase" refers to a polypeptide that catalyzes the oxidation of a primary alcohol. In general, the dehyrogenases used in the methods of the invention convert the hydroxymethyl group of a hexose (i.e. the C6-OH moiety) to a carboxylic acid. Dehydrogenases useful in the methods of the invention include, but are not limited to, UDP-glucose dehydrogenases (Ugds).

As used herein, the term "nucleotide-sugar pyrophosphorylase" refers to a polypeptide that catalyzes the conversion of a sugar-1-phosphate to a UDP-sugar. In general, a uridine-5'-monophosphate moiety is transferred from uridine-5'-triphosphate to the sugar-1-phosphate to form the UDP-sugar. Examples of nucleotide-sugar pyrophosphorylases include glucosamine uridylyltransferases (GlmUs) and glucose-1-phosphate uridylyltransferases (GalUs). Nucleotide-sugar pyrophosphorylases also include promiscuous UDP-sugar pyrophosphorylases, termed "USPs," that can catalyze the conversion of various sugar-1-phosphates to UDP-sugars including UDP-Glc, UDP-GlcNAc, UDP-GlcNH$_2$, UDP-Gal, UDP-GalNAc, UDP-GalNH$_2$, UDP-Man, UDP-ManNAc, UDP-ManNH$_2$, UDP-GlcA, UDP-IdoA, UDP-GalA, and their substituted analogs.

As used herein, the term "pyrophosphatase" (abbreviated as PpA) refers to a polypeptide that catalyzes the conversion of pyrophosphate (i.e., $P_2O_7^{4-}$, $HP_2O_7^{3-}$, $H_2P_2O_7^{2-}$, $H_3P_2O_7$) to two molar equivalents of inorganic phosphate (i.e., $PO_4^{3-}$, $HPO_4^{2-}$, $H_2PO_4$).

As used herein, the term "glycosyltransferase" refers to a polypeptide that catalyzes the formation of an oligosaccharide from a nucleotide-sugar an acceptor sugar. Nucleotide-sugars include, but are not limited to, nucleotide diphosphate sugars (NDP-sugars) and nucleotide monophosphate sugars (NMP-sugars) such as a cytidine monophophate sugar (CMP-sugar). In general, a glycosyltransferase catalyzes the transfer of the monosaccharide moiety of an NDP-sugar or CMP-sugar to a hydroxyl group of the acceptor sugar. The covalent linkage between the monosaccharide and the acceptor sugar can be a 1-3 linkage, a 1-4 linkage, a 1-6-linkage, a 1-2 linkage, a 2-3 linkage, a 2-6 linkage, a 2-8 linkage, or a 2-9 linkage as described above. The linkage may be in the α- or β-configuration with respect to the anomeric carbon of the monosaccharide. Other types of linkages may be formed by the glycosyltransferases in the methods of the invention. Glycosyltransferases include, but are not limited to, heparosan synthases (HSs) glucosaminyltransferases, N-acetylglucosaminyltransferases, glucosyltransferasess, glucuronyltransferases, and sialyltransferases.

The glycosyltransferases useful in the present invention include those in Glycosyltransferase family 80 (GT80 using CAZy nomenclature) and include beta-galactoside alpha-2, 3-sialyltransferases that catalyze the following conversion: CMP-sialic acid+β-D-galactosyl-R=CMP+α-sialic acid-(2→3)-β-D-galactosyl-R, where the acceptor is GalβOR, where R is H, a monosaccharide, an oligosaccharide, a polysaccharide, a glycopeptide, a glycoprotein, a glycolipid, or a hydroxyl-containing compound. GT80 family sialyltransferases also include galactoside or N-acetylgalactosaminide alpha-2,6-sialyltransferases that catalyze the following conversion: CMP-sialic acid+galactosyl/GalNAc-R=CMP+α-sialic acid-(2→6)-β-D-galactosyl/GalNAc-R, where the acceptor is GalOR or GalNAcOR, where R is H, serine or threonine on a peptide or protein, a monosaccharide, an oligosaccharide, a polysaccharide, a glycopeptide, a glycoprotein, a glycolipid, or a hydroxyl-containing compound.

As used herein, the term "CMP-sialic acid synthetase" refers to a polypeptide that catalyzes the synthesis of cytidine monophosphate sialic acid (CMP-sialic acid) from cytidine triphosphate (CTP) and sialic acid.

As used herein, the term "sialic acid aldolase" refers to an aldolase that catalyzes a reversible reaction that converts a suitable hexosamine, hexose, pentose, or derivative (such as N-acetyl mannosamine) to sialic acid via reaction with pyruvate.

As used herein, the term "substrate sugar" refers to a sugar that accepts a sialic acid moiety from a CMP-sialic acid. The substrate sugar can contain a monosaccharide, an oligosaccharide, or a polysaccharide.

As used herein, the term "couple" refers to catalyzing the formation of a covalent bond between enzyme substrates. The coupling can take place via the direct reaction of two substrates with each other. Alternatively, the coupling can include the formation of one or more enzyme-substrate intermediates. An enzyme-substrate intermediate can, in turn, react with another substrate (or another enzyme-substrate intermediate) to form the bond between the substrates.

As used herein, the terms "treat", "treating" and "treatment" refer to any indicia of success in the treatment or amelioration of an injury, pathology, condition, or symptom thereof, including any objective or subjective parameter such as abatement; remission; diminishing of symptoms or making the symptom, injury, pathology or condition more tolerable to the subject; decreasing the duration of the symptom or condition; or, in some situations, preventing the onset of the symptom or condition. The treatment or amelioration of symptoms can be based on any objective or subjective parameter; including, e.g., the result of a physical examination.

As used herein, "necrotizing enterocolitis" refers to the death of intestinal tissue in a subject.

As used herein, the term "subject" refers to a human or animal. In certain embodiments, the subject is a human infant.

III. Mono- and Oligo-Saccharides

A number of UDP-sugars can be synthesized according to the methods of the invention. In general, the UDP-sugars have structures according to Formula I:

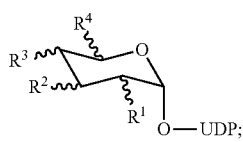

(I)

wherein each of $R^1$, $R^2$, and $R^3$ is independently selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; and $R^4$ is selected from $CH_2OH$, $CO_2^-$, $CO_2H$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, and $CH_2NHC(O)CH_2N_3$.

In some embodiments, the UDP-sugars have structures according to formula Ia:

(Ia)

A range of oligosaccharides can also be prepared using the methods of the invention. In general, the oligosaccharides contain one or more unit according to Formula II:

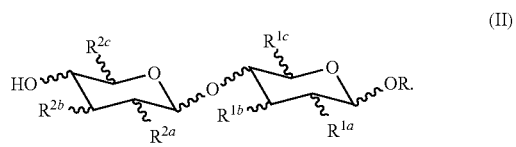

(II)

In oligosaccharide units according to Formula II, each of $R^{1a}$, $R^{1b}$, $R^{2a}$, and $R^{2b}$ is independently selected from OH, $N_3$, $NH_2$, $NHSO_3^-$, $OSO_3^-$, $NHC(O)CH_3$, $NHC(O)CF_3$, $NHC(O)CH_2OH$, or $NHC(O)CH_2N_3$; and each of $R^{1c}$ and $R^{2c}$ is independently selected from $CH_2OH$, $CO_2^-$, $CO_2H$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$. In some embodiments, one of $R^{1c}$ and $R^{2c}$ can be $CO_2^-$ or $CO_2H$, while the other of $R^{1c}$ and $R^{2c}$ can be $CH_2OH$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$. R includes but not is limited to H, $CH_3$, $CH_2CH_3$, $CH_2CH_2N_3$, $CH_2CH_2CH_2N_3$, an aglycon according to Formula B, Formula C, Formula D, or Formula E below, substituted or unsubstituted GlcNAc, substituted or unsubstituted GlcNH$_2$, substituted or unsubstituted GlcA, or substituted or unsubstituted Ido:

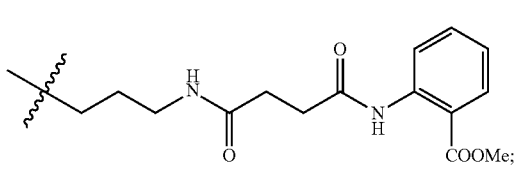

(B)

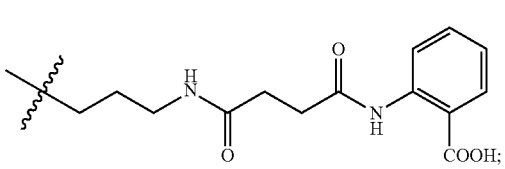

(C)

-continued

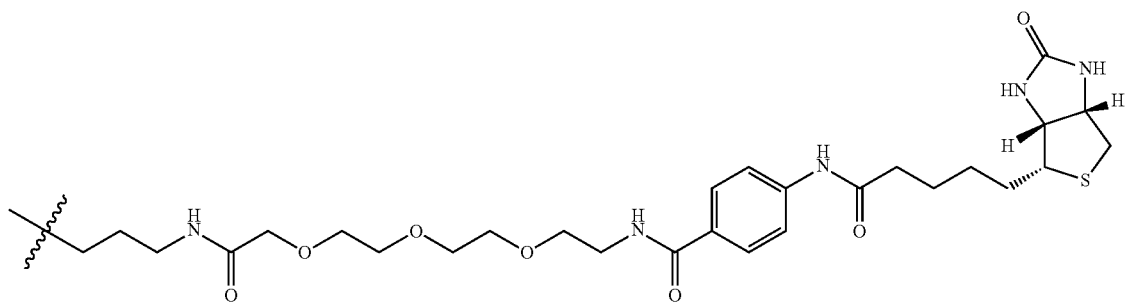

In some embodiments, the oligosaccharides have the structure of formula IIa:

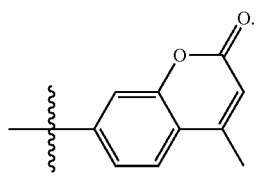

In some embodiments, the method provides oligosaccharides with structures according to Formula III:

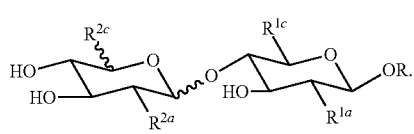

wherein each of $R^{1a}$, $R^{1b}$, and $R^{2a}$ is independently selected from OH, $N_3$, $NH_2$, $NHSO_3^-$, $OSO_3^-$, $NHC(O)CH_3$, $NHC(O)CF_3$, $NHC(O)CH_2OH$, or $NHC(O)CH_2N_3$; and $R^{1c}$ is selected from $CH_2OH$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$.

In some embodiments, the method provides oligosaccharides with structures according to Formula IV:

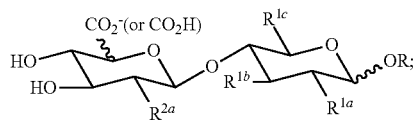

wherein each of $R^{1a}$, $R^{2a}$, and $R^{2b}$ is independently selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; and $R^{2c}$ is selected from $CH_2OH$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$.

In some embodiments, the present invention provides oligosaccharides having the structure of formula IVa:

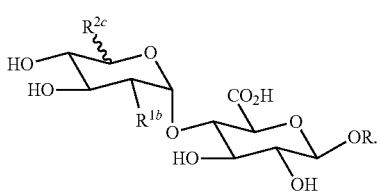

In some embodiments, the method provides oligosaccharides with structures according to Formula (V):

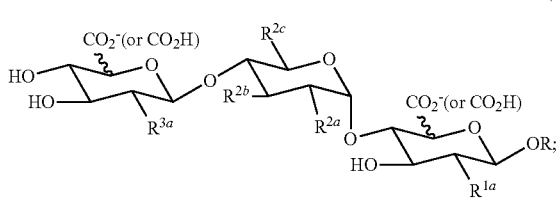

wherein each of $R^{1a}$, $R^{2a}$, $R^{2b}$, and $R^{3a}$ is independently selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; and $R^{2c}$ is selected from $CH_2OH$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$.

In some embodiments, the present invention provides oligosaccharides having a structure of formula Va:

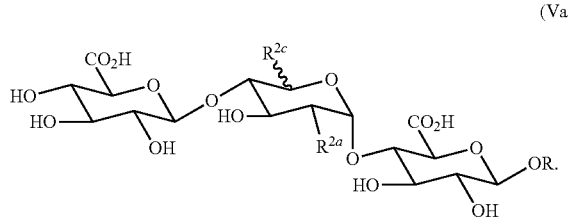

(Va)

In some embodiments, the method provides oligosaccharides with structures according to Formula VI:

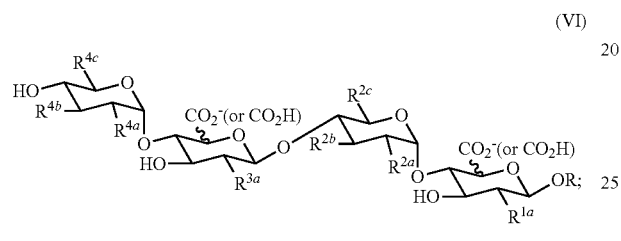

(VI)

wherein each of $R^{1a}$, $R^{2a}$, $R^{2b}$, $R^{3a}$, $R^{4b}$, and $R^{4b}$ is independently selected from OH, $N_3$, $NH_2$, $NHSO_3^-$, $OSO_3^-$, $NHC(O)CH_3$, $NHC(O)CF_3$, $NHC(O)CH_2OH$, or $NHC(O)CH_2N_3$; and each of $R^{2c}$, $R^{4c}$ is independently selected from $CH_2OH$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, or $CH_2NHC(O)CH_2N_3$.

In some embodiments, the oligosaccharides has the structure of formula VIa:

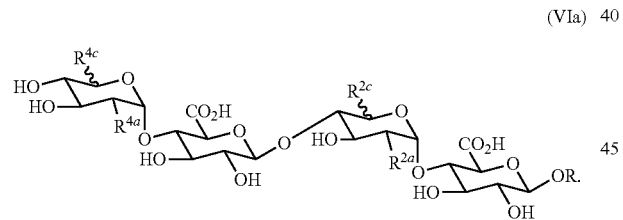

(VIa)

IV. One-Pot Method of Making UDP-Sugars

In a first embodiment, the invention provides a method of synthesizing a UDP-sugar. The method includes forming a reaction mixture comprising a first sugar, a nucleotide-sugar pyrophosphorylase, and a first enzyme selected from a kinase and a dehydrogenase under conditions sufficient to form the UDP-sugar.

In some embodiments, the first sugar is selected from substituted or unsubstituted glucose (Glc), substituted or unsubstituted glucose-1-phosphate (Glc-1-P), substituted or unsubstituted glucuronic acid (GlcA), substituted or unsubstituted glucuronic acid-1-phosphate (GlcA-1-P), substituted or unsubstituted iduronic acid (IdoA), substituted or unsubstituted iduronic acid-1-phosphate (IdoA-1-P), substituted or unsubstituted N-acetylglucosamine (GlcNAc), substituted or unsubstituted N-acetylglucosamine-1-phosphate (GlcNAc-1-P), substituted or unsubstituted glucosamine (GlcNH$_2$), substituted or unsubstituted glucosamine-1-phosphate (GlcNH$_2$-1-P), substituted or unsubstituted galactose (Gal), substituted or unsubstituted galactose-1-phosphate (Gal-1-P), substituted or unsubstituted galacturonic acid (GalA), substituted or unsubstituted galacturonic acid-1-phosphate (GalA-1-P), substituted or unsubstituted N-acetylgalactosamine (GalNAc), substituted or unsubstituted N-acetylgalactosamine-1-phosphate (GalNAc-1-P), substituted or unsubstituted galactosamine (GalNH$_2$), substituted or unsubstituted galactosamine-1-phosphate (GalNH$_2$-1-P), substituted or unsubstituted mannose (Man), substituted or unsubstituted mannose-1-phosphate (Man-1-P), substituted or unsubstituted N-acetylmannosamine (ManNAc), substituted or unsubstituted N-acetylmannosamine-1-phosphate (ManNAc-1-P), substituted or unsubstituted mannosamine (ManNH$_2$), substituted or unsubstituted mannosamine-1-phosphate (ManNH$_2$-1-P). In some embodiments, the first sugar is selected from GlcNAc, Glc-1-P, GlcA, and IdoA.

In some embodiments, the first sugar has the formula VII:

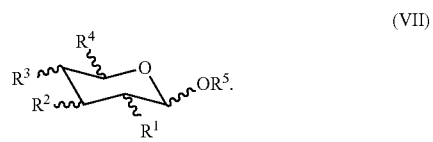

(VII)

Wherein each of $R^1$, $R^2$, and $R^3$ is selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; $R^4$ is selected from $CH_2OH$, $CO_2^-$, $CO_2H$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, and $CH_2NHC(O)CH_2N_3$; and $R^5$ can be H, $PO_3^{2-}$, or $HPO_3^-$. In some embodiments, the first sugar has the formula VIII or IX:

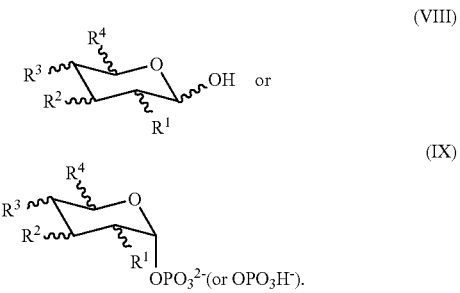

(VIII)

(IX)

In general, the reaction mixture formed in the methods of the invention contains a nucleotide-sugar pyrophosphorylase. The nucleotide-sugar pyrophosphorylase can be, but is not limited to, a glucosamine uridyltransferase (GlmU), a Glc-1-P uridylyltransferase (GalU), or a promiscuous UDP-sugar pyrophosphorylase (USP). The present inventors have cloned and characterized a GlmU from *P. multocida* (PmGlmU) that is useful for the synthesis of UDP-sugars according to the methods of the invention. Suitable GalUs can be obtained, for example, from yeasts such as *Saccharomyces fragilis*, pigeon livers, mammalian livers such as bovine liver, Gram-positive bacteria such as *Bifidobacterium bifidum*, and Gram-negative bacteria such as *Escherichia coli* (EcGalU) (Chen X, Fang J W, Zhang J B, Liu Z Y, Shao J, Kowal P, Andreana P, and Wang P G. J. Am. chem. Soc. 2001, 123, 2081-2082). In some embodiments, the nucleotide-sugar pyrophosphorylase is a USP. USPs include, but are not limited to, those obtained from *Pisum sativum* L. (PsUSP) and *Arabidopsis thaliana* (AtUSP), as well as enzymes obtained from protozoan parasites (such as *Leishmania major* and *Trypanosoma cruzi*) and hyperthermophilic archaea (such as *Pyrococcus furiosus* DSM 3638). USPs also include human UDP-GalNAc pyrophosphorylase AGX1, *E. coli* EcGlmU, and *Bifidobacterium longum* BLUSP. BLUSP was cloned and characterized by the inventors. In some embodiments, the nucleotide-sugar pyrophosphorylase is selected from AGX1, EcGlmU, EcGalU, PmGlmU, and BLUSP. In some embodiments, the nucleotide-sugar pyrophosphorylase is selected from EcGalU, PmGlmU, and BLUSP. In some embodiments, the nucleotide-sugar pyrophosphorylase is EcGalU. In some embodiments, the nucleotide-sugar pyrophosphorylase is PmGlmU. In some embodiments, the nucleotide-sugar pyrophosphorylase is BLUSP.

The reaction mixture formed in the methods of the invention also contains a kinase or a dehydrogenase. In some embodiments, the first enzyme in the reaction mixture is a kinase. The kinase can be, but is not limited to, an N-acetylhexosamine 1-kinase (NahK), a galactokinase (GalK), or a glucuronokinase (GlcAK). In some embodiments, the kinase is an NahK. The NahK can be, for example, *Bifidobacterium infantis* NahK_ATCC15697 or *Bifidobacterium longum* NahK_ATCC55813. NahK_ATCC15697 and NahK_ATCC55813 were cloned and characterized by the inventors. In some embodiments, the kinase is a GalK. The GalK can be, for example, *Escherichia coli* EcGalK (Chen X, Fang J W, Zhang J B, Liu Z Y, Shao J, Kowal P, Andreana P, and Wang P G. J. Am. chem. Soc. 2001, 123, 2081-2082) and *Streptococcus pneumoniae* TIGR4 SpGalK (Chen M, Chen L L, Zou Y, Xue M, Liang M, Jing L, Guan W Y, Shen J, Wang W, Wang L, Liu J, and Wang P G. Carbohydr. Res. 2011, 346, 2421-2425).

In some embodiments, the UDP-sugar is a substituted or unsubstituted UDP-GlcA. The first sugar employed in the synthesis of UDP-GlcA may vary depending on the enzymes that are used in the one-pot reaction. For example, Glc-1-P can be converted to UDP-Glc using a UDP-sugar pyrophosphorylase. UDP-GlcA can be obtained from UDP-Glc using a dehydrogenase. Accordingly, the reaction mixture in some embodiments of the invention includes a dehydrogenase. The dehydrogenase can be, but is not limited to, a UDP-glucose dehydrogenase (Ugd). In some embodiments, the dehydrogenase is *Pasteurella multocida* PmUgd. The PmUgd was cloned and characterized by the inventors. Alternatively, GlcA can be converted to GlcA-1-P using a GlcAK. In some embodiments, therefore, the kinase in the reaction mixture is a GlcAK. The GlcAK can be, for example, *Arabidopsis thaliana* AtGlcAK. The GlcA-1-P is then converted to UDP-GlcA by a UDP-sugar pyrophosphorylase such as *Arabidopsis thaliana* AtUSP. The AtGlcAK was cloned and characterized by the inventors. Other sugars, including iduronic acid (IdoA) and galacturonic acid (GalA), can also be used as substrates for GlcAKs in the methods of the invention.

Various UDP-sugars can be synthesized using the methods of the invention. In some embodiments, the UDP-sugar is selected from substituted or unsubstituted UDP-Glc, substituted or unsubstituted UDP-GlcA, substituted or unsubstituted UDP-IdoA, substituted or unsubstituted UDP-GalA, substituted or unsubstituted UDP-GlcNAc, substituted or unsubstituted UDP-GlcNH$_2$, substituted or unsubstituted UDP-Gal, substituted or unsubstituted UDP-GalNAc, substituted or unsubstituted UDP-GalNH$_2$, substituted or unsubstituted UDP-Man, substituted or unsubstituted UDP-ManNAc, and substituted or unsubstituted UDP-ManNH$_2$. In some embodiments, the UDP-sugar is selected from UDP-GlcNAc, UDP-GlcNH$_2$, UDP-GlcA, UDP-IdoA, UDP-GalA, UDP-Gal, UDP-Man, and UDP-Glc. The UDP-sugar can also have the structure of formula I described above.

The hydroxyl groups, the amino group, and the N-acetyl amino group in UDP-sugar can be substituted with any suitable substituent. In some embodiments, the hydroxyl groups, the amino group, and the N-acetyl amino group in UDP-sugar can be substituted with an azide, an amine, an N-trifluoroacetyl group, an N-acyl group, an O-sulfate, or an N-sulfate.

The reaction mixture formed in the methods of the invention can further include an inorganic pyrophosphatase (PpA). PpAs can catalyze the degradation of the pyrophosphate (PPi) that is formed during the conversion of a sugar-1-phosphate to a UDP-sugar. PPi degradation in this manner can drive the reaction towards the formation of the UDP-sugar products. The pyrophosphatase can be, but is not limited to, *Pasteurella multocida* PmPpA (Lau K, Thon V, Yu H, Ding L, Chen Y, Muthana M M, Wong D, Huang R, and Chen X. Chem. Commun. 2010, 46, 6066-6068).

The reaction mixture in the present methods can be formed under any conditions sufficient to convert the first sugar to a UDP-sugar or an intermediate such as a sugar-1-phosphate. The reaction mixture can include, for example, buffering agents to maintain a desired pH, as well as salts and/or detergents to adjust the solubility of the enzymes or other reaction components. In general, the reaction mixture also includes one or more nucleotide triphosphates (NTPs), such as UTP or ATP, that are consumed during sugar phosphorylation and UDP-sugar formation. The reaction mixture can contain a stoichiometric amount of an NTP, with respect to the first sugar, or an excess of the NTP. Divalent metal ions, such as magnesium ions, manganese ions, cobalt ions, or calcium ions, may be required to maintain the catalytic activity of certain enzymes. Enzyme cofactors, including but not limited to nicotinamide adenine dinucleotide (NAM, can also be included in the reaction mixture. In some embodiments, the reaction mixture further includes at least one component selected from UTP, ATP, $Mn^{2+}$, $Co^{2+}$, $Ca^{2+}$, and $Mg^{2+}$. After the reaction mixture is formed, it is held under conditions that allow for the conversion of the first sugar to the UDP sugar. For example, the reaction mixture can be held at 37° C. for 1 min-72 hr to form the UDP-sugar. The reaction mixture can also be held at 25° C. to form the UDP-sugar. Other temperatures and conditions may be suitable for forming the UDP-sugar, depending on the nature of the first sugar and the enzymes used for the synthesis.

In some embodiments, the invention provides a method of synthesizing a UDP-sugar of Formula I:

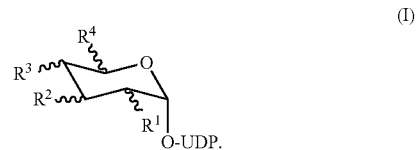

The method includes forming a reaction mixture comprising a first sugar, a nucleotide-sugar pyrophosphorylase, and a first enzyme selected from the group consisting of a kinase and a dehydrogenase under conditions sufficient to form the UDP-sugar. In some embodiments, the first sugar has the formula VII:

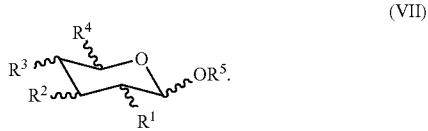

(VII)

Wherein each of $R^1$, $R^2$, and $R^3$ is selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; $R^4$ is selected from $CH_2OH$, $CO_2^-$, $CO_2H$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, and $CH_2NHC(O)CH_2N_3$; and $R^5$ can be H, $PO_3^{2-}$, or $HPO_3^-$.

Certain enzymes that are useful in the methods of the invention are characterized by a level of substrate promiscuity that allows for the synthesis of various natural and non-natural UDP-sugars. The scope of the products can be widened further by chemically appending a range of functionality to common enzymatically synthesized UDP-sugars. A UDP-sugar containing an azido moiety, for example, can be reduced to form an amino moiety which can be further elaborated via amide bond formation or N-sulfation to install various functional groups in the UDP-sugar. Similarly, trifluoracetamido moieties can also be converted to amino moieties for further derivitization. Accordingly, some embodiments of the invention include converting a UDP-azido-sugar or a UDP-trifluoroacetamido-sugar to a UDP-amino-sugar. In some embodiments, the UDP amino-sugar is further converted to a UDP-acylamido-sugar or a UDP-N-sulfated-sugar.

V. One-Pot Method of Making Oligosaccharides

The method described above for preparing UDP-sugars can be extended by incorporating additional enzymes that incorporate the sugar in UDP-sugars into oligosaccharide products. Accordingly, some embodiments of the invention provide a method of preparing an oligosaccharide. The method includes forming a first reaction mixture containing a first sugar, an acceptor sugar, a glycosyltransferase, a nucleotide-sugar pyrophosphorylase, and an enzyme selected from a kinase and a dehydrogenase. The first sugar is selected from a substituted or unsubstituted N-acetylglucosamine (2-acetamido-2-deoxy glucose, GlcNAc), a substituted or unsubstituted glucosamine ($GlcNH_2$), a substituted or unsubstituted glucuronic acid (GlcA), a substituted or unsubstituted iduronic acid (IdoA), and a substituted or unsubstituted glucose-1-phosphate (Glc-1-P), and the acceptor sugar includes at least one member selected from a substituted or unsubstituted N-acetylglucosamine (GlcNAc), a substituted or unsubstituted glucosamine ($GlcNH_2$), a substituted or unsubstituted glucuronic acid (GlcA), and a substituted or unsubstituted iduronic acid (IdoA). The reaction mixture is formed under conditions sufficient to convert the first sugar to a UDP-sugar, and sufficient to couple the sugar in the UDP-sugar to the acceptor sugar. When the first sugar is substituted or unsubstituted GlcNAc or $GlcNH_2$, the sugar in the UDP-sugar is coupled to a substituted or unsubstituted GlcA or a substituted or unsubstituted IdoA of the acceptor sugar. When the first sugar is substituted or unsubstituted Glc-1-P, substituted or unsubstituted GlcA, or substituted or unsubstituted IdoA, the sugar in the UDP-sugar is coupled to a substituted or unsubstituted $GlcNH_2$ or a substituted or unsubstituted GlcNAc of the acceptor sugar.

In some embodiments, the first sugar has the formula:

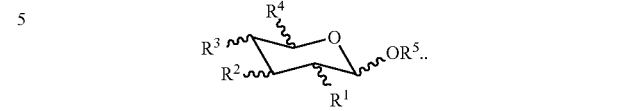

(VII)

Wherein each of $R^1$, $R^2$, and $R^3$ is selected from OH, $N_3$, $NH_2$, $NHSO_3^-$, $OSO_3^-$, $NHC(O)CH_3$, $NHC(O)CF_3$, $NHC(O)CH_2OH$, and $NHC(O)CH_2N_3$; $R^4$ is selected from $CH_2OH$, $CO_2^-$, $CO_2H$, $CH_2N_3$, $CH_2NH_2$, $CH_2NHSO_3^-$, $CH_2OSO_3^-$, $CH_2NHC(O)CH_3$, $CH_2NHC(O)CF_3$, $CH_2NHC(O)CH_2OH$, and $CH_2NHC(O)CH_2N_3$; and $R^5$ can be H, $PO_3^{2-}$, or $HPO_3^-$. In some embodiments, the first sugar has the formula VIII or IX:

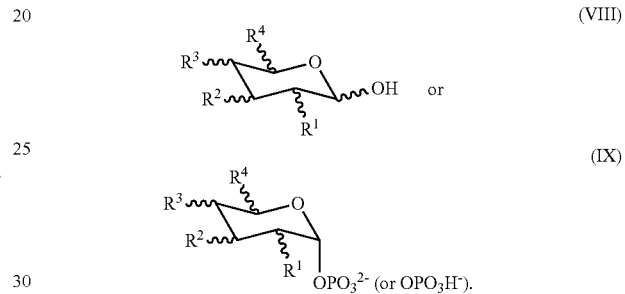

The first sugar is converted to the UDP-sugar by the UDP-sugar pyrophosphorylase and the kinase/dehydrogenase as described above. In some embodiments, the first sugar is selected from substituted or unsubstituted glucose (Glc), substituted or unsubstituted glucose-1-phosphate (Glc-1-P), substituted or unsubstituted glucuronic acid (GlcA), substituted or unsubstituted iduronic acid (IdoA), substituted or unsubstituted glucuronic acid-1-phosphate (GlcA-1-P), substituted or unsubstituted iduronic acid (IdoA), substituted or unsubstituted iduronic acid-1-phosphate (IdoA-1-P), substituted or unsubstituted N-acetylglucosamine (GlcNAc), substituted or unsubstituted N-acetylglucosamine-1-phosphate (GlcNAc-1-P), substituted or unsubstituted glucosamine ($GlcNH_2$), substituted or unsubstituted glucosamine-1-phosphate ($GlcNH_2$-1-P), substituted or unsubstituted galactose (Gal), substituted or unsubstituted galactose-1-phosphate (Gal-1-P), substituted or unsubstituted galacturonic acid (GalA), substituted or unsubstituted galacturonic acid-1-phosphate (GalA-1-P), substituted or unsubstituted N-acetylgalactosamine (GalNAc), substituted or unsubstituted N-acetylgalactosamine-1-phosphate (GalNAc-1-P), substituted or unsubstituted galactosamine ($GalNH_2$), substituted or unsubstituted galactosamine-1-phosphate ($GalNH_2$-1-P), substituted or unsubstituted mannose (Man), substituted or unsubstituted mannose-1-phosphate (Man-1-P), substituted or unsubstituted N-acetylmannosamine (ManNAc), substituted or unsubstituted N-acetylmannosamine-1-phosphate (ManNAc-1-P), substituted or unsubstituted mannosamine ($ManNH_2$), substituted or unsubstituted mannosamine-1-phosphate ($ManNH_2$-1-P). In some embodiments, the UDP-sugar is a compound of Formula I.

The sugar in the UDP-sugar is, in turn, coupled to an acceptor sugar to form an oligosaccharide product. A variety of sugars can be used as the acceptor sugar. For example, the acceptor sugar can be a monosaccharide, a disaccharide, a trisaccharide, or a tetrasaccharide. Longer oligosaccharides may also be used as the acceptor sugar in the methods of the invention. In some embodiments, the oligosaccharide can be a compound of Formula II, III, IV, V, or VI.

In general, the sugar in a UDP-sugar is coupled to an acceptor sugar by the glycosyltransferase in the reaction mixture. Any suitable glycosyltransferase can be used in the methods of the invention. Certain glycosyltransferases have exhibited a level of substrate promiscuity that are particularly useful for preparing a variety of oligosaccharide products. Promiscuous glycosyltransferases can utilize a range of UDP-sugars and/or a range of acceptor sugars. The glycosyltransferase can be, for example, *P. multocida* PmHS1 or PmHS2. The glycosyltransferase can also be *E. coli* KfiA or KfiC. Other glycosyltransferases can also be useful in the methods of the invention. In some embodiments, the glycosyltransferase is selected from PmHS1, PmHS2 and KfiA. In some embodiments, the glycosyltransferase is selected from PmHS1, PmHS2, NmLgtA, NmLgtB, PmCS, PmHAS, KfiC, and KfiA.

In general, the UDP-sugar can be formed enzymatically in the one-pot reaction mixture as described above. The nucleotide-sugar pyrophosphorylase can be, but is not limited to, a glucosamine uridyltransferase (GlmU), a Glc-1-P uridylyltransferase (GalU), or a promiscuous UDP-sugar pyrophosphorylase (USP). In some embodiments, the nucleotide-sugar pyrophosphorylase is selected from AGX1, EcGlmU, EcGalU, PmGlmU, and BLUSP. In some embodiments, the nucleotide-sugar pyrophosphorylase is selected from AGX1, EcGalU, and BLUSP. In some embodiments, the nucleotide-sugar pyrophosphorylase is selected from EcGalU, PmGlmU, and BLUSP. In some embodiments, the nucleotide-sugar pyrophosphorylase is EcGalU. In some embodiments, the nucleotide-sugar pyrophosphorylase is PmGlmU. In some embodiments, the nucleotide-sugar pyrophosphorylase is BLUSP.

In some embodiments, the kinase in the reaction mixture is selected from an N-acetylhexosamine 1-kinase (NahK), a galactokinase (GalK), and a glucuronokinase (GlcAK). In some embodiments, the kinase is selected from NahK_ATCC15697, NahKATCC55813, EcGalK, SpGalK, and AtGlcAK. In some embodiments, the kinase is selected from NahK_ATCC15697, NahK_ATCC55813, EcGalK, and AtGlcAK. In some embodiments, the kinase is selected from NahK_ATCC15697, NahK_ATCC55813, and AtGlcAK. In some embodiments, the kinase is EcGa1K. In some embodiments, the kinase is NahK_ATCC15697. In some embodiments, the kinase is NahK_ATCC55813. In some embodiments, the kinase is AtGlcAK. In some embodiments, the kinase is NahK_ATCC55813.

In some embodiments, the dehydrogenase in the reaction mixture is UDP-glucose dehydrogenase (Ugd). In some embodiments, the Ugd is PmUgd.

In some embodiments, the UDP-sugar formed in the one-pot reaction mixture is selected from substituted or unsubstituted UDP-GlcNAc, substituted or unsubstituted UDP-Glc, substituted or unsubstituted UDP-GlcA, and substituted or unsubstituted UDP-IdoA. In some embodiments, the UDP-sugar is substituted with at least one moiety selected from an azide, an amine, an N-trifluoroacetyl group, an N-acylamido group, an O-sulfate, and an N-sulfate.

In some embodiments, the reaction mixture further contains a pyrophosphatase. In some embodiments, the pyrophosphatase is PmPpA.

The reaction mixture in the present methods can be formed under any suitable conditions sufficient to prepare an oligosaccharide. The reaction mixture can include, for example, buffering agents to maintain a desired pH, as well as salts and/or detergents to adjust the solubility of the enzymes or other reaction components. In general, the reaction mixture also includes one or more nucleotide triphosphates (NTPs), such as UTP or ATP, that are consumed during sugar phosphorylation and UDP-sugar formation. The reaction mixture can contain a stoichiometric amount of an NTP, with respect to the first sugar, or an excess of the NTP. Divalent metal ions, such as magnesium ions, manganese ions, cobalt ions, or calcium ions, may be required to maintain the catalytic activity of certain enzymes. Enzyme cofactors, including but not limited to nicotinamide adenine dinucleotide (NAM, can also be included in the reaction mixture. In some embodiments, the reaction mixture further includes at least one component selected from UTP, ATP, $Mn^{2+}$, $Co^{2+}$, $Ca^{2+}$, and $Mg^{2+}$. After the reaction mixture is formed, it is held under conditions that allow for preparation of the oligosaccharide. For example, the reaction mixture can be held at 37° C. for 1 min-72 hr. The reaction mixture can also be held at 25° C. Other temperatures and conditions may be suitable for forming the oligosaccharide, depending on the nature of the sugars and the enzymes used for the synthesis.

Heparin and heparan sulfate (HS) oligosaccharides have particularly important biological, pathological, and therapeutic properties. Heparin and HS are sulfated linear polysaccharides composed of alternating α1-4 linked D-glucosamine ($GlcNH_2$) residues and 1-4 linked uronic acid residues (α-linkage for iduronic acid, IdoA, and β-linkage for glucuronic acid, GlcA]. In order to prepare heparin and HS oligosaccharides and their analogs, the methods of the invention can be used to prepare oligosaccharides containing alternating glucosamine and uronic acid residues. The oligosaccharides can contain, for example, alternating GlcNAc residues and GlcA residues. In some embodiments, the oligosaccharide is selected from: GlcNAc-GlcA; GlcA-GlcNAc-GlcA; GlcNAc-GlcA-GlcNAc-GlcA; GlcA-GlcNAc-GlcA-GlcNAc-GlcA; GlcNAc-GlcA-GlcNAc-GlcA-GlcNAc-GlcA; GlcA-GlcNAc-GlcA-GlcNAc-GlcA-GlcNAc-GlcA; GlcNAc-GlcA-GlcNAc-GlcA-GlcNAc-GlcA-GlcNAc-GlcA; GlcA-GlcNAc-GlcA-GlcNAc-GlcA-GlcNAc-GlcA-GlcNAc-GlcA; GlcA-GlcNAc; GlcNAc-GlcA-GlcNAc; GlcA-GlcNAc-GlcA-GlcNAc; GlcNAc-GlcA-GlcNAc-GlcA-GlcNAc; GlcA-GlcNAc-GlcA-GlcNAc-GlcA-GlcNAc; GlcNAc-GlcA-GlcNAc-GlcA-GlcNAc-GlcA-GlcNAc; GlcA-GlcNAc-GlcA-GlcNAc-GlcA-GlcNAc-GlcA-GlcNAc; GlcNAc-GlcA-GlcNAc-GlcA-GlcNAc-GlcA-GlcNAc-GlcA-GlcNAc; and GlcA-GlcNAc-GlcA-GlcNAc-GlcA-GlcNAc-GlcA-GlcNAc-GlcA-GlcNAc. In some embodiments, each GlcA and GlcNAc are optionally independently mono- or multi-substituted with a moiety selected from an azide, an amine, an N-trifluoroacetyl group, an N-acyl group, and an N-sulfate.

Other oligosaccharides can also be prepared using the methods of the invention. Oligosaccharides of arbitrary length can be prepared by repeating the one-pot reaction methods as described above. Accordingly, some embodiments of the invention provide a method for preparing an oligosaccharide as described above, wherein the method is repeated with a second sugar in place of the first sugar and the oligosaccharide in place of the acceptor sugar. In this manner, a variety of products can be prepared. In some embodiments, the oligosaccharides of the present invention can be a compound of any of Formulas II, III, IV, V, or VI.

In some embodiments, the present invention provides a method of preparing an oligosaccharide of formula II:

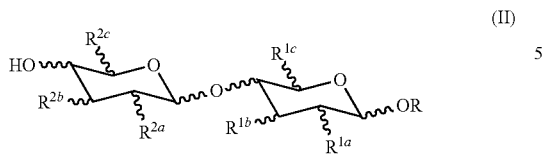
(II)

wherein the method includes forming a first reaction mixture containing a first sugar, an acceptor sugar, a glycosyltransferase, a UDP-sugar pyrophosphorylase, and/or one enzyme selected from a kinase and a dehydrogenase. The first sugar is selected from a substituted or unsubstituted N-acetylglucosamine (GlcNAc), a substituted or unsubstituted glucosamine (GlcNH$_2$), a substituted or unsubstituted glucoronic acid (GlcA), a substituted or unsubstituted iduronic acid (IdoA), and a substituted or unsubstituted glucose-1-phosphate (Glc-1-P), and the acceptor sugar includes at least one member selected from a substituted or unsubstituted N-acetylglucosamine (GlcNAc), a substituted or unsubstituted glucosamine (GlcNH$_2$), a substituted or unsubstituted glucuronic acid (GlcA), and substituted or unsubstituted iduronic acid (IdoA). The reaction mixture is formed under conditions sufficient to convert the first sugar to a UDP-sugar having a structure of formula I:

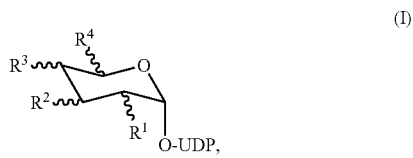
(I)

and sufficient to couple the sugar in the UDP-sugar to the acceptor sugar. The first sugar can have a structure of the formula VII:

(VII)

Each of $R^1$, $R^2$, $R^3$, $R^{1a}$, $R^{1b}$, $R^{2a}$, and $R^{2b}$ is independently selected from OH, N$_3$, NH$_2$, NHSO$_3^-$, OSO$_3^-$, NHC(O)CH$_3$, NHC(O)CF$_3$, NHC(O)CH$_2$OH, or NHC(O)CH$_2$N$_3$; each of $R^4$, $R^{1c}$, and $R^{2c}$ is independently selected from CH$_2$OH, CO$_2^-$, CO$_2$H, CH$_2$N$_3$, CH$_2$NH$_2$, CH$_2$NHSO$_3^-$, CH$_2$OSO$_3^-$, CH$_2$NHC(O)CH$_3$, CH$_2$NHC(O)CF$_3$, CH$_2$NHC(O)CH$_2$OH, or CH$_2$NHC(O)CH$_2$N$_3$; R includes but not is limited to H, CH$_3$, CH$_2$CH$_3$, CH$_2$CH$_2$N$_3$, CH$_2$CH$_2$CH$_2$N$_3$, an aglycon according to Formula B, Formula C, Formula D, or Formula E below, substituted or unsubstituted GlcNAc, substituted or unsubstituted GlcNH$_2$, substituted or unsubstituted GlcA, or substituted or unsubstituted IdoA. When $R^4$ is CO$_2^-$ or CO$_2$H, then $R^{2c}$ is CO$_2^-$ or CO$_2$H, and $R^{1c}$ is selected from CH$_2$OH, CH$_2$N$_3$, CH$_2$NH$_2$, CH$_2$NHSO$_3^-$, CH$_2$OSO$_3^-$, CH$_2$NHC(O)CH$_3$, CH$_2$NHC(O)CF$_3$, CH$_2$NHC(O)CH$_2$OH, and CH$_2$NHC(O)CH$_2$N$_3$. Alternatively, when $R^4$ is CH$_2$OH, CH$_2$N$_3$, CH$_2$NH$_2$, CH$_2$NHSO$_3^-$, CH$_2$OSO$_3^-$, CH$_2$NHC(O)CH$_3$, CH$_2$NHC(O)CF$_3$, CH$_2$NHC(O)CH$_2$OH, or CH$_2$NHC(O)CH$_2$N$_3$, then $R^{1c}$ is CO$_2$ or CO$_2$H, and $R^{2c}$ is $R^4$.

(B)
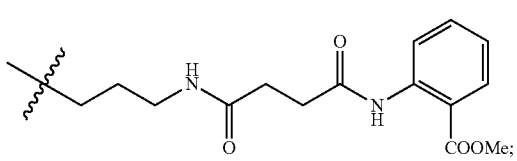

(C)
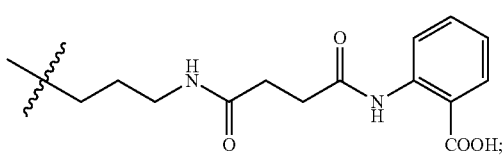

(D)
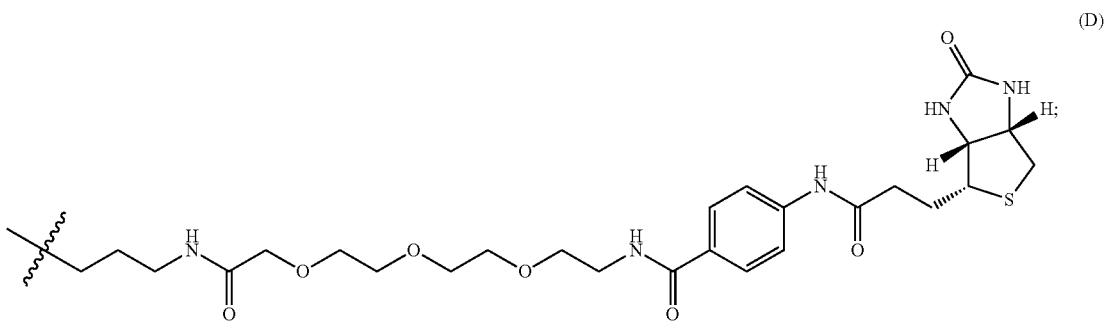

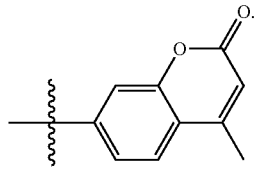

(E)

Heparin and HS generally contain varying levels of sulfated sugar residues. Examples of sulfated sugar residues include, but are not limited to, GlcNS, containing an N-sulfate at the 2 position of glucosamine (GlcNH$_2$); GlcNS3S, containing an N-sulfate at the 2 position and an O-sulfate at the 3 position of glucosamine (GlcNH$_2$); GlcNS6S, containing an N-sulfate at the 2 position and an O-sulfate at the 6 position of glucosamine (GlcNH$_2$); GlcNS3S6S, containing an N-sulfate at the 2 position, an O-sulfate at the 3 position, and an O-sulfate at the 6 position of glucosamine (GlcNH$_2$); GlcNAc3S, containing an O-sulfate at the 3 position of N-acetylglucosamine (GlcNAc); GlcNAc6S, containing an O-sulfate at the 6 position of N-acetylglucosamine (GlcNAc); GlcNAc3S6S, containing an O-sulfate at the 3 position and an O-sulfate at the 6 position of N-acetylglucosamine (GlcNAc); GlcNH$_2$3S, containing an O-sulfate at the 3 position of glucosamine (GlcNH$_2$); GlcNH$_2$6S, containing an O-sulfate at the 6 position of glucosamine (GlcNH$_2$); GlcNH$_2$3S6S, containing an O-sulfate at the 3 position and an O-sulfate at the 6 position of glucosamine (GlcNH$_2$); GlcA2S, containing an O-sulfate at the 2 position of glucuronic acid (GlcA); and IdoA2S, containing an O-sulfate at the 2 position of iduronic acid (IdoA). Substrate preferences for the methods of the invention will vary depending on the specific enzymes employed in the one-pot reactions. As described above, various substituted and unsubstituted sugars can be used in the methods of the invention.

The present inventors have discovered enzymes that exhibit catalytic activity for a number of natural and non-natural UDP-sugar and acceptor sugar substrates. The oligosaccharides that are prepared using these enzymes can contain functional moieties that can be chemically modified to diversify the structure of the products. For example, azido-sugar residues or trifluoroacetamido-sugar residues can be converted to amino-sugar residues. Azido groups and trifluoracetamos groups can be manipulated independently using orthogonal chemical methods to selectively install desired functionality at specific sites on a given oligosaccharide. Amine-containing oligosaccharides can be further elaborated to form acylamino groups and sulfamate groups. Sulfamate (i.e. N-sulfate) groups, in particular, can be installed to form heparin and HS analogs.

The inventors have discovered that certain oligosaccharides containing N-sulfate groups (where O-sulfate groups would normally be present in heparin and HS) demonstrate inhibitory activity against the binding of fibroblast growth factors (FGFs) to heparin. FGFs, in turn, have a role in regulating a number of processes including angiogenesis, cell proliferation, differentiation, morphogenesis, and wound healing. As such, the invention provides convenient and flexible methods for preparation of oligosaccharides with useful biological activity.

VI. One-Pot Method of Preparing Sialylated Oligosaccharides

The methods described above for preparing oligosaccharides can be further extended by incorporating sialyltransferases that convert the oligosaccharides into sialylated oligosaccharides. Sialyltransferases are the key enzymes that catalyze the transfer of a sialic acid residue from cytidine 5'-monophosphate-sialic acid (CMP-sialic acid) to an acceptor. Resulting sialic acid-containing products have been implicated in various biological and pathological processes, including cell-cell recognition, cell growth and differentiation, cancer metastasis, immunological regulation, as well as bacterial and viral infection. Besides being prevalent in mammals, sialyltransferases have been found in some pathogenic bacteria. They are mainly involved in the formation of sialic acid-containing capsular polysaccharides (CPS) and lipooligo(poly)saccharides (LOS/LPS), serving as virulence factors, preventing recognition by host's immune system, and modulating interactions with the environment.

Human Milk Oligosaccharides

Human milk oligosaccharides (HMOs) are a mixture of more than 100 glycans which constitute the third major component of human milk. They have been found to contribute significantly to the gut health of breastfed infants. Strong evidences are available now to support the roles of HMOs on promoting the growth of beneficial gut bacteria; inhibiting the binding of pathogenic bacteria, human immunodeficiency virus (HIV), or protozoan parasites to gut epithelial cells; modulating immune responses; and influencing the functions of gut epithelium.

Among individual HMOs with known functions, disialyl-lacto-N-tetraose (DSLNT), but not its non-sialylated (LNT) or mono-sialylated (sialyllacto-N-tetraose b or LSTb, with a sialic acid α2-6-linked to an internal glycan) analog, was previously identified as a specific human milk oligosaccharide (HMOs) component that is effective for preventing necrotizing enterocolitis (NEC) in a neonatal rat model. The hexasaccharide is presented at a level of 0.2-0.6 gram in a liter of human milk. However, it is not presented in porcine milk, and either is not presented or exists only in trace amount in bovine milk. Due to the limited availability of human milk and the absence or the low abundance of DSLNT in bovine milk, it is impractical to obtain the compound in large scale for potential clinical therapeutic applications. The present invention provides useful methods for preparing sialylated HMOs and novel sialylated HMO-type oligosaccharides. The methods are based in part on the surprising discovery that *Photobacterium damselae* α2-6-sialyltransferase (Pd2,6ST) can be used to transfer sialic acid moieties to internal monosaccharide subunits as well as to terminal monosaccharide subunits in complex substrate sugars.

Accordingly, some embodiments of the invention provide a method of preparing a sialylated oligosaccharide having at least two sialic acid moieties. The method includes forming a reaction mixture containing: a substrate sugar; cytidine-5'-monophospho-sialic acid (CMP-sialic acid or CMP-Sia) or derivatives; and *Photobacterium damselae* α2-6-sialyltransferase (Pd2,6ST) under conditions sufficient to form the sialylated oligosaccharide.

Any suitable substrate sugar can be used in the methods of the invention. In some embodiments, the substrate sugar is a monosaccharide. In some embodiments, the substrate sugar is selected from a disaccharide, a trisaccharide, a tetrasaccharide, a pentasaccharide, a hexasaccharide, a heptasaccharide, an octasaccharide, a nonasaccharide, a decasaccharide, an undecasaccharide, a dodecasaccharide, a tridecasaccharide, a tetradecasaccharide, a pentadecasaccharide, and a hexadecasaccharide.

The substrate sugar can contain a variety of monosaccharide subunits. The substrate sugar can contain, for example, one or more moieties selected from substituted or unsubstituted glucose (Glc), substituted or unsubstituted glucose-1-phosphate (Glc-1-P), substituted or unsubstituted glucuronic acid (GlcA), substituted or unsubstituted glucuronic acid-1-phosphate (GlcA-1-P), substituted or unsubstituted iduronic acid (IdoA), substituted or unsubstituted iduronic acid-1-phosphate (IdoA-1-P), substituted or unsubstituted N-acetylglucosamine (GlcNAc), substituted or unsubstituted N-acetylglucosamine-1-phosphate (GlcNAc-1-P), substituted or unsubstituted glucosamine (GlcNH$_2$), substituted or unsubstituted glucosamine-1-phosphate (GlcNH$_2$-1-P), substituted or unsubstituted galactose (Gal), substituted or unsubstituted galactose-1-phosphate (Gal-1-P), substituted or unsubstituted galacturonic acid (GalA), substituted or unsubstituted galacturonic acid-1-phosphate (GalA-1-P), substituted or unsubstituted N-acetylgalactosamine (GalNAc), substituted or unsubstituted N-acetylgalactosamine-1-phosphate (GalNAc-1-P), substituted or unsubstituted galactosamine (GalNH$_2$), substituted or unsubstituted galactosamine-1-phosphate (GalNH$_2$-1-P), substituted or unsubstituted mannose (Man), substituted or unsubstituted mannose-1-phosphate (Man-1-P), and substituted or unsubstituted N-acetylmannosamine (ManNAc), substituted or unsubstituted N-acetylmannosamine-1-phosphate (ManNAc-1-P), substituted or unsubstituted mannosamine (ManNH$_2$), substituted or unsubstituted mannosamine-1-phosphate (ManNH$_2$-1-P), and substituted or unsubstituted 2-keto-3-deoxy-D-glycero-D-galactonononic acid (KDN).

In some embodiments, the substrate sugar contains one or more moieties selected from substituted or unsubstituted galactose (Gal) and substituted or unsubstituted N-acetylgalactosamine (GalNAc).

In some embodiments, the substrate sugar is selected from galactose, lactose, N-acetyllactosamine, Galβ1-3GalNAc, Galβ1-3GlcNAc, Galα1-3Gal, Galα1-4Gal, Galα1-3Lac, Galα1-4Lac, Galβ1-4LacNAc, Galβ1-4GlcNAcβ1-3Galβ1-4Glc, Galβ1-3GlcNAcβ1-3Galβ1-4Glc, GalNAcβ1-4Galβ31-4Glc, Neu5Acα2-3(GalNAcβ1-4)Galβ1-4Glc, GalNAcβ1-4GlcAβ1-3GalNAcβ1-4GlcA, Galβ1-4GlcNAcβ1-3Galβ1-4GlcNAc, GlcNAcβ1-3Galβ1-4GlcNAcβ1-3Gal, and Galβ1-9KDN.

In some embodiments, the substrate sugar is prepared by any of the methods for preparing oligosaccharides described above.

Sialic acid is a general term for N- and O-substituted derivatives of neuraminic acid, and includes, but is not limited to, 5-hydroxyl (Kdn), N-acetyl (Neu5Ac), or N-glycolyl (Neu5Gc) derivatives, as well as O-acetyl, O-lactyl, O-methyl, O-sulfate and O-phosphate derivatives. In some embodiments, the sialic acid can be a compound of the formula:

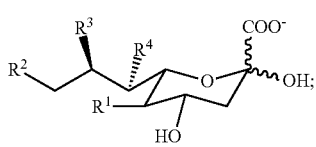

wherein R$^1$ is selected from H, OH, N$_3$, NHC(O)Me, NHC(O)CH$_2$OH, NHC(O)CH$_2$N$_3$, NHC(O)OCH$_2$C=CH$_2$, NHC(O)OCHC=CH, NHC(O)CH$_2$F, NHC(O)CH$_2$NHCbz, NHC(O)CH$_2$OC(O)Me, and NHC(O)CH$_2$OBn; and R$^2$, R$^3$, and R$^4$ are independently selected from H, OH, N$_3$, OMe, F, OSO$_3^-$, OPO$_3$H$^-$, and OC(O)Me. In some embodiments, the CMP-sialic acid is cytidine 5'-monophosphate N-acetylneuraminic acid (CMP-Neu5Ac) or a CMP-Neu5Ac analog. Other sialic acid forms are useful in the methods of the present invention. In some embodiments, the sialic acid can be a compound of the formula:

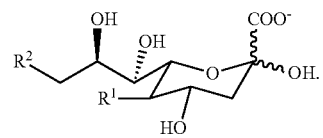

In some embodiments, the sialic acid can be a compound of the formula:

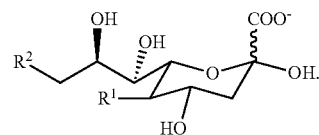

The CMP-sialic acid can be prepared prior to preparation of the oligosaccharide, or prepared in situ immediately prior to preparation of the oligosaccharide. In some embodiments, the method of the present invention also includes forming a reaction mixture including a CMP-sialic acid synthetase, cytidine 5'-triphosphate, and N-acetylneuraminic acid (Neu5Ac) or a Neu5Ac analog, under conditions suitable to form CMP-Neu5Ac or a CMP-Neu5Ac analog. Any suitable CMP-sialic acid synthetase (i.e., N-acylneuraminate cytidylyltransferase, EC 2.7.7.43) can be used in the methods of the invention. For example, CMP-sialic acid synthetases from *E. coli, C. thermocellum, S. agalactiae*, or *N. meningitidis* can be used. In some embodiments, the step of forming the CMP-sialic acid and the step of forming the sialylated oligosaccharide are performed in one pot.

In some embodiments, the sialic acid moiety of the CMP-sialic acid is prepared separately prior to use in the methods of the present invention. Alternatively, the sialic acid moiety can be prepared in situ immediately prior to use in the methods of the present invention. In some embodiments, the method also includes forming a reaction mixture including a sialic acid aldolase, pyruvic acid or derivatives thereof, and N-acetylmannosamine or derivatives thereof, under conditions suitable to form Neu5Ac or a Neu5Ac analog. Any suitable sialic acid aldolase (i.e., N-Acetylneuraminate pyruvate lyase, EC 4.1.3.3) can be used in the methods of the invention. For example, sialic acid aldolases from *E. coli, L. plantarum, P. multocida*, or *N. meningitidis* can be used. In some embodiments, the step of forming the sialic acid moiety, the step of forming the CMP-sialic acid, and the step of forming the sialylated oligosaccharide are performed in one pot.

In some embodiments, the CMP-sialic acid is prepared by a process including: i) forming a reaction mixture containing a CMP-sialic acid synthetase, cytidine triphosphate, and sialic acid (Sia) under conditions sufficient to form the CMP-sialic acid.

In some embodiments, the sialic acid is prepared by a processing including: ii) forming a reaction mixture containing a sialic acid aldolase, pyruvic acid or a salt thereof, and N-acetylmannosamine or derivatives under conditions sufficient to form the sialic acid.

In some embodiments, steps i) and ii) are conducted in one pot.

In some embodiments, the sialylated oligosaccharide has a structure according to Formula 1:

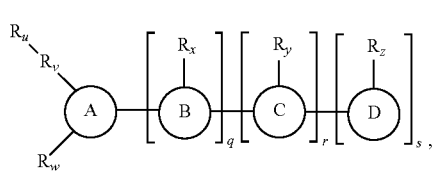

(1)

wherein
each of A, B, C, and D is a monosaccharide moiety independently selected from Gal, GalNAc, Glc, GlcNAc, GlcA, and KDN;
each R is a sialic acid moiety;
each of subscripts q, r, and s is independently selected from 0 and 1; and
each of subscripts u, v, w, x, y, and z is selected from 0 and 1, and the sum of subscripts u, v, w, x, y, and z is equal to 2.

In some embodiments, A is independently selected from Gal, GalNAc, and GlcNAc; B is independently selected from Gal, GalNAc, Glc, GlcNAc, GlcA, and KDN; C is independently selected from Gal, GalNAc, Glc, and GlcNAc; and D is independently selected from Gal, Glc, GlcNAc, and GlcA.

In some embodiments, A is Gal; and each of subscripts q, r, and s is 0.

In some embodiments, the moiety A-B is selected from Galβ1-4Glc, Galβ1-4GlcNAc, Galβ1-3GalNAc, Galβ1-3GlcNAc, Galα1-3Gal, Galα1-4Gal, and Galβ1-9KDN; subscript q is 1; and each of subscripts r and s is 0.

In some embodiments, the moiety A-B-C is selected from Galα1-3Galβ1-4Glc, Galα1-4Galβ1-4Glc, Galβ1-4Galβ1-4GlcNAc, GalNAcβ1-4Galβ1-4Glc, and GalNAcβ1-4Galβ1-4Glc; each of subscripts q and r is 1; and subscript s is 0.

In some embodiments, the moiety A-B-C-D is selected from Galβ1-4GlcNAcβ1-3Galβ1-4Glc, Galβ1-3GlcNAcβ1-3Galβ1-4Glc, GalNAcβ1-4GlcAβ1-3GalNAcβ1-4GlcA, Galβ1-4GlcNAcβ1-3Galβ1-4GlcNAc, and GlcNAcβ1-3Galβ1-4GlcNAcβ1-3Gal; and each of subscripts q, r, and s is 1.

In some embodiments, each R is independently selected from an α2-3 linked Neu5Ac moiety, an α2-6 linked Neu5Ac moiety, and an α2-8 linked Neu5Ac moiety.

In some embodiments, the sialylated oligosaccharide is selected from:
Neu5Acα2-3(Neu5Acα2-6)Galβ1-4GlcNAc;
Neu5Acα2-6Galβ1-4GlcNAcβ1-3(Neu5Acα2-6)Galβ1-4Glc;
Neu5Acα2-6Galβ1-4(Neu5Acα2-6)Galβ1-4GlcNAc;
Neu5Acα2-6Galβ1-3GlcNAcβ1-3(Neu5Acα2-6)Galβ1-4Glc;
Neu5Acα2-6Galβ1-4GlcNAcβ1-3(Neu5Acα2-6)Galβ1-4GlcNAc;
GlcNAcβ1-3(Neu5Acα2-6)Galβ1-4GlcNAcβ1-3 (Neu5Acα2-6)Gal;
Neu5Acα2-6GalNAcβ1-4GlcAcβ1-3(Neu5Acα2-6)GalNAcβ1-4GlcA;
Neu5Acα2-3(Neu5Acα2-6)Gal;
Neu5Acα2-3(Neu5Acα2-6)Galβ1-4Glc;
Neu5Acα2-8Neu5Acα2-3 Galβ1-4Glc;
Neu5Acα2-8Neu5Acα2-6 Galβ1-4Glc;
Neu5Acα2-3(Neu5Acα2-6)Galβ1-3GalNAc;
Neu5Acα2-6Galβ1-3(Neu5Acα2-6)GalNAc;
Neu5Acα2-3Galβ1-3(Neu5Acα2-6)GalNAc;
Neu5Acα2-3(Neu5Acα2-6)Galβ1-3GlcNAc;
Neu5Acα2-6Galα1-3(Neu5Acα2-6)Gal;
Neu5Acα2-6Galα1-4(Neu5Acα2-6)Gal;
Neu5Acα2-6Galα1-3 (Neu5Acα2-6)Galβ1-4Glc;
Neu5Acα2-6Galα1-4(Neu5Acα2-6)Galβ1-4Glc;
Neu5Acα2-6GalNAcβ1-4(Neu5Acα2-6)Galβ1-4Glc;
Neu5Acα2-3GalNAcβ1-4(Neu5Acα2-6)Galβ1-4Glc; and
Neu5Acα2-3(Neu5Acα2-6)Galβ1-9KDN.

The methods of the invention include forming reaction mixtures that contain *Photobacterium damselae* α2-6-sialyltransferase (Pd2,6ST). The Pd2,6ST can be, for example, purified prior to addition to the reaction mixture or secreted by a cell present in the reaction mixture. Alternatively, the Pd2,6ST can catalyze the reaction within a cell expressing the enzyme.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, CaCl$_2$, and salts of Mn$^{2+}$ and Mg$^{2+}$), chelators (e.g., ethylene glycol-bis(2-aminoethylether)-N,N,N',N'-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, chelators, reducing agents, and labels can be used at any suitable concentration, which can be readily determined by one of skill in the art. In general, buffers, cosolvents, salts, chelators, reducing agents, and labels are included in reaction mixtures at concentrations ranging from about 1 µM to about 1 M. For example, a buffer, a cosolvent, a salt, a chelator, a reducing agent, or a label can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M.

Reactions are conducted under conditions sufficient to form the sialylated oligosaccharide. Generally, the conditions are sufficient to transfer the sialic acid from the CMP-sialic acid to the substrate sugar. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 5.5 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions can be employed in the methods of the invention, depending on the identity of the particular CMP-sialic acid or substrate sugar. Additional aspects of sialylation reactions are described in WO 2013/022836, WO 2013/070677, and US 2013/0196385, the entirety of which publications are incorporated herein by reference in their entirety.

In a related aspect, the invention provides a sialylated oligosaccharide prepared according to any of the methods described herein. In certain embodiments, the invention provides novel sialylated saccharides. In some embodiments, the sialylated oligosaccharide is selected from:

Neu5Acα2-3(Neu5Acα2-6)Galβ1-4Glc;
Neu5Acα2-8Neu5Acα2-3 Galβ1-4Glc;
Neu5Acα2-3(Neu5Acα2-6)Galβ1-3GalNAc;
Neu5Acα2-3(Neu5Acα2-6)Galβ1-3GalNAc;
Neu5Acα2-6Galβ1-4GlcNAcβ1-3(Neu5Acα2-6)Galβ1-4Glc (DSLNnT);
Neu5Acα2-6Galβ1-3GlcNAcβ1-3(Neu5Acα2-6)Galβ1-4Glc; and
Neu5Acα2-3(Neu5Acα2-6)Galβ1-9KDN.

In some embodiments, the sialylated oligosaccharide is selected from:

Neu5Acα2-6Galβ1-4GlcNAcβ1-3(Neu5Acα2-6)Galβ1-4Glc; and
Neu5Acα2-6Galβ1-3GlcNAcβ1-3(Neu5Acα2-6)Galβ1-4Glc In some embodiments, the sialylated oligosaccharide is Neu5Acα2-6Galβ1-4GlcNAcβ1-3(Neu5Acα2-6)Galβ1-4Glc.

VII. Methods for Treating Necrotizing Enterocolitis

In another aspect, the invention provides a method for treating necrotizing enterocolitis (NEC). The method includes administering to a subject in need thereof a sialylated oligosaccharide of the invention.

Necrotizing enterocolitis refers to a condition most often observed in very young infants, newborn infants, and prematurely-born infants. Possible causes include decreased blood flow to the bowel and reduced production of protective mucus, as well as bacteria in the intestine. NEC is considered to be the most serious gastrointestinal disorder among preterm infants.

The sialylated oligosaccharides can be administered at any suitable dose in the methods of the invention. In general, the sialylated oligosaccharides are administered at a dose ranging from about 1 microgram to about 1000 milligrams per kilogram of a subject's body weight (i.e., about 1 μg/kg-1000 mg/kg). The dose of a sialylated oligosaccharide can be, for example, about 1 μg/kg-1 mg/kg, or about 1-500 μg/kg, or about 25-250 μg/kg, or about 50-100 μg/kg. The dose of a sialylated oligosaccharide can be about 0.1-1000 mg/kg, or about 1-500 mg/kg, or about 25-250 mg/kg, or about 50-100 mg/kg. The dose of the sialylated oligosaccharide can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, or 950 μg/kg. The dose of the sialylated oligosacharide can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg.

The dosages can be varied depending upon the requirements of the subject, the severity of the disorder being treated, and the particular formulation being administered. The dose administered to a subject should be sufficient to result in a beneficial therapeutic response in the subject. In certain instances, the dose administered to a subject will be sufficient to prevent the occurrence of NEC in the subject. The size of the dose will also be determined by the existence, nature, and extent of any adverse side-effects that accompany the administration of the compound in a particular subject. Determination of the proper dosage for a particular situation is within the skill of the typical practitioner. Those of skill in the art are aware of the routine experimentation that will produce an appropriate dosage range for a subject in need of treatment by oral administration or any other method of administration of a compound, e.g., intravenous administration or parenteral administration, for example. Those of skill are also aware that results provided by in vitro or in vivo experimental models can be used to extrapolate approximate dosages for a subject in need of treatment. The total dosage can be divided and administered in portions over a period of time suitable to treat NEC.

Administration of a sialylated oligosaccharide can be conducted for a period of time which will vary depending upon the nature of the particular disorder, its severity and the overall condition of the subject. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours. Following treatment, a subject can be monitored for changes in his or her condition and for alleviation of the symptoms of the disorder. The dosage of the sialylated oligosaccharide can either be increased in the event the subject does not respond significantly to a particular dosage level, or the dose can be decreased if an alleviation of the symptoms of the disorder is observed, or if the disorder has been ablated, or if unacceptable side effects are seen with a particular dosage.

In a related aspect, the invention provides pharmaceutical compositions for the administration of the sialylated oligosaccharides. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing the sialylated oligosaccharides can be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewable tablets, and the like. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations. The sialylated oligosaccharides can be added, for example, to human milk, bovine milk, or infant formula.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Transdermal delivery of the sialylate oligosaccharides can be accomplished by means of iontophoretic patches and the like. The compounds can also be administered in the form of suppositories for rectal administration. These compositions can be prepared by mixing the compound with a suitable non-irritating excipient which is solid at ordinary temperatures but liquid at the rectal temperature and will therefore melt in the rectum to release the compound. Such materials include cocoa butter and polyethylene glycols.

VIII. EXAMPLES

Example 1

Enzymes

NahK_ATCC15697 and NahK_ATCC55813 N-acetylhexosamine 1-Kinases

NahK (EC 2.7.1.162) catalyzes the direct addition of a phosphate from adenosine 5'-triphosphate (ATP) to the anomeric position of N-acetylhexosamine for the formation of N-acetylhexosamine-1-phosphate and adenosine 5'-diphosphate (ADP). The only characterized NahK to date is encoded by the lnpB gene in the lnpABCD operon of *Bifidobacterium longum* JCM1217. Herein we report the cloning and characterization of two new NahKs from *Bifidobacterium infantis* (ATCC15697) and *Bifidobacterium longum* (ATCC55813), respectively. A new capillary electrophoresis-based assay method has been developed for biochemical characterization of NahKs. We found that in addition to previously reported NahK substrates, various GlcNAc derivatives including those with C2-azido, C6-azido, and 6-O-sulfate groups are tolerable substrates for the newly cloned NahKs. In addition, despite of their low activities toward glucose and galactose, the activities of both NahKs are much higher for mannose and some of its C-2, C-4, and C-6 derivatives including 2-deoxy-mannose or 2-deoxy-glucose.

Experimental

Bacterial Strains, Plasmids, and Materials. Electrocompetent DH5α and chemically competent BL21 (DE3) *E. coli* cells were from Invitrogen (Carlsbad, Calif.). *Bifidobacterium longum* Reuter ATCC #55813 was from American Type Culture Collection (ATCC, Manassas, Va.). Genomic DNA of *Bifidobacterium longum* subsp. *infantis* (ATCC #15697) was a kind gift from Professor David Mills (University of California, Davis). Vector plasmid pET22b(+) was from Novagen (EMD Biosciences Inc. Madison, Wis.). $Ni^{2+}$-NTA agarose (nickel-nitrilotriacetic acid agarose), QIAprep spin miniprep kit, and QIAEX II gel extraction kit were from Qiagen (Valencia, Calif.). Herculase-enhanced DNA polymerase was from Stratagene (La Jolla, Calif.). T4 DNA ligase and 1 kb DNA ladder were from Promega (Madison, Wis.). NdeI and XhoI restriction enzymes were from New England Biolabs Inc. (Beverly, Mass.). Adenosine-5'-triphosphate disodium salt (ATP), GlcNAc, and GalNAc were from Sigma (St. Louis, Mo.). GlcNAc, GalNAc, mannose, and ManNAc derivatives were synthesized according to reported procedures.

Cloning. NahK_ATCC15697 and NahK_ATCC55813 were each cloned as a C-$His_6$-tagged (SEQ ID NO:22) fusion protein in pET22b(+) vector using genomic DNAs of *Bifidobacterium longum* subsp. infantis ATCC#15697 and *Bifidobacterium longum* ATCC#55813, respectively, as the template for polymerase chain reactions (PCR). The primers used for NahK_ATCC15697 were: forward primer 5' ACCCCATATGAACAACACCAATGAAGCCCTG 3' (SEQ ID NO:23) (NdeI restriction site is underlined) and reverse primer 5' TGACCTCGAGCTTGGTCGTCTCCAT-GACGTCG 3' (SEQ ID NO:24) (XhoI restriction site is underlined). The primers used for NahK_ATCC55813 were: forward primer 5' ACCCCATATGACCGAAAGCAAT-GAAGTTTTATTC 3' (SEQ ID NO:25) (NdeI restriction site is underlined) and reverse primer 5' TGACCTCGAGCCTG-GCAGCCTCCATGATG 3' (SEQ ID NO:26(XhoI restriction site is underlined). PCR was performed in a 50 µL reaction mixture containing genomic DNA (1 µg), forward and reverse primers (1 µM each), 10×Herculase buffer (5 µL), dNTP mixture (1 mM), and 5 U (1 µL) of Herculase-enhanced DNA polymerase. The reaction mixture was subjected to 35 cycles of amplification with an annealing temperature of 52° C. The resulting PCR product was purified and digested with NdeI and XhoI restriction enzymes. The purified and digested PCR product was ligated with predigested pET22b(+) vector and transformed into electrocompetent *E. coli* DH5α cells. Selected clones were grown for minipreps and characterization by restriction mapping and DNA sequencing performed by Davis Sequencing Facility at the University of California-Davis.

Expression and purification. Positive plasmids were selected and transformed into BL21(DE3) chemically competent cells. The plasmid-bearing *E. coli* cells were cultured in LB rich medium (10 g/L tryptone, 5 g/L yeast extract, and 10 g/L NaCl) supplied with ampicillin (100 µg/mL). Overexpression of the target protein was achieved by inducing the *E.* coli culture with 0.1 mM of isopropyl-1-thio-β-D-galactopyranoside (IPTG) when the $OD_{600\,nm}$ of the culture reaches 0.8-1.0 followed by incubation at 20° C. for 24 h with vigorous shaking at 250 rpm in a C25KC incubator shaker (New Brunswick Scientific, Edison, NJ). To obtain the cell lysate, cells were harvested by centrifuge cell culture at 4000×g for 2 h. The cell pellet was re-suspended in lysis buffer (pH 8.0, 100 mM Tris-HCl containing 0.1% Triton X-100, 20 mL/L cell culture) containing lysozyme (100 μg/mL) and DNaseI (3 μg/mL). After incubating at 37° C. for 60 min with vigorous shaking (250 rpm), the lysate was collected by centrifugation at 12,000 g for 30 min. $His_6$-tagged (SEQ ID NO:22) target proteins were purified from cell lysate using an ÄKTA FPLC system (GE Healthcare, Piscataway, N.J., USA). To do this, the lysate was loaded to a HisTrap™ FF 5 mL column (GE Healthcare) pre-washed and equilibrated with binding buffer (0.5 M NaCl, 20 mM Tris-HCl, pH 7.5). The column was then washed with 8 volumes of binding buffer, 10 volumes of washing buffer (10 mM imidazole, 0.5 M NaCl, 20 mM Tris-HCl, pH 7.5) and eluted with 8 volumes of elute buffer (200 mM imidazole, 0.5 M NaCl, 20 mM Tris-HCl, pH 7.5). Fractions containing the purified enzyme were combined and dialyzed against dialysis buffer (Tris-HCl containing 10% glycerol, pH 7.5, 20 mM) and stored at 4° C.

Quantification of Purified Protein. Protein concentration was determined in a 96-well plate using a Bicinchoninic Acid (BCA) Protein Assay Kit (Pierce Biotechnology, Rockford, Ill.) with bovine serum albumin as a protein standard. The absorbance of each sample was measured at 562 nm by a BioTek Synergy™ HT Multi-Mode Microplate Reader.

pH Profile by Capillary Electrophoresis (CE) Assays. Typical enzymatic assays were performed in a 20 μL reaction mixture containing a buffer (200 mM) with a pH in the range of 6.0-11.0, GlcNAc (1 mM), ATP (1 mM), $MgCl_2$ (5 mM), and a NahK (0.75 μM). Buffers used were: MES, pH 6.0; Tris-HCl, pH 7.0-9.0; CAPS, pH 10.0-11.0. Reactions were allowed to proceed for 10 min at 37° C. and were stopped by adding 20 μL of cold ethanol to each reaction mixture. Samples were centrifuged and the supernatants were analyzed by a P/ACE™ Capillary Electrophoresis (CE) system equipped with a Photodiode Array (PDA) detector (Beckman Coulter, Inc., Fullerton, Calif.). CE conditions were as follows: 75 μm i.d. capillary, 25 KV/80 μA, 5 s vacuum injections, monitored at 254 nm, the running buffer used was sodium tetraborate (25 mM, pH 10.0).

Effect of $MgCl_2$ on the Enzymatic Activity. Different concentrations of $MgCl_2$ were used in a Tris-HCl buffer (pH 8.0, 200 mM) containing GlcNAc (1 mM), ATP (1 mM), and a NahK (0.75 μM). Reactions were allowed to proceed for 10 min at 37° C. Reaction without $MgCl_2$ was used as a control.

Substrates Specificity Assays. GlcNAc, GalNAc, and their derivatives (1 mM) were used as substrates in the presence of ATP (1 mM) and $MgCl_2$ (5 mM) in a Tris-HCl buffer (pH 8.0, 200 mM) to analyze the substrate specificity of NahKs. Two concentrations (0.75 μM or 15 μM) of each NahK were used and the reactions were allowed to proceed for 10 min (for 0.75 μM NahK) or 30 min (for 15 μM NahK) at 37° C. For substrate specificity studies of Glc, Gal, mannose, ManNAc, and their derivatives, 15 μM of NahK was used for each reaction and the reactions were carried out at 37° C. for 30 min. All other conditions were the same as for GlcNAc, GalNAc, and their derivatives.

Kinetics by CE Assays. Reactions were carried out in duplicate at 37° C. for 10 min in a total volume of 20 μL in Tris-HCl buffer (200 mM, pH 7.5) containing $MgCl_2$ (1 mM), ATP, GlcNAc or GalNAc, and NahK (0.25 μM when GlcNAc and ATP were used as substrates, 0.5 μM when GalNAc and ATP were used as substrates). Apparent kinetic parameters were obtained by varying the ATP concentration from 0.1-5.0 mM (0.1 mM, 0.2 mM, 0.4 mM, 1 mM, 2 mM, and 5 mM) at a fixed concentration of GlcNAc or GalNAc (1 mM), or varying the concentration of GlcNAc or GalNAc (0.1 mM, 0.2 mM, 0.4 mM, 1 mM, 2 mM, and 5 mM) at a fixed concentration of ATP (1 mM) and fitting the data to the Michaelis-Menten equation using Grafit 5.0.

Results and Discussion

Cloning, expression, and purification. NahKs from *Bifidobacterium infantis* ATCC#15697 (NahK_ATCC15697) and *Bifidobacterium longum* ATCC#55813 (NahK_ATCC55813) were each cloned as a C-$His_6$-tagged (SEQ ID NO:22) fusion protein in a pET22b(+) vector. Sequence alignment (FIG. 1) indicates that NahK_ATCC55813 is almost identical to the NahK from *Bifidobacterium longum* JCM1217 (NahK_JCM1217, GenBank accession no. BAF73925) except for a single amino acid difference R348H (R is in NahK_JCM1217). In comparison, NahK_ATCC15697 shares 90% amino acid sequence identity with NahK_JCM1217.

Both NahKs were expressed by induction with 0.1 mM of isopropyl-1-thio-β-D-galactopyranoside (IPTG) followed by incubation at 20° C. for 24 h with vigorous shaking (250rpm). Up to 180 mg and 185 mg of $Ni^{2+}$-column purified NahK_ATCC15697 and NahK_ATCC55813, respectively, could be obtained from one liter of *E. coli* culture. SDS-PAGE analysis shows that both purified proteins migrated to around 41 kDa, matching well to the calculated molecular weights of the translated $His_6$-tagged (SEQ ID NO:22) fusion proteins of 41.4 and 40.9 kDa for NahK_ATCC15697 and NahK_ATCC55813, respectively.

Capillary Electrophoresis (CE) Assays. Based on the detection of ADP and ATP in the reaction mixture by a UV detector, a capillary electrophoresis-based method was developed to directly measure the formation of ADP and N-acetylhexosamine-1-phosphate from ATP and N-acetylhexosamine for characterizing the activities of NahKs. Both ATP and ADP gave absorbance at 254 nm with equal signal responses.

pH Profile. As shown in FIG. 2, both NahKs are highly active in a pH range of 7.0-8.0 with slight variations. The activities of both NahKs drop quickly with either decrease of the pH to lower than 7.0 or increase of the pH to higher than 8.0. About 50% of the optimal activity was observed at pH 6.0 and pH 8.5 for NahK_ATCC15697. In comparison, about 70% of the optimal activity was observed at pH 6.0 and pH 8.5 for NahK_ATCC55813. The pH optima of these two enzymes are slight different from that (pH 8.5) of NahK_JCM1217. Overall, the activity of NahK_ATCC55813 is higher than that of NahK_ATCC15697 in the pH range of 6.0-10.0 when GlcNAc was used as the substrate and the same molar concentrations of the enzymes were used.

Figure 3:
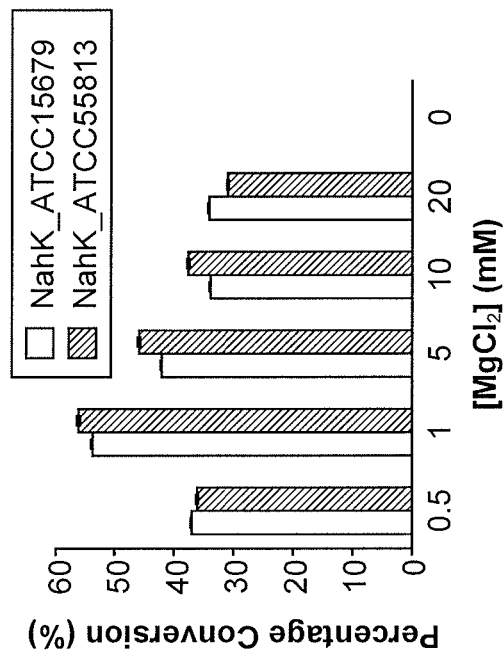
FIG. 3 shows the effect of MgCl$_2$ on the activity of NahKs.

Effect of $MgCl_2$. Similar to NahK_JCM1217 and other kinases, both NahK_ATCC15697 and NahK_ATCC55813 require a divalent metal ion for activity. As shown in FIG. 3, the optimal concentration of $Mg^{2+}$ was determined to be 1 mM. The activities of both NahKs in the presence of 0.5 mM of $Mg^{2+}$ were about two thirds of those in the presence of 1.0 mM of $Mg^{2+}$. Increasing the concentration of $Mg^{2+}$ from 1 mM to 20 mM caused a slight decrease of the activities of both NahKs.

Kinetics. The apparent kinetic parameters shown in Table 1 indicate that the activities of two NahKs are close, with NahK_ATCC55813 having 16% or 39% higher activity than NahK_ATCC15697 when GlcNAc or GalNAc was used as the substrate in the presence of ATP. Overall, GlcNAc is a more efficient (3.1-fold for NahK_ATCC15697 and 2.6-fold for NahK_ATCC55813) substrate than GalNAc for both NahKs due to relatively lower $K_m$ values and higher (~2-fold) $k_{cat}$ values obtained when GlcNAc was used. Using ATP and GlcNAc as the substrates, the $K_m$ values of ATP (0.10±0.03 mM and 0.11±0.03 mM) and GlcNAc (0.06±0.01 mM) for both NahKs are lower than those for NahK_JCM1217 (0.172 mM for ATP and 0.118 mM for GlcNAc) determined by high performance ion chromatography (HPIC) with a pulsed amperometric detector (DX500, Dionex Corporation, Sunnyvale, Calif.) using a Dionex CarboPac PA1 column (4 mm×250 mm). The discrepancies of the parameters may be due to the differences in the assay conditions used.

TABLE 1

Apparent kinetic parameters of NahKs.

| Enzymes Substrate | NahK1_ATCC15697 | | | NahK_ATCC55813 | | |
|---|---|---|---|---|---|---|
| | $K_m$ (mM) | $k_{cat}$ (s$^{-1}$) | $k_{cat}/K_m$ (s$^{-1}$ mM$^{-1}$) | $K_m$ (mM) | $K_{cat}$ (s$^{-1}$) | $k_{cat}/K_m$ (s$^{-1}$ mM$^{-1}$) |
| ATP[a] | 0.10 ± 0.03 | 1.1 ± 0.1 | 11.0 | 0.11 ± 0.03 | 1.3 ± 0.1 | 11.8 |
| GlcNAc | 0.06 ± 0.01 | 0.95 ± 0.01 | 15.8 | 0.06 ± 0.01 | 1.1 ± 0.1 | 18.3 |
| ATP[b] | 0.08 ± 0.03 | 0.38 ± 0.02 | 4.8 | 0.06 ± 0.02 | 0.48 ± 0.03 | 8.0 |
| GalNAc | 0.09 ± 0.05 | 0.46 ± 0.07 | 5.1 | 0.08 ± 0.03 | 0.57 ± 0.04 | 7.1 |

[a]The other substrate is GlcNAc;
[b]The other substrate is GalNAc.

Substrate Specificity. The substrate specificity studies using GlcNAc, GalNAc, and their derivatives (Table 2) indicate that both NahKs exhibit promiscuous substrate specificity and have comparable levels of activity toward GlcNAc and GalNAc derivatives. Compared to NahK_ATCC15697, NahK_ATCC55813 is more reactive towards non-modified GlcNAc (T2-1), GalNAc (T2-11), and some of their C2-modified derivatives with an N-trifluoroacetyl (GlcNTFA T2-2 and GalNTFA T2-12), an N-azidoacetyl group (GlcNAcN$_3$ T2-3 and GalNAcN$_3$ T2-13), or an N-butanoyl group (GlcNBu T2-4 and GalNBu T2-14). Nevertheless, NahK_ATCC15697 is more reactive than NahK_ATCC55813 for some of C2-modified GlcNAc and GalNAc derivatives such as those with a bulky N-benzoyl group (GlcNBz T2-5 and GalNBz T2-15) and a C2-azido group (GlcN$_3$ T2-6 and GalN$_3$ T2-16). NahK_ATCC15697 is also more reactive towards 2-amino-2-deoxy-glucose (GlcNH$_2$ T2-7), 2-N-sulfo-glucose (GlcNS T2-8), as well as C6-modified GlcNAc derivatives such as 6-deoxy-GlcNAc (GlcNAc6Me T2-9), 6-azido-6-deoxy-GlcNAc (GlcNAc6N$_3$ T2-10), and 6-O-sulfo-GlcNAc (GlcNAc6S T2-17). Both C2 and C6-modified derivatives GlcNAc such as 6-O-sulfo-N-trifluoroacetyl glucosamine (GlcNTFA6S T2-18) and 6-O-sulfo-2-azido-2-deoxy glucose (GlcN$_3$ T2-19) as well as both C2 and C3-modified GlcNAc derivative 3-O-sulfo-2-azido-2-deoxy glucose (GlcN$_3$S T2-20) are poor but acceptable substrates for both enzymes. Overall, some of the C2-modified GlcNAc and GalNAc (T2-1-T2-5 and T2-11-T2-14) are relatively good substrates for both NahKs with yields varied from 5.2-42.3% in a 10 min reaction containing 0.75 μM of enzyme. In comparison, other C2-modified GlcNAc and GalNAc (T2-6-T2-8, 15, T2-16), C6-(T2-9, T2-10, T2-17), both C2- and C6-(T2-18, T2-19), as well both C2- and C3-modified GlcNAc (T2-20) derivatives are poor but tolerable substrates for both NahKs and the assays have to be carried out for a longer reaction time (30 min) with a 20-fold higher concentration (15 μM) of enzyme.

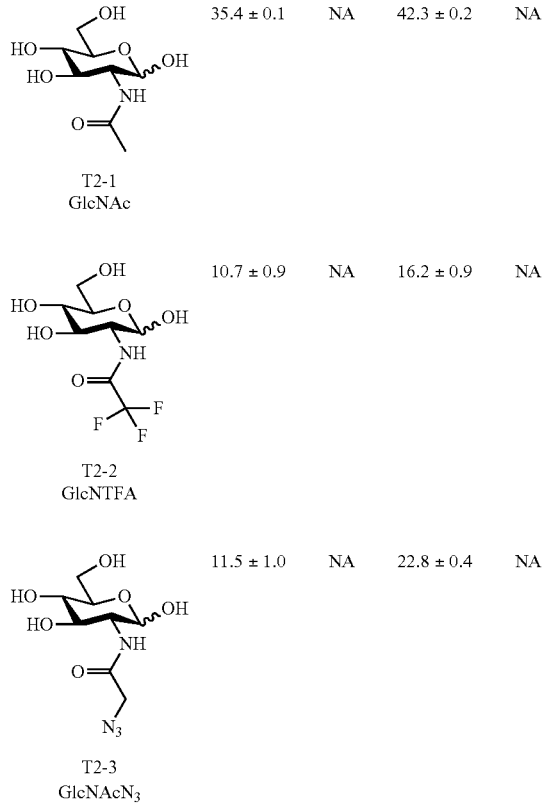

TABLE 2

Substrate specificity of NahKs using GlcNAc, GalNAc, and their derivatives.

| | Percentage Conversion (%) | | | |
|---|---|---|---|---|
| | NahK ATCC156 | | NahK ATCC5581 | |
| | 97 | | 3 | |
| | [a]0.75 μM | [b]15 μM | [a]0.75 μM | [b]15 μM |
| T2-1 GlcNAc | 35.4 ± 0.1 | NA | 42.3 ± 0.2 | NA |
| T2-2 GlcNTFA | 10.7 ± 0.9 | NA | 16.2 ± 0.9 | NA |
| T2-3 GlcNAcN$_3$ | 11.5 ± 1.0 | NA | 22.8 ± 0.4 | NA |

TABLE 2-continued

| Compound | NahK ATCC15 697 a 0.75 μM | NahK ATCC15 697 b 15 μM | NahK ATCC5581 3 a 0.75 μM | NahK ATCC5581 3 b 15 μM |
|---|---|---|---|---|
| T2-4 GlcNBu | 20.9 ± 0.6 | NA | 35.0 ± 2.0 | NA |
| T2-5 GlcNBz | 10.3 ± 0.4 | NA | 5.2 ± 0.2 | NA |
| T2-6 GlcN$_3$ | 0 | 14.5 ± 0.1 | 0 | 7.0 ± 0.1 |
| T2-7 GlcNH$_2$ | 0 | 15.0 ± 0.1 | 0 | 8.4 ± 0.1 |
| T2-8 GlcNS | 0 | 6.4 ± 0.2 | 0 | 4.0 ± 0.1 |
| T2-9 GlcNAc6Me | 4.4 ± 1.2 | 41.8 ± 0.3 | 2.1 ± 0.2 | 36.3 ± 0.3 |
| T2-10 GlcNAc6N$_3$ | 0 | 37.2 ± 0.5 | 0 | 23.4 ± 0.1 |
| T2-11 GalNAc | 12.5 ± 0.1 | NA | 19.9 ± 0.1 | NA |
| T2-12 GalNTFA | 11.2 ± 1.6 | NA | 21.8 ± 0.2 | NA |
| T2-13 GalNAcN$_3$ | 9.9 ± 0.6 | NA | 21.0 ± 1.2 | NA |
| T2-14 GalNBu | 12.1 ± 0.3 | NA | 24.0 ± 0.1 | NA |
| T2-15 GalNBz | 0 | 62.2 ± 1.0 | 0 | 51.9 ± 0.5 |
| T2-16 GalN$_3$ | 0 | 7.6 ± 0.1 | 0 | 4.3 ± 0.1 |

TABLE 2-continued

| Structure | | | | |
|---|---|---|---|---|
| 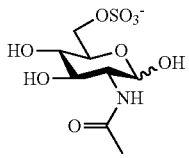 T2-17 GlcNAc6S | 0 | 11.7 ± 0.2 | 0 | 6.6 ± 0.1 |
| 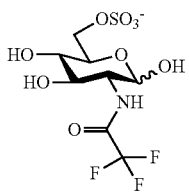 T2-18 GlcNTFA6S | 0 | 7.2 ± 0.1 | 0 | 3.3 ± 0.2 |
| 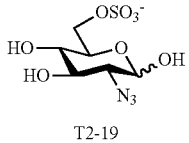 T2-19 GlcN36S | 0 | 6.9 ± 0.1 | 0 | 4.4 ± 0.1 |
| 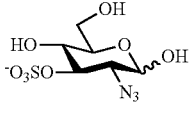 T2-20 GlcN₃3S | 0 | 4.9 ± 0.1 | 0 | 3.9 ± 0.1 |

NA: not assayed;
[a]Reactions were allowed to proceed for 10 min at 37° C.;
[b]Reactions were allowed to proceed for 30 min at 37° C.

Among twenty compounds of GlcNAc, GalNAc and their derivatives tested, compounds T2-1, T2-3-T2-5, T2-9-T2-11, T2-13-T2-15 have been reported before as suitable substrates for NahK_JCM1217 [11-12], while other compounds including T2-2, T2-6-T2-8, T2-12, and T2-16-T2-20 are newly identified substrates for NahKs. It is worth to note that some of these compounds have negatively charged O-sulfate group at different positions of GlcNAc or its derivatives.

Quite interestingly, the substrate specificity studies using glucose (Glc T3-21), galactose (Gal T3-28), mannose (Man T3-23), N-acetylmannosamine (ManNAc T3-29), and derivatives of mannose and ManNAc (Table 3) indicate that while both Glc (T3-21) and Gal (T3-28) are poor substrates for both NahKs, 2-deoxy glucose (2-deoxyGlc T3-22) or 2-deoxymannose is a better substrate. In addition, mannose (T3-23), its 2-fluoro- (2F-Man T3-24) and 2-azido- (2N₃-Man T3-26) derivatives, as well as its 4-deoxy (4-deoxyMan T3-27) derivative are relatively good substrates. In comparison, 2-methyl modification of mannose (2Me-Man T3-25) decreases its tolerance as the substrate for both NahKs. Quite surprisingly, while ManNAc (T3-29) and some of its C-2 derivatives (T3-30-T3-32) are poor substrates for the NahKs, N-azidoacetylmannosamine (ManNAcN₃ T3-33, a C2-derivative of ManNAc) and its C6-derivative N-acetyl-6-O-methylmannosamine (ManNAc6OMe T3-34) are better substrates for both NahKs. Overall, except for 2-fluoro-mannose (2F-Man T3-24), NahK_ATCC15697 shows higher activity than NahK_ATCC55813 for mannose, ManNAc, and their derivatives.

TABLE 3

Substrate specificity of NahKs using Glc, Gal, Man, ManNAc, and their derivatives.

| | Percentage Conversion (%) | |
|---|---|---|
| Substrates | NahK_ATCC15697 | NahK_ATCC55813 |
| 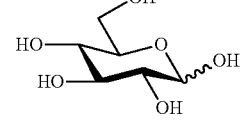 T3-21 Glc | 9.1 ± 0.1 | 4.7 ± 0.1 |
| 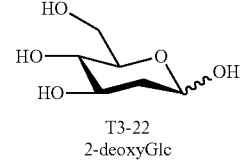 T3-22 2-deoxyGlc | 44.8 ± 0.2 | 28.4 ± 0.1 |
| 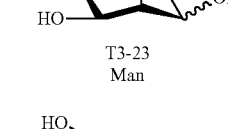 T3-23 Man | 68.0 ± 1.7 | 37.1 ± 0.4 |
| 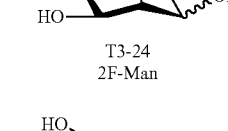 T3-24 2F-Man | 44.4 ± 0.2 | 47.0 ± 0.1 |
| 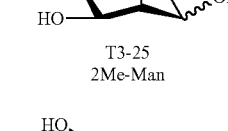 T3-25 2Me-Man | 9.4 ± 0.5 | 0 |
| 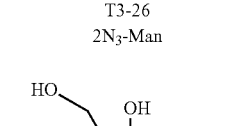 T3-26 2N₃-Man | 53.3 ± 0.1 | 40.2 ± 0.2 |
| 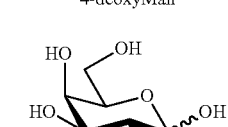 T3-27 4-deoxyMan | 37.1 ± 0.2 | 23.9 ± 0.1 |
| 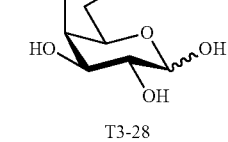 T3-28 Gal | 7.3 ± 0.2 | 4.4 ± 0.1 |

TABLE 3-continued

Substrate specificity of NahKs using Glc, Gal, Man, ManNAc, and their derivatives.

| Substrates | Percentage Conversion (%) | |
| --- | --- | --- |
| | NahK_ATCC15697 | NahK_ATCC55813 |
| 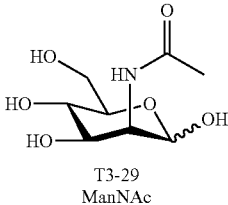 T3-29 ManNAc | 8.9 ± 0.1 | 5.5 ± 0.1 |
| 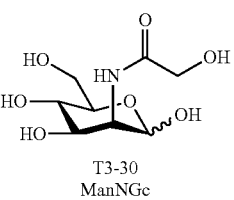 T3-30 ManNGc | 7.6 ± 0.1 | 5.4 ± 0.2 |
| 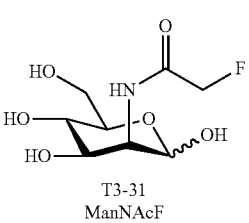 T3-31 ManNAcF | 12.0 ± 0.1 | 9.1 ± 0.2 |
| 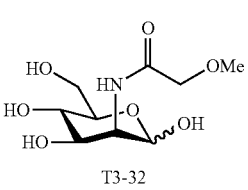 T3-32 ManNAcOMe | 12.0 ± 0.4 | 7.4 ± 0.3 |
| 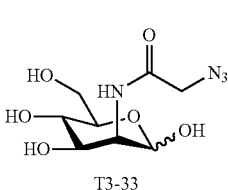 T3-33 ManNAcN$_3$ | 20.3 ± 0.3 | 18.6 ± 0.4 |
| 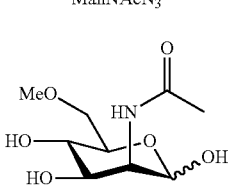 T3-34 ManNAc6OMe | 32.6 ± 0.1 | 28.9 ± 0.1 |

The concentration of the enzyme used was 15 µM. Reactions were allowed to proceed at 37° C. for 30 min.

AtGlcAK—*Arabidopsis thaliana* glucuronokinase (EC 2.7.1.43)

Experimental

Cloning, expression, and purification. Full length *Arabidopsis thaliana* glucuronokinase (EC 2.7.1.43) (AtGlcAK) (encoded by gene GlcAK1, DNA GenBank accession number: GU599900; protein GenBank accession number: NP_566144) was cloned in pET15b vector from a cDNA library of *Arabidopsis thaliana* and expressed as an N-His$_6$-tagged fusion protein. The primers used were: forward primer 5' GGAATTCCATATGGATCCGAATTCCACGG 3' (SEQ ID NO:27) (NdeI restriction site is bold and underlined) and reverse primer 5' CCGCTCGAGTCATAAGGTCTGAAT-GTCAGAATCATTC 3' (SEQ ID NO:28) (XhoI restriction site is bold and underlined). The resulting PCR products were digested with restriction enzymes, purified, and ligated with pET15b vector predigested with Ndel and XhoI restriction enzymes. The ligated product was transformed into electrocompetent *E. coli* DH5α cells. Selected clones were grown for minipreps and positive clones were verified by restriction mapping and DNA sequencing performed by Davis Sequencing Facility. The DNA sequence of the insert matched to GlcAK1.

The plasmid was transformed into *E. coli* BL21 (DE3) chemically competent cells for protein expression. *E. coli* cells harboring the pET15b-AtGlcAK plasmid were cultured in LB medium (10 g/L tryptone, 5 g/L yeast extract, and 10 g/L NaCl) with ampicillin (100 µg/mL) at 37° C. with rigorous shaking at 250 rpm in a C25KC incubator shaker (New Brunswick Scientific, Edison, N.J.) until the OD600 nm of the culture reached 0.8-1.0. Overexpression of the targeted proteins was achieved by adding 0.15 mM of isopropyl-1-thio-β-D-galactopyranoside (IPTG) followed by incubation at 18° C. for 20 h with rigorous shaking at 250 rpm.

His$_6$-tagged (SEQ ID NO:22) protein was purified from cell lysate using Ni$^{2+}$-NTA affinity column. To obtain cell lysate, cells were harvested by centrifugation at 4,000 rpm (Sorvall) at 4° C. for 2 h. The cell pellet was resuspended in lysis buffer (pH 8.0, 100 mM Tris-HCl containing 0.1% Triton X-100). Lysozyme (100 µg/mL) and DNaseI (5µg/mL) were added to the cell suspension. The mixture was incubated at 37° C. for 1 hr with vigorous shaking (200rpm). Cell lysate was obtained as the supernatant by centrifugation at 11,000 rpm (Sorvall) at 4° C. for 45 min. Purification was performed by loading the supernatant onto a Ni$^{2+}$-NTA column preequilibrated with 10 column volumes of binding buffer (10 mM imidazole, 0.5 M NaCl, 50 mM Tris-HCl, pH 7.5). The column was wash with 10 column volumes of binding buffer and 10column volumes of washing buffer (40 mM imidazole, 0.5 M NaCl, 50 mM Tris-HCl, pH 7.5). Protein of interest was eluted with Tris-HCl (pH 7.5, 50 mM) containing imidazole (200 mM) and NaCl (0.5 M). The fractions containing the purified enzyme were collected and dialyzed against Tris-HCl buffer (pH 7.5, 20 mM) containing 30% glycerol. Dialyzed proteins were stored at -20° C. Alternatively, fractions containing purified enzyme were dialyzed against Tris-HCl buffer (pH 7.5, 20 mM) and freeze dried. On average, 57 mg of purified protein was obtained from 1 liter of cell culture.

Substrates Specificity Assays by Thin-Layer Chromatography (TLC).

Enzymatic assays were carried out in a total volume of 10 µL in Tris-HCl buffer (100 mM, pH 7.5) containing GlcA (or GalA, IdoA, xylose) (10 mM), ATP (20 mM), MgCl$_2$ (20 mM), and AtGlcAK (22 µg). Reactions were allowed to proceed at 37° C. for 15 hr and monitored using thin-layer chromatographic (TLC) analysis using n-PrOH:H$_2$O:NH$_4$OH=7:4:2 (by volume) as a developing solvent. For visualizing compounds on TLC plate, p-anisaldehyde sugar stain was used.

LC-MS Assays for AtGlcAK Reactions. The AtGlcAK reaction mixtures above were also analyzed by LC-MS. 2 µL of sample was diluted 100 fold and 8 µL was injected into a Waters spherisorb ODS-2 column (5 µm particles, 250 mm length, 4.6 mm I.D.). The sample was eluted with 30% acetonitrile in H$_2$O with 0.1% formic acid and detected by ESI-MS in negative mode.

Results and Discussion

Figure 25:
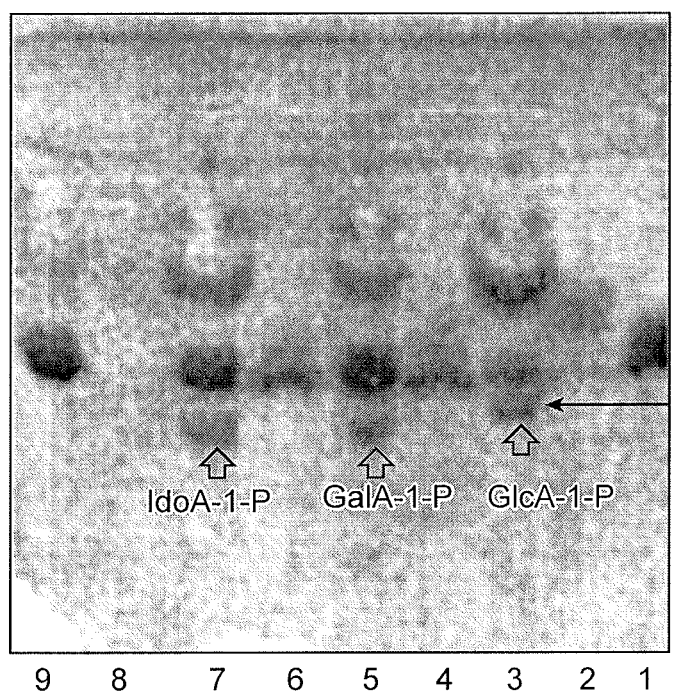
FIG. 25 shows thin-layer chromatography (TLC) analysis data for AtGlcAK reactions. Lanes: 1, ATP; 2, GlcA; 3, reaction with GlcA and ATP; 4, GalA; 5, reaction with GalA and ATP; 6, IdoA; 7, reaction with IdoA and ATP; 8, xylose; 9, reaction with xylose and ATP. Developing solvent used for running TLC: n-PrOH:H$_2$O:NH$_4$OH=7:4:2 (by volume).

Substrates Specificity Assays. As shown in FIG. 25 and FIG. 26, thin-layer chromatography results and mass spectrometry (MS) results showed that GlcA, GalA, and IdoA are acceptable substrates for AtGlcAK for the formation of GlcA-1-P, GalA-1-P, and IdoA-1P, respectively.

**PmGlmU—*Pasteurella multocida* Glucosaminyl Uridyltransferase**

Glycosyltranferases are key enzymes for the formation of oligosaccharides and glycoconjugates in nature. Most glycosyltransferases require sugar nucleotides as donor substrates and catalyze the transfer of monosaccharides from sugar nucleotides to acceptors in high regio- and stereoselective manner. Some carbohydrate structures contain post-glycosylational modifications (modifications on carbohydrates and glycoconjugates which take place after the formation of glycosidic bonds). One strategy to obtain naturally existing oligosaccharides and glycoconjugates with modified sugar moieties is to develop novel chemoenzymatic methods using structurally modified monosaccharides as starting materials and carbohydrate biosynthetic enzymes (the simplest carbohydrate biosynthetic route usually involves a monosaccharide kinase, a nucleotidyltransferase, and a glycosyltransferase) with substrate promiscuities. Carbohydrates with non-natural modifications can be synthesized similarly. Some of these compounds are potential drug candidates as they can effectively interfere with carbohydrate-dependent biological processes.

Glycosaminoglycans including keratan sulfate, heparan sulfate, and heparin are N-acetylglucosamine (GlcNAc)-containing polysaccharides with post-glycosylational modifications. While GlcNAc and 6-O-sulfo-GlcNAc are commonly found in kearatan sulfate, additional modified GlcNAc forms such as N-sulfo- and 3-O-sulfo-GlcNAc are common for heparan sulfate and heparin. In addition, 6-O-sulfation on GlcNAc is also common in Lewis x and sialyl Lewis x structures and has been shown to affect the binding affinity of the related carbohydrate-binding proteins such as Selectins and Siglecs. In attempts to synthesizing glycans containing naturally modified GlcNAc and their non-natural derivatives using glycosyltransferase-catalyzed reactions, we applied an efficient one-pot three-enzyme approach to synthesize UDP-GlcNAc derivatives including UDP-6-O-sulfo-GlcNAc, UDP-GlcNTFA, and azido-containing UDP-GlcNAc derivatives. Additional UDP-GlcNAc derivatives, including UDP-N-sulfo-glucosamine, were also produced by chemical diversification from enzymatically produced UDP-GlcNAc derivatives. These compounds will be tested as potential donor substrates for GlcNAc-glycosyltransferases.

Experimental

Cloning, expression, and purification of PmG1mU. The gene sequence of Pm1806 from *Pasteurella multocida* subsp. multocida strain Pm70 (GenBank accession no. AAK03890) was used as a reference for designing primers. The genomic DNA of *Pasteurella multocida* strain P-1059 (ATCC 15742) was used as a template for polymerase chain reaction (PCR). Full length *Pasteurella multocida* N-acetylglucosamine-1-phosphate uridylyltransferase (PmGlmU) was cloned in pET15b and pET22b(+) vectors as N-His$_6$-(SEQ ID NO:22) and C-His$_6$-tagged (SEQ ID NO:22) fusion proteins, respectively. For cloning into pET15b vector as an N-His$_6$-tagged (SEQ ID NO:22) protein, the primers used were: forward primer 5' GATCCATATG AAAGAGAAAGCATTAAG-TATCGTG 3' (SEQ ID NO:29) (NdeI restriction site is bold and underlined) and reverse primer 5' CCGCTCGAGT-TACTTTTTCGTTTGTTTAGTAGGGCG 3' (SEQ ID NO:30) (XhoI restriction site is bold and underlined). For cloning into pET22b(+) vector as a C-His$_6$-tagged (SEQ ID NO:22) protein, the primers used were: forward primer 5' GATCCATATGAAAGAGAAAGCATTAAGTATCGTG 3' (SEQ ID NO:31) (NdeI restriction site is bold and underlined) and reverse primer 5' CCGCTCGAG CTTTTTCGTTTGTT-TAGTAGGGCGTTGC 3' (SEQ ID NO:32) (XhoI restriction site is bold and underlined). The resulting PCR products were digested with restriction enzymes, purified, and ligated with pET15b or pET22b(+) vector predigested with NdeI and XhoI restriction enzymes. The ligated product was transformed into electrocompetent *E. coli* DH5α cells. Selected clones were grown for minipreps and positive clones were verified by restriction mapping and DNA sequencing performed by Davis Sequencing Facility.

Positive plasmids were transformed into *E. coli* BL21 (DE3) chemically competent cells. *E. coli* cells harboring the pET15b-PmGlmU or pET22b(+)-PmGlmU plasmid were cultured in LB medium (10 g/L tryptone, 5 g/L yeast extract, and 10 g/L NaCl) with ampicillin (100 µg/mL) until the OD$_{600\,nm}$ of the culture reached 0.8-1.0. Overexpression of the targeted proteins was achieved by adding 0.1 mM of isopropyl-1-thio-β-D-galactopyranoside (IPTG) followed by incubation at 25° C. for 18 h with rigorous shaking at 250 rpm in a C25KC incubator shaker (New Brunswick Scientific, Edison, N.J.).

His$_6$-tagged (SEQ ID NO:22) proteins were purified from cell lysate using Ni$^{2+}$-NTA affinity column. To obtain cell lysate, cells were harvested by centrifugation at 4,000 rpm (Sorvall) at 4° C. for 2 hr. The cell pellet was resuspended in lysis buffer (pH 8.0, 100 mM Tris-HCl containing 0.1% Triton X-100). Lysozyme (100 µg/mL) and DNaseI (5 µg/mL) were then added to the cell suspension. The mixture was incubated at 37° C. for 1 hr with vigorous shaking (200 rpm). Cell lysate was obtained as the supernatant by centrifugation at 11,000 rpm (Sorvall) at 4° C. for 45 min. Purification is performed by loading the supernatant onto a Ni$^{2+}$-NTA column pre-equilibrated with 10 column volumes of binding buffer (10 mM imidazole, 0.5 M NaCl, 50mM Tris-HCl, pH 7.5). The column was wash with 10 column volumes of binding buffer and 10 column volumes of washing buffer (40 mM imidazole, 0.5 M NaCl, 50 mM Tris-HCl, pH 7.5). Protein of interest was eluted with Tris-HCl (pH 7.5,50 mM) containing imidazole (200 mM) and NaCl (0.5 M). The fractions containing the purified enzymes were collected and dialyzed against Tris-HCl (pH 7.5,25 mM) buffer containing 10% glycerol. Dialyzed proteins were stored at 4° C.

Results and Discussion

DNA and Protein Sequences of PmGlmU Cloned from *Pasteurella multocida* Strain P-1059 (ATCC 15742). Compared to the sequences of GlmU (gene Pm1806) from *Pasteurella multocida* genomic strain Pm70 (GenBank accession numbers: AE004439 for gene and AAK03890 for protein), there are 13 base differences (C39A, T195C, A333G, G334A, T339C, G636A, G655A, G817C, T882A, A1006G, A1008T, G1071A, and G1266T) and four amino acid differences (E112K, D219N, E273Q, and T336A) (italicized and underlined) in *Pasteurella multocida* strain P-1059 (ATCC 15742).

Expression level and SDS-PAGE of PmGlmU. The N-His$_6$-tagged (SEQ ID NO:22) PmGlmU has a higher expression level than the C-His$_6$-tagged (SEQ ID NO:22) PmGlmU. On average, 170 mg of purified N-His$_6$-tagged (SEQ ID NO:22) PmG1mU was obtained from 1 liter of cell culture. SDS-PAGE analysis shows that both the purified protein migrated to around 55 kDa.

**BLUSP—*Bifidobacterium longum* UDP-sugar Pyrophosphorylase**

Carbohydrates are widespread in nature and play pivotal roles in biological systems. The key enzymes for the formation of glycosidic bonds in carbohydrates are glycosyltransferases. Most glycosyltransferases require monosaccharide nucleotides as the common activated donor substrates. Among monosaccharide nucleotides used by mammalian glycosyltransferases, many are uridine 5'-diphosphate (UDP)-monosaccharides such as UDP-glucose (UDP-Glc), UDP-galactose (UDP-Gal), UDP-glucuronic acid (UDP-GlcA), UDP-N-acetylglucosamine (UDP-GlcNAc), UDP-N-acetylgalactosamine (UDP-GalNAc), and UDP-xylose (UDP-Xyl). In addition, UDP-mannose (UDP-Man) has been isolated from *Mycobacterium smegmatis* and proposed to be an intermediate in the biosynthesis of mycobacterial polysaccharides. Furthermore, UDP-N-acetylmannosamine (UDP-ManNAc) and UDP-N-acetylmannosaminuronic acid (UDP-ManNAcA) have been used by some bacteria for producing capsular polysaccharides containing ManNAc or ManNAcA residues or forming ManNAcβ1-4GlcNAc-PP-undecaprenol (lipid II) for the biosynthesis of cell wall teichoic acids of Gram-positive bacteria.

The simplest biosynthetic route for obtaining monosaccharide nucleotides such as UDP-monosaccharides usually involves the formation of a monosaccharide-1-phosphate catalyzed by a monosaccharide-1-phosphate kinase followed by the formation of monosaccharide nucleotides catalyzed by a nucleotidyltransferase (or pyrophosphorylase). However, the simplest route has not been applied routinely for the formation of UDP-Gal due to the less common access to UTP:galactose-1-phosphate uridylyltransferases or UDP-Gal pyrophosphorylase (EC 2.7.7.10) for direct formation of UDP-Gal from Gal-1-phosphate and UTP. For example, UDP-Gal used in galactosyltransferase-catalyzed enzymatic synthesis of galactosides has been more frequently obtained from UDP-Glc by reactions catalyzed by UDP-Gal 4-epimerases or UDP-glucose:galactose-1-phosphate uridylyltransferases (EC 2.7.7.12, GalT or GalPUT) in the Leloir pathway.

Nevertheless, UDP-galactose pyrophosphorylase activity was identified from yeast *Saccharomyces fragilis*, pigeon liver, and mammalian livers. The enzyme was purified from bovine liver and Gram-positive bacterium *Bifidobacterium bifidum*. Recently, promiscuous UDP-sugar pyrophosphorylases (USPs) (EC 2.7.7.64) that can use various monosaccharide 1-phosphates in the presence of UTP for direct synthesis of UDP-monosaccharides including UDP-Glc, UDP-Gal, and UDP-GlcA, etc. were cloned from plants such as pea (*Pisum sativum* L.) sprouts (PsUSP) and *Arabidopsis thaliana* (AtUSP). Enzymes which share sequence homology to plant USPs were also cloned from *Leishmania major* and *Trypanosoma cruzi*, two trypanosomatid protozoan parasites, and were shown to have good activity towards Gal-1-P and Glc-1-P and weaker activity towards xylose-1-phosphate and GlcA-1-P. A USP with broad substrate specificity and optimal activity at 99° C. was also cloned from a hyperthermophile archaea *Pyrococcus furiosus* DSM 3638 for which Glc-1-P, Man-1-P, Gal-1-P, Fuc-1-P, GlcNH$_2$-1-P, GalNH$_2$-1-P, and GlcNAc-1-P were all shown to be tolerable substrate, and both UTP and dTTP could be used as nucleotide triphosphate substrates by the enzyme. Nevertheless, none of these enzymes has been used in preparative-scale or large-scale synthesis of sugar nucleotides and non-natural derivatives of monosaccharide-1-P have not been tested as substrates for DSPs.

Here we report the cloning of a promiscuous USP from a probiotic *Bifidobacterium longum* strain ATCC55813 and its application in an efficient one-pot three-enzyme system for preparative-scale synthesis of UDP-monosaccharides and their derivatives from simple monosaccharides or derivatives (except for UDP-Glc which was synthesized from Glc-1-P in a one-pot two-enzyme system as discussed below). These compounds will be tested as potential donor substrates for various glycosyltransferases.

Experimental

Cloning, expression, and purification of BLUSP. Full length *Bifidobacterium longum* UDP-sugar pyrophosphorylase (EC 2.7.7.64) (BLUSP) (encoded by gene ugpA, DNA GenBank accession number: ACHI01000119, locus tag: HMPREF0175_1671; protein GenBank accession number: EEI80102) was cloned from the genomic DNA of *Bifidobacterium longum* strain ATCC55813 in pET15b vector as an N-His$_6$-tagged (SEQ ID NO:22) fusion protein. The primers used were: forward primer 5' GGAATTCCATATGACA-GAAATAAACGATAAGGCC 3' (SEQ ID NO:33) (NdeI restriction site is bold and underlined) and reverse primer 5' CGCGGATCCTCACACCCAATCGTCCG 3' (SEQ ID NO:34) (BamHI restriction site is bold and underlined). The resulting PCR products were digested with restriction enzymes, purified, and ligated with pET15b vector predigested with NdeI and BamHI restriction enzymes. The ligated product was transformed into electrocompetent *E. coli* DH5α cells. Selected clones were grown for minipreps and positive clones were verified by restriction mapping and DNA sequencing performed by Davis Sequencing Facility. The DNA sequence of the insert matched to BL0739 (ugpA) gene in the genomic sequence of *Bifidobacterium longum* NCC2705. Compared to the BL0739 (ugpA) gene sequence of *Bifidobacterium longum* NCC2705 (GenBank accession number: AE014295) which was annotated to encoding a hypothetical UTP:glucose-1-phosphate uridylyltransferase (GenBank accession number: AAN24556), there are 4 base differences (T35C, A47G, C228T, A465C) resulting in one amino acid difference (D16G) in the protein sequence of BLUSP.

The plasmid was transformed into *E. coli* BL21 (DE3) chemically competent cells for protein expression. *E. coli* cells harboring the pET15b-BLUSP plasmid were cultured in LB medium (10 g/L tryptone, 5 g/L yeast extract, and 10 g/L NaCl) with ampicillin (100 µg/mL) at 37° C. with rigorous shaking at 250 rpm in a C25KC incubator shaker (New Brunswick Scientific, Edison, N.J.) until the OD$_{600\ nm}$ of the culture reached 0.8-1.0. Overexpression of the targeted proteins was achieved by adding 0.15 mM of isopropyl-1-thio-β-D-galactopyranoside (IPTG) followed by incubation at 18° C. for 20 hr with rigorous shaking at 250 rpm.

His$_6$-tagged (SEQ ID NO:22) protein was purified from cell lysate using Ni$^{2+}$-NTA affinity column. To obtain cell lysate, cells were harvested by centrifugation at 4,000 rpm (Sorvall) at 4° C. for 2 hr. The cell pellet was resuspended in lysis buffer (pH 8.0,100 mM Tris-HCl containing 0.1% Triton X-100). Lysozyme (100 µg/mL) and DNaseI (5 µg/mL) were added to the cell suspension. The mixture was incubated at 37° C. for 1 hr with vigorous shaking (200rpm). Cell lysate was obtained as the supernatant by centrifugation at 11,000 rpm (Sorvall) at 4° C. for 45 min. Purification was performed by loading the supernatant onto a Ni$^{2+}$-NTA column pre-equilibrated with 10 column volumes of binding buffer (10 mM imidazole, 0.5 M NaCl, 50 mM Tris-HCl, pH 7.5). The column was wash with 10 column volumes of binding buffer and 10 column volumes of washing buffer (40 mM imidazole, 0.5 M NaCl, 50 mM Tris-HCl, pH 7.5). Protein of interest was eluted with Tris-HCl (pH 7.5,50 mM) containing imidazole (200 mM) and NaCl (0.5 M). The fractions containing the purified enzyme were collected and dialyzed against Tris-HCl buffer (pH 7.5,25 mM) containing 10% glycerol and 0.25 M NaCl. Dialyzed proteins were stored at 4° C. Alternatively, fractions containing purified enzyme were dialyzed against Tris-HCl buffer (pH 7.5,25 mM) and freeze dried. On average, 167 mg of purified protein was obtained from 1 liter of cell culture. Protein concentration was determined in a 96-well plate using bicinchoninic acid with BSA as standard. The absorbance was measured at 562 nm using a plate reader.

pH Profile Study for BLUSP. Typical enzymatic assays for pH profile studies were carried out for 10 min at 37° C. in a total volume of 20 µL containing Glc-1-P (1 mM), UTP (1 mM), Mg$^{2+}$ (20 mM), and BLUSP (10 ng) in a buffer (100 mM) with pH varying from 3.0 to 9.5. The reaction mixture was quenched by boiling for 5 min followed by adding 20 µL of pre-chilled 95% (v/v) ethanol. The samples were then kept on ice until analyzed by a Beckman Coulter P/ACE MDQ Capillary Electrophoresis system equipped with a UV detector and a 50 cm capillary tubing (75 µm I.D., Beckman Coulter). Assays were run at 25 kV with 25 mM sodium borate buffer (pH 9.8) for 22 min. Percent conversions were calculated from peak areas of UDP-sugar and UTP monitored by UV absorbance at 254 nm. All assays were carried out in duplicate.

Effects of Metal Ions and EDTA. EDTA (5 mM), different concentrations (0.5, 1, 5, 10, 20, 50 mM) of $MgCl_2$, and various divalent metal cations ($CaCl_2$, $CoCl_2$, $CuSO_4$, $MnCl_2$, $ZnCl_2$) were used in a MES buffer (pH 6.5, 100 mM) to analyze their effects on the uridylyltransferase activity of BLUSP (10 ng in 20 μL total volume) using Glc-1-P (1 mM) as the acceptor. Other components are the same as those described for the pH profile studies. Reaction without EDTA or metal ions was used as a control.

Capillary electrophoresis (CE) and thin-layer chromatograph (TLC) assays for kinase reactions. Kinase reactions were carried out at 37° C. in a total volume of 30 μL in Tris-HCl buffer (100 mM, pH 8.0) containing monosaccharide (15 mM), ATP (18 mM, 1.2 eq.), $MgCl_2$ (10 mM), and a kinase (6 μg). These conditions were similar to those used for preparative-scale synthesis. After 1 hr, 4 hr, and 24 hr, an aliquot of 8 μL was withdrawn from each reaction mixture, boiled in a water bath for 5 min and stored at −20° C. until being analyzed by capillary electrophoresis (CE) and TLC. For TLC analysis, 0.5 μL of each sample was directly spotted on TLC plates, developed using suitable developing solvents, and stained with anisaldehyde sugar stain. For CE analysis, 1.5 μL of each sample was diluted into 30 μL and subjected to CE analysis as described above for pH profile studies.

Results and Discussion

Figure 6:
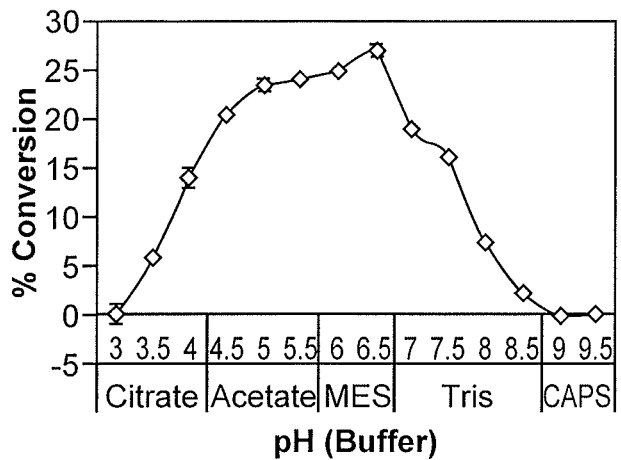
FIG. 6 shows the pH profile of *Bifidobacterium longum* UDP-sugar pyrophosphorylase (BLUSP).

SDS-PAGE Analysis of BLUSP. SDS-PAGE analysis shows that the recombinant BLUSP has a very good expression level in E. coli and has a high solubility. It consists of about 90% of the total protein extracts from E. coli host cells and more than 90% of the soluble protein. The protein size observed is about 60 kDa which is close to 59.7 kDa calculated molecular weight.

pH Profile of BLUSP. As shown in FIG. 6, BLUSP is active in a broad pH range of 4.0-8.0 and with optimal activity at pH 6.5 in MES buffer.

Figure 7:
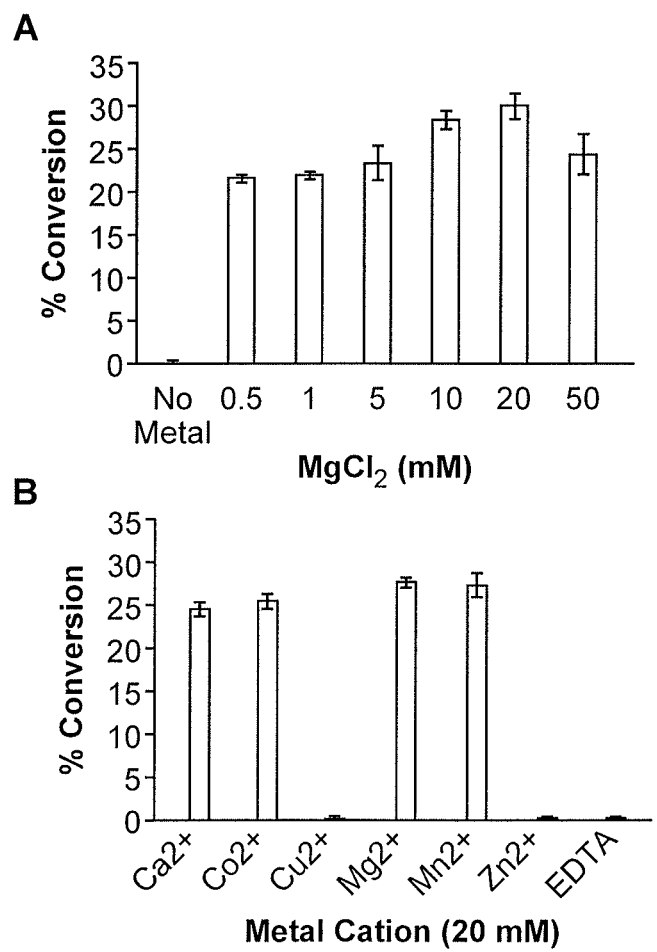
FIG. 7 shows the metal requirements of BLUSP.

Effects of Metal Ions and EDTA. As shown in FIG. 7, a divalent metal cation such as $Ca^{2+}$, $Co^{2+}$, $Mg^{2+}$, or $Mn^{2+}$ is required for the activity of BLUSP. BLUSP is inactive in the absence of a divalent metal cataion or in the presence of EDTA. At 20 mM concentration, $Mg^{2+}$ was the best among all divalent metal cations tested including $Ca^{2+}$, $Co^{2+}$, $Mg^{2+}$, or $Mn^{2+}$, $Cu^{2+}$, and $Zn^{2+}$. The optimal $Mg^{2+}$ concentration for BLUSP activity was found to be 20 mM.

PmUgd—Pasteurella multocida UDP-Glucose Dehydrogenase

Cloning of PmUgd. PmUgd was cloned as a C-His$_6$-tagged (SEQ ID NO:22) fusion protein in pET22b(+) vector using the genomic DNA of P. multocida P-1059 (ATCC#15742) as the template for polymerase chain reactions (PCR). Primers used for cloning were: forward primer 5'-GATCCATAT-GAAGAAAATTACAATTGCTGGGGC-3' (SEQ ID NO:35)(NdeI restriction site is underlined) and reverse primer 5'- CCGCTCGAGAGCATCACCGC-CAAAAATATCTCTTG-3'(SEQ ID NO:36) (XhoI restriction site is underlined). PCR was performed in a reaction mixture of 50 μl containing genomic DNA (1 μg), forward and reverse primers (1 μM each), 10×Herculase buffer (5 μl), dNTP mixture (1 mM), and 5 U (1 μl) of Herculase-enhanced DNA polymerase. The reaction mixture was subjected to 30 cycles of amplification with an annealing temperature of 55° C. The resulting PCR products were purified, digested, and ligated with the corresponding pre-digested vector. The ligation products were transformed into electrocompetent E. coli DH5αcells. Plasmids containing the target genes as confirmed by DNA sequencing (performed by UC-Davis Sequencing Facility) were selected and transformed into E. coli BL21(DE3) chemically competent cells.

Compared to the DNA sequence of PM0776 gene from P. multocida strain Pm70 (its genomic DNA sequence is available on NCBI), the obtained gene of PmUgd has 19 base differences (A357G, C381A, A390G, A397C, C404A, A406G, T408A, C414T, A420T, A426G, C430T, G438A, C447A, T451C, C453T, T456C, A464T, C582T, and G807A, the nucleotide before the number is from the DNA sequence of PM0776, the number is based on PM0776 gene) compared to publically available PM0776 gene sequence. Furthermore, the C at position 401 in PM0776 is missing in PmUgd and PmUgd has an extra A between 408 and 409 of PM0776. Overall, there are five amino acid differences in PmUgd (N127K, N133H, L1371, Y151H and Y155F, the amino acid residue before the number is from the protein sequence deduced from PM0776, the number is based on the protein sequence deduced from PM0776) compared to the deduced protein sequence from PM0776 gene.

Expression and Purification. E. coli strains were cultured in LB rich medium (10 g/L tryptone, 5 g/L yeast extract, and 10 g/L NaCl) supplemented with ampicillin (100 μg/mL). Overexpression of PmUgd was achieved by inducing the E. coli BL21(DE3) cell culture with 0.1 mM of isopropyl-1-thio-β-D-galactopyranoside (IPTG) when the $OD_{600\,nm}$ of the culture reached 0.8-1.0 followed by incubation at 20° C. for 20 h.

Bacterial cells were harvested by centrifugation at 4° C. in a Sorvall Legend RT centrifuge with a hanging bucket rotor at 4000×rpm for 2 h. Harvested cells were resuspended in lysis buffer (Tris-HCl buffer, 100 mM, pH 8.0 containing 0.1% Triton X-100) (20 mL for cells collected from one liter cell culture). Lysozyme (100 μg/mL) and DNaseI (5 μg/mL) were added to the cell resuspension. The resulting mixture was incubated at 37° C. for 1 h with shaking at 200 rpm. Cell lysate (supernatant) was obtained by centrifugation at 12000×rpm for 15 min. Purification was carried out by loading the supernatant onto a $Ni^{2+}$-NTA column pre-equilibrated with 8 column volumes of binding buffer (10 mM imidazole, 0.5 M NaCl, 50 mM Tris-HCl, pH 7.5). The column was washed with 8 column volumes of binding buffer and 8 column volumes of washing buffer (40 mM imidazole, 0.5 M NaCl, 50 mM Tris-HCl, pH 7.5). The target protein was eluted with Tris-HCl buffer (50 mM, pH 7.5) containing imidazole (200 mM) and NaCl (0.5 M). The fractions containing the purified enzymes were collected and dialyzed against Tris-HCl buffer (20 mM, pH 7.5) containing 10% glycerol. Dialyzed proteins were stored at 4° C.

About 23 mg PmUgd can be routinely expressed and purified from 1 L of E. coli culture under expression conditions described above.

PmHS1, PmHS2, KfiA

Materials and Methods

Bacterial Strains, Plasmids, and Materials. E. coli electrocompetent DH5α and chemically competent BL21 (DE3) cells were from Invitrogen (Carlsbad, Calif.). P. multocida P-934 (ATCC #12948) and P. multocida P-1059 (ATCC #15742) were from American Type Culture Collection (ATCC, Manassas, Va., USA). KfiA synthetic gene with codons optimized for E. coli expression was synthesized by GeneArt (Grand Island, N.Y.) based on KfiA gene sequence from E. coli Nissle 1917 (GenBank accession number: AJ586888, ORF79). Vector plasmid pET15b was from Novagen (EMD Biosciences Inc. Madison, Wis., USA). Vector pMAL-c4X was purchased from New England Biolabs (Ipswich, Mass.). Nickel-nitrilotriacetic acid agarose ($Ni^{2+}$-NTA agarose), QIAprep spin miniprep kit, and QIAEX II gel extraction kit were from Qiagen (Valencia, Calif., USA). Herculase-enhanced DNA polymerase was from Stratagene (La Jolla, Calif., USA). T4 DNA ligase and 1 kb DNA ladder were from Promega (Madison, Wis., USA). NdeI, BamHI, EcoRI, and HindIII restriction enzymes were from New England Biolabs Inc. (Beverly, Mass., USA).

Cloning of PmHS1, PmHS2 and KfiA. PmHS2 was cloned as N- and C-His$_6$-tagged (SEQ ID NO:22) fusion proteins in pET15b and pET22b(+) vector, respectively, using genomic DNAs of P. multocida P-1059 (ATCC#15742) as the template for polymerase chain reactions (PCR). PmHS 1 and KfiA were cloned as a fusion protein of an N-terminal with a maltose-binding protein (MBP) and a C-terminal His$_6$ tag (SEQ ID NO:22) in pMAL-c4X vector using the *P. multocida* P-934 (ATCC#12948) and KfiA synthetic gene as template, respectively. Primers used for cloning are summarized in Table 8. PCR was performed in a reaction mixture of 50μL containing genomic DNA (1 μg), forward and reverse primers (1 μM each), 10×Herculase buffer (5 μL), dNTP mixture (1 mM), and 5 U (1μL) of Herculase-enhanced DNA polymerase. The reaction mixture was subjected to 30 cycles of amplification with an annealing temperature of 55° C. (for PmHS1 and PmHS2) or 52° C. (for KfiA). The resulting PCR products were purified, digested, and ligated with the corresponding pre-digested vector. The ligation products were transformed into electrocompetent *E. coli* DH5α cells. Plasmids containing the target genes as confirmed by DNA sequencing (performed by UC-Davis Sequencing Facility) were selected and transformed into *E. coli* BL21(DE3) chemically competent cells.

washed with 10 column volumes of binding buffer and 10 column volumes of washing buffer (20-50 mM imidazole, 0.5 M NaCl, 50 mM Tris-HCl, pH 7.5). The target protein was eluted with Tris-HCl buffer (50 mM, pH 7.5) containing imidazole (200 mM) and NaCl (0.5 M). The fractions containing the purified enzymes were collected and dialyzed against Tris-HCl buffer (20 mM, pH 7.5) containing 10% glycerol. Dialyzed proteins were stored at 4° C.

pH Profile by HPLC. Typical enzymatic assays were performed in a 10 μl reaction mixture containing a buffer (100 mM) with a pH in the range of 4.0-10.0, UDP-GlcNAc (1 mM), GlcAβ132AA (1 mM), MnCl$_2$ (10 mM) and KfiA (9.0 μg) or PmHS2 (0.25 μg). Buffers used were: Na$_2$HPO$_4$/citric acid, pH 4.0; MES, pH 5.0-6.5; TrisHCl, pH 7.0-9.0; and CAPS, pH 10.0. Reactions were allowed to proceed for 30 min at 37° C. and were quenched by adding ice-cold 10% (v/v) acetonitrile to make 100-fold dilutions. The samples were then kept on ice until an aliquot of 8 μl was injected and analyzed by a Shimadzu LC-2010A system equipped with a membrane on-line degasser, a temperature control unit and a

TABLE 4

Primers used for cloning PmHS1, PmHS2 and KfiA.

| Primers | Sequences (5'-3') (SEQ ID NO:) |
|---|---|
| KfiA_pMAL-c4X_F_EcoRI | GACCGAATTCATGATTGTTGCAAATATGAGC (37) |
| KfiA_pMAL-c4X_R_HindIII | GTCGAAGCTTTTAGTGGTGGTGGTGGTGGTGACCTT CCACATTATAC (38) |
| PmHS1_pMAL-c4X_F_BamHI | CGCGGATCCATGAGCTTATTTAAACGTGCTAC (39) |
| PmHS1_pMAL-c4X_R_HindIII | GATCAAGCTTTTAGTGATGATGATGATGATGCTCGT TATAAAAAGATAAACACGG (40) |
| PmHS2_pET15b/22b+_F_NdeI | GATCCATATGAAGGGAAAAAAAGAGATGAC (41) |
| PmHS2_pET15b_R_BamHI | AAGGGATCCTTATAAAAAATAAAAAGGTAAACAGG (42) |
| PmHS2_pET22b+_R_BamHI | AAGGGATCCTTAGTGGTGGTGGTGGTGGTGTAAAA AATAAAAAGGTAAACAGG (43) |

Expression and Purification. *E. coli* strains were cultured in LB rich medium (10 g/L tryptone, 5 g/L yeast extract, and 10 g/L NaCl) supplemented with ampicillin (100 μg/mL). Overexpression of PmHS1 and PmHS2 were achieved by inducing the *E. coli* BL21(DE3) cell culture with 0.1 mM of isopropyl-1-thio-β-D-galactopyranoside (IPTG) when the OD$_{600\ nm}$ of the culture reached 0.8-1.0 followed by incubation at 20° C. for 20 h. Overexpression of KfiA was performed by inoculating 10 mL of a fresh overnight bacterial culture grown in LB containing 50 μg/mL ampicillin and 20 μg/mL chloramphenicol into 1 L of LB (containing 50 μg/mL of ampicillin, 20 μg/mL of chloramphenicol and 2 mg/mL of L-arabinose). The culture was incubated at 37° C. with shaking at 250 rpm. When the OD$_{600}$ of the culture reached 0.4-0.6, expression was induced by adding IPTG to a final concentration of 0.3 mM and then the cell was cultured at 20° C. for 20 h.

Bacterial cells were harvested by centrifugation at 4° C. in a Sorvall Legend RT centrifuge with a hanging bucket rotor at 4000×rpm for 2 h. Harvested cells were resuspended in lysis buffer (Tris-HCl buffer, 100 mM, pH 8.0 containing 0.1% Triton X-100) (20 mL for cells collected from one liter cell culture). Lysozyme (100 μg/mL) and DNaseI (5 μg/in L) were added to the cell resuspension. The resulting mixture was incubated at 37° C. for 1 h with shaking at 200 rpm. Cell lysate (supernatant) was obtained by centrifugation at 12000×rpm for 15 min. Purification was carried out by loading the supernatant onto a Ni$^{2+}$-NTA column pre-equilibrated with 10 column volumes of binding buffer (10 mM imidazole, 0.5 M NaCl, 50 mM Tris-HCl, pH 7.5). The column was fluorescence detector. A reverse phase Premier C18 column (250 9 4.6 mm I.D., 5 μm particle size, Shimadzu) protected with a C18 guard column cartridge was used. The mobile phase was 25% (v/v) acetonitrile. The fluorescent compounds GlcAβ2AA and GlcNAcα1-4GlcAβ2AA were detected by excitation at 315 nm and emission at 400 nm.

Effects of Metal Ions. Different concentrations (1, 5, 10, and 20 mM) of MgCl$_2$, MnCl$_2$, CaCl$_2$, or CuCl$_2$ were used in a MES buffer (pH 6.5, 100 mM) to analyze their effects on the activity of KfiA (0.9 μg μl$^{-1}$) or PmHS2 (2.5×10$^{-2}$ μg μl$^{-1}$). Reaction without metal ions was used as a control. The assay was performed as above pH profile.

Substrate Specificity of KfiA and PmHS2. All reactions were carried out in duplicate at 37° C. in MES (100 mM, pH 6.5) containing an UDP-GlcNAc or its derivatives (1 mM), GlcAα2AA (1 mM), MnCl$_2$(10 mM) and KfiA (1.08 μg μl$^{-1}$) or PmHS2 (2.5×10$^{-2}$ μg μl$^{-1}$). At 30 min, 4 h or 16 h, aliquots of reaction mixture were withdrawn and were quenched by adding ice-cold 10% (v/v) acetonitrile to make 100-fold dilutions. The assays were analyzed by HPLC.

Results

Figure 27:
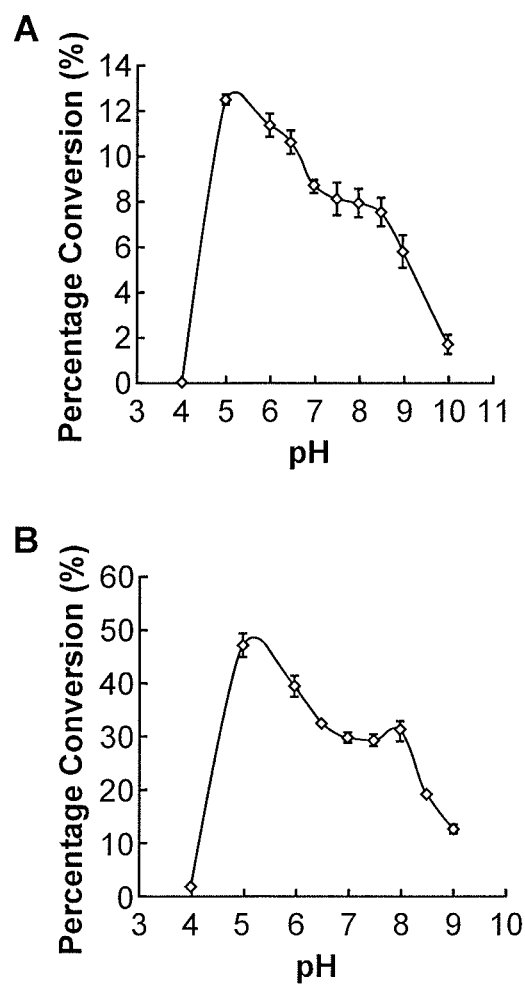
FIG. 27 shows pH profiles of KfiA (FIG. 27A) and PmHS2 (FIG. 27B). Buffers used were: Na$_2$HPO$_4$/citric acid, pH 4.0; MES, pH 5.0-6.5; TrisHCl, pH 7.0-9.0; and CAPS, pH 10.0.

Cloning, expression and purification of recombinant proteins. PmHS2 was cloned as an N- or a C-His$_6$-tagged (SEQ ID NO:22) protein using pET15b and pET22b (+) vectors, respectively. Both N- and C-His$_6$-tagged (SEQ ID NO:22) proteins were able to be expressed as soluble forms in *E. coli* BL21(DE3) cells by induction 0.1 mM IPTG. Both could be easily purified using Ni$^{2+}$-affinity chromatography. The expression level of the soluble and active N-His$_6$-tagged (SEQ ID NO:22) form was relatively higher than its C-His$_6$-tagged (SEQ ID NO:22) counterpart and N-His$_6$-PmHS2 was studied in detail. About 11 mg of N-His$_6$-PmHS2 was routinely obtained from the cell lysate of one liter E. coli cell culture. KfiA was expressed in an N-terminal MBP and a C-terminal six-His fusion protein in BL21(DE3) cells coexpressed with chaperone protein pGro7. The recombinant KfiA was purified to homogeneity with a Ni$^{2+}$-affinity column. About 8.0 mg of MBP-KfiA-His$_6$ was routinely obtained from the cell lysate of one liter E. coli cell culture. Sodium dodecylsulfate-polyacrylamide gel electrophoresis (SDS-PAGE) analysis indicated that one-step Ni$^{2+}$-column purification was efficient to provide pure PmHS2 and KfiA. As expected from the calculated molecular weight of PmHS2 and KfiA, the size of the protein shown by SDS-PAGE was about 75 kDa and 69 kDa, respectively. To obtain a soluble and active recombinant PmHS 1 in E. coli expression system, the MBP tag was introduced by using pMAL-c4X vector, while the C-His$_6$-tag (SEQ ID NO:22) was introduced by including the His$_6$-tag (SEQ ID NO:22) codons in the 3'-primer used for cloning. Expression was achieved by incubating E. coli BL21(DE3) cells at 20° C. for 20 h with vigorous shaking (250 rpm) after the addition of IPTG (0.1 mM) for induction. Although it has activity, SDS-PAGE analysis indicated that only a small portion of the recombinant protein was seen in the cell lysate, the soluble portion of the cell extraction.

pH Profile of KfiA and the N-Acetylglucosaminyltransferase Activity of PmHS2. As shown in FIG. 27, when GlcAB2AA was used as an acceptor, both KfiA and PmSH2 were found to be active in a pH range of 5.0-9.0 with an optimal activity at pH 5.0. The activities of both enzymes decreased dramatically when pH was below 5.0.

Effects of Metal Ions on the Heparosan Synthase Activity of KfiA and PmHS2. The effects of different metal ions, Mg$^{2+}$, Mn$^{2+}$, Ca$^{2+}$ and Cu$^{2+}$ on the heparosan synthase activity of KfiA and PmHS2 were investigated. Reaction without metal ions was used as a control. As shown in FIG. 28, no activity was detected without metals. Both enzymes showed best activities in the presence of Mn$^{2+}$. Increasing Mn$^{2+}$ from 1 mM to 20 mM increased the activity of both KfiA and PmHS2 first and then decreased the activity of both enzymes. Compared with Mn$^{2+}$, Mg$^{2+}$ and Ca$^{2+}$ showed much less efficiency for the activity of KfiA and PmHS2. No activity was shown in the presence of Cu$^{2+}$.

Figure 11:
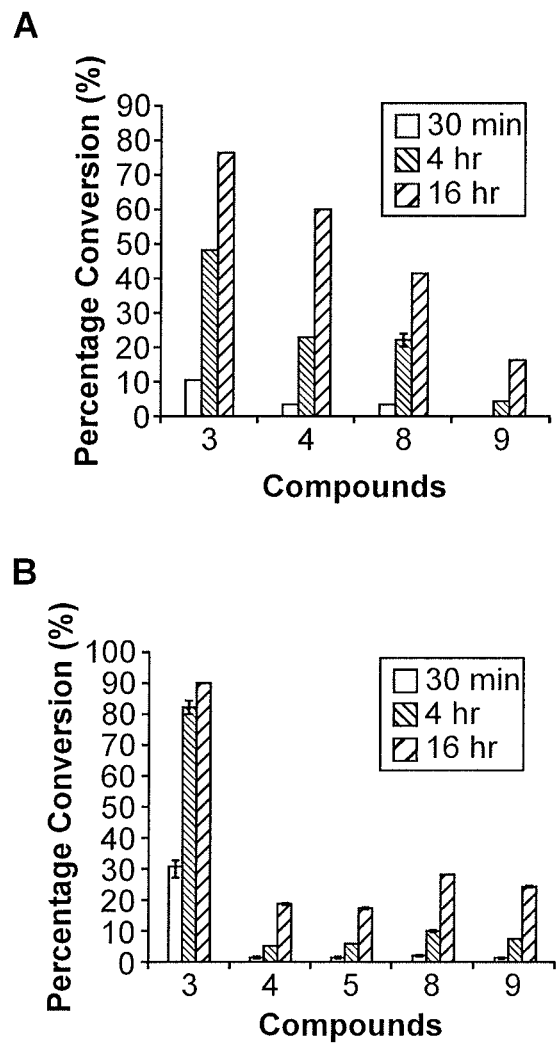
FIG. 11 shows the results of the substrate specificity assay for the heparosan synthase activity of KfiA (FIG. 11A) and PmHS2 (FIG. 11B). Each reaction was performed at 37° C. in MES buffer (100 mM, pH 6.5) for 30 min, 4 h or 16 h. Enzyme used: KfiA (1.08 μg/μL), PmHS2 (2.5×10$^{-2}$ μg/μL).
Figure 12:
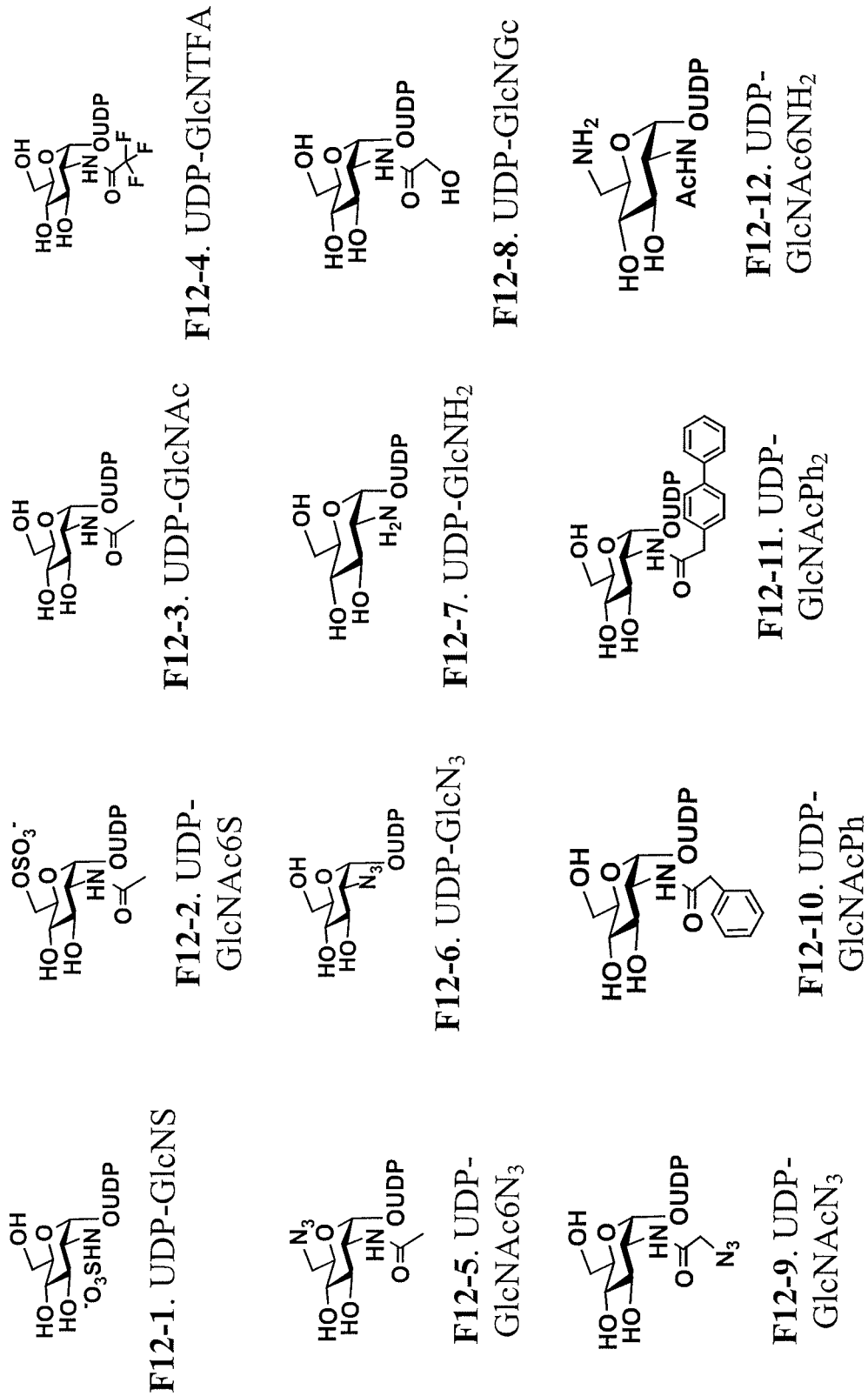
FIG. 12 shows the structures of the substrates tested in the substrate specificity assay for KfiA and PmHS2 in FIG. 11.
Figure 12:
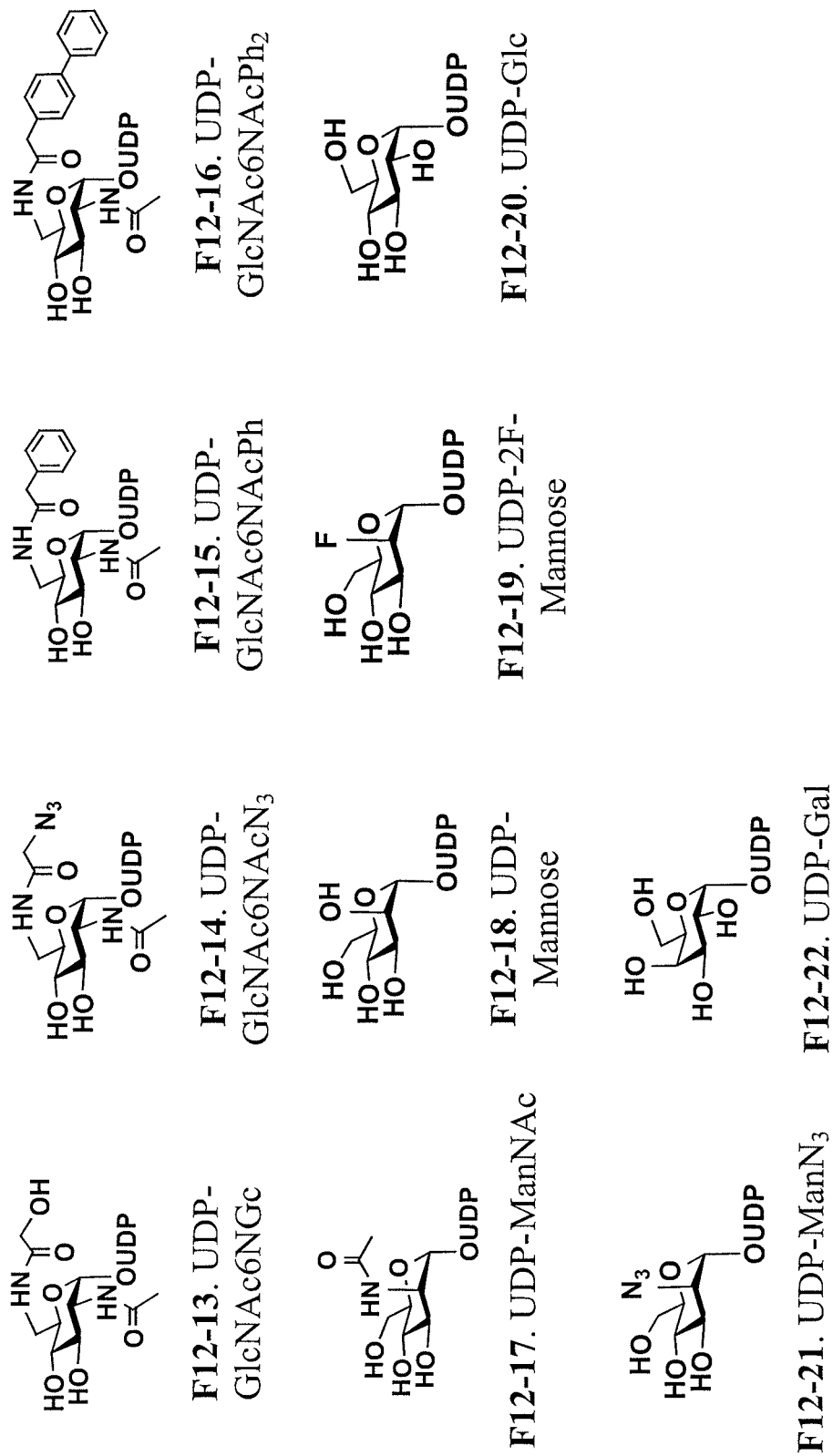

Substrate Specificity of KfiA and PmHS2. Using the HPLC method described above, the substrate specificities of KfiA and PmHS2 were examined using GlcAa2AA and twenty two compounds of UDP-GlcNAc or UDP-Mannose or their derivatives. Experimental data is shown in FIG. 11. Among the tested compounds (see FIG. 12), both enzymes exhibited quite narrow substrate specificities. However, the catalytic efficiency of PmHS2 was much high than that of KfiA. Both enzymes can use the UDP-GlcNAc (F12-3), UDP-GlcNTFA (F12-4), UDP-GlcNGc (F12-8), UDP-GlcNAcN$_3$ (F12-9), among which the UDP-GlcNAc (F12-3) is the best substrate for both enzymes. Besides these four compounds, UDP-GlcNAc6N$_3$ (F12-5) is a substrate for PmHS2 but not for KfiA.

Example 2

Preparation of UDP-GlcNAc and Derivatives

General Methods for Compound Purification and Characterization. Chemicals were purchased and used without further purification. $^1$H NMR and $^{13}$C NMR spectra were recorded on a 600 MHz NMR spectrometer. High resolution electrospray ionization (ESI) mass spectra were obtained at the Mass Spectrometry Facility in the University of California, Davis. Silica gel 60 Å (Sorbent Technologies) was used for flash column chromatography. Analytical thin-layer chromatography (Sorbent Technologies) was performed on silica gel plates using anisaldehyde sugar stain for detection. Gel filtration chromatography was performed with a column (100 cm×2.5 cm) packed with BioGel P-2 Fine resins. ATP, UTP, and GlcNAc were purchased from Sigma. GlcNTFA, GlcN$_3$, GlcNAc6N$_3$, GlcNAc6S, GlcNS were synthesized as described previously. NanK_ATCC55813 and PmPpA were overexpressed as discussed previously.

Synthesis of GlcNTFA6S T5b-6. GlcNTFA T5b-2 (300 mg, 1.09 mmol) was dissolved in 15 mL of anhydrous DMF. Anhydrous Et$_3$N (5 mL) and sulfur trioxide pyridine complex (1.2 eq.) were added at 0° C. After being stirred at room temperature for overnight, the reaction was stopped by adding MeOH and concentrated. The residue was purified by flash column chromatography (EtOAc:MeOH:H$_2$O=8:2:1, by volume) to afford 6-O-sulfo-GlcNTFA T5b-6 (243 mg, 63%). $^1$H NMR (600 MHz, D$_2$O) δ 5.25 (d, J=2.4 Hz, 0.6H), 4.84 (d, J=8.4 Hz, 0.4H), 4.26-3.51 (m, 6H). $^{13}$C NMR (150 MHz, D$_2$O) δ 159.75 (J=37.5 Hz), 159.69 (J=37.5 Hz), 117.01 (J=284.7 Hz), 116.93 (J=284.7 Hz), 94.46, 80.59, 74.03, 73.24, 70.21, 70.00, 69.84, 96.75, 67.22, 67.18, 57.34, 54.87.

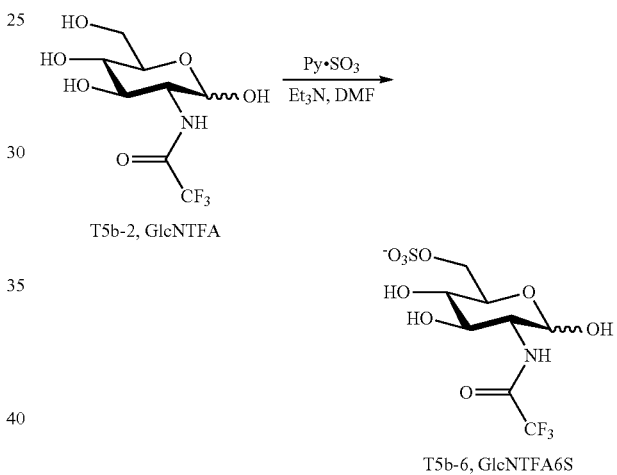

T5b-2, GlcNTFA

T5b-6, GlcNTFA6S

Synthesis of GlcN$_3$6S T5b-7. 6-O-Sulfo-GlcN$_3$ T5b-7 was synthesized from GlcN$_3$ T5b-3 (300 mg, 1.46 mmol) in 54% yield (224 mg) and the procedures were similarly as described above for GlcNTFA6S T5b-6. $^1$H NMR (600 MHz, D$_2$O) δ 5.35 (d, J=2.9 Hz, 0.4H), 4.71 (d, J=8.4 Hz, 0.6H), 4.21-3.82 (m, 3H), 3.65-3.28 (m, 3H). $^{13}$C NMR (150 MHz, D$_2$O) δ 95.31, 91.39, 74.32, 73.94, 71.55, 69.80, 69.61, 69.27, 67.15, 67.12, 66.85, 63.55.

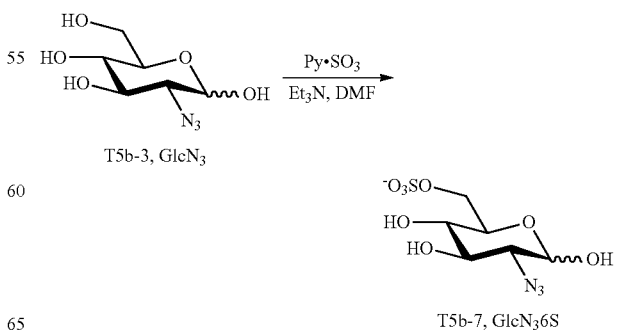

T5b-3, GlcN$_3$

T5b-7, GlcN$_3$6S

Figure 4:
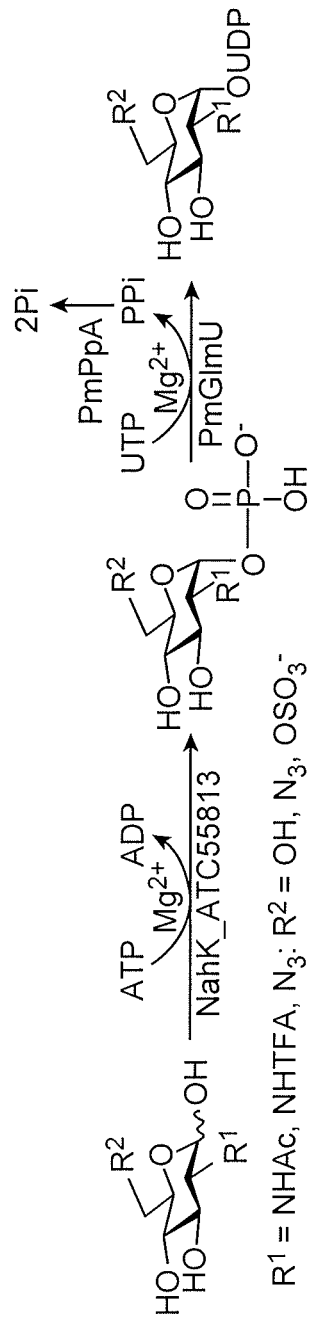
FIG. 4 shows the one-pot three-enzyme synthesis of UDP-GlcNAc and derivatives. Enzyme used: NahK_ATCC55813, an N-acetylhexosamine 1-kinase cloned from *Bifidobacterium longum* ATCC55813; PmGlmU, *Pasteurella multocida* N-acetylglucosamine-1-phosphate uridylyltransferase; PmPpA, *Pasteurella multocida* inorganic pyrophosphatase.

One-Pot Three-Enzyme Synthesis of UDP-Sugars T5b-9-T5b-13. This was carried out as shown in FIG. 4. Glucosamine derivatives T5b-1-T5b-5 (50 to 300 mg, 1.0 eq.), ATP (1.2 eq.), and UTP (1.2 eq.) were dissolved in water in a 50 mL centrifuge tube containing Tris-HCl buffer (100 mM, pH 8.0) and $MgCl_2$ (10 mM). After the addition of appropriate amount of NanK_ATCC55813 (3.2-4.8 mg), PmGlmU (5-7.5 mg), and PmPpA (2.5-5 mg), water was added to bring the volume of the reaction mixture to 20 mL. The reaction was carried out by incubating the solution in an isotherm incubator for 24 hr to 48 hr at 37° C. with gentle shaking. Product formation was monitored by TLC (EtOAc:MeOH:$H_2O$=3:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. Silica gel column purification (EtOAc:MeOH:$H_2O$=4:2:1) was applied when necessary to achieve further purification.

Figure 29:
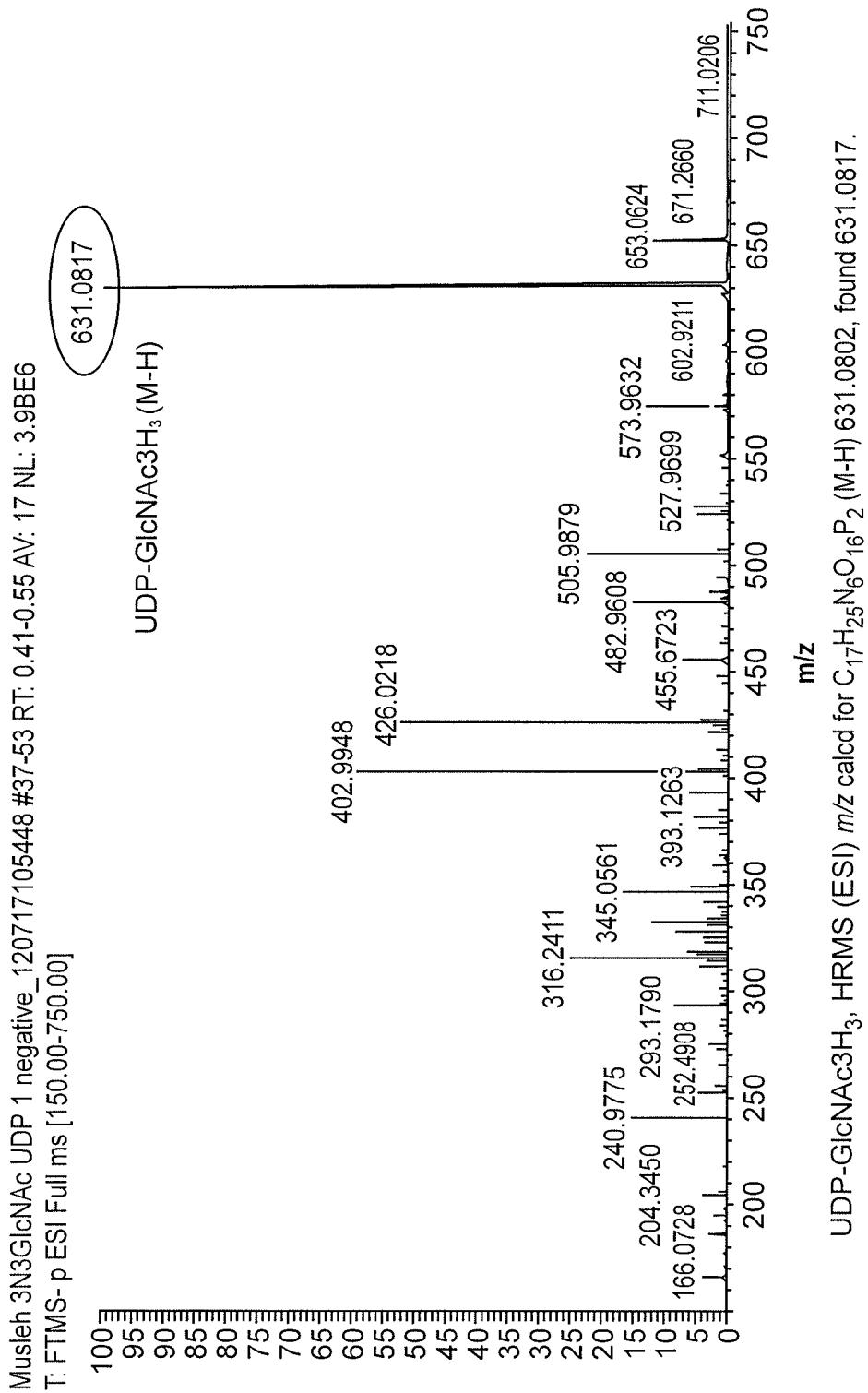
FIG. 29 shows high-resolution mass spectrometry (Orbitrap HRMS) assay for the synthesis of UDP-GlcNAc3N$_3$ from GlcNAc3N$_3$, ATP, and UTP using one-pot three-enzyme reactions containing NahK, PmGlmU, and PmPpA.

One-pot three-enzyme synthesis of UDP-GlcNAc3$N_3$ was also conducted using GlcNAc3$N_3$ as the staring sugar (See Table 5a) for reaction conditions). As shown in FIG. 29, the formation of UDP-GlcNAc3$N_3$ was confirmed by high-resolution mass spectrometry [HRMS (ESI) m/z calcd for $C_{17}H_{25}N_6O_{16}P_2$ (M–H) 631.0802, found 631.0817].

TABLE 5a

Reaction conditions for the synthesis of UDP-GlcNAc3$N_3$.

| | GlcNAc3$N_3$ (10 mM) |
|---|---|
| Tris-HCl (pH 7.5) | 100 mM |
| $MgCl_2$ | 10 mM |
| ATP | 20 mM |
| UTP | 20 mM |
| NahK_ATCC15697 | 17 µg |
| PmGlmU | 12.5 µg |
| PmPpA | 23 µg |
| Total volume | 20 µL |
| reaction time/Temp | 18 hr/37° C. |

Uridine 5'-diphospho-2-acetamido-2-deoxy-α-D-glucopyranoside (UDP-GlcNAc, T5b-9). Yield, 81% (445 mg); white foam. $^1$H NMR (600 MHz, $D_2O$) δ 7.97 (d, J=8.4 Hz, 1H), 5.97-6.00 (m, 2H), 5.53 (dd, J=6.6, 3.0 Hz, 1H), 4.37-4.40 (m, 2H), 4.21-4.31 (m, 3H), 3.81-3.75 (m, 5H), 3.58 (t, J=9.0 Hz, 1H), 2.09 (s, 3H). $^{13}$C NMR (150 MHz, $D_2O$) δ 174.94, 166.39, 151.99, 141.82, 102.85, 94.68, 88.72, 83.40 (d, J=8.7 Hz), 73.96, 73.20, 71.13, 69.83, 65.18, 65.15, 60.53, 53.88 (d, J=8.4 Hz), 22.29. HRMS (ESI) m/z calcd for $C_{17}H_{27}N_3O_{17}P_2$ (M+H) 608.0894, found 608.0906.

Uridine 5'-diphospho-2-deoxy-2-trifluoroacetamido-α-D-glucopyranoside (UDP-GlcNTFA, T5b-10). Yield, 97% (699 mg); white foam. $^1$H NMR (600 MHz, $D_2O$) δ 7.95 (d, J=7.8 Hz, 1H), 5.97-5.98 (m, 2H), 5.64 (dd, J=6.6, 3.0 Hz, 1H), 4.35-4.39 (m, 2H), 4.18-4.29 (m, 3H), 4.12 (d, J=10.8 Hz, 1H), 3.93-3.98 (m, 2H), 3.91 (dd, J=12.6, 1.8 Hz, 1H), 3.85 (dd, J=12.0, 4.2 Hz, 1H), 3.61 (t, J=9.0 Hz, 1H). $^{13}$C NMR (150 MHz, $D_2O$) δ 166.39, 159.73 (d, J=37.5 Hz), 151.94, 141.83, 116.88 (d, J=284.6 Hz), 102.79, 93.91, 88.79, 83.22 (d, J=9.0 Hz), 73.92, 73.23, 70.35, 69.76, 69.68, 65.12, 60.42, 54.53 (d, J=8.9 Hz). HRMS (ESI) m/z calcd for $C_{17}H_{24}F_3N_3O_{17}P_2$ (M+H) 662.0611, found 662.0615.

Uridine 5'-diphospho-2-azido-2-deoxy-α-D-glucopyranoside (UDP-GlcN$_3$, T5b-11). Yield, 54% (124 mg); white foam. $^1$H NMR (600 MHz, $D_2O$) δ 7.96 (d, J=8.4 Hz, 1H), 5.97-5.96 (m, 2H), 5.68 (dd, J=7.2, 3 Hz, 1H), 4.34-4.37 (m, 2H), 4.18-4.27 (m, 3H), 3.89-3.93 (m, 3H), 3.85 (dd, J=12.6, 2.4 Hz, 1H), 3.79 (dd, J=12.0, 4.2 Hz, 1H), 3.54 (t, J=9.6 Hz, 1H), 3.38 (d, J=10.2 Hz, 1H). $^{13}$C NMR (150 MHz, $D_2O$) δ 166.39, 151.96, 141.84, 102.79, 94.60, 88.64, 83.34 (d, J=9 Hz), 73.91, 73.07, 70.85, 69.77, 69.49, 65.07, 62.93 (d, J=8.6 Hz), 60.29. HRMS (ESI) m/z calcd for $C_{15}H_{23}N_5O_{16}P_2$ (M+H) 633.0959, found 633.0960.

Uridine 5'-diphospho-2-acetamido-6-azido-2,6-dideoxy-α-D-glucopyranoside (UDP-GlcNAc6$N_3$, T5b-12). Yield, 72% (462 mg); white foam. $^1$H NMR (600 MHz, $D_2O$) δ 7.93 (d, J=7.8 Hz, 1H), 5.96-5.94 (m, 2H), 5.15 (s, 1H), 4.32-4.36 (m, 2H), 4.17-4.24 (m, 3H), 4.00-4.04 (m, 2H), 3.79 (t, J=9.6 Hz, 1H), 3.72 (dd, J=13.2, 2.4 Hz, 1H), 3.55-3.62 (m, 2H), 2.06 (s, 3H). $^{13}$C NMR (150 MHz, $D_2O$) δ 174.86, 166.33, 151.86, 141.82, 102.76, 94.53, 88.92, 83.15 (d, J=8.9 Hz), 73.93, 71.85, 70.28, 70.28, 69.68, 65.16, 53.77 (d, J=7.4 Hz), 50.71, 22.22. HRMS (ESI) m/z calcd for $C_{17}H_{26}N_6O_{16}P_2$ (M+H) 592.0693, found 592.0698.

Uridine 5'-diphospho-2-acetamido-2-deoxy-6-O-sulfo-α-D-glucopyranoside (UDP-GlcNAc6S, T5b-13). Yield, 62% (70 mg); white foam. $^1$H NMR (600 MHz, $D_2O$) δ 7.96 (d, J=7.8 Hz, 1H), 5.97-5.99 (m, 2H), 5.55 (dd, J=7.2, 3.0 Hz, 1H), 4.35-4.38 (m, 3H), 4.26-4.30 (m, 3H), 4.18-4.22 (m, 1H), 4.12 (d, J=9.6 Hz, 1H), 4.04 (d, J=10.8 Hz, 1H), 3.84 (t, J=9.6 Hz, 1H), 3.68 (t, J=9.6 Hz, 1H), 2.09 (s, 3H). $^{13}$C NMR (150 MHz, $D_2O$) δ 174.84, 166.40, 151.93, 141.73, 102.76, 94.57, 88.72, 83.15 (d, J=9.3 Hz), 73.89, 70.83, 69.70, 69.04, 66.56, 65.16, 65.13, 53.67 (d, J=8.1 Hz), 22.17. HRMS (ESI) m/z calcd for $C_{17}H_{27}N_3O_{20}P_2S$ (M+H) 688.0462, found 688.0471.

Chemical Derivatization of UDP-Sugars F5-2F5-8, and F5-10F5-15.

Uridine 5'-diphospho-2-amino-2-deoxy-α-D-glucopyranoside (UDP-GlcN$H_2$, F5-2). UDP-GlcNTFA F5-1 (150 mg, 0.22 mmol) was dissolved in 25 mL of methanol and 5 mL of $H_2O$. The pH of the solution was adjusted to 9.5 by adding $K_2CO_3$. After being vigorously stirred at r.t. for overnight, the reaction mixture was neutralized with DOWEX HCR-W2 ($H^+$) resin, filtered and concentrated. The residue was purified by flash column chromatography (EtOAc:MeOH:$H_2O$=1:1:1, by volume) to afford UDP-GlcN$H_2$ F5-2 as white solid in 98% yield (122 mg). $^1$H NMR (600 MHz, $D_2O$) δ 7.90 (d, J=7.8 Hz, 1H), 5.89-5.92 (m, 2H), 5.79 (dd, J=6.0, 3.0 Hz, 1H), 4.30-4.32 (m, 2H), 4.16-4.24 (m, 3H), 3.86-3.90 (m 2H), 3.81 (dd, J=12.6, 1.8 Hz, 1H), 3.77 (dd, J=12.6, 4.2 Hz, 1H), 3.52 (t, J=9.6 Hz, 1H), 3.33 (d, J=10.8 Hz, 1H). $^{13}$C NMR (150 MHz, $D_2O$) δ 166.40, 151.93, 141.75, 102.71, 92.87, 88.74, 83.21 (d, J=9 Hz), 73.91, 73.39, 69.85, 69.69, 69.16, 65.23, 60.09, 54.27 (d, J=8.4 Hz). HRMS (ESI) m/z calcd for $C_{15}H_{25}N_3O_{16}P_2$ (M+H) 566.0788, found 566.0791.

Uridine 5'-diphospho-2-sulfoamino-2-deoxy-α-D-glucopyranoside (UDP-GlcNS, F5-3). UDP-GlcN$H_2$ F5-2 (50 mg, 0.082 mmol) was dissolved in 30 mL of water. The pH of the solution was adjusted to 9.5 by adding 2 N NaOH (aq). Sulfur trioxide-pyridine complex (65 mg, 0.41 mmol) was added in three equal portions during 35 minutes intervals at room temperature, and the pH was maintained at 9.5 throughout the whole process using 2 N NaOH (aq). After being stirred at r.t. for overnight, the reaction mixture was neutralized with DOWEX HCR-W2 ($H^+$) resin, filtered, concentrated, and purified using silica gel column (EtOAc:MeOH:$H_2O$=3:2:1, by volume) to obtain the UDP-GlcNS F5-3 in 86% yield (46 mg). $^1$H NMR (600 MHz, $D_2O$) δ 7.90 (d, J=7.8 Hz, 1H), 5.92-5.93 (m, 2H), 5.71 (s, 1H), 4.31-4.33 (m, 2H), 4.16-4.23 (m, 3H), 3.73-3.86 (m, 3H), 3.66 (t, J=9.6 Hz, 1H), 3.51 (t, J=9.6 Hz, 1H), 3.24 (d, J=9.6 Hz, 1H). $^{13}$C NMR (150 MHz, $D_2O$) δ 166.49, 152.13, 141.99, 103.04, 95.50, 88.86, 83.53 (J=8.9 Hz), 74.02, 73.06, 71.73, 69.98, 69.96, 65.38, 60.73, 58.11 (J=9.2 Hz). HRMS (ESI) m/z calcd for $C_{15}H_{25}N_3O_{19}P_2S$ (M+H) 646.0356, found 646.0373.

Uridine 5'-diphospho-2-hydroxyacetamido-2-deoxy-α-D-glucopyranoside (UDP-GlcNGc, F5-5). To a solution of UDP-GlcN$H_2$ F5-2 (30 mg, 0.049 mmol) in $CH_3CN$—$H_2O$ (30 mL, 1:1, v/v) in the presence of $NaHCO_3$ (40 mg, 0.49 mmol), the Acetoxyacetyl chloride (6.9 µL, 0.098 mmol) in $CH_3CN$ (5 mL) was added. The reaction mixture was stirred for 4 hours at 0° C. and was neutralized with DOWEX HCR- W2 (Fr) resin, filtered, and concentrated. The residue was purified by flash column chromatography (EtOAc:MeOH:H$_2$O=5:2:1, by volume) to afford UDP-GlcNGcAc F5-4 in 95% yield (31 mg). $^1$H NMR (600 MHz, D$_2$O) δ 7.99 (d, J=7.8 Hz, 1H), 6.03-6.04 (m, 2H), 5.62 (dd, J=6.6, 3.6 Hz, 1H), 4.41-4.45 (m, 2H), 4.24-4.35 (m, 3H), 4.13 (d, J=10.2 Hz, 1H), 4.01 (d, J=7.8 Hz, 1H), 3.86-3.96 (m, 3H), 3.63 (t, J=9.6 Hz, 1H), 2.25 (s, 3H). UDP-GlcNGcAc F5-4 was dissolved in dry methanol (50 mL) containing analytic amount of sodium methoxide. The resulted mixture was stirred at r.t. for overnight. The reaction mixture was then neutralized with DOWEX HCR-W2 (H$^+$) resin, filtered, and concentration to give product UDP-GlcNGc F5-5 in 98% yield (28 mg). $^1$H NMR (600 MHz, D$_2$O) δ 7.92 (d, J=7.8 Hz, 1H), 5.93-5.95 (m, 2H), 5.52 (dd, J=7.2, 3.0 Hz, 1H), 4.31-4.35 (m, 2H), 4.09-4.25 (m, 5H), 4.02 (d, J=10.2 Hz, 1H), 3.83-3.91 (m, 3H), 3.79 (dd, J=12.6, 4.2 Hz, 1H), 3.55 (t, J=9.6 Hz, 1H). $^{13}$C NMR (150 MHz, D$_2$O) δ 175.47, 166.37, 151.92, 141.74, 101.73, 94.36, 88.53, 83.28 (d, J=8.4 Hz), 73.86, 73.09, 70.69, 69.71, 69.54, 65.05, 61.11, 60.36, 53.68, 53.46 (d, J=7.7 Hz). HRMS (ESI) m/z calcd for C$_{17}$H$_{27}$N$_3$O$_{18}$P$_2$ (M+H) 624.0843, found 624.0847.

Uridine 5'-diphospho-2-azidoxyacetamido-2-deoxy-α-D-glucopyranoside (UDP-GlcNAz, F5-6). Sodium azide (62 mg, 0.98 mmol) was dissolved in 5 mL of distilled H$_2$O and the mixture was cooled to 0° C. Bromoacetic acid (68 mg, 0.49 mmol) was then added over 10 min and the reaction was allowed to slowly warm up to r.t. for overnight. The reaction was acidified to pH 1.0 and extracted three times with 5 mL of diethyl ether. The organic portions were combined, dried over MgSO$_4$ and concentrated. The crude mixture was dissolved in 10 mL of CH$_2$Cl$_2$ and two drops of DMF and cooled to 0° C. Oxalyl chloride (54 μL, 0.64 mmol) was slowly added over 15 min using a syringe. The reaction was allowed to warm up to r.t. for overnight. The solvent was removed under reduced pressure to afford the crude oil azidoacetyl chloride. To a solution of UDP-GlcNH$_2$ F5-2 (30 mg, 0.049 mmol) in CH$_3$CN—H$_2$O (30 mL, 1:1, v/v) in the presence of NaHCO$_3$ (40 mg, 0.49 mmol), the azidoacetyl chloride in CH$_3$CN (5 mL) was added. The reaction mixture was stirred for 4 hours at 0° C. and was neutralized with DOWEX HCR-W2 (H$^+$) resin, filtered, and concentrated. The residue was purified by flash column chromatography (EtOAc:MeOH:H$_2$O=5:2:1, by volume) to afford UDP-GlcNAz F5-6 in 68% yield (22 mg). $^1$H NMR (600 MHz, D$_2$O) δ 7.92 (d, J=8.4 Hz, 1H), 5.91-5.94 (m, 2H), 5.49 (dd, J=7.2, 3.6 Hz, 1H), 4.30-4.36 (m, 2H), 4.00-4.24 (m, 6H), 3.75-3.89 (m, 4H), 3.53 (t, J=9.6 Hz, 1H). $^{13}$C NMR (150 MHz, D$_2$O) δ 171.13, 166.41, 151.98, 141.86, 102.84, 94.59, 88.80, 83.34 (d, J=9.0 Hz), 73.94, 73.25, 71.02, 69.81, 69.66, 65.24, 60.51, 53.94 (d, J=9.0 Hz), 52.69, 51.80. HRMS (ESI) m/z calcd for C$_{17}$H$_{26}$N$_6$O$_{17}$P$_2$ (M+H) 649.0908, found 649.0917.

Uridine 5'-diphospho-2-phenylacetamido-2-deoxy-α-D-glucopyranoside (UDP-GlcNAcPh, F5-7). 2-Phenylacetyl acid (33 mg, 0.25 mmol) was dissolved in 10 mL of CH$_2$Cl$_2$ and two drops of DMF. The mixture was cooled to 0° C. Oxalyl chloride (28 μL, 0.33 mmol) was slowly added over 15 min using a syringe. The reaction was allowed to warm up to r.t. for overnight. The solvent was then removed under reduced pressure to afford 2-phenylacetyl chloride as a light pink solid. To a solution of UDP-GlcNH$_2$ F5-2 (30 mg, 0.049 mmol) in CH$_3$CN—H$_2$O (30 mL, 1:1, v/v) in the presence of NaHCO$_3$ (40 mg, 0.49 mmol), the 2-phenylacetyl chloride in CH$_3$CN (5 mL) was added. The reaction mixture was stirred for 4 hours at 0° C. and was neutralized with DOWEX HCR-W2 (H$^+$) resin, filtered, and concentrated. The residue was purified by flash column chromatography (EtOAc:MeOH:H$_2$O=6:2:1, by volume) to afford white solid UDP-GlcNAcPh F5-7 in 79% yield (26 mg). $^1$H NMR (600 MHz, D$_2$O) δ 7.83 (d, J=8.4 Hz, 1H), 7.32-7.35 (m, 2H), 7.26-7.29 (m, 3H), 5.90 (d, J=3.6 Hz, 1H), 5.83 (d, J=7.8 Hz, 1H), 5.54 (dd, J=6.6, 3.0 Hz, 1H), 4.16-4.30 (m, 5H), 3.77-4.00 (m, 5H), 3.67 (s, 2H), 3.54 (t, J=9.6 Hz, 1H). $^{13}$C NMR (150 MHz, D$_2$O) δ 175.33, 166.16, 151.75, 141.64, 135.13, 129.36, 128.90, 127.26, 102.74, 94.77, 88.80, 83.08 (d, J=9 Hz), 73.80, 73.25, 70.97, 69.74, 69.65, 65.07, 60.50, 53.89 (d, J=8.7 Hz), 42.21. HRMS (ESI) m/z calcd for C$_{23}$H$_{31}$N$_3$O$_{17}$P$_2$ (M+H) 684.1207, found 684.1215.

Uridine 5'-diphospho-2-(1,1'-biphenyl-4-yl)acetamido-2-deoxy-α-D-glucopyranoside (UDP-GlcNAcPh$_2$, F5-8). UDP-GlcNAcPh$_2$ F5-8 was synthesized from UDP-GlcNH$_2$ F5-2 using a similar procedure as described above for UDP-GlcNAcPh F5-7 g except that the reagent 2-phenylacetyl acid was replaced by 2-([1,1'-biphenyl]-4-yl)acetic acid. UDP-GlcNAcPh$_2$ F5-8 was obtained as a white solid in 82% yield (31 mg). $^1$H NMR (600 MHz, D$_2$O) δ 7.69 (d, J=8.4 Hz, 1H), 7.64 (d, J=8.4 Hz, 2H), 7.59 (d, J=7.2 Hz, 2H), 7.45-7.47 (m, 2H), 7.34-7.41 (m, 3H), 5.79 (d, J=4.2 Hz, 1H), 5.64 (d, J=7.2 Hz, 1H), 5.53 (dd, J=6.6, 3.0 Hz, 1H) 4.14-4.19 (m, 5H), 4.01 (d, J=10.2 Hz, 1H), 3.92 (d, J=9.6 Hz, 1H), 3.65-3.85 (m, 5H), 3.53 (t, J=9.0 Hz, 1H). $^{13}$C NMR (150 MHz, D$_2$O) δ 175.19, 165.92, 151.44, 141.31, 140.08, 139.12, 134.51, 129.30, 129.16, 127.75, 127.14, 126.80, 102.49, 94.76, 88.77, 82.87 (d, J=8.6 Hz), 73.82, 73.22, 71.01, 69.70, 69.44, 64.89, 60.46, 53.88 (d, J=8.4 Hz), 41.80. HRMS (ESI) m/z calcd for C$_{29}$H$_{35}$N$_3$O$_{17}$P$_2$(M+H) 760.1520, found 760.1534.

Uridine 5'-diphospho-2-acetamido-6-amino-2,6-dideoxy-α-D-glucopyranoside (UDP-GlcNAc6NH$_2$, F5-10). UDP-GlcNAc6N$_3$ (T5b-12 or F5-9) (100 mg, 0.16 mmol) was dissolved in MeOH—H$_2$O (10 mL, 1:1, v/v) and 20 mg of Pd/C was added. The mixture was shaken under H$_2$ gas (4 Bar) for 1 hr, filtered, and concentrated. The residue was purified by flash column chromatography (EtOAc:MeOH:H$_2$O=3:2:1, by volume) to afford UDP-GlcNAc6NH$_2$ F5-10 in 96% yield (93 mg). $^1$H NMR (600 MHz, D$_2$O) δ 7.90 (d, J=8.4 Hz, 1H), 5.89-5.93 (m, 2H), 5.48 (dd, J=6.6, 3.0 Hz, 1H), 4.30-4.32 (m, 2H), 4.20-4.23 (m, 2H), 4.08-4.15 (m, 2H), 3.99 (d, J=10.8 Hz, 1H), 3.77 (t, J=9.6 Hz, 1H), 3.45 (d, J=13.2 Hz, 1H), 3.40 (t, J=9.6 Hz, 1H), 3.11 (t, J=12.6 Hz, 1H), 2.02 (s, 3H). $^{13}$C NMR (150 MHz, D$_2$O) δ 174.94, 166.39, 151.96, 141.84, 102.79, 94.33, 88.82, 83.29 (J=9.0 Hz), 73.92, 71.82, 69.80, 69.28, 65.30, 53.64 (J=8.9 Hz), 40.70, 22.21. HRMS (ESI) m/z calcd for C$_{17}$H$_{28}$N$_4$O$_{16}$P$_2$ (M+H)$^-$ 607.1054, found 607.1068.

Uridine 5'-diphospho-2-acetamido-6-hydroxyacetamido-2,6-dideoxy-α-D-glucopyranoside (UDP-GlcNAc6NGc, F5-12). UDP-GlcNAc6NGcAc F5-11 was synthesized from UDP-GlcNAc6NH$_2$ F5-10 using the same process as described above for UDP-GlcNAcNGcAc F5-4. UDP-GlcNAc6NGcAc F5-11 was obtained as a white solid in 91% yield (31 mg). $^1$H NMR (600 MHz, D$_2$O) δ 7.91 (d, J=7.8 Hz, 1H), 5.91-5.93 (m, 2H), 5.46 (dd, J=6.6, 3.0 Hz, 1H), 4.62 (s, 2H), 4.30-4.34 (m, 2H), 4.14-4.24 (m, 3H), 3.95 (m, 2H), 3.76 (t, J=9.0 Hz, 1H), 3.61 (dd, J=14.4, 6.0 Hz, 1H), 3.54 (dd, J=14.4, 2.4 Hz, 1H), 3.35 (dd, J=14.4, 4.2 Hz, 1H), 2.15 (s, 3H), 2.03 (s, 3H). $^{13}$C NMR (150 MHz, D$_2$O) δ 174.85, 173.43, 170.60, 166.44, 151.95, 141.74, 102.70, 94.40, 88.70, 83.16, 73.87, 71.33, 70.89, 70.68, 69.66, 65.05, 62.88, 53.67, 39.59, 22.14, 20.13. UDP-GlcNAc6NGc F5-12 was synthesized from UDP-GlcNAc6NGcAc F5-11 using the same process as described above for UDP-GlcNGc F5-5 and obtained as a white solid in 98% yield (29 mg). $^1$H NMR (600 MHz, D$_2$O) δ 8.09 (d, J=7.8 Hz, 1H), 6.11-6.13 (m, 2H), 5.66 (dd, J=6.6, 3.0 Hz, 1H), 4.50-4.53 (m, 2H), 4.33-4.43 (m, 3H), 4.26 (s, 2H), 4.14-4.16 (m, 2H), 3.95 (t, J=9.9 Hz, 1H), 3.82 (d, J=14.4 Hz, 1H), 3.73 (dd, J=13.8, 6 Hz, 1H), 3.56 (t, J=10.2 Hz, 1H), 2.22 (s, 3H). $^{13}$C NMR (150 MHz, D$_2$O) δ 175.55, 175.05, 166.60, 152.20, 141.97, 102.99, 94.62, 88.99, 83.50 (d, J=8.9 Hz), 74.06, 71.47, 71.06, 69.97, 65.33, 61.35, 53.98 (d, J=8.4 Hz), 39.76, 22.42. HRMS (ESI) m/z calcd for C$_{19}$H$_{30}$N$_4$O$_{18}$P$_2$(M+H) 665.1109, found 665.1113.

Uridine 5'-diphospho-2-acetamido-6-azidoacetamido-2,6-dideoxy-α-D-glucopyranoside (UDP-GlcNAc6NAcN$_3$, F5-13). UDP-GlcNAc6NAcN$_3$(F5-13) was synthesized from UDP-GlcNAc6NH$_2$ (F5-10) using the same process as described above for UDP-GlcNAcN$_3$ (F5-6). UDP-GlcNAc6NAcN$_3$ (F5-13) was obtained as a white solid in 61% yield (21 mg). $^1$H NMR (600 MHz, D$_2$O) δ 7.89 (d, J=7.8 Hz, 1H), 5.91 (m, 2H), 5.43 (dd, J=6.6, 3.0 Hz, 1H), 4.32-4.29 (m, 2H), 4.19-4.22 (m, 3H), 4.00 (s, 2H), 3.92-3.95 (m, 2H), 3.74 (t, J=10.2 Hz, 1H), 3.54 (s, 1H), 3.34 (t, J=9.6 Hz, 1H), 2.01 (s, 3H). $^{13}$C NMR (150 MHz, D$_2$O) δ 174.85, 170.93, 166.40, 151.92, 141.75, 104.99, 102.71, 94.42, 88.71, 83.16 (J=8.9 Hz), 73.87, 71.27, 71.01, 70.71, 69.67, 65.10, 53.72 (J=8.1 Hz), 51.80, 39.92, 22.14. HRMS (ESI) m/z calcd for C$_{19}$H$_{29}$N$_7$O$_{17}$P$_2$ (M+H) 690.1173, found 690.1180.

Uridine 5'-diphospho-2-acetamido-6-phenylacetamido-2,6-dideoxy-α-D-glucopyranoside (UDP-GlcNAc6NAcPh, F5-14). UDP-GlcNAc6NAcPh F5-14 was synthesized from UDP-GlcNAc6NH$_2$ F5-10 using the same way as described above for UDP-GlcNAcPh (F5-7). UDP-GlcNAc6NAcPh (F5-14) was obtained as a white solid in 86% yield (30 mg). $^1$H NMR (600 MHz, D$_2$O) δ 7.87 (d, J=8.4 Hz, 1H), 7.36-7.38 (m, 2H), 7.29-7.32 (m, 3H), 5.87-5.89 (m, 2H), 5.48 (dd, J=6.6, 2.4 Hz, 1H), 4.16-4.29 (m, 5H), 3.92-3.98 (m, 2H), 3.78 (t, J=9.6 Hz, 1H), 3.53-3.65 (m, 4H), 3.30 (t, J=9.6 Hz, 1H), 2.05 (s, 3H). $^{13}$C NMR (150 MHz, D$_2$O) δ 175.37, 174.89, 166.26, 151.75, 141.64, 135.34, 129.22, 129.05, 127.38, 102.66, 94.50, 88.93, 83.12 (J=8.6 Hz), 73.94, 71.48, 71.06, 70.60, 69.51, 64.99, 53.79 (J=8.3 Hz), 42.43, 40.01, 22.19. HRMS (ESI) m/z calcd for C$_{25}$H$_{34}$N$_4$O$_{17}$P$_2$(M+H) 725.1473, found 725.1484.

Uridine 5'-diphospho-2-acetamido-6-(1,1'-biphenyl-4-yl)-acetamido-2,6-dideoxy-α-D-glucopyranoside (UDP-GlcNAc6NAcPh$_2$, F5-15). UDP-GlcNAc6NAcPh$_2$ (F5-15) was synthesized from UDP-GlcNAc6NH$_2$ using the same way as described above for UDP-GlcNAcPh$_2$ (F5-8). UDP-GlcNAc6NAcPh$_2$ (F5-15) was obtained as a white solid in 88% yield (35 mg). $^1$H NMR (600 MHz, D$_2$O) δ 7.75 (d, J=7.8 Hz, 1H), 7.63 (d, J=7.2 Hz, 2H), 7.60 (d, J=7.2 Hz, 2H), 7.44-7.45 (m, 2H), 7.34-7.45 (m, 3H), 5.77-5.80 (m, 2H), 5.44 (dd, J=7.2, 3.6 Hz, 1H), 4.03-4.18 (m, 5H), 3.89-3.96 (m, 2H), 3.75 (t, J=9.6 Hz, 1H), 3.49-3.63 (m, 4H), 3.28 (t, J=9.0 Hz, 1H), 2.01 (s, 3H). $^{13}$C NMR (150 MHz, D$_2$O) δ 175.17, 174.79, 166.28, 151.63, 141.34, 140.12, 139.31, 134.70, 129.74, 129.18, 127.75, 127.30, 126.88, 102.44, 94.39, 88.87, 82.62 (d, J=8.7 Hz), 73.93, 71.18, 70.54, 69.27, 64.80, 53.77 (d, J=8.4 Hz), 42.03, 40.16, 22.09. HRMS (ESI) m/z calcd for C$_{31}$H$_{38}$N$_4$O$_{17}$P$_2$ (M+H) 801.1785, found 801.1807.

Results and Discussion

As shown in FIG. 4, three enzymes were used in one-pot to synthesize UDP-GlcNAc and derivatives. The first enzyme was an N-acetylhexosamine 1-kinase cloned from *Bifidobacterium longum* strain ATCC55813 (NahK_ATCC55813) which showed promiscuous substrate specificity and were able to use N-sulfated, 3-O-sulfated, or 6-O-sulfated GlcNAc and derivatives as substrates for the formation of GlcNAcα1-phosphate derivatives. The second enzyme was an N-acetylglucosamine-1-phosphate uridylyltransferase that we cloned from *Pasteurella multocida* strain P-1059 (ATCC15742) (PmGlmU). It catalyzes the reversible formation of UDP-GlcNAc and pyrophosphate from UTP and GlcNAcα1-phosphate with tolerance on some substrate modifications. The third enzyme was an inorganic pyrophosphatase also cloned from *Pasteurella multocida* strain P-1059 (PmPpA) for hydrolyzing the pyrophosphate by-product formed to drive the reaction towards the formation of UDP-GlcNAc and derivatives. A recombinant NahK cloned from another strain of *Bifidobacterium longum* (NahK_JCM1217) was used in the synthesis of GlcNAc-1-phosphate, GalNAc-1-phosphate, and their derivatives. The purified HexNAc-1-phosphates were then used in a one-pot two-enzyme system containing a commercially available inorganic pyrophosphatase (PpA) and a GlmU cloned from *E. coli* (EcGlmU) or an AGX1 cloned from human for the synthesis of UDP-GlcNAc, dNDP-GlcNAc, dNDP-Glc, UDP-GalNAc, and derivatives. Nevertheless, chemoenzymatic synthesis of UDP-GlcNAc derivatives using all three enzymes in one-pot has not been reported. In addition, UDP-GlcNAc derivatives containing N-sulfated glucosamine or O-sulfated GlcNAc have not been synthesized using the combination of these three enzymes.

As shown in Table 5b, the one-pot three-enzyme system (FIG. 4) was quite efficient in synthesizing UDP-GlcNAc (T5b-9, 81%), its C-2 derivatives such as UDP-N-trifluoroacetylglucosamine (UDP-GlcNTFA, T5b-10, 97%) and UDP-2-azido-2-deoxy-glucose (UDP-GlcN$_3$, T5b-11, 54%), as well as its C-6 derivatives including UDP-N-acetyl-6-azido-6-deoxy-glucosamine (UDP-GlcNAc6N$_3$, T5b-12, 72%) and UDP-N-acetyl-6-O-sulfo-glucosamine (UDP-GlcNAc6S, T5b-13, 62%) from GlcNAc (T5b-1) and derivatives (T5b-2-T5b-5). An interesting observation was that the yield of the one-pot three-enzyme reaction was improved from 81% to 97% when the N-acetyl group of GlcNAc was substituted by an N-trifluoroacetyl group in GlcNTFA (T5b-2). However, while 6-O-sulfated GlcNAc (GlcNAc6S, T5b-5) was used as a substrate to produce UDP-GlcNAc6S (T5b-13) in 62% yield, the synthesis of its N-trifluoroacetyl analogue UDP-6-O-sulfo-GlcNTFA (UDP-GlcNTFA6S, T5b-14) from 6-O-sulfo-GlcNTFA (GlcNTFA6S, T5b-6) was not successful. In addition, although both 2-azido-2-deoxy-glucose (T5b-3) and 6-O-sulfo-GlcNAc (T5b-5) could be used for the synthesis of the corresponding UDP-GlcNAc derivatives UDP-GlcN$_3$ T5b-11 and UDP-GlcNAc6S T5b-13 in 54% and 62% yields, respectively, the synthesis of UDP-2-azido-2-deoxy-6-O-sulfo-glucose (UDP-GlcN$_3$6S, T5b15) from GlcN$_3$6S (T5b-7) with the combined modifications at C-2 and C-6 was not successful. Furthermore, the one-pot three-enzyme synthesis of UDP-N-sulfo-glucosamine (UDP-GlcNS, T5b-16) from N-sulfo-glucosamine (GlcNS, T5b-8) was not achieved. As compounds T5b-3-T5b-8 have all been shown to be weak substrates for NahK_ATCC55813, the successful synthesis of compounds T5b-11-T5b-13 and the unsuccessful synthesis of compounds T5b-14-T5b-16 by the one-pot three-enzyme system indicate that the substrate specificity of PmGlmU is most likely the limiting factor.

TABLE 5b

Synthesis of UDP-GlcNAc and its derivatives using the one-pot three-enzyme system shown in Figure 4. ND, not detected.

| Substrates | Products | Yields (%) |
|---|---|---|
| T5b-1 GlcNAc | T5b-9 UDP-GlcNAc | 81 |

TABLE 5b-continued

Synthesis of UDP-GlcNAc and its derivatives using the one-pot three-enzyme system shown in Figure 4. ND, not detected.

| Substrates | Products | Yields (%) |
|---|---|---|
| T5b-2 GlcNTFA | T5b-10 UDP-GlcNTFA | 97 |
| T5b-3 GlcN$_3$ | T5b-11 UDP-GlcN$_3$ | 54 |
| T5b-4 GlcNAc6N$_3$ | T5b-12 UDP-GlcNAc6N$_3$ | 72 |
| T5b-5 GlcNAc6S | T5b-13 UDP-GlcNAc6S | 62 |
| T5b-6 GlcNTFA6S | T5b-14 UDP-GlcNTFA6S | ND |
| T5b-7 GlcN$_3$6S | T5b-15 UDP-GlcN$_3$6S | ND |
| T5b-8 GlcNS | T5b-16 UDP-GlcNS | ND |

Taking advantage of the substrate promiscuity of Nah-K_ATCC55813 and PmGlmU, UDP-GlcNAc and a number of its natural and non-natural derivatives were synthesized efficiently by the one-pot three-enzyme system illustrated in Scheme 1. However, the success of the approach relied on the substrate promiscuity of all enzymes used. In order to increase the size of the library of UDP-GlcNAc derivatives with various modifications that can be used to test the activity of diverse GlcNAc-transferases, we further carried out chemical diversification of chemoenzymatically-produced UDP-GlcNAc derivatives.

Figure 5:
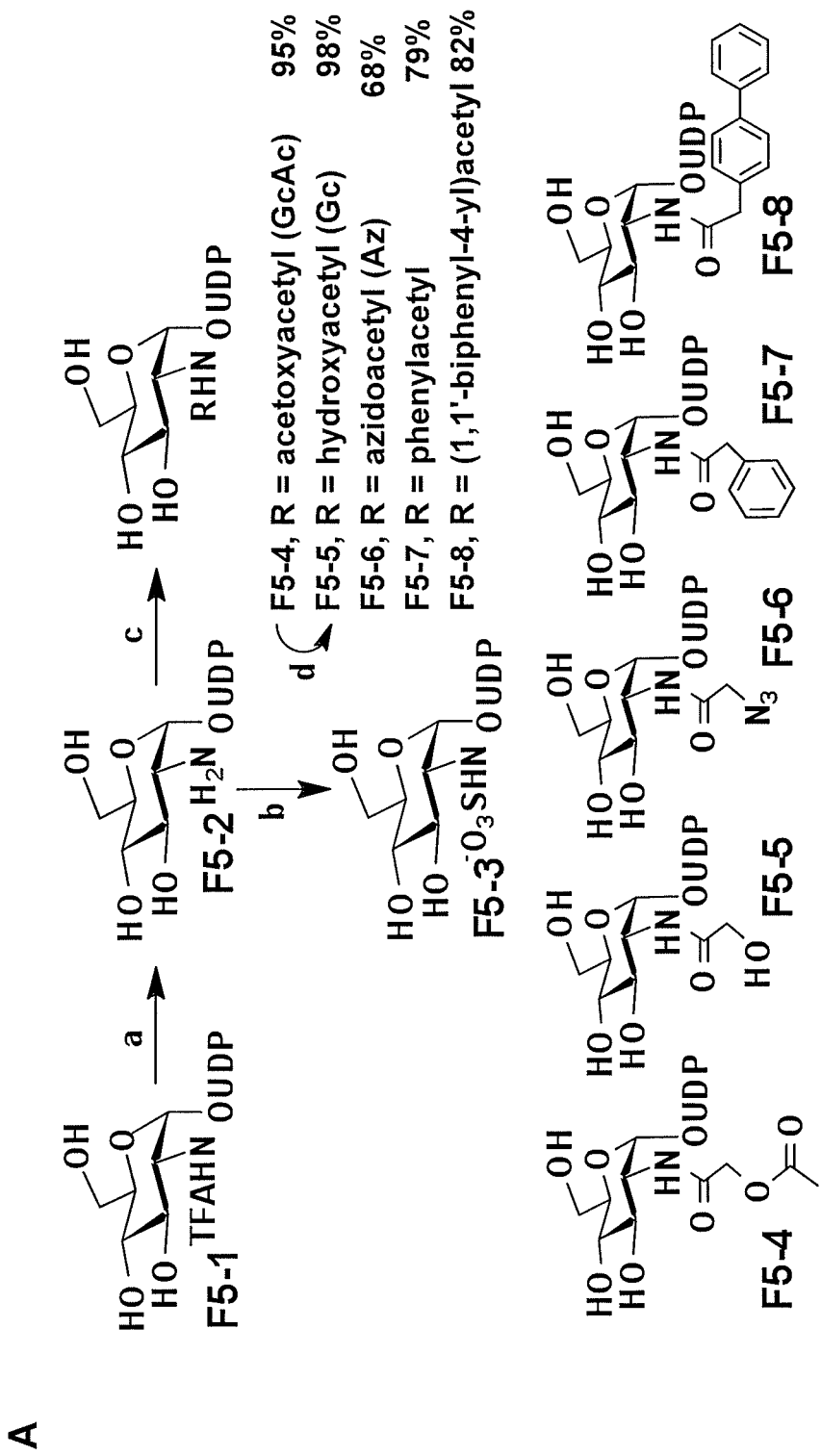
FIG. 5 shows the chemical diversification at (A) the C-2 of glucosamine and (B) the C-6 of N-acetylglucosamine in UDP-sugar nucleotides. Reagents and conditions: a) K$_2$CO$_3$, CH$_3$OH, H$_2$O, 20° C., overnight, 98%; b) Py.SO$_3$, 2 M NaOH, H$_2$O, overnight, 86%; c) RCOCl, NaHCO$_3$, CH$_3$CN, H$_2$O; d) NaOMe, MeOH; e) H$_2$, Pd/C, MeOH, H$_2$O, 1 h, 96%.
Figure 5:
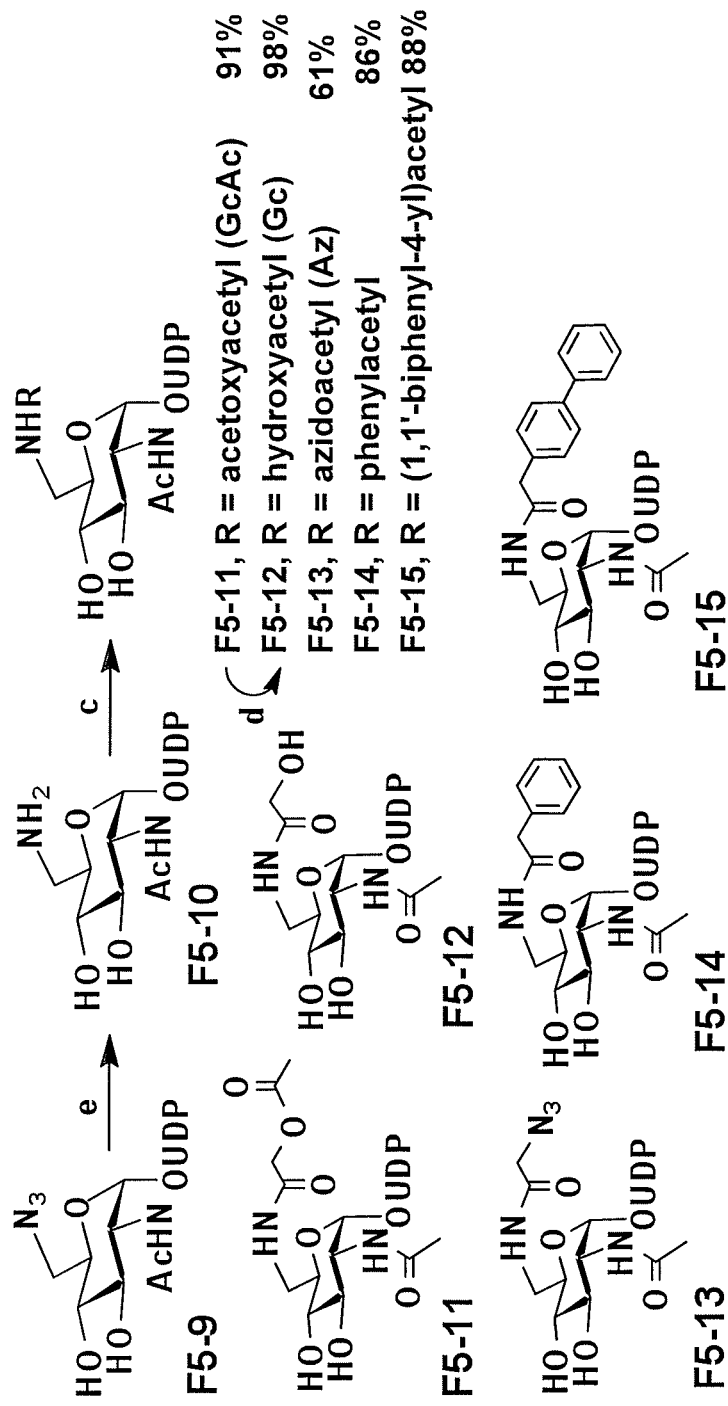

The N-TFA group in UDP-GlcNTFA (T5b-10) as well as the N$_3$ group in UDP-GlcN$_3$ (T5b-11) UDP-GlcNAc6N$_3$ (T5b-12), and UDP-GlcN$_3$6S (T5b-15) can be easily converted to a free amine, allowing further modifications to generate a diverse array of N-substituted UDP-GlcNAc derivatives. As shown in FIG. 5A, the N-TFA group at C2 of UDP-GlcNTFA T5b-10 (or F5-1) was removed under mild basic condition to produce UDP-glucosamine (UDP-GlcNH$_2$, F5-2) in 98% yield. Selective acylation of the free amine group in F5-2 using various acyl chlorides produced C-2 modified UDP-GlcNAc derivatives UDP-N-acetoxyacetyl-glucosamine (UDP-GlcNGcAc, F5-4), UDP-N-azidoacetyl-glucosamine (UDP-GlcNAz, F5-6), UDP-N-phenylacetyl-glucosamine (UDP-GlcNPh, F5-7), and UDP-N-(1,1'-biphenyl-4-yl)acetylglucosamine (UDP-GlcNPh$_2$, F5-8) in 68-95% yields. Deacetylation of compound F5-4 using catalytic amount of NaOMe in MeOH provided UDP-N-hydroxyacetylglucosamine (UDP-GlcNGc, F5-5) in 98% yield. In addition, although UDP-GlcNS T5b-16 (or F5-3) was unable to be prepared from GlcNS (T5b-8) (Table 5b) in the one-pot three-enzyme system, it was readily obtained by N-sulfation of compound F5-2 with Py.SO$_3$ in 2 M of NaOH aqueous solution in a very good yield (86%) (FIG. 5A). Similarly as shown in FIG. 5B, catalytic hydrogenation of the azido group at the C-6 of UDP-GlcNAc6N$_3$ T5b-12 (or F5-9) generated UDP-6-amino-6-deoxyl-N-acetylglucosamine (UDP-GlcNAc6NH$_2$, F5-10) with an excellent yield (96%). Selective acylation of the free amino group of F5-10 using various acyl chlorides produced C-6 modified UDP-GlcNAc derivatives including UDP-6-acetoxyacetamido-N-acetylglucosamine (UDP-GlcNAc6NGcAc, F5-11), UDP-6-azidoacetamido-N-acetylglucosamine (UDP-GlcNAc6NAz, F5-13), UDP-6-phenylacetamido-N-acetylglucosamine (UDP-GlcNAc6NPh, F5-14), and UDP-N-(1,1'-biphenyl-4- yl)acetamido-N-acetylglucosamine (UDP-GlcNAc6NPh$_2$, F5-15) in 61-91% yields. Finally, C-6 modified derivative UDP-N-hydroxyacetamido-N-acetylglucosamine (UDP-GlcNAc6NGc, F5-12) was obtained in 98% yield by treating compound F5-11 in NaOMe and methanol.

Example 3

Preparation of UDP-GalNAc

One-Pot Three-Enzyme Synthesis of uridine 5'-diphospho-2-acetamido-2-deoxy-α-D-glacopyranoside (UDP-GalNAc). GalNAc (100 mg, 1.0 eq), ATP (1.2 eq.), and UTP (1.2 eq.) were dissolved in water in a 50 mL centrifuge tube containing Tris-HCl buffer (100 mM, pH 8.0) and MgCl$_2$ (10 mM). After the addition of NanK_ATCC55813 (3.5 mg), PmGlmU (5 mg), and PmPpA (2.5 mg), water was added to bring the volume of the reaction mixture to 20 mL. The reaction was carried out by incubating the solution in an isotherm incubator at 37° C. for 24 h with gentle shaking. Product formation was monitored by TLC (EtOAc:MeOH: H$_2$O=3:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. Silica gel column purification (EtOAc:MeOH:H$_2$O=4:2:1) was applied for further purification to give pure target compound. Yield, 83% (228 mg); white foam. $^1$H NMR (600 MHz, D$_2$O) δ 7.93 (d, J=8.4 Hz, 1H), 5.94-5.96 (m, 2H), 5.55 (dd, J=6.6, 3.0 Hz, 1H), 4.27-4.36 (m, 2H), 4.22-4.27 (m, 3H), 4.16-4.18 (m, 2H), 4.02 (d, J=3.0 Hz, 1H), 3.95 (dd, J=10.8, 3.0 Hz, 1H), 3.71-3.78 (m, 2H), 2.06 (s, 3H). $^{13}$C NMR (150 MHz, D$_2$O) δ 175.05, 166.31, 151.85, 141.89, 102.82, 94.75, 88.70, 83.03 (d, J=8.6 Hz), 73.97, 72.32, 69.79, 68.50, 67.64, 65.14, 61.17, 49.95 (d, J=7.8 Hz), 22.24. HRMS (ESI) m/z calcd for C$_{17}$H$_{28}$N$_3$O$_{17}$P$_2$ (M+H) 608.0894, found 608.0906.

Example 4

Preparation of UDP-Sugars Using Sugar-1-P Kinases, BLUSP, and PmPpA

General Methods for Compound Purification and Characterization. Chemicals were purchased and used without further purification. $^1$H NMR and $^{13}$C NMR spectra were recorded on a Varian Mercury 600 NMR spectrometer. High resolution electrospray ionization (ESI) mass spectra were obtained in negative mode using Thermo Electron LTQ-Orbitrap mass spectrometer. Silica gel 60 Å (Sorbent Technologies) was used for flash column chromatography. Thin-layer chromatography (TLC) was performed on silica gel plates 60 GF254 (Sorbent Technologies) using anisaldehyde sugar stain for detection. Gel filtration chromatography was performed with a column (100 cm×2.5 cm) packed with BioGel P-2 Fine resins (Bio-Rad). GlcN$_3$ (T6-9) (Lau K, Thon, V, Yu H, Ding L, Chen Y, Muthana M M, Wong D, Huang R, and Chen X. Chem. Commun. 2010, 46, 6066-6068), ManF (T6-11) (Burkart M D, Zhang Z, Hung S-C, and Wong C-H. J. Am. Chem. Soc. 1997, 119, 11743-11746; Cao H, Li Y, Lau K, Muthana S, Yu H, Cheng J, Chokhawala H A, Sugiarto G, Zhang L, and Chen X. Org. Biomol. Chem. 2009, 7, 5137-5145), GalN$_3$ (T6-4) and ManN$_3$ (T6-14) (Yu H, Yu H, Karpel R, cand Chen X. Bioorg. Med. Chem. 2004, 12, 6427-6435) were previously synthesized using reported methods. NahK_ATCC15697, EcGalK, SpGalK, and PmPpA were over-expressed as described previously.

One-Pot Multienzyme Synthesis of UDP-Sugars. Monosaccharides and derivatives (30-100 mg, 1.0 eq.), ATP (1.2 eq.), and UTP (1.3 eq.) were dissolved in water in a 15 mL centrifuge tube containing Tris-HCl buffer (100 mM, pH 8.0) and MgCl$_2$ (10 mM). After the addition of appropriate amount of NahK_ATCC15697, EcGalK, or SpGalK (1.3-4.5 mg), BLUSP (1.0-2.5 mg), and PmPpA (1.5-2.5 mg), millipore water was added to bring the total volume of the reaction mixture to 10 mL. The reaction was carried out by incubating the solution in an isotherm incubator for 24 hr at 37° C. with gentle shaking or without shaking. In the synthesis of UDP-Glc, commercially available Glc-1-P (55.2 mg), UTP (1.2 eq.), Tris-HCl buffer (100 mM, pH 8.0), and MgCl$_2$ (10 mM) were used along with BLUSP (1 mg) and PmPpA (1.5 mg). The reaction was left for 2 hr at 37° C. in isotherm with gentle shaking. Product formation was monitored by TLC (EtOAc: MeOH:H$_2$O:AcOH=5:3:3:0.3 by volume) with p-anisaldehyde sugar staining. The reaction was terminated by adding the same volume of ice-cold ethanol and incubating at 4° C. for 30 min followed by centrifugation remove the enzymes. The supernatant was collected and concentrated and passed through a BioGel P-2 gel filtration column to afford the product. Silica gel column purification (EtOAc:MeOH:H$_2$O=7:3: 2) was applied when necessary to achieve further purification.

Uridine 5'-diphospho-α-D-galactopyranoside (UDP-Gal, T6-16). 135 mg. Yield, 86%; white foam. $^1$H NMR (600 MHz, D$_2$O) δ 7.93 (d, J=8.4 Hz, 1H), 5.97-5.95 (m, 2H), 5.63 (dd, J=7.2, 3.6 Hz, 1H), 4.37-4.35 (m, 2H), 4.28-4.18 (m, 3H), 4.16 (t, J=6 Hz, 1H), 4.02 (d, J=3 Hz, 1H), 3.90 (dd, J=10.2, 3.6 Hz, 1H), 3.80 (dt, J=10.2, 3.3 Hz, 1H), 3.76-3.71 (m, 2H). $^{13}$C NMR (150 MHz, D$_2$O) δ 166.39, 151.96, 141.78, 102.80, 96.01 (d, J=6.6 Hz), 88.65, 83.32 (d, J=8.9 Hz), 73.93, 72.11, 69.78, 69.43, 69.24, 68.50 (d, J=7.8 Hz), 65.15 (d, J=5.0 Hz), 61.16. HRMS (ESI) m/z calcd for C$_{15}$H$_{24}$N$_2$O$_{17}$P$_2$ (M−H) 565.0472, found 565.0453.

Uridine 5'-diphospho-α-D-glucopyranoside (UDP-Glc, T6-21). 82 mg. Yield, 99%; white foam. $^1$H NMR (600 MHz, D$_2$O) δ 7.94 (d, J=8.4 Hz, 1H), 5.98-5.96 (m, 2H), 5.59 (dd, J=7.2, 3.6 Hz, 1H), 4.37-4.35 (m, 2H), 4.28-4.18 (m, 3H), 3.9-3.83 (m, 2H), 3.78-3.74 (m, 2H), 3.53 (dt, J=9.6, 3.3 Hz, 1H), 3.46 (t, J=9.6 Hz, 1H). $^{13}$C NMR (150 MHz, D$_2$O) δ 166.20, 151.75, 141.52, 102.57, 95.51 (d, J=6.8 Hz), 88.35, 83.07 (d, J=8.9 Hz), 73.67, 72.72 (2C), 71.45 (d, J=8.4 Hz), 69.52, 69.05, 64.86 (d, J=5.6 Hz), 60.20. HRMS (ESI) m/z calcd for C$_{15}$H$_{24}$N$_2$O$_{17}$P$_2$ (M−H) 565.0472, found 565.0458.

Uridine 5'-diphospho-2-deoxy-α-D-glucopyranoside (UDP-2-deoxyGlc, T6-22). 96 mg. Yield, 56%; white foam. $^1$H NMR (600 MHz, D$_2$O) δ 7.95 (d, J=8.4 Hz, 1H), 5.96-5.95 (m, 2H), 5.70 (dd, J=7.2, 1.8 Hz, 1H), 4.36-4.33 (m, 2H), 4.27-4.16 (m, 3H), 4.0-3.95 (m, 1H), 3.86-3.75 (m, 3H), 3.39 (t, J=9.6 Hz, 1H), 2.28-2.24 (m, 1H), 1.74-1.68 (m, 1H), (150 MHz, D$_2$O) δ 168.99, 154.54, 144.38, 105.38, 97.63 (d, J=5.7 Hz), 91.25, 85.86 (d, J=9.0 Hz), 76.51, 76.13, 73.33, 72.32, 70.46, 67.63 (d, J=5.0 Hz), 63.21, 40.18 (d, J=7.2 Hz), HRMS (ESI) m/z calcd for C$_{15}$H$_{24}$N$_2$O$_{16}$P$_2$ (M−H) 549.0523, found 549.0513.

Uridine 5'-diphospho-2-amino-2-deoxy-α-D-glucopyranoside (UDP-GlcNH$_2$, T6-23). 56 mg. Yield, 43%; white foam. $^1$H NMR (600 MHz, D$_2$O) δ 7.93 (d, J=7.8 Hz, 1H), 5.97-5.94 (m, 2H), 5.82 (d, J=6.0 Hz, 1H), 4.36-4.34 (m, 2H), 4.28-4.17 (m, 3H), 3.92-3.90 (m 2H), 3.86 (dd, J=12.0, 2.4 Hz, 1H), 3.81 (dd, J=12.6, 4.2 Hz, 1H), 3.55 (t, J=9.9 Hz, 1H), 3.37 (d, J=10.8 Hz, 1H). $^{13}$C NMR (150 MHz, D$_2$O) δ 166.40, 151.93, 141.75, 102.71, 92.87, 88.74, 83.21 (d, J=9 Hz), 73.91, 73.39, 69.85, 69.69, 69.16, 65.23, 60.09, 54.27 (d, J=8.4 Hz). HRMS (ESI) m/z calcd for C$_{15}$H$_{25}$N$_3$O$_{16}$P$_2$ (M−H) 564.0632, found 564.0619.

Uridine 5'-diphospho-2-azido-2-deoxy-α-D-glucopyranoside (UDP-GlcN$_3$, T6-24). 88 mg, Yield, 61%; white foam. $^1$H NMR (600 MHz, D$_2$O) δ 7.95 (d, J=8.4 Hz, 1H), 5.96-5.95 (m, 2H), 5.67 (dd, J=7.2, 3 Hz, 1H), 4.36-4.33 (m, 2H), 4.27-4.18 (m, 3H), 3.93-3.88 (m, 2H), 3.85-3.76 (m, 2H), 3.53 (t, J=9.6 Hz, 1H), 3.38 (d, J=10.8 Hz, 1H). $^{13}$C NMR (150 MHz, D$_2$O) δ 166.14, 151.75, 141.61, 102.79, 94.39 (d, J=4.5 Hz), 88.47, 83.48 (d, J=8.4 Hz), 73.68, 72.85, 70.61, 69.53, 69.24, 64.87, 62.71 (d, J=7.8 Hz), 60.05. HRMS (ESI) m/z calcd for $C_{15}H_{23}N_5O_{16}P_2$ (M−H) 590.0537, found 590.0524.

Uridine 5'-diphospho-α-D-mannopyranoside (UDP-Man, T6-26)

60 mg. Yield, 60%; white foam. $^1$H NMR (600 MHz, $D_2O$) δ 7.93 (d, J=8.4 Hz, 1H), 5.96-5.94 (m, 2H), 5.51 (d, J=7.2, 1H), 4.35-4.18 (m, 5H), 4.02 (m, 1H), 3.89-3.82 (m, 3H), 3.75 (dd, J=12, 4.8 Hz, 1H), 3.67 (t, J=9.9 Hz, 1H). $^{13}$C NMR (150 MHz, $D_2O$) δ 166.40, 151.94, 141.77, 102.79, 96.64 (d, J=5.5), 88.70, 83.24 (d, J=8.7 Hz), 73.93, 73.91, 70.38 (d, J=9.3 Hz), 69.98, 69.74, 66.56, 65.15 (d, J=4.7 Hz), 60.92. HRMS (ESI) m/z calcd for $C_{15}H_{24}N_2O_{17}P_2$ (M−H) 565.0472, found 565.0467.

Uridine 5'-diphospho-2-fluoro-2-deoxy-α-D-mannopyranoside (UDP-ManF, T6-27). 142 mg. Yield, 92%; white foam. $^1$H NMR (600 MHz, $D_2O$) δ 7.94 (d, J=8.4 Hz, 1H), 5.97-5.95 (m, 2H), 5.70 (t, J=6.3 Hz, 1H), 4.39-4.35 (m, 2H), 4.36-4.33 (m, 2H), 4.28-4.16 (m, 3H), 4.00 (ddd, J=30.6, 9.6, 2.4 Hz, 1H), 3.88-3.86 (m, 2H), 3.79 (d, J=12.6, 4.8 Hz, 1H), 3.74 (t, J=9.9 Hz, 1H). $^{13}$C NMR (150 MHz, $D_2O$) δ 166.42, 151.98, 141.80, 102.84, 93.75 (dd, J=31.2, 5.7 Hz), 89.75 (dd, J=173.6, 10.5 Hz), 88.75, 83.26 (d, J=9.0 Hz), 73.95, 73.84, 69.76, 69.32 (d, J=17.3 Hz), 66.46, 65.15 (d, J=5.1 Hz) 60.46. HRMS (ESI) m/z calcd for $C_{15}H_{23}PN_2O_{16}P_2$ (M−H) 567.0429, found 567.0426.

Uridine 5'-diphospho-2-azido-2-deoxy-α-D-mannopyranoside (UDP-ManN$_3$, T6-29). 259 mg, Yield, 90%; white foam. $^1$H NMR (600 MHz, $D_2O$) δ 7.96 (d, J=8.4 Hz, 1H), 6.00-5.98 (m, 2H), 5.62 (d, J=7.2 Hz, 1H), 4.39-4.35 (m, 2H), 4.31-4.18 (m, 3H), 4.16-4.13 (m, 2H), 3.87-3.83 (m, 2H), 3.77 (dd, J=12.6, 4.8 Hz, 1H), 3.70 (t, J=9.6 Hz, 1H). $^{13}$C NMR (150 MHz, $D_2O$) δ 166.42, 151.97, 141.81, 102.84, 94.86 (d, J=5.7 Hz), 88.80, 83.24 (d, J=8.9 Hz), 73.96, 73.95, 70.09, 69.74, 66.49, 65.16 (d, J=5.0 Hz), 64.18 (d, J=9.5 Hz) 60.64. HRMS (ESI) m/z calcd for $C_{15}H_{23}N_5O_{16}P_2$ (M−H) 590.0537, found 590.0532.

Uridine 5'-diphospho-2-acetamido-2-deoxy-α-D-mannopyranoside (UDP-ManNAc, T6-30). Yield for two steps from UDP-ManN$_3$ (T6-29), 79%; white foam. $^1$H NMR (600 MHz, $D_2O$) δ 7.96 (d, J=7.8 Hz, 1H), 5.98-5.95 (m, 2H), 5.44 (dd, J=7.8, 1.8 Hz, 1H), 4.43 (dd, J=4.8, 1.8 Hz, 1H), 4.37-4.34 (m, 2H), 4.28-4.22 (m, 2H), 4.19-4.15 (m, 1H), 4.11 (dd, J=10.2, 4.8 Hz, 1H), 3.90 (dt, J=10.2, 3.0 Hz, 1H), 3.85 (d, J=3.6 Hz, 1H), 3.62 (t, J=10.2 Hz, 1H), 2.03 (s, 3H). $^{13}$C NMR (150 MHz, $D_2O$) δ 175.59, 166.16, 151.75, 141.55, 102.57, 95.35, 88.23, 83.17 (d, J=8.9 Hz), 73.73, 73.20, 69.58, 68.72, 66.29, 64.82, 59.23, 52.94 (d, J=8.9 Hz), 21.85. HRMS (ESI) m/z calcd for $C_{17}H_{27}N_3O_{17}P_2$ (M−H) 606.0737, found 606.0723.

TABLE 6

Figure 9:
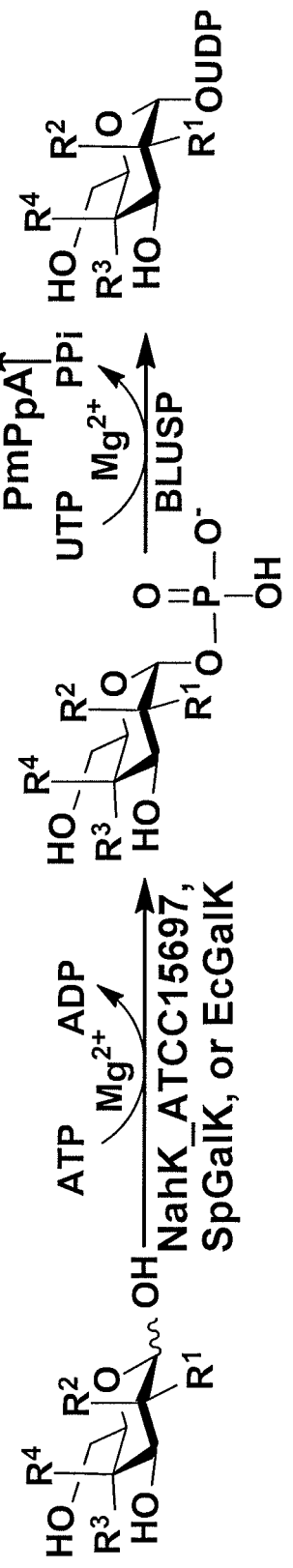
FIG. 9 shows a one-pot, three-enzyme system for the synthesis of UDP-monosaccharides and derivatives. Enzymes used: NahK_ATCC15697, *Bifidobacterium infantis* strain ATCC15697 N-acetylhexosamine 1-kinase; SpGalK, *Streptococcus pneumoniae* TIGR4 galactokinase; EcGalK, *Escherichia coli* galactokinase; BLUSP, *Bifidobacterium longum* UDP-sugar pyrophosphorylase; PmPpA, *Pasteurella multocida* inorganic pyrophosphatase.

Synthesis of UDP-monosaccharides using the one-pot three-enzyme system shown in Figure 9. ND, not detected.

| Substrate | Kinase | Product | Yield (%) |
|---|---|---|---|
| 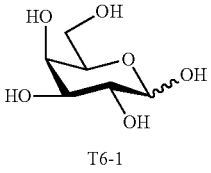<br>T6-1<br>Gal | EcGalK or SpGalK | 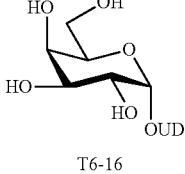<br>T6-16<br>UDP-Gal | 86 |
| 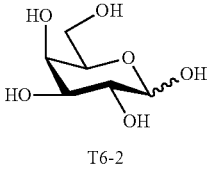<br>T6-2<br>2-deoxyGal | EcGalK or SpGalK | 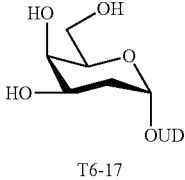<br>T6-17<br>UDP-2-deoxyGal | ND |
| 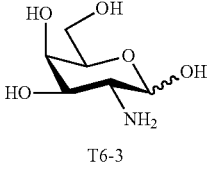<br>T6-3<br>GalNH$_2$ | EcGalK | 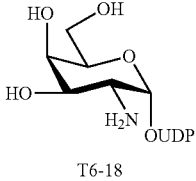<br>T6-18<br>UDP-GalNH$_2$ | ND |
| 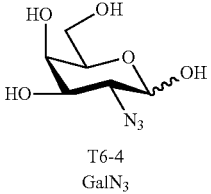<br>T6-4<br>GalN$_3$ | SpGalK | 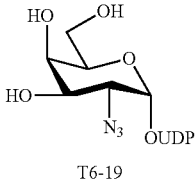<br>T6-19<br>UDP-GalN$_3$ | ND |

TABLE 6-continued
Synthesis of UDP-monosaccharides using the one-pot three-enzyme system shown in Figure 9.
ND, not detected.
| Substrate | Kinase | Product | Yield (%) |
|---|---|---|---|
| 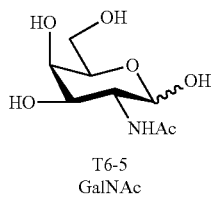<br>T6-5<br>GalNAc | SpGalK | 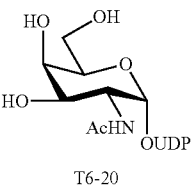<br>T6-20<br>UDP-GalNAc | ND |
| 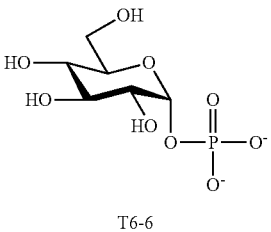<br>T6-6<br>Glc-1-P | None | 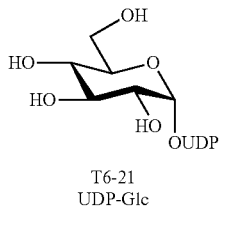<br>T6-21<br>UDP-Glc | 99 |
| 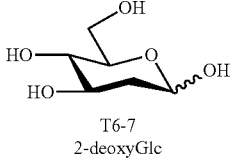<br>T6-7<br>2-deoxyGlc | NahK | 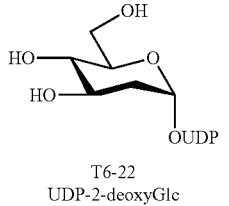<br>T6-22<br>UDP-2-deoxyGlc | 56 |
| 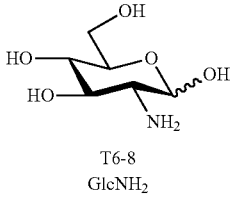<br>T6-8<br>GlcNH$_2$ | NahK | 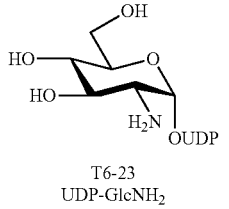<br>T6-23<br>UDP-GlcNH$_2$ | 43 |
| 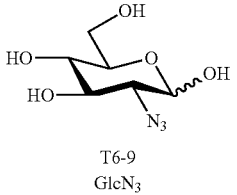<br>T6-9<br>GlcN$_3$ | NahK | 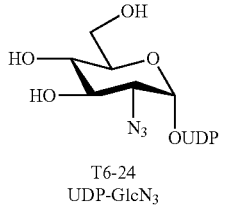<br>T6-24<br>UDP-GlcN$_3$ | 61 |

TABLE 6-continued
Synthesis of UDP-monosaccharides using the one-pot three-enzyme system shown in Figure 9. ND, not detected.
| Substrate | Kinase | Product | Yield (%) |
|---|---|---|---|
| 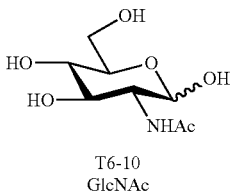 T6-10 GlcNAc | NahK | 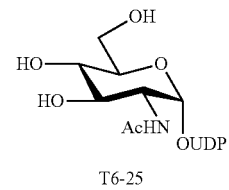 T6-25 UDP-GlcNAc | ND |
| 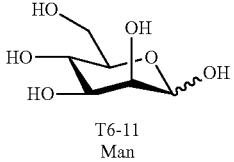 T6-11 Man | NahK | 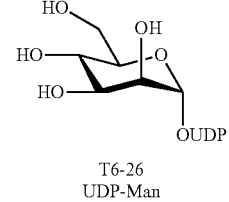 T6-26 UDP-Man | 60 |
| 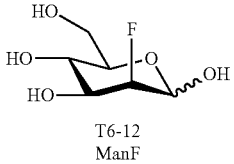 T6-12 ManF | NahK | 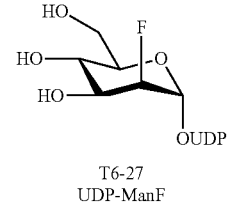 T6-27 UDP-ManF | 92 |
| 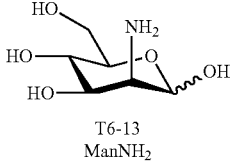 T6-13 ManNH$_2$ | NahK | 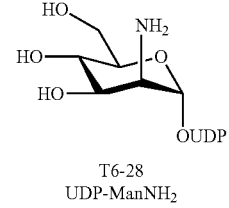 T6-28 UDP-ManNH$_2$ | ND |
| 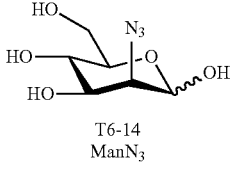 T6-14 ManN$_3$ | NahK | 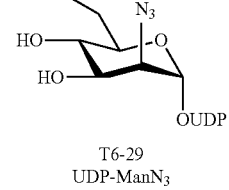 T6-29 UDP-ManN$_3$ | 90 |
| 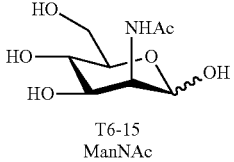 T6-15 ManNAc | NahK | 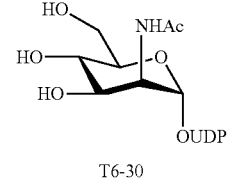 T6-30 UDP-ManNAc | ND |

We were able to identify at least one of these kinases for each monosaccharide that gave a yield higher than 58% for the formation of the corresponding monosaccharide-1-phosphate. The observed results from thin-layer chromotography (TLC) and capillary electrophoresis (CE) (Table 7) confirmed the previously reported activities of NahK, SpGalK, and EcGalK toward their respective substrates except for mannosamine (T6-13), a NahK substrate which was not previously tested.

TABLE 7

Yields of the kinase reactions monitored by the conversion of ATP to ADP in capillary electrophoresis (CE) assays.

| Substrate | Kinase | ATP Conversion (%) | | |
|---|---|---|---|---|
| | | 1 hr | 4 hr | 24 hr |
| No | No | <2 | <5 | 11.1 |
| T6-1 Gal | SpGalK | 92.2 | NA | NA |
| T6-1 Gal | EcGalK | 90.3 | NA | NA |
| T6-2 2-deoxyGal | SpGalK | 80.3 | 89.5 | NA |
| T6-2 2-deoxyGal | EcGalK | 78.5 | 87.6 | NA |
| T6-3 GalNH$_2$ | EcGalK | 90.2 | NA | NA |
| T6-4 GalN$_3$ | SpGalK | 45.7 | 79.0 | 81.2 |
| T6-5 GalNAc | SpGalK | 11.8 | 24.7 | 69.5 |
| Glc | EcGalK | 8.2 | 13.0 | 66.4 |
| Glc | SpGalK | 6.9 | 13.8 | 75.5 |
| Glc | NahK | 10.3 | 18.6 | 82.2 |
| T6-7 2-deoxyGlc | NahK | 36.8 | 69.6 | 79.4 |
| T6-8 GlcNH$_2$ | NahK | 11.9 | 28.0 | 67.1 |
| T6-9 GlcN$_3$ | NahK | 12.4 | 25.9 | 71.2 |
| T6-10 GlcNAc | NahK | 72.6 | 84.6 | 85.5 |
| T6-11 Man | NahK | 29.6 | 69.3 | 75.1 |
| T6-12 Man2F | NahK | 57.9 | 67.9 | 78.2 |
| T6-13 ManNH$_2$ | NahK | 10.3 | 22.8 | 58.0 |
| T6-14 ManN$_3$ | NahK | 34.9 | 65.9 | 76.4 |
| T6-15 ManNAc | NahK | 11.4 | 26.1 | 73.8 |

Abbreviation:
NA, not assayed.

The synthesis of all other UDP-sugars in Table 6 was carried out using the one-pot three-enzyme system shown in FIG. 9. As shown in Table 6, the one-pot three-enzyme system provided excellent yields for the formation of UDP-Gal (T6-16, 86%), UDP-ManF (T6-27, 92%), and UDP-ManN$_3$ (T6-29, 90%) from the corresponding monosaccharides Gal (T6-1), ManF (T6-12), and ManN$_3$ (T6-14), respectively. Three of the derivatives of UDP-Glc including UDP-2-deoxyGlc (T6-22), UDP-GlcNH$_2$ (T6-23), and UDP-GlcN$_3$ (T6-24) were obtained from 2-deoxyGlc (T6-7), glucosamine (GlcNH$_2$, T6-8) and GlcN$_3$ (T6-9) in 56%, 43%, and 61% yields, respectively. The moderate yields for these three compounds may be attributed by less optimal NahK kinase activity for GlcNH$_2$ (T6-8) and GlcN$_3$ (T6-9), and the less optimal BLUSP activity for 2-deoxyGlc (T6-7). UDP-Man (T6-26) was synthesized from Man (T6-11) in moderate 60% yield using the one-pot three-enzyme system and the moderate yield was most likely due to the less optimal activity of BLUSP towards Man-1-P. The synthesis of four UDP-Gal derivatives including its 2-deoxy, 2-deoxy-2-amido-, 2-deoxy-2-azido-, and 2-deoxy-2-acetamido-derivatives (T6-17-T6-20) using the one-pot three-enzyme system was not successful. In addition, UDP-GlcNAc (T6-25), UDP-ManNH$_2$ (T6-28), and UDP-ManNAc (T6-30) could not be produced from the corresponding monosaccharides (T6-10, T6-13, and T6-15) using the one-pot three-enzyme system. These were most likely due to the substrate restriction of BLUSP instead of kinases used.

Figure 8:
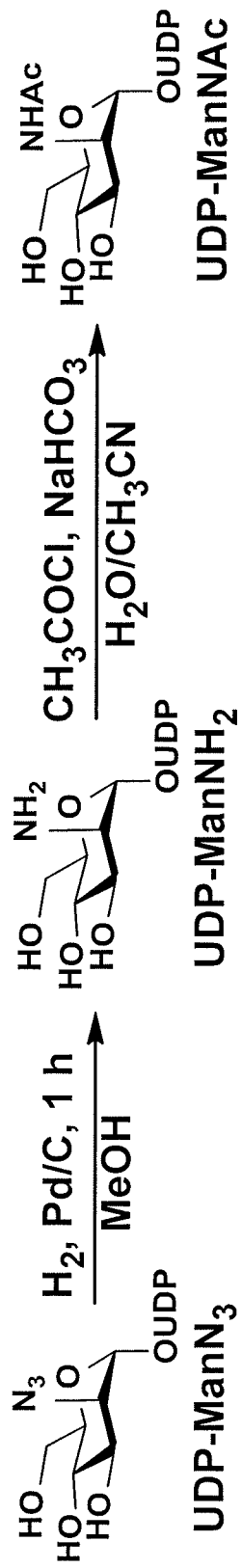
FIG. 8 shows the synthesis of UDP-ManNAc from UDP-ManN$_3$ in 79% yield via the formation of UDP-ManNH$_2$ by catalytic hydrogenation followed by acetylation.

Although UDP-ManNH$_2$ (T6-28) and UDP-ManNAc (T6-30) were not directly available from ManNH$_2$ (T6-13) and ManNAc (T6-15), respectively, via the one-pot three-enzyme reaction shown in FIG. 9, they can be readily prepared via simple chemical modification reactions from UDP-ManN$_3$ (T6-29) obtained from the one-pot three-enzyme system. As shown in FIG. 8, a simple one-step catalytic hydrogenation of UDP-ManN$_3$ (T6-29) produced UDP-ManNH$_2$ (T6-28). Acetylation of the amino group in UDP-ManNH$_2$ (T6-28) provided an easy access of UDP-ManNAc (T6-30). The similar chemical acylation of UDP-ManNH$_2$ can be used to synthesize other acyl derivatives of UDP-ManNAc.

Example 5

Synthesis of UDP-Uronic Acids Using AtGlcAK, BLUSP, and PmPpA

Mass Spectrometry Analysis of One-Pot Multienzyme Synthesis of UDP-GlcA, UDP-IdoA, and UDP-GalA. Enzymatic assays were carried out at in a total volume of 10 µL in Tris-HCl buffer (100 mM, pH 7.5) containing GlcA (GalA, or IdoA) (10 mM), ATP (20 mM), MgCl$_2$ (20 mM), and AtGlcAK (23 µg). Reactions were allowed to proceed at 37° C. for 15 hr and monitored using thin-layer chromatographic analysis using n-PrOH:H$_2$O:NH$_4$OH=7:4:2 (by volume) as a developing solvent. p-Anisaldehyde sugar stain followed by heating the TLC plates on hot plate was used for visualizing compounds on the TLC plates. After 24 hr, BLUSP (5 µg), PmPpA (5 µg) and UTP (12 mM) were added to the reaction mixture. The reactions were allowed to proceed at 37° C. for another 24 hr. The reactions were then quenched with the same volume of 100% ethanol, centrifuged at 13000 rpm for 2 min, and the reaction mixtures were stored at −20° C.

For LC-MS analysis, 2 µL of each sample was diluted 100-fold and 8 µL was injected to a Waters spherisorb ODS-2 column (5 µm particles, 250 mm length, 4.6 mm I.D.). Each sample was eluted with 30% acetonitrile in H$_2$O and detected by ESI-MS in the negative mode.

Figure 10:
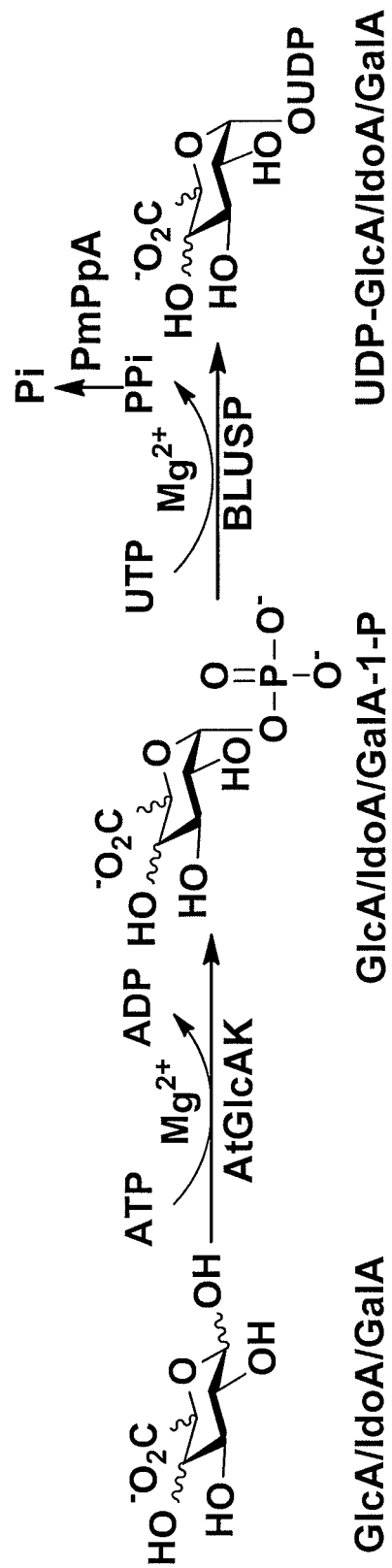
FIG. 10 shows the one-pot multienzyme synthesis of UDP-glucuronic acid, UDP-iduronic acid, and UDP-galacturonic acid.

AtGlcAK was shown to be active on GlcA, GalA, and IdoA by TLC and LC-MS analyses. One-pot three-enzyme strategy containing AtGlcAK, BLUSP, and PmPpA (FIG. 10) was shown to be able to produce UDP-GlcA, UDP-GalA, and UDP-IdoA from their corresponding monosaccharides GlcA, GalA, and IdoA respectively in small-scale assays confirmed by LC-MS or HRMS (FIG. 30).

Example 6

Preparation of GlcNAcα1-4GlcA Disaccharide Derivatives

General Methods for Compound Purification and Characterization. Chemicals were purchased and used without further purification. $^1$H NMR and $^{13}$C NMR spectra were recorded on Varian VNMRS 600 MHz and Bruker Avance 800 MHz spectrometer. High resolution electrospray ionization (ESI) mass spectra were obtained at the Mass Spectrometry Facility in the University of California, Davis. Silica gel 60 Å (Sorbent Technologies) was used for flash column chromatography. Analytical thin-layer chromatography (Sorbent Technologies) was performed on silica gel plates using anisaldehyde sugar stain for detection. Gel filtration chromatography was performed with a column (100 cm×2.5 cm) packed with BioGel P-2 Fine resins. ATP, UTP, GlcNAc, Glc-1-P, NAD$^+$, and glucuronolactone were purchased from Sigma. GlcNTFA, GlcNAc6N$_3$, UDP-GlcNAc, UDP-GlcNAz, UDP-GlcNAc6NGc were synthesized as described previously. NanK_ATCC55813, PmGlmU and PmPpA were overexpressed as reported.

Figure 13:
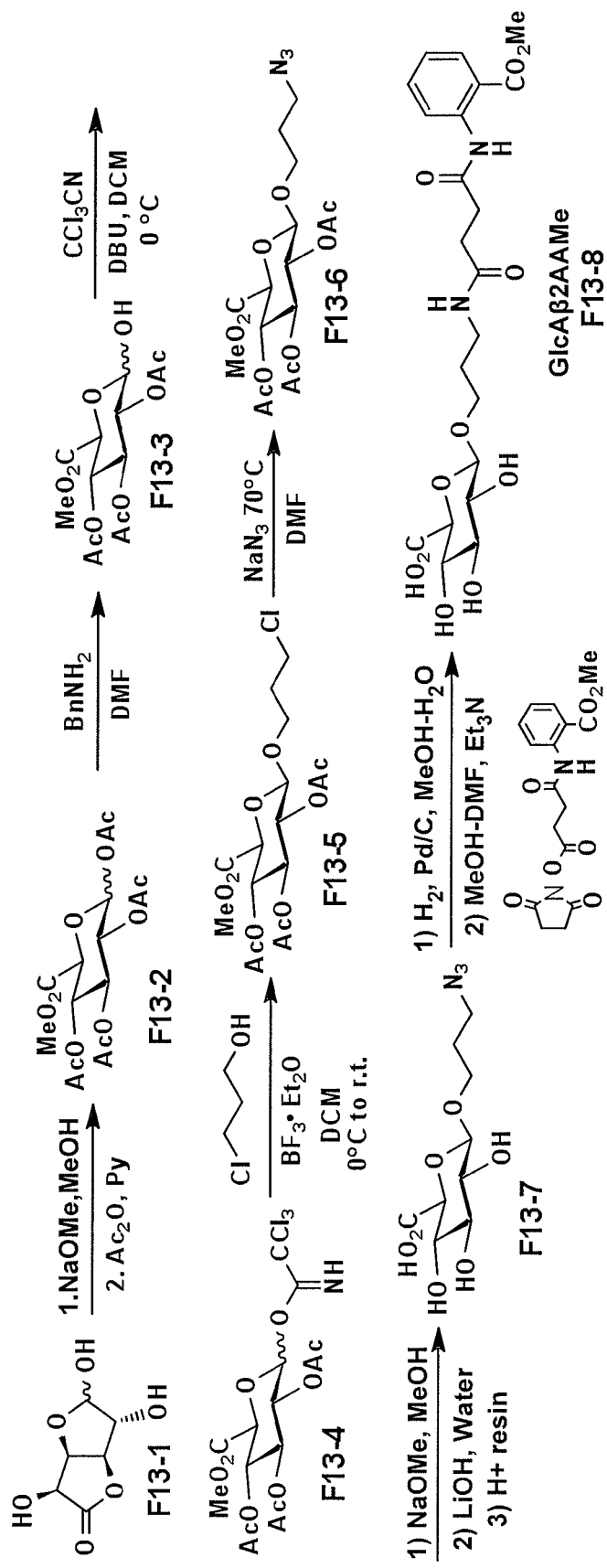
FIG. 13 shows the synthetic scheme for preparation of fluorescently labeled GlcA GlcAβ2AAMe.

Chemical Synthesis of GlcAβ2AAMe. GlcAβ2AAMe was synthesized as outlined in FIG. 13.

Synthesis of F13-2. Glucuronolactone F13-1 (2.0 g, 11.3 mmol) was dissolved in dry MeOH (12 mL) under N$_2$. To the solution, 20 mg of sodium methoxide was added. The reaction was stirred at room temperature for 3 hours, and then MeOH was removed in vacuo. The resulting syrup was further dried under high-vacuum. The above product was dissolved in pyridine (10 mL) and acetic anhydride (8 mL) under 0° C. and $N_2$. The reaction was stirred from 0° C. to room temperature overnight. The mixture was concentrated and purified by flash column chromatography (Hexane:EtOAc=1:1, by volume) to provide white solid F13-2 in 67% yield. β-isomer: $^1$H NMR (600 MHz, $CDCl_3$) δ 5.76 (d, J=7.8 Hz, 1H), 5.30 (t, J=9.6 Hz, 1H), 5.25 (t, J=9.6 Hz, 1H), 5.13 (t, J=7.8 Hz, 1H), 4.17 (d, J=9.6 Hz, 1H), 3.73 (s, 3H), 2.10 (s, 3H), 2.03 (s, 6H), 2.02 (s, 3H). $^{13}$C NMR (150 MHz, $D_2O$) δ 170.13, 169.65, 169.53, 168.61, 167.37, 88.90, 70.51, 69.24, 69.07, 69.00, 53.17, 20.95, 20.79, 20.61, 20.55. α-isomer: $^1$H NMR (600 MHz, $CDCl_3$) δ 6.39 (d, J=3.6 Hz, 1H), 5.51 (t, J=10.2 Hz, 1H), 5.22 (t, J=10.2 Hz, 1H), 5.12 (dd, J=10.2, 3.6 Hz, 1H), 4.41 (d, J=10.2 Hz, 1H), 3.74 (s, 3H), 2.15 (s, 3H), 2.04 (s, 3H), 2.03 (s, 3H), 2.01 (s, 3H). $^{13}$C NMR (150 MHz, $CDCl_3$) δ 170.04, 169.56, 169.32, 168.98, 166.95, 91.48, 73.11, 71.94, 70.27, 69.06, 53.18, 20.93, 20.72, 20.70, 20.63.

Synthesis of methyl 2,3,4-tri-O-acetyl-D-glucopyranuronate F13-3. Methyl 1,2,3,4-tetra-O-acetyl-D-glucopyranuronate F13-2 (1.2 g, 3.2 mmol) was dissolved in dry DMF (10 mL) under $N_2$. To the solution, benzylamine (0.42 mL, 3.8 mmol) was added. The mixture was stirred at r.t. for 16 hours. The solvent was removed under reduced pressure and the residue was purified by flash chromatography (Hexane:EtOAc=1:2, by volume) to afford a white solid F13c in 84% yield. $^1$H NMR (600 MHz, $CDCl_3$) δ 5.50-5.55 (m, 1H), 5.11-5.27 (m, 1H), 4.85-4.91 (m, 1H), 5.39-4.56 (m, 2H), 3.70-3.72 (m, 3H), 1.99-2.05 (m, 9H). $^{13}$C NMR (150 MHz, $CDCl_3$) δ 170.68, 170.45, 170.34, 170.30, 169.94, 169.81, 168.77, 167.83, 95.59, 90.36, 72.98, 72.66, 71.81, 70.97, 69.73, 69.61, 69.34, 68.12, 53.21, 53.11, 20.85, 20.84, 20.77, 20.70, 20.66, 20.65.

Synthesis of methyl 2,3,4-tetra-O-acetyl-1-O-(3-chloropropyl)-β-D-glucopyranuronate F13-5. Methyl 2,3,4-tri-O-acetyl-D-glucopyranuronate F13-3 (800 mg, 2.4 mmol) was dissolved in 8 mL dichloromethane. Trichloroacetonitrile (1.3 mL, 12 mmol) was added under $N_2$. After cooling to 0° C., 1,8-diazabicyclo[5.4.0]undec-7-ene (1,8-DBU) was added in a drop-wise manner until the color of sodium changes to brown. The reaction mixture was allowed to stir for 1 h and the mixture was concentrated to afford a sticky dark brown residue. The flash column chromatography (Hexane:EtOAc=3:7, by volume) gives an off-white product F13-4 in 88% yield. To the mixture of S4 (200 mg, 0.42 mmol) and MS 4 Å, 8 mL dichloromethane was added, followed by 3-chloropropanol (0.25 mL, 2.1 mmol). The mixture was stirred for 30 min at room temperature under $N_2$. After cooling to 0° C., boron trifluoride ether complex (0.06 mL, 0.42 mmol) was added drop-wisely. The reaction was stirred at 0° C. for 3 hours. After the TLC showed the reaction is completed, the mixture was filtered and the filtrate was washed with saturated $NaHCO_3$. The organic layer was evaporated to give a crude residue which was purified by silica gel chromatography (Hexane:EtOAc=3:2, by volume) to provide the product F13-5 in 64% yield. $^1$H NMR (600 MHz, $CDCl_3$) δ 5.17-5.28 (m, 2H), 4.97-5.00 (dd, J=9.6, 7.8 Hz, 1H), 4.53-4.54 (d, J=7.8 Hz, 1H), 4.02-4.04 (d, J=9.6 Hz, 1H), 3.99-4.01 (dd, J=9.6, 4.8 Hz, 1H), 3.27 (s, 3H), 3.66-3.70 (m, 1H), 3.57-3.59 (m, 2H), 2.05-2.09 (m, 1H), 2.04 (s, 3H), 2.01 (s, 3H), 2.00 (s, 3H), 1.91-1.95 (m 1H). $^{13}$C NMR (150 MHz, $CDCl_3$) δ 170.30, 169.59, 169.52, 167.37, 101.21, 72.78, 72.14, 71.33, 69.62, 66.79, 53.13, 41.48, 32.29, 20.83, 20.82, 20.71.

Synthesis of methyl 2,3,4-tetra-O-acetyl-1-O-(3-azidopropyl)-β-D-glucopyranuronate F13-6. Methyl 2,3,4-tetra-O-acetyl-1-O-(3-chloropropyl)-β-D-glucopyranuronate F13-5 (412 mg, 1.0 mmol) was dissolved in 10 mL of DMF. To the solution, sodium azide (325 mg, 5.0 mmol) was added. The reaction was stirred at 65° C. overnight. The solvent was removed under reduced pressure and the residue was purified by flash chromatography (Hexane:EtOAc=3:2, v/v) to afford a white solid in 92% yield. $^1$H NMR (600 MHz, $CDCl_3$) δ 5.19-5.27 (m, 2H), 4.99-5.02 (t, J=7.8 Hz, 1H), 4.54-4.55 (d, J=7.8 Hz, 1H), 4.02-4.04 (d, J=9.6 Hz, 1H), 3.94-3.95 (m, 1H), 3.75 (s, 3H), 3.58-3.62 (m, 1H), 3.32-3.39 (m, 2H), 2.04 (s, 3H), 2.01 (s, 3H), 1.78-1.89 (m 2H). $^{13}$C NMR (150 MHz, $CDCl_3$) δ 170.27, 169.53, 169.40, 167.34, 101.01, 72.82, 72.23, 71.39, 69.60, 66.92, 53.09, 48.10, 29.11, 20.81, 20.79, 20.68.

Synthesis of 1-O-(3-azidopropyl)-β-D-glucopyranuronic acid F13-7. Methyl 2,3,4-tetra-O-acetyl-1-O-(3-azidopropyl)-⊕-D-glucopyranuronate F13-6 (350 mg, 0.84 mmol) was dissolved in 5 mL MeOH. To the solution, sodium methoxide was added until the pH go to 9.5. The reaction was stirred at room temperature for 1 hr. After the TLC showed the reaction is completed, potassium hydroxide (60 mg, 2.52 mmol) and 10 mL water was added. After stirred at r.t. for 3 hours, the mixture was neutralized with DOWEX HCR-W2 (Fr) resin, filtered, and concentrated. The residue was purified by flash column chromatography (EtOAc:MeOH:$H_2O$=6:2:1, by volume) to afford white solid F13-7 in 79% yield. $^1$H NMR (600 MHz, $D_2O$) δ 4.45-4.47 (d, J=7.8 Hz, 1H), 3.95-3.99 (m, 1H), 3.81-3.82 (d, J=9.0 Hz, 1H), 3.71-3.75 (m, 1H), 3.49-3.54 (m, 2H), 3.42-3.45 (t, J=6.6 Hz, 2H), 3.28-3.31 (t, J=8.4 Hz, 1H), 1.86-1.91 (m, 2H). $^{13}$C NMR (150 MHz, $D_2O$) δ 175.17, 102.36, 75.91, 75.64, 73.06, 71.86, 67.57, 48.05, 28.39.

Synthesis of GlcAβAAMe (F13-8). 1-O-(3-Azidopropyl)-β-D-glucopyranuronic acid F13-7 (100 mg, 0.44 mmol) was dissolved in 10 mL MeOH and 20 mg of Pd/C was added. The mixture was shaken under $H_2$ gas (4 Bar) for 1 h, filtered, and concentrated. The residue was further dried in high-vacuum. To a solution of the amine residue in 10 mL of DMF-MeOH (1:1, v/v), dry triethylamine (61 µL) was added under $N_2$. Then 2-(methoxycarbonyl) succinanilic acid NHS ester[3] (2AA-OSu, 306 mg, 0.88 mmol) was added at 0° C. The reaction mixture was stirred at room temperature for overnight. The reaction mixture was concentrated and the residue was purified by silica gel chromatography (EtOAc:MeOH:$H_2O$=8:2:1, by volume) to afford white solid GlcAβ2AAMe (F13-8) in 83% yield. $^1$H NMR (600 MHz, $D_2O$) δ 7.88-7.89 (d, J=8.4 Hz, 1H), 7.79-7.80 (d, J=7.8 Hz, 1H), 7.48-7.51 (t, J=7.8 Hz, 1H), 7.12-7.15 (t, J=7.8 Hz, 1H), 4.27-4.29 (d, J=7.8 Hz, 1H), 3.83-3.86 (m, 1H), 3.81 (s, 3H), 3.58-3.60 (d, J=9.6 Hz, 1H), 3.53-3.57 (m, 1H), 3.40-3.47 (m, 2H), 3.24-3.30 (m, 2H), 3.18-3.22 (m, 1H), 2.61-2.64 (t, J=7.2 Hz, 2H), 2.52-2.54 (t, J=7.2 Hz, 2H), 1.72-1.77 (m, 2H). $^{13}$C NMR (150 MHz, $D_2O$) δ 175.17, 174.18, 172.66, 168.75, 137.89, 134.16, 130.81, 124.41, 121.83, 118.36, 101.96, 75.66, 75.46, 72.83, 71.68, 67.35, 52.63, 36.04, 32.61, 30.83, 28.23.

One-Pot Four-Enzyme Synthesis of Disaccharides F18a-F18c. As shown in FIG. 18A, GlAβ2AAMe (F13-8) (5 to 30 mg, 1 eq.), glucosamine derivatives (1.5 eq.), ATP (1.8 eq.), and UTP (1.8 eq.) were dissolved in water in a 15 mL centrifuge tube containing Tris-HCl buffer (100 mM, pH 7.5) or MES buffer (100 mM, pH 6.5) and $MgCl_2$ (10 mM). After the addition of appropriate amount of NanK_ATCC55813 (0.5-2.1 mg), PmGlmU (1-3 mg), PmPpA (0.5-1.5 mg), and PmHS2 (1-6 mg), water was added to bring the concentration of GlAβ2AAMe (F13-8) to 5 mM. The reaction was carried out by incubating the solution in an isotherm incubator for 12-36 h at 37° C. with gentle shaking. Product formation was monitored by TLC (EtOAc:MeOH:$H_2O$=4:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. Silica gel column purification (EtOAc:MeOH:$H_2O$=5:2:1) was applied when necessary to achieve further purification.

GlcNAcα1-4GlcAβ2AAMe F18-1. Yield: 95%; white foam. $^1$H NMR (600 MHz, $D_2O$) δ 7.95-7.96 (d, J=8.4 Hz, 1H), 7.81-7.83 (d, J=8.4 Hz, 1H), 7.61-7.64 (t, J=7.8 Hz, 1H), 7.29-7.32 (t, 0.1=8.4 Hz, 1H), 5.38-5.39 (d, J=3.6 Hz, 1H), 4.32-4.33 (d, 0.1=7.8 Hz, 1H), 3.89 (s, 3H), 3.79-3.88 (m, 4H), 3.70-3.73 (m, 4H), 3.60-3.63 (m, 1H), 3.55-3.58 (m, 1H), 3.45-3.48 (t, J=9.6 Hz, 1H), 3.20-3.32 (m, 3H), 2.73-2.75 (t, J=6.6 Hz, 2H), 2.58-2.61 (t, J=7.2 Hz, 2H), 2.04 (s, 3H), 1.73-1.78 (m, 2H). $^{13}$C NMR (150 MHz, D$_2$O) δ 175.15, 174.61, 174.51, 173.61, 169.24, 137.16, 134.12, 130.99, 125.45, 123.57, 121.10, 102.21, 96.98, 76.96, 76.69, 75.90, 73.56, 72.01, 70.86, 69.80, 67.58, 66.22, 53.83, 52.93, 36.23, 32.59, 31.20, 28.40, 22.06. HRMS (ESI) m/z calcd for C$_{29}$H$_{42}$N$_3$O$_{16}$ (M+H) 688.2560, found 688.2563.

GlcNTFAα1-4GlcAβ2AAMe F18-2. Yield: 84%; white foam. $^1$H NMR (600 MHz, D$_2$O) δ 7.95-7.97 (d, J=7.8 Hz, 1H), 7.88-7.89 (d, J=7.8 Hz, 1H), 7.62-7.65 (t, J=7.8 Hz, 1H), 7.30-7.32 (t, J=7.8 Hz, 1H), 5.50-5.51 (d, J=3.6 Hz, 1H), 4.34-4.35 (d, J=7.8 Hz, 1H), 4.02-4.04 (dd, J=10.8, 4.2 Hz, 1H), 3.91 (s, 3H), 3.83-3.88 (m, 4H), 3.75-3.77 (m, 3H), 3.63-3.66 (m, 1H), 3.57-3.61 (m, 1H), 3.51-3.55 (t, J=9.6 Hz, 1H), 3.23-3.34 (m, 3H), 2.74-2.76 (t, J=6.6 Hz, 2H), 2.61-2.63 (t, J=7.2 Hz, 2H), 1.77-1.81 (m, 2H). $^{13}$C NMR (150 MHz, D$_2$O) δ 175.15, 174.63, 173.50, 169.26, 159.45 (q, J=37.6 Hz), 137.49, 134.28, 131.09, 125.33, 123.27, 120.52, 117.02 (q, J=284.7 Hz), 102.29, 96.51, 76.90, 76.73, 76.13, 73.61, 72.21, 70.40, 69.85, 67.73, 60.32, 54.54, 53.00, 36.34, 32.75, 31.26, 28.51. HRMS (ESI) m/z calcd for C$_{29}$H$_{39}$F$_3$N$_3$O$_{16}$ (M+H) 742.2277, found 742.2284.

GlcNAc$_3$Nα1-4GlcAβ2AAMe F18-3. Yield: 89%; white foam. $^1$H NMR (600 MHz, D$_2$O) δ 7.97-7.98 (d, J=7.8 Hz, 1H), 7.82-7.84 (d, J=8.4 Hz, 1H), 7.63-7.66 (t, J=7.2 Hz, 1H), 7.32-7.34 (t, J=7.2 Hz, 1H), 5.40-5.41 (d, J=3.6 Hz, 1H), 4.34-4.35 (d, J=7.8 Hz, 1H), 3.91 (s, 3H), 3.83-3.90 (m, 3H), 3.70-3.73 (m, 3H), 3.57-3.63 (m, 4H), 3.47-3.51 (t, J=9.6 Hz, 1H), 3.22-3.33 (m, 3H), 2.74-2.77 (t, J=6.6 Hz, 2H), 2.60-2.62 (t, J=7.2 Hz, 2H), 2.05 (s, 3H), 1.75-1.79 (m, 2H). $^{13}$C NMR (150 MHz, D$_2$O) δ 175.06, 174.64, 174.53, 173.69, 169.28, 137.07, 134.10, 130.99, 125.54, 123.75, 121.38, 102.21, 97.07, 76.88, 76.80, 76.04, 73.57, 70.85, 70.65, 70.44, 67.60, 53.76, 52.94, 50.62, 36.26, 32.58, 31.23, 28.41, 22.07. HRMS (ESI) m/z calcd for C$_{29}$H$_{41}$N$_6$O$_{15}$ (M+H) 713.2625, found 713.2630.

Chemical Derivatization of GlcNTFAα1-4GlcAβ2AAMe (F18-2) to form disaccharide GlcNH$_2$α1-4GlcAβ2AA (F24-9). Disaccharide GlcNTFAα1-4GlcAβ2AAMe (F18-2) (20 mg, 0.027 mmol) was dissolved in 8 mL of H$_2$O. The pH of the solution was adjusted to 10 by adding 1 N NaOH. After being vigorously stirred at r.t. for 1.5 hr, the reaction mixture was neutralized with DOWEX HCR-W2 (H$^+$) resin, filtered and concentrated. The residue was purified by flash column chromatography (EtOAc:MeOH:H$_2$O=3:2:1, by volume) to obtain a white solid GlcNH$_2$α1-4GlcAβ2AA (F24-9) in 86% yield. $^1$H NMR (600 MHz, D$_2$O) δ 8.14-8.15 (d, J=8.4 Hz, 1H), 7.87-7.88 (d, J=7.8 Hz, 1H), 7.49-7.51 (t, J=7.8 Hz, 1H), 7.20-7.22 (t, J=6.6 Hz, 1H), 5.65-5.66 (d, J=3.0 Hz, 1H), 4.26-4.27 (d, J=7.8 Hz, 1H), 3.72-3.85 (m, 8H), 3.66-3.67 (t, J=8.4 Hz, 1H), 3.46-3.52 (m, 2H), 3.20-3.35 (m, 3H), 2.74-2.76 (t, J=6.6 Hz, 2H), 2.61-2.63 (t, J=6.6 Hz, 2H), 1.73-1.74 (m, 2H). $^{13}$C NMR (150 MHz, D$_2$O) δ 175.15, 174.77, 174.68, 173.01, 137.67, 131.91, 130.82, 125.32, 124.25, 120.95, 102.28, 97.77, 76.77, 76.51, 76.32, 73.27, 72.32, 69.60, 67.61, 61.37, 60.24, 54.95, 36.21, 33.50, 31.57, 28.43. HRMS (ESI) m/z calcd for C$_{26}$H$_{38}$N$_3$O$_{15}$ (M+H) 632.2303, found 632.2321.

PmHS2-Catalyzed Synthesis of Disaccharides F18-4-F186. As shown in FIG. 18B, GlAβ2AAMe (F13-8) (5 to 10 mg, 1 eq.) and UDP-GlcNAc derivatives (1.2 eq.) were dissolved in water in a 15 mL centrifuge tube containing Tris-HCl buffer (100 mM, pH 7.5) and MgCl$_2$ (10 mM). After the addition of appropriate amount PmHS2 (1-2 mg), water was added to bring the volume of the reaction mixture to 10 mL. The reaction was carried out by incubating the solution in an isotherm incubator for 12 to 36 h at 37° C. with gentle shaking. Product formation was monitored by TLC (EtOAc:MeOH:H$_2$O=4:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. Silica gel column purification (EtOAc:MeOH:H$_2$O=5:2:1) was applied when necessary to achieve further purification.

GlcNGcα1-4GlcAβ2AAMe F18-4. Yield: 92%; white foam. $^1$H NMR (600 MHz, D$_2$O) δ 7.97-7.98 (d, J=7.8 Hz, 1H), 7.81-7.82 (d, J=8.4 Hz, 1H), 7.62-7.65 (t, J=7.2 Hz, 1H), 7.31-7.34 (t, J=8.4 Hz, 1H), 5.39-5.40 (d, J=3.6 Hz, 1H), 4.32-4.33 (d, J=7.8 Hz, 1H), 4.13 (s, 2H), 3.94-3.96 (dd, J=10.8, 4.2 Hz, 1H), 3.90 (s, 3H), 3.77-3.86 (m, 4H), 3.71-3.75 (m, 3H), 3.61-3.64 (m, 1H), 3.55-3.59 (m, 1H), 3.48-3.51 (t, J=9.6 Hz, 1H), 3.20-3.30 (m, 3H), 2.74-2.76 (t, J=6.6 Hz, 2H), 2.59-2.61 (t, J=7.2 Hz, 2H), 1.74-1.78 (m, 2H). $^{13}$C NMR (150 MHz, D$_2$O) δ 175.18, 175.12, 174.62, 173.67, 169.26, 137.05, 134.08, 130.97, 125.52, 123.72, 121.35, 102.19, 97.05, 76.93, 76.66, 76.03, 73.48, 72.06, 70.81, 69.72, 67.57, 61.03, 60.17, 53.45, 52.92, 36.22, 32.56, 31.20, 28.38. HRMS (ESI) m/z calcd for C$_{29}$H$_{42}$N$_3$O$_{17}$ (M+H) 704.2509, found 704.2516.

GlcNAzα1-4GlcAβ2AAMe F18-5. Yield: 91%; white foam. $^1$H NMR (600 MHz, D$_2$O) δ 7.97-7.99 (d, J=7.8 Hz, 1H), 7.82-7.83 (d, J=7.8 Hz, 1H), 7.64-7.66 (t, J=7.2 Hz, 1H), 7.33-7.35 (t, J=7.8 Hz, 1H), 5.41-5.42 (d, J=3.6 Hz, 1H), 4.33-4.34 (d, J=7.8 Hz, 1H), 4.08 (s, 2H), 3.95-3.97 (dd, J=7.8, 3.6 Hz, 1H), 3.91 (s, 3H), 3.82-3.86 (m, 1H), 3.73-3.80 (m, 6H), 3.62-3.65 (m, 1H), 3.56-3.60 (m, 1H), 3.48-3.51 (t, J=9.0 Hz, 1H), 3.22-3.33 (m, 3H), 2.75-2.77 (t, J=6.6 Hz, 2H), 2.60-2.62 (t, J=6.6 Hz, 2H), 1.75-1.79 (m, 2H). $^{13}$C NMR (150 MHz, D$_2$O) δ 175.15, 174.64, 173.71, 170.83, 169.28, 137.04, 134.09, 130.98, 125.56, 123.77, 121.44, 102.21, 96.88, 76.90, 76.70, 75.99, 73.52, 72.06, 70.72, 69.77, 67.60, 60.20, 53.87, 52.93, 51.93, 36.24, 32.57, 31.23, 28.40. HRMS (ESI) m/z calcd for C$_{29}$H$_{41}$N$_6$O$_{16}$ (M+H) 729.2574, found 729.2582.

GlcNAc6NGcα1-4GlcAβ2AAMe F18-6. Yield: 74%; white foam. $^1$H NMR (600 MHz, D$_2$O) δ 7.98-7.99 (d, J=7.8 Hz, 1H), 7.82-7.83 (d, J=7.8 Hz, 1H), 7.64-7.66 (t, J=7.8 Hz, 1H), 7.33-7.35 (t, J=7.8 Hz, 1H), 5.31-5.32 (d, J=3.6 Hz, 1H), 4.33-4.35 (d, J=8.4 Hz, 1H), 4.12 (s, 2H), 3.91 (s, 3H), 3.81-3.90 (m, 4H), 3.68-3.74 (m, 3H), 3.56-3.63 (m, 3H), 3.50-3.53 (dd, J=13.8, 2.4 Hz, 1H), 3.22-3.32 (m, 3H), 2.76-2.78 (t, J=6.6 Hz, 2H), 2.60-2.63 (t, J=7.2 Hz, 2H), 2.04 (s, 3H), 1.75-1.79 (m, 2H). $^{13}$C NMR (150 MHz, D$_2$O) δ 175.48, 175.29, 174.65, 174.55, 173.71, 169.28, 137.03, 134.09, 130.99, 125.57, 123.81, 121.48, 102.16, 97.49, 77.08, 76.86, 76.73, 73.57, 71.51, 70.72, 70.51, 67.57, 61.18, 53.77, 52.94, 39.62, 36.24, 32.57, 31.24, 28.41, 22.08. HRMS (ESI) m/z calcd for C$_{31}$H$_{45}$N$_4$O$_{17}$ (M+H) 745.2780, found 745.2787.

Example 7

Preparation of Trisaccharide Derivatives

Figure 19:
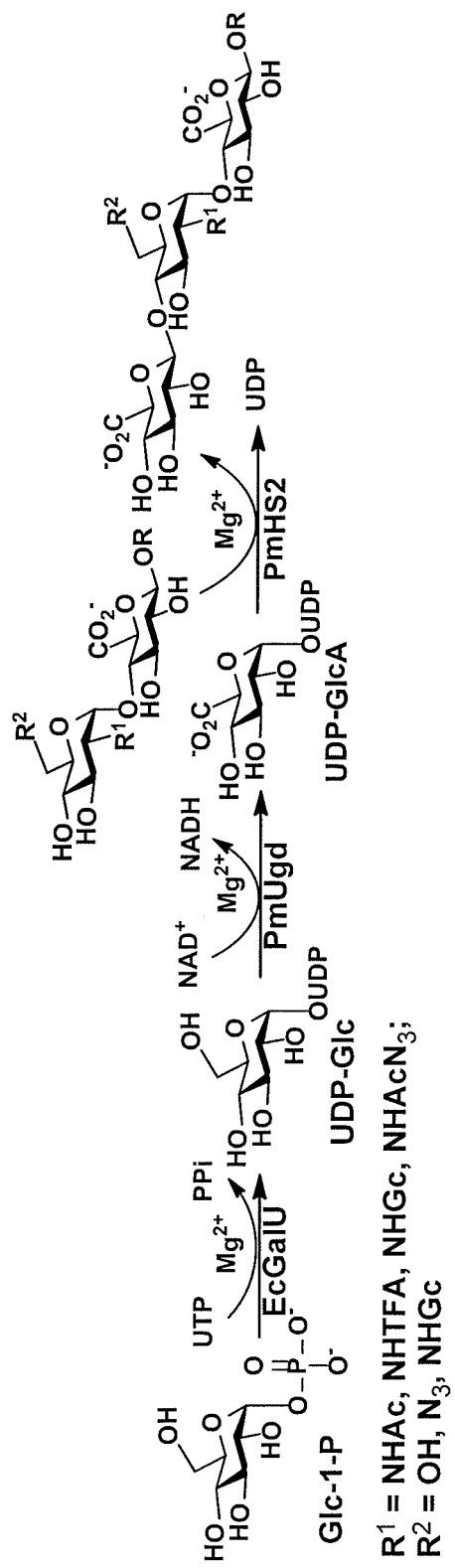
FIG. 19 shows the enzymatic synthesis of trisaccharides from disaccharides via in situ generation of UDP-GlcA from Glc-1-P catalyzed by *Echerichia coli* glucose-1-phosphate uridylyltransferase (EcGalU), *Pasteurella multocida* UDP-glucose dehydrogenase (PmUgd), and PmHS2.

Small Scale One-Pot Three-Enzyme Synthesis of Trisaccharides F20-1-F20-6 by HPLC and MALDI-TOF MS Analysis. As shown in FIG. 19, Typical enzymatic assays were performed in a total volume of 20 μL in Tris-HCl buffer (100 mM, pH 7.5) containing MgCl$_2$ (10 mM), UTP (7.5 mM), disaccharides (5 mM), Glc-1-P (6 mM), NAD$^+$ (12 mM), GalU (2.5 μg), PmUgd (8 μg) and PmHS2 (11.5 μg). Reactions were allowed to proceed for 12 hr at 37° C. and quenched by adding ice-cold ethanol (20 μL) and water (1.96 mL) to make 100-fold dilution. The samples were then kept on ice until aliquots of 5 μL were injected and analyzed by a Shimadzu LC-2010A system equipped with a membrane on-line degasser, a temperature control unit (maintained at 30° C. throughout the experiment), and a fluorescence detector. A reverse phase Premier C18 column (250×4.6 mm I.D., 5 µm particle size, Shimadzu) protected with a C18 guard column cartridge was used. The mobile phase was 10% acetonitrile. The fluorescent compounds 2AA derivatives were detected by excitation at 305 nm and emission at 415 nm. The MS data of the products were acquired using MALDI Mass. See Table 8.

TABLE 8

HPLC and MALDI-TOF MS analysis data for the synthesis of trisaccharides F20-1-F20-6

| Starting Material | Retention Time (min) | Product (Yield) | Retention Time (min) | Cal. Mass M + Na$^+$ | Measured Mass* M + Na$^+$ – H$^+$ | M + 2Na$^+$ – 2H$^+$ | M + 3Na$^+$ – 3H$^+$ |
|---|---|---|---|---|---|---|---|
| Compound F18-1 | 8.8 | Compound F20-1 (100%) | 4.7 | 885.2627 | 885.4562 | 907.4189 | 929.2829 |
| Compound F18-2 | 13.5 | Compound F20-2 (72%) | 4.8 | 940.2423 | 939.3854 | 961.3454 | 983.3108 |
| Compound F18-3 | 9.3 | Compound F20-3 (100%) | 3.9 | 911.277 | 910.4507 | 932.4137 | 954.3776 |
| Compound F18-4 | 8.1 | Compound F20-4 (75%) | 4.9 | 902.2655 | 901.4351 | 923.3950 | 945.3587 |
| Compound F18-5 | 10.5 | Compound F20-5 (95%) | 4.8 | 927.2719 | 926.4009 | 948.3610 | 970.3205 |
| Compound F18-6 | 9.2 | Compound F20f (14%) | 5.1 | 943.2920 | 942.4578 | 964.4117 | — |

*Measured values represent M + Na$^+$, M + 2Na$^+$ – H$^+$, M + 3Na$^+$ – 2H$^+$.

Preparative-Scale Preparation of Trisaccharide GlcAβ1-4GlcNTFAα1-4GlcAβ2AAMe F20-2 in a One-Pot Three-Enzyme System as Shown in FIG. 19.

Disaccharide GlcNTFAα1-4GlcAβAAMe F18-2 (30 mg, 1 eq.), Glc-1-P (1.2 eq), UTP (1.5 eq) and NAD$^+$ (2.4 eq.) were dissolved in water in a 15 mL centrifuge tube containing Tris-HCl buffer (100 mM, pH 7.0) and MgCl$_2$ (10 mM). After the addition of appropriate amount of GalU (1 mg), PmUgd (3 mg), PmHS2 (4.5 mg), water was added to bring the volume of the reaction mixture to 8 mL. The reaction was carried out by incubating the solution in an isotherm incubator at 37° C. for 12 hr with gentle shaking. Product formation was monitored by TLC (EtOAc:MeOH:H$_2$O=3:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. The trisaccharide was further purified by silica gel column chromatography (EtOAc:MeOH:H$_2$O=4:2:1) to obtain white solid trisaccharide GlcAβ1-4GlcNTFAα1-4GlcAβ2AAMe F20-2 in 87% yield. $^1$H NMR (600 MHz, D$_2$O) δ 7.96-7.97 (d, J=7.8 Hz, 1H), 7.80-7.82 (d, J=8.4 Hz, 1H), 7.61-7.64 (t, J=7.8 Hz, 1H), 7.31-7.33 (t, J=7.2 Hz, 1H), 5.44-5.45 (d, J=3.6 Hz, 1H), 4.94-4.51 (d, J=7.8 Hz, 1H), 4.30-4.31 (d, J=7.8 Hz, 1H), 3.99-4.01 (dd, J=11.4, 3.6 Hz, 1H), 3.94-3.97 (m, 1H), 3.90 (s, 3H), 3.80-3.85 (m, 4H), 3.70-3.75 (m, 4H), 3.57-3.60 (m, 1H), 3.53-3.56 (m, 1H), 3.48-3.52 (m, 2H), 3.35-3.37 (t, J=7.8 Hz, 1H), 3.20-3.31 (m, 3H), 2.73-2.76 (t, J=7.2 Hz, 2H), 2.58-2.61 (t, J=7.2 Hz, 2H), 1.73-1.77 (m, 2H). $^{13}$C NMR (150 MHz, D$_2$O) δ 174.88 (2C), 174.40, 173.45, 169.04, 159.11 (q, f=37.7 Hz), 136.81, 133.86, 130.75, 125.31, 123.50, 121.14, 116.69 (q, J=284.6 Hz), 102.27, 101.95, 96.01, 78.16, 76.60, 76.50, 76.02, 75.75, 75.05, 73.31, 72.82, 71.68, 70.58, 68.59, 67.36, 59.22, 53.85, 52.70, 36.00, 32.34, 30.99, 28.16. HRMS (ESI) m/z calcd for C$_{35}$H$_{47}$F$_3$N$_3$O$_{22}$ (M+H) 918.2603, found 918.2613.

Preparative-Scale Preparation of Trisaccharide GlcAβ1-4GlcNH$_2$α1-4GlcAβ2AA (F24-11) in a One-Pot Three-Enzyme System as Shown in FIG. 19.

Disaccharide GlcNH$_2$α1-4GlcAβ2AA (F24-9) (15 mg, 1 eq.), Glc-1-P (1.2 eq), UTP (1.5 eq), and NAD$^+$ (2.4 eq.) were dissolved in water in a 15 mL centrifuge tube containing Tris-HCl buffer (100 mM, pH 7.0) and MgCl$_2$ (10 mM). After the addition of appropriate amount of GalU (0.5 mg), PmUgd (1.5 mg), PmHS2 (2.5 mg), water was added to bring the volume of the reaction mixture to 4 mL. The reaction was carried out by incubating the solution in an isotherm incubator at 37° C. for 12 hr with gentle shaking. Product formation was monitored by TLC (EtOAc:MeOH:H$_2$O=3:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. The trisaccharide was further purified by silica gel column chromatography (EtOAc:MeOH:H$_2$O=3:2:1) to obtain white solid GlcAβ1-4GlcNH$_2$α1-4GlcAβ2AA (F24-11) in 84% yield. $^1$H NMR (600 MHz, D$_2$O) δ 7.96-7.97 (d, J=6.6 Hz, 1H), 7.81-7.82 (d, J=6.6 Hz, 1H), 7.62-7.65 (t, J=6.6 Hz, 1H), 7.31-7.34 (d, J=6.6 Hz, 1H), 5.63-5.64 (d, J=3.6 Hz, 1H), 4.49-4.50 (d, J=6.6 Hz, 1H), 4.35-4.37 (d, J=7.8 Hz, 1H), 3.9-3.98 (t, J=9.0 Hz, 1H), 3.91 (s, 3H), 3.82-3.88 (m, 4H), 3.67-3.78 (m, 6H), 3.49-3.59 (m, 3H), 3.28-3.38 (m, 3H), 3.21-3.25 (m, 1H), 2.74-2.76 (t, J=7.2 Hz, 2H), 2.60-2.62 (t, J=6.6 Hz, 2H), 1.75-1.77 (m, 2H). $^{13}$C NMR (150 MHz, D$_2$O) δ 175.82, 175.08, 174.65, 173.66, 169.27, 137.14, 134.14, 131.01, 125.51, 123.66, 121.23, 102.52, 102.23, 97.66, 78.32, 76.76, 76.61, 76.51, 75.90, 75.33, 73.20, 73.09, 71.93, 70.99, 67.62, 59.48, 58.73, 54.66, 52.95, 36.24, 32.60, 31.23, 28.41. HRMS (ESI) m/z calcd for C$_{32}$H$_{46}$N$_3$O$_{21}$ (M+H) 807.2546, found 807.2557.

Example 8

Preparation of Tetrasaccharides

One-Pot Four-Enzyme Synthesis of Tetrasaccharide GlcNAc6N$_3$α1-4GlcAβ1-4GlcNTFAα1-4GlcAβ2AAMe F21-1. Trisaccharide GlcAβ1-4GlcNTFAα1-4GlcAβ2AAMe F20-2 (30 mg, 1 eq.), GlcNAc6N$_3$ (1.5 eq.), ATP (1.8 eq.), and UTP (1.8 eq.) were dissolved in water in a 15 mL centrifuge tube containing MES buffer (100 mM, pH 6.5) and MgCl$_2$ (10 mM). After the addition of appropriate amount of NanK_ATCC55813 (2.5 mg), PmGlmU (3 mg), PmPpA (1.5 mg), and PmHS2 (4 mg), water was added to bring the volume of the reaction mixture to 6.5 mL. The reaction was carried out by incubating the solution in an isotherm incubator for 18 h at 37° C. with gentle shaking. Product formation was monitored by TLC (EtOAc:MeOH:H$_2$O=4:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. The tetrasaccharide was further purified by silica gel column chromatography (EtOAc:MeOH:H$_2$O=5:2:1) to obtain white solid tetrasaccharide GlcNAc6N$_3$α1-4GlcAβ1-4GlcNTFAα1-4GlcAβ2AAMe F21-1 in 93% yield. $^1$H NMR (600 MHz, D$_2$O) δ 7.94-7.96 (d, J=7.8 Hz, 1H), 7.81-7.83 (d, J=8.4 Hz, 1H), 7.60-7.63 (t, J=7.8 Hz, 1H), 7.29-7.31 (t, J=7.2 Hz, 1H), 5.43-5.44 (d, J=3.6 Hz, 1H), 5.40-5.41 (d, J=4.2 Hz, 1H), 4.47-4.49 (d, J=7.8 Hz, 1H), 4.29-4.31 (d, J=8.4 Hz, 1H), 3.93-4.00 (m, 2H), 3.88-3.90 (m, 4H), 3.78-3.86 (m, 6H), 3.66-3.75 (m, 6H), 3.61-3.62 (d, J=2.4 Hz, 2H), 3.57-3.60 (m, 114), 3.53-3.56 (m, 1H), 3.45-3.48 (t, J=9.0 Hz, 1H), 3.34-3.36 (t, J=7.8 Hz, 1H), 3.19-3.30 (m, 3H), 2.72-2.74 (t, J=6.6 Hz, 2H), 2.57-2.60 (t, J=6.6 Hz, 2H), 2.03 (s, 3H), 1.72-1.76 (m, 2H). $^{13}$C NMR (150 MHz, D$_2$O) δ 174.85, 174.78, 174.36, 174.29, 173.36, 169.00, 159.08 (q, J=284.4 Hz), 136.91, 133.88, 130.75, 125.20, 123.30, 120.83, 116.67 (q, J=37.7 Hz), 102.29, 101.93, 96.83, 96.00, 78.08, 76.57, 76.46, 76.30, 76.28, 76.01, 75.77, 73.36, 73.29, 70.65, 70.55, 70.35, 70.22, 68.47, 67.35, 59.17, 53.76, 53.47, 52.67, 50.38, 35.98, 32.35, 30.95, 28.15, 21.79. HRMS (ESI) m/z calcd for C$_{43}$H$_{59}$F$_3$N$_7$O$_{26}$ (M+H) 1146.3462, found 1146.3478.

Synthesis of Tetrasaccharide GlcNAc6N$_3$α1-4GlcAβ1-4GlcNH$_2$α1-4GlcAβ2AA F22-1. Compound GlcNAc6N$_3$α1-4GlcAβ1-4GlcNTFAα1-4GlcAβ2AAMe F21-1 (30 mg, 0.029 mmol) was dissolved in 8 mL of H$_2$O. The pH of the solution was adjusted to 10 by adding 1 N NaOH. After being vigorously stirred at r.t. for 1.5 hr, the reaction mixture was neutralized with DOWEX HCR-W2 (H$^+$) resin, filtered and concentrated. The residue was purified by flash column chromatography (EtOAc:MeOH:H$_2$O=4:2:1, by volume) to obtain a white solid GlcNAc6N$_3$α1-4GlcAβ1-4GlcNH$_2$α1-4GlcAβ2AA F22-1 in 81% yield. $^1$H NMR (600 MHz, D$_2$O) δ 8.12-8.13 (d, J=7.8 Hz, 1H), 7.85-7.87 (d, J=7.8 Hz, 1H), 7.48-7.50 (t, J=7.2 Hz, 1H), 7.20-7.22 (t, J=7.8 Hz, 1H), 5.59-5.60 (d, J=3.6 Hz, 1H), 5.41-5.40 (d, J=4.2 Hz, 1H), 4.45-4.47 (d, J=7.8 Hz, 1H), 4.27-4.28 (d, J=7.8 Hz, 1H), 3.88-3.94 (m, 2H), 3.79-3.88 (m, 6H), 3.66-3.78 (m, 8H), 3.62-3.64 (m, 2H), 3.46-3.52 (m, 2H), 3.34-3.37 (t, J=7.8 Hz, 1H), 3.19-3.33 (m, 3H), 2.73-2.75 (t, J=6.6 Hz, 2H), 2.60-2.62 (t, J=6.6 Hz, 2H), 2.03 (s, 3H), 1.71-1.75 (m, 2H). $^{13}$C NMR (150 MHz, D$_2$O) δ 174.89, 174.87, 174.67, 174.47, 174.29, 172.74, 137.25, 131.59, 130.48, 125.10, 124.00, 120.70, 102.27, 101.92, 96.84, 95.32, 77.32, 76.22, 76.15, 76.10, 76.07, 75.79, 73.38, 73.03, 70.90, 70.65, 70.34, 70.20, 68.24, 68.22, 67.30, 58.92, 53.82, 53.45, 50.38, 35.90, 33.19, 31.28, 28.10, 21.77. HRMS (ESI) m/z calcd for C$_{40}$H$_{58}$N$_7$O$_{25}$ (M+H) 1036.3482, found 1036.3497.

Synthesis of Tetrasaccharide GlcNAc6N$_3$α1-4GlcAβ1-4GlcNSα1-4GlcAβ2AA F22-2. Compound GlcNAc6N$_3$α1-4GlcAβ1-4GlcNH$_2$α1-4GlcAβ2AA F22-1 (20 mg, 0.018 mmol) was dissolved in 10 mL of H$_2$O. The pH of the solution was adjusted to 9.5 by adding 2 N NaOH (aq). Sulfur trioxide-pyridine complex (58 mg, 0.36 mmol) was added in three equal portions during 35 minutes intervals at room temperature, and the pH was maintained at 9.5 throughout the whole process using 2 N NaOH (aq). After being stirred at r.t. for 24 hr, the reaction mixture was neutralized with DOWEX HCR-W2 (H$^+$) resin, filtered, concentrated. The process has been repeated for three times and purified using silica gel column (EtOAc:MeOH:H$_2$O=5:2:1, by volume) to obtain a light yellow solid GlcNAc6N$_3$α1-4GlcAβ1-4GlcNSα1-4GlcAβ2AA F22-2 in 70% yield. $^1$H NMR (800 MHz, D$_2$O) δ 8.13-8.14 (d, J=8.0 Hz, 1H), 7.87-7.88 (d, J=7.2 Hz, 1H), 7.52-7.50 (t, J=8.0 Hz, 1H), 7.22-7.24 (t, J=7.2 Hz, 1H), 5.60-5.61 (d, J=4.0 Hz, 1H), 5.42-5.43 (d, J=3.2 Hz, 1H), 4.50-4.51 (d, J=8.0 Hz, 1H), 4.34-4.35 (d, J=8.0 Hz, 1H), 3.86-3.92 (m, 3H), 3.80-3.83 (m, 4H), 3.73-3.79 (m, 4H), 3.68-3.72 (m, 4H), 3.64-3.65 (d, J=3.2 Hz, 2H), 3.56-3.53 (m, 1H), 3.48-3.50 (t, J=9.6 Hz, 1H), 3.36-3.39 (t, J=8.0 Hz, 1H), 3.19-3.28 (m, 4H), 2.75-2.77 (t, J=7.2 Hz, 2H), 2.62-2.63 (t, J=7.2 Hz, 2H), 2.04 (s, 3H), 1.75-1.77 (m, 1H). $^{13}$C NMR (200 MHz, D$_2$O) δ 174.89, 174.51, 174.32, 174.30, 172.82, 172.78, 137.13, 131.55, 130.41, 125.21, 124.02, 120.77, 102.11, 101.88, 96.88, 96.79, 77.70, 76.48, 76.29, 76.15, 76.11, 75.77, 73.28, 72.51, 70.58, 70.30, 70.21, 70.15, 69.38, 67.25, 59.16, 57.45, 53.43, 50.30, 35.89, 33.09, 31.19, 28.09, 21.73. HRMS (ESI) m/z calcd for C$_{40}$H$_{58}$N$_7$O$_{28}$S (M+H) 1116.3051, found 1116.3076.

Synthesis of Tetrasaccharide GlcNAc6NH$_2$α1-4GlcAβ1-4GlcNSα1-4GlcAβ2AA F22-3. Compound GlcNAc6N$_3$α1-4GlcAβ1-4GlcNSα1-4GlcAβ2AA F22-2 (17 mg, 0.015 mmol) was dissolved in 10 mL H$_2$O/MeOH (1:1) and 20 mg of Pd/C was added. The mixture was shaken under H$_2$ gas (4 Bar) for 1 hr, filtered, and concentrated to produce F22-3 as a white solid in quantitative yield. $^1$H NMR (800 MHz, D$_2$O) δ 8.04-8.05 (d, J=8.0 Hz, 1H), 8.02-8.03 (d, J=8.0 Hz, 1H), 7.64-7.67 (t, J=8.0 Hz, 1H), 7.32-7.34 (t, J=7.2 Hz, 1H), 5.56-5.57 (d, J=4.0 Hz, 1H), 5.34-5.35 (d, J=4.0 Hz, 1H), 4.56-4.57 (d, J=8.0 Hz, 1H), 4.34-4.35 (d, J=8.0 Hz, 1H), 3.92-3.95 (m, 3H), 3.88-3.90 (dd, J=12.0, Hz, 2.4H), 3.76-4.84 (m, 4H), 3.68-3.75 (m, 4H), 3.55-3.58 (m, 1H), 3.42-3.45 (dd, J=13.6, 3.2 Hz, 1H), 3.35-3.38 (m, 2H), 3.30-3.32 (m, 2H), 3.19-3.27 (m, 4H), 3.12-3.15 (dd, J=12.8, 8.8 Hz, 1H), 2.77-2.79 (t, J=6.4 Hz, 1H), 2.61-2.62 (t, J=6.4 Hz, 1H), 2.05 (s, 3H), 1.75-1.78 (m, 2H). $^{13}$C NMR (200 MHz, D$_2$O) δ 174.77, 174.47, 174.42, 173.26, 172.64, 170.76, 137.73, 133.92, 131.18, 127.27, 124.85, 122.56, 102.18, 102.87, 97.64, 97.48, 77.66, 77.32, 76.56, 75.76, 75.73, 75.70, 74.58, 73.42, 72.45, 71.70, 70.65, 70.08, 69.22, 68.16, 67.53, 59.22, 57.60, 53.33, 46.57, 40.22, 35.88, 31.12, 28.13, 21.78. HRMS (ESI) m/z calcd for C$_{40}$H$_{60}$N$_5$O$_{28}$S (M+H) 1090.3146, found 1190.3171.

Synthesis of Tetrasaccharide GlcNAc6NSα1-4GlcAβ1-4GlcNSα1-4GlcAβ2AA F22-4. Compound GlcNAc6NH$_2$α1-4GlcAβ1-4GlcNSα1-4GlcAβ2AA F22-3 (14 mg, 0.013 mmol) was dissolved in 5 mL of H$_2$O. The pH of the solution was adjusted to 9.5 by adding 2 N NaOH. Sulfur trioxide-pyridine complex (30 mg, 0.18 mmol) was added in three equal portions during 1 hr intervals at rt. The pH was maintained at 9.5 throughout the whole process by adding 2 N NaOH. After being stirred at r.t. for overnight, the reaction mixture was neutralized with DOWEX HCR-W2 (H$^+$) resin, filtered, concentrated. The process has been repeated for three times and purified by preparative HPLC using C18 column to give white solid GlcNAc6NSα1-4GlcAβ1-4GlcNSα1-4GlcAβ2AA F22-4 in 65% yield. $^1$H NMR (800 MHz, D$_2$O) δ 8.06-8.07 (d, J=8.0 Hz, 1H), 8.03-8.04 (d, J=8.0 Hz, 1H), 7.66-7.68 (t, J=7.2 Hz, 1H), 7.33-7.34 (d, J=7.2 Hz, 1H), 5.54-5.55 (d, J=3.2 Hz, 1H), 5.35-5.36 (d, J=3.2 Hz, 1H), 4.61-4.62 (d, J=8.0 Hz, 1H), 4.34-4.35 (d, J=8.0 Hz, 1H), 4.11-4.12 (d, J=9.6 Hz, 1H), 3.81-3.93 (m, 4H), 3.73-3.81 (m, 5H), 3.64-3.71 (m, 5H), 3.55-3.58 (m, 1H), 3.50-3.53 (t, J=9.6 Hz, 1H), 3.39-3.41 (t, J=8.0 Hz, 1H), 3.28-3.33 (m, 3H), 3.21-3.27 (m, 3H), 2.77-2.79 (t, J=7.2 Hz, 2H), 2.61-2.62 (t, J=6.4 Hz, 2H), 2.05 (s, 3H), 1.75-1.78 (m, 2H). $^{13}$C NMR (200 MHz, D$_2$O) δ 174.48, 174.34, 173.25, 171.88, 171.81, 170.41, 137.88, 134.18, 131.28, 127.18, 124.87, 122.59, 102.27, 102.04, 97.78, 97.46, 77.88, 76.83, 76.46, 75.65, 75.49, 73.91, 73.88, 73.14, 72.41, 70.83, 70.69, 70.46, 70.13, 69.14, 67.62, 59.21, 59.15, 57.67, 53.42, 43.29, 35.85, 32.71, 31.09, 28.13, 21.81. HRMS (ESI) m/z calcd for C$_{40}$H$_{60}$N$_5$O$_{31}$S$_2$ (M+H) 1170.2714, found 1170.2730.

Alternative Route for Synthesizing Tetrasaccharide F22-4 from F21-1.

Compound GlcNAc6N$_3$α1-4GlcAβ1-4GlcNH$_2$α1-4GlcAβ2AAMe F21-1 (10 mg, 0.009 mmol) was dissolved in 5 mL of H$_2$O/MeOH (1:1) and 5 mg of Pd/C was added. The mixture was shaken under H$_2$ gas (4 Bar) for 1 hr, filtered and concentrated to provide GlcNAc6NH$_2$α1-4GlcAβ1-4GlcNH$_2$α1-4GlcAβ2AA. The residue was dissolved in 5 mL of H$_2$O. The pH of the solution was adjusted to 9.5 by adding 2 N NaOH. Sulfur trioxide-pyridine complex (15 mg, 0.09 mmol) was added in three equal portions during 1 h intervals at rt. The pH was maintained at 9.5 throughout the whole process by adding 2 N NaOH. After being stirred at r.t. for overnight, the reaction mixture was neutralized with DOWEX HCR-W2 (H$^+$) resin, filtered, and concentrated to give a mixture of GlcNAc6NSα1-4GlcAβ1-4GlcNH$_2$α1-4GlcAβ2AA, GlcNAc6NH$_2$α1-4GlcAβ1-4GlcNSα1-4GlcAβ2AA (F22-3), and GlcNAc6NSα1-4GlcAβ1-4GlcNSα1-4GlcAβ2AA (F22-4) which can be separated by HPLC using a C18 column.

Figure 14:
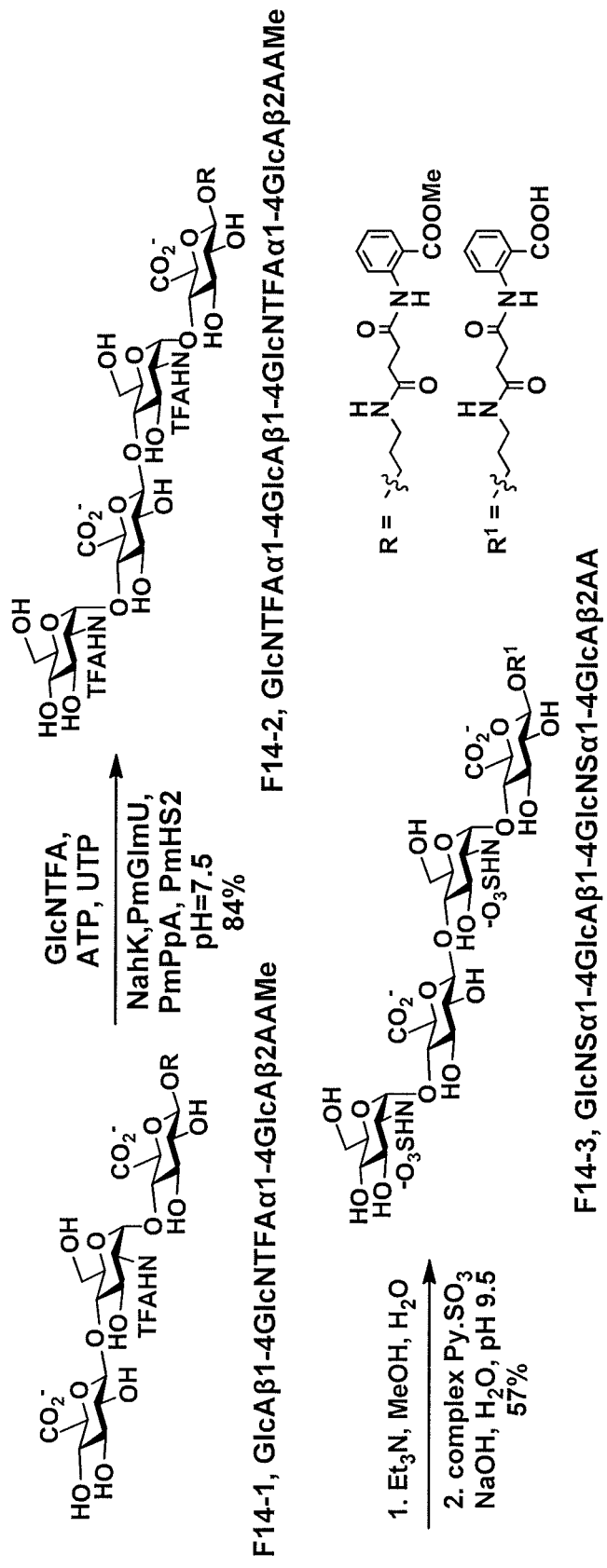
FIG. 14 shows the synthesis of tetrasaccharides GlcNTFAα1-4GlcAβ1-4GlcNTFAα1-4GlcAβ2AAMe (F14-2) and GlcNSα1-4GlcAβ1-4GlcNSα1-4GlcAβ2AA (F14-3) from trisaccharide GlcAβ1-4GlcNTFAα1-4GlcAβ2AAMe (F14-1).

Synthesis of GlcNSα1-4GlcAβ1-4GlcNSα1-4GlcAβ2AA. The synthesis was conducted as outlined in FIG. 14.

Trisaccharide GlcAβ1-4GlcNTFAα1-4GlcAβ2AAMe (Compound F14-1 or F20-2, FIG. 14) (11 mg, 1 eq.), GlcNTFA (1.5 eq.), ATP (1.8 eq.), and UTP (1.8 eq.) were dissolved in water in a 15 mL centrifuge tube containing tris buffer (100 mM, pH 7.0) and MgCl$_2$ (10 mM). After the addition of NanK_ATCC55813 (2.5 mg), PmGlmU (3 mg), PmPpA (1.5 mg), and PmHS2 (2 mg), water was added to bring the volume of the reaction mixture to 10 mL. The reaction was carried out by incubating the solution in an isotherm incubator at 37° C. for 20 hr with gentle shaking. Product formation was monitored by TLC (EtOAc:MeOH:H$_2$O=4:2:1 by volume) with p-anisaldehyde sugar staining. The reaction was stopped by adding the same volume of ice-cold ethanol and incubating at 4° C. for 30 min. The mixture was concentrated and passed through a BioGel P-2 gel filtration column to obtain the desired product. The tetrasaccharide was further purified by silica gel column chromatography (EtOAc:MeOH:H$_2$O=5:2:1) to obtain a white solid of GlcNTFAα1-4GlcAβ1-4GlcNTFAα1-4GlcAβ2AAMe (Compound F14-2, FIG. 14). 11.8 mg, 84% yield. $^1$H NMR (600 MHz, D$_2$O) δ 8.04-8.03 (d, J=8.4 Hz, 1H), 7.87-7.85 (d, J=7.8 Hz, 1H), 7.72-7.69 (t, J=7.2 Hz, 1H), 7.41-7.38 (t, J=7.8 Hz, 1H), 5.54-5.53 (d, J=4.2 Hz, 1H), 5.50-5.49 (d, J=3.6 Hz, 1H), 4.56-4.55 (d, J=7.8 Hz, 1H), 4.38-4.36 (d, J=7.8 Hz, 1H), 4.00-3.26 (m, 24H), 2.83-2.81 (t, J=6.9 Hz, 2H), 2.68-2.66 (t, J=6.9 Hz, 2H), 1.82-1.80 (m, 2H).

GlcNTFAα1-4GlcAβ1-4GlcNTFAα1-4GlcAβ2AAMe (Compound F14-2, FIG. 14) (11 mg) was dissolved in 7.5 mL solution of (MeOH:H$_2$O:triethylamine=1:1:0.5). The reaction was stirred overnight and monitored until completion as indicated by TLC. The solution was then rotovaped and re-dissolved in water and lyophilized to afford free amines as a white foam. The free amine was then dissolved in 7 mL of water and the pH of the solution was adjusted to 9.5 by adding 2 N NaOH (aq). Sulfur trioxide-pyridine complex (60 mg, 0.37 mmol) was added in three equal portions during 35 minutes intervals at room temperature, and the pH was maintained at 9.5 throughout the whole process using 2 N NaOH (aq). After being stirred at r.t. for 24 hr, the reaction mixture was neutralized with DOWEX HCR-W2 (H$^+$) resin, filtered, concentrated. The crude product was purified using silica gel column (EtOAc:MeOH:H$_2$O=5:3:2, v/v) to obtain a light yellow solid GlcNSα1-4GlcAβ1-4GlcNSα1-4GlcAβ2AA (tetrasaccharide F14-3, FIG. 14). MS (ESI) m/z calcd for C$_{38}$H$_{56}$N$_4$O$_{31}$S$_2$ (M−H) 1127.23, found 1127.23. C$_{38}$H$_{56}$N$_4$O$_{31}$S$_2$ (M/2−H) 563.11, found 563.11.

Results and Discussion

As shown in FIG. 16, four enzymes were used in one-pot to synthesize GlcNAcα1-4GlcA disaccharide derivatives. The first enzyme was an N-acetylhexosamine 1-kinase cloned from *Bifidobacterium infantis* strain ATCC15697 (NahK_ATCC15697). The second enzyme was an N-acetylglucosamine-1-phosphate uridylyltransferase that we cloned from *Pasteurella multocida* strain P-1059 (ATCC15742) (PmGlmU). The third enzyme was an inorganic pyrophosphatase that we cloned from *Pasteurella multocida* strain P-1059 (PmPpA) for hydrolyzing the pyrophosphate by-product formed to drive the reaction towards the formation of UDP-GlcNAc and derivatives.

The fourth enzyme is a heparosan synthase 2 cloned from *Pasteurella multocida* strain P-1059 (PmHS2) for the formation of α1-4 linkage. PmHS2 is a bifunctional enzyme which demonstrates α1-4GlcNAc and β1-4GlcA transferase activity. It not only uses UDP-GlcNAc as donor, transferring GlcNAc to GlcA to form α1-4 linkage, but also transfers GlcA from donor UDP-GlcA to acceptor GlcNAc to form β1-4 linkage. Although PmHS2 has been shown to be able to synthesize heparosan polysaccharides, its donor and acceptor specificity has not been investigated in detail.

Prior to applying the one-pot three-enzyme system shown in FIG. 16 to the preparative-scale synthesis of the disaccharides, UDP-GlcNAc and derivatives F17-1-F17-12 were tested as donor substrates for PmHS2 in small-scale reaction containing Tris-HCl buffer (100 mM, pH 7.5), GlcAβ2AAMe (10 mM), UDP-GlcNAc or a derivative (15 mM), MgCl$_2$ (10 mM), and PmHS2 (0.5 mg/mL). See FIG. 17. The reactions were carried out at 37° C. for 12 hr and analyzed by thin layer chromatography (TLC). UDP-GlcNAc F17-1 and some of its C2-(UDP-GlcNTFA F17-2, UDP-GlcNGc F17-3, and UDP-GlcNAcN$_3$ F17-4), and C6-(UDP-GlcNAc6N$_3$ F17-8 and UDP-GlcNAc6NGc F17-9) derivatives are tolerable donor substrates for PmHS2. UDP-GlcNH$_2$ F17-5, UDP-GlcN$_3$ F17-6, UDP-GlcNS F17-7, UDP-GlcNAc6NH$_2$ F17-10, UDP-GlcNAc6NAcN$_3$ F17-11 and UDP-GlcNAc6S F17-12 did not serve as donor substrates for PmHS2.

Figure 18:
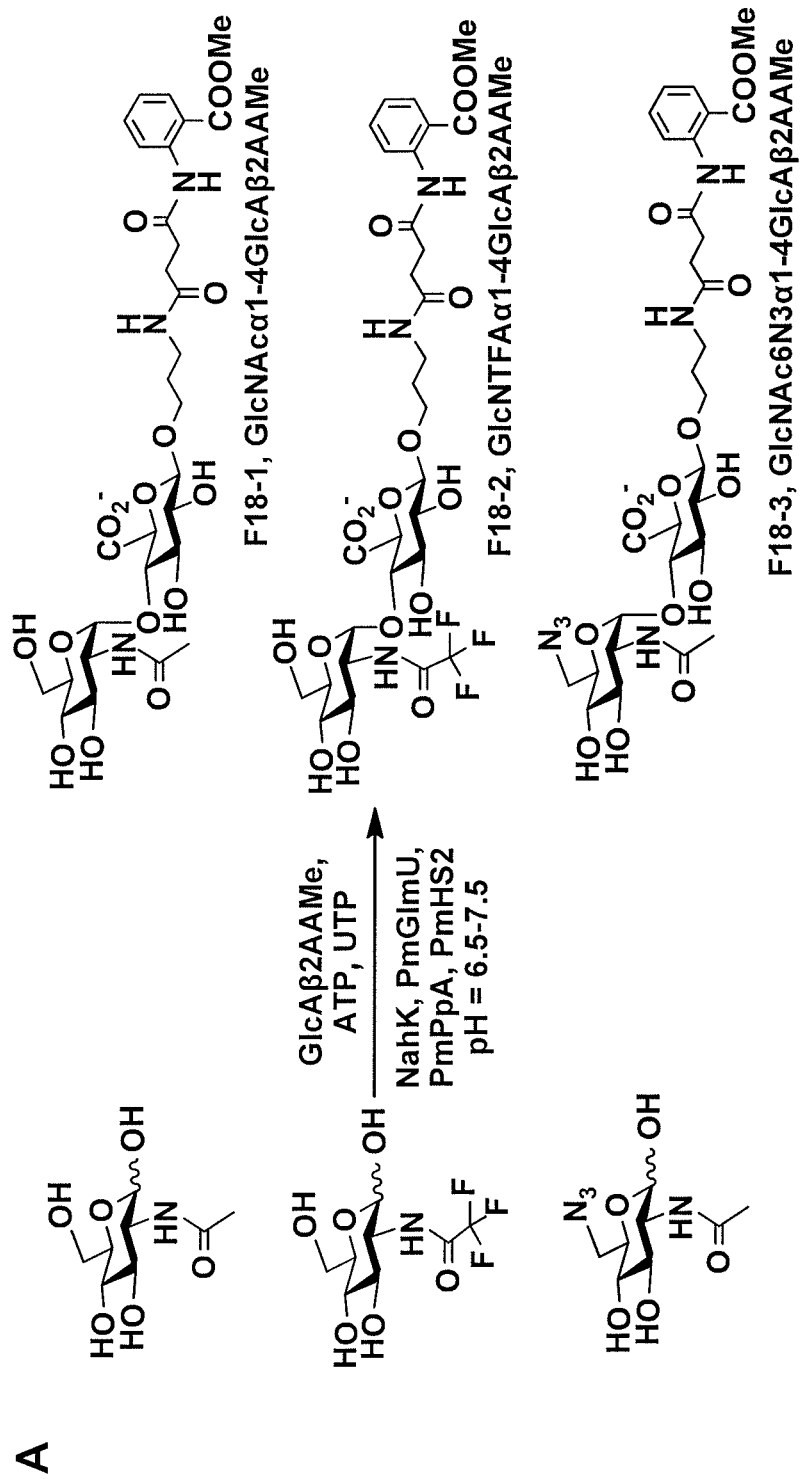
FIG. 18 shows the enzymatic synthesis of the disaccharides.
Figure 18:
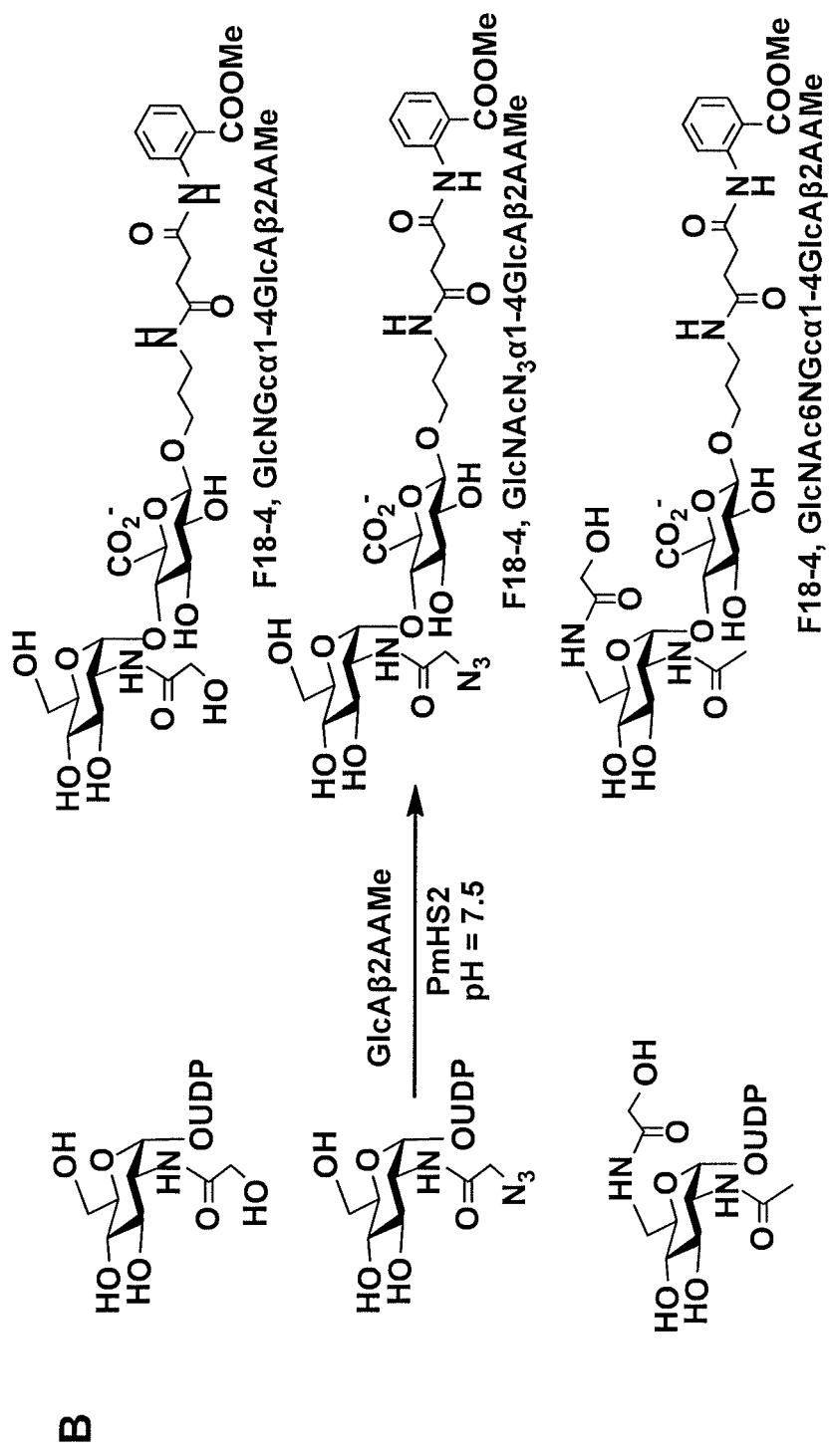

As shown in FIG. 18, preparative-scale transfer of monosaccharide GlcNAc, GlcNTFA and GlcNAc6N$_3$ to fluorescent labeled glucuronide GlcAβ2AAMe as an acceptor for PmHS2 successfully produced disaccharides GlcNAcα1-4GlcAβ2AAMe F18-1, GlcNTFAα1-4GlcAβ2AAMe F18-2, and GlcNAc6N$_3$α1-4GlcAβ2AAMe F18-3 in 95%, 84%, and 89% yields, respectively. It was found that the N-TFA group removal was significant at pH 7.5. Nevertheless, the removal of N-TFA was not significant when the pH of the reaction mixture was changed from 7.5 to 6.5 and the reaction time was shortened. Three additional disaccharides (supporting information) were also synthesized by PmHS2-catalyzed reaction using UDP-GlcNAc derivatives UDP-GlcNGc F17-3, UDP-GlcNAcN$_3$ F17-4, and UDP-GlcNAc6NGc F17-9, since the three sugar nucleotides were prepare form UDP-GlcNTFA F17-2 by the removal of TFA and acylation of amine with proper acyl chloride. GlcNGcα1-4GlcAβ2AAMe F18-4, GlcNAcN$_3$α1-4GlcAβ2AAMe F18-5, and GlcNAc6NGcα1-4GlcAβ2AAMe F18-6 are prepared in 92%, 91%, and 74% yields, respectively. See FIG. 18.

Figure 20:
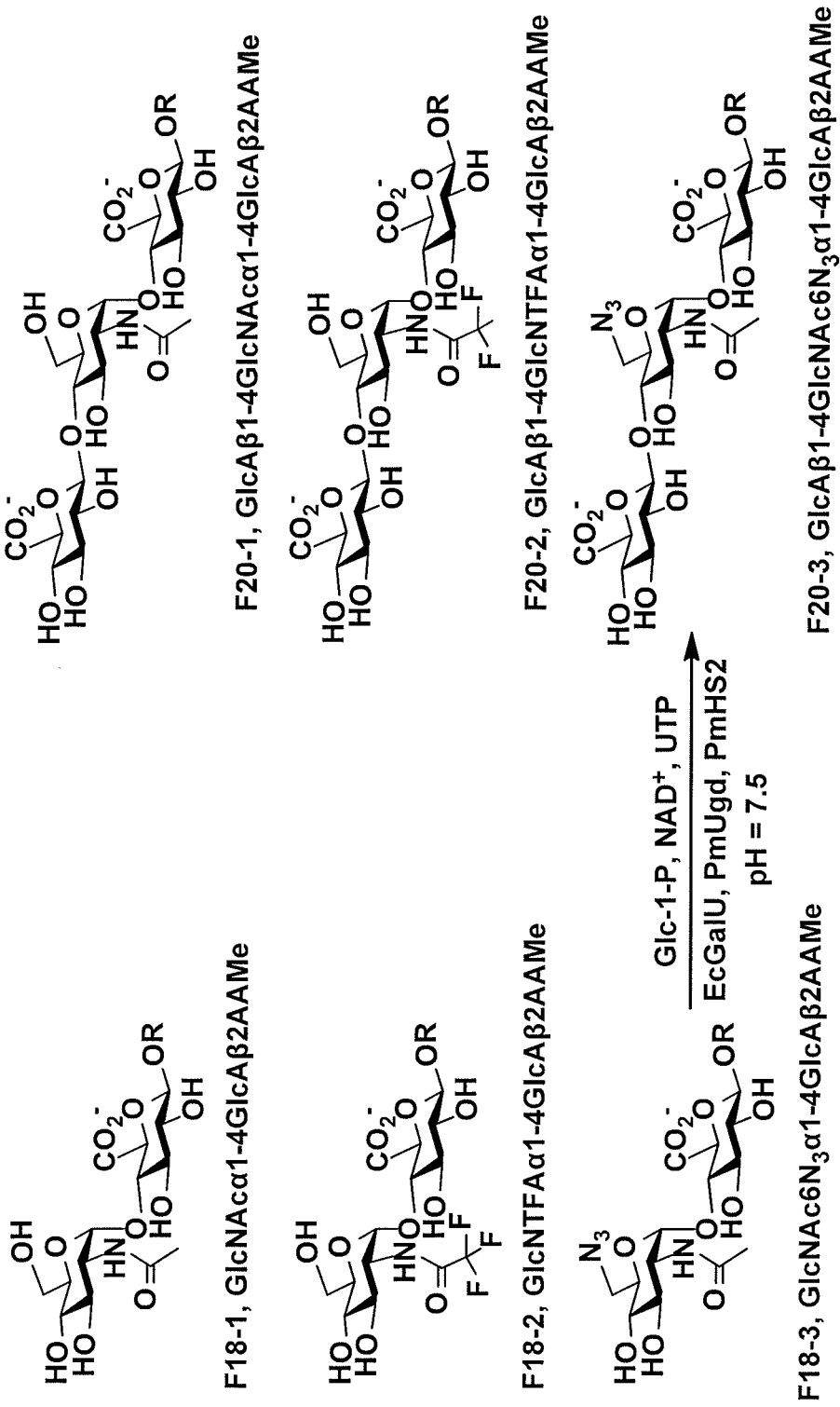
FIG. 20 shows the one-pot three-enzyme synthesis of trisaccharides GlcAβ1-4GlcNAcα1-4GlcAβ2AAMe (F20-1), GlcAβ1-4GlcNTFAα1-4GlcAβ2AAMe (F20-2), GlcAβ1-4GlcNAc6N$_3$α1-4GlcAβ2AAMe (F20-3), GlcAβ1-4GlcNGcα1-4GlcAβ2AAMe (F20-4), GlcAβ1-4GlcNAcN$_3$α1-4GlcAβ2AAMe (F20-5), GlcAβ1-4GlcNAc6NGcα1-4GlcAβ2AAMe (F20-6).

Acceptor specificity of the β1-4GlcA transferase activity of PmHS2 was also explored in one-pot three-enzyme system, as shown in FIG. 19. The first enzyme was a glucose-1-phosphate uridylyltransferase (GalU) which catalyzes the reversible conversion of Glc-1-P in the presence of UTP to produce UDP-Glc and inorganic pyrophosphate. The second enzyme was a UDP-glucose dehydrogenase (Ugd) for oxidation of 6-OH in glucose residue of UDP-Glc to form the UDP-glucuronic acid (UDP-GlcA) in the presence of its coenzyme NAD$^+$. The third enzyme is PmHS2 transferring GlcA from UDP-GlcA for the formation of β1-4 linkage. As shown in FIG. 20, trisaccharides GlcAβ1-4GlcNAcα1-4GlcAβ2AAMe F20-1, GlcAβ1-4GlcNAc6N$_3$α1-4GlcAβ2AAMe F20-3, GlcAβ1-4GlcNAcN$_3$α1-4GlcAβ2AAMe F20-5 were synthesis by small-scale reaction and analyzed by HPLC method in 100%, 100% and 95% yields, respectively. The relative low yield (72%) for the formation of GlcAβ1-4GlcNTFAα1-4GlcAβ2AAMe F20-2 was due to the formation of byproduct GlcAβ1-4GlcNH$_2$α1-4GlcAβ2AAMe in which the TFA group was removed. Disaccharide F18-4 with N-glycolyl group in C2 position of glucosamine residue acts as a good acceptor for PmHS2, leading to the formation of GlcAβ1-4GlcNGcα1-

4GlcAβ2AAMe F20-4 in 75% yield, but the disaccharide F18-6 with N-glycolyl group in C6 position of GlcNAc was converted to trisaccharide GlcAβ1-4GlcNAc6NGcα1-4GlcAβ2AAMe F20-6 only in 14% yield. Taken together, these results indicate that the donor and acceptor substrate activity of PmHS2 can tolerate a limited number of modifications on C-2 and C-6 position of glucosamine residue.

Figure 21:
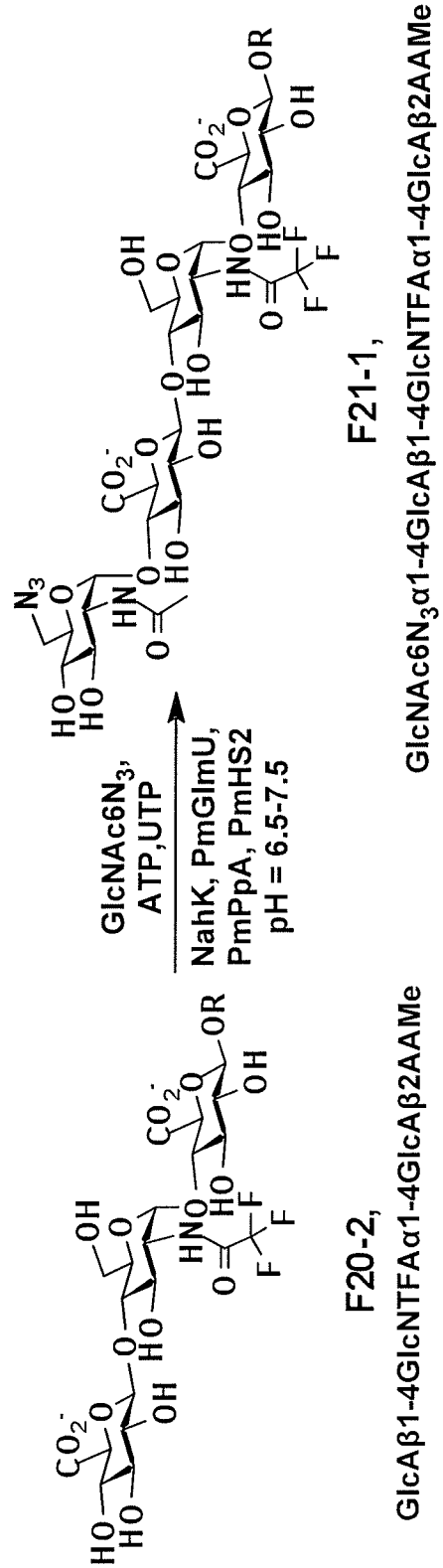
FIG. 21 shows the one-pot four-enzyme synthesis of tetrasaccharide GlcNAc6N$_3$α1-4GlcAβ1-4GlcNTFAα1-4GlcAβ2AAMe (F21-1) from trisaccharide GlcAβ1-4GlcNTFAα1-4GlcAβ2AAMe (F20-1).

Preparative-scale synthesis of trisaccharide F20-2 was also achieved. The removal of TFA group was significantly reduced when the pH of the reaction mixture was change for 7.5 to 7.0, and the yield increased to 87% from 72%. Trisaccharide F20-2 was used as the starting material for the synthesis of the tetrasaccharide F21-1 (FIG. 21). In the one-pot four-enzyme system, monosaccharide GlcNAc6N$_3$ was converted to GlcNAc6N$_3$-1-P by NanK, followed by the formation of UDP-GlcNAc6N$_3$ by PmGlmU, and transferred to trisaccharide F20-2 to obtain GlcNAc6N$_3$α1-4GlcAβ1-4GlcNTFAα1-4GlcAβ2AAMe F21-1 in 93% yield.

Figure 22:
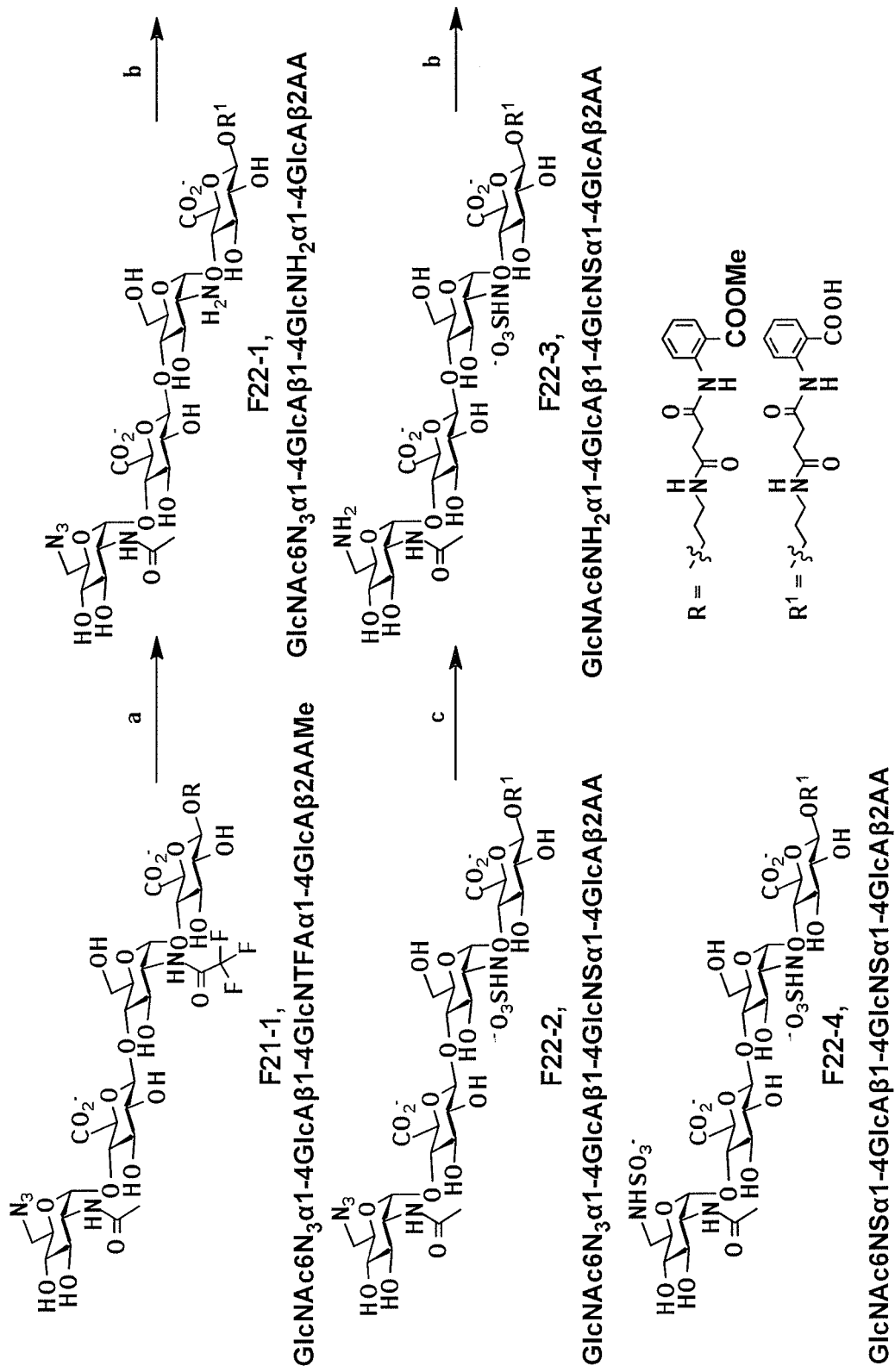
FIG. 22 shows the synthesis of tetrasaccharides GlcNAc6N$_3$α1-4GlcAβ1-4GlcNH$_2$α1-4GlcAβ2AA (F22-1), GlcNAc6N$_3$α1-4GlcAβ1-4GlcNSα1-4GlcAβ2AA (F22-2), GlcNAc6NH$_2$α1-4GlcAβ1-4GlcNSα1-4GlcAβ2AA (F22-3), GlcNAc6NSα1-4GlcAβ1-4GlcNSα1-4GlcAβ2AA (F22-4) from GlcNAc6N$_3$α1-4GlcAβ1-4GlcNTFAα1-4GlcAβ2AAMe (F21-1) by chemical modifications. Reagents and conditions: (a) K$_2$CO$_3$, H$_2$O, r.t. overnight, 81%; (b) Py.SO$_3$, 2 M NaOH, H$_2$O, 3d, 70%; (c) H$_2$, Pd/C, MeOH, H$_2$O, 1 h.

The N-TFA group as well as the N$_3$ group can be easily converted to a free amine, allowing sequential sulfation to generate a diverse array of HS tetrasaccharides. As shown in FIG. 22, the N-TFA group at C2 of internal GlcNTFA residue of tetrasaccharide F21-1 was removed under mild basic conditions to produce GlcNAc6N$_3$α1-4GlcAβ1-4GlcNH$_2$α1-4GlcAβ2AA F22-1 in 81% yield. As the removal of TFA group was accompanied by demethylation in methyl carboxylic ester, tetrasaccharide F22-1 contain a free carboxyl acid in 2AA motif instead of carboxylic ester in tetrasaccharide F21-1. Conversion of F22-1 to GlcNAc6N$_3$α1-4GlcAβ1-4GlcNSα1-4GlcAβ2AA F22-2 (70%) needed a larger excess of sulfating reagent (60 equiv.) and prolonged reaction time (3 d). Catalytic hydrogenation of the azido group at the C6 of non-reduced end GlcNAc6N$_3$ generated GlcNAc6NH$_2$α1-4GlcAβ1-4GlcNSα1-4GlcAβAA F22-3 and followed by the sulfation to produce GlcNAc6NSα1-4GlcAβ1-4GlcNSα1-4GlcAβ2AA F22-4.

Example 9

Preparation of GlcA-TEG-PABA-Biotin

Figure 15:
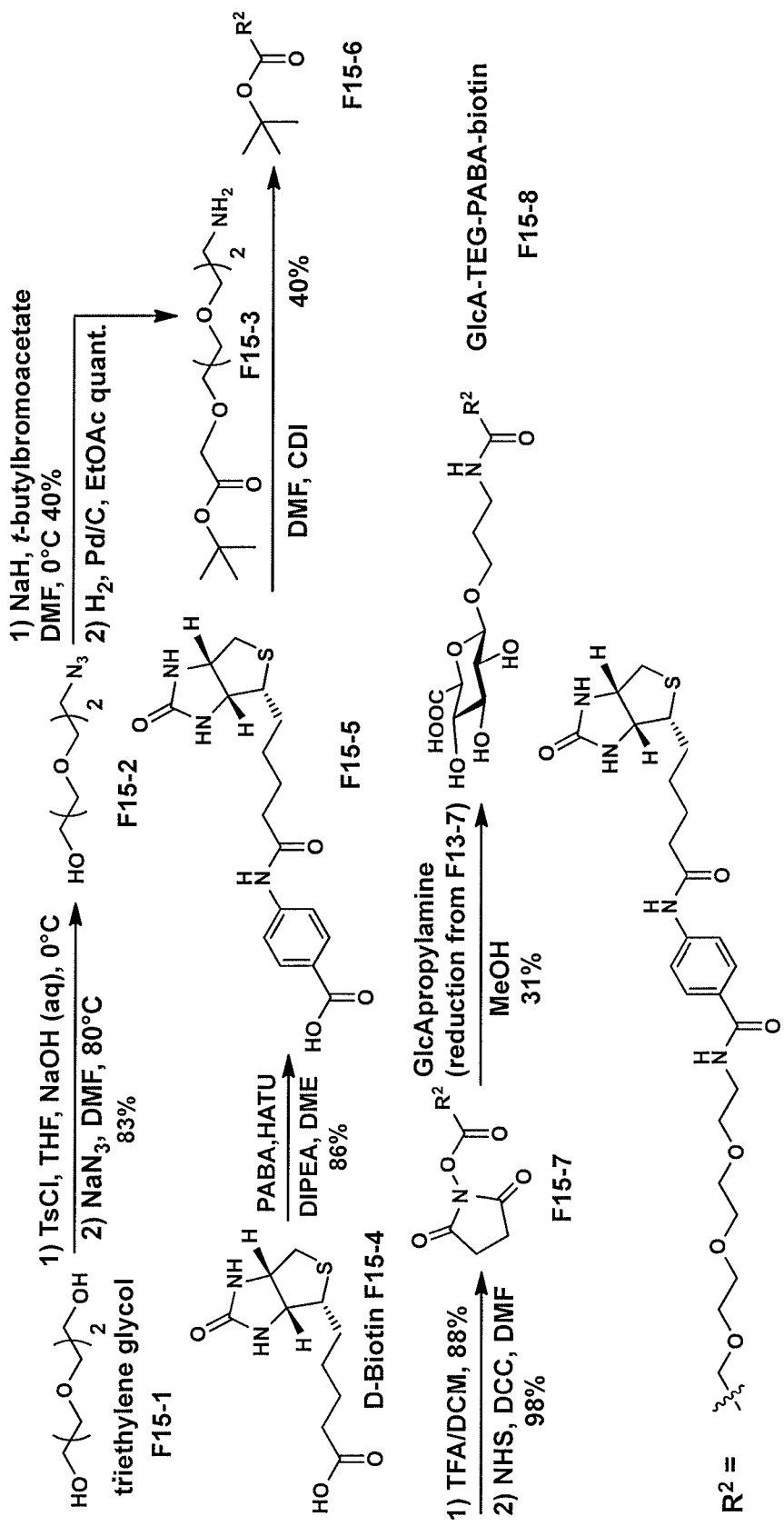
FIG. 15 shows the synthesis of GlcA-TEG-PABA-biotin (F15-8).

The synthesis was conducted as outlined in FIG. 15.

2-(2-(2-Tosylethoxy)ethoxy)ethanol. Compound F15-1 (51 grams) was dissolved in 10 mL of water containing 2.2 grams of NaOH. The reaction mixture was cooled in an ice bath. To the reaction mixture tosyl chloride (6.5 g, 34.1 mmol) in 80 mL of THF was added drop-wisely in 1 hr period. The reaction was left in ice bath off for 2 hr. The reaction was worked up with 150 mL of DCM and 150 mL of cold water. The organic layer was collected and saved. The aqueous layer was extracted twice with DCM (150 mL) and the organic layers were collected and washed twice with water (200 mL). The organic portions were combined, dried with magnesium sulfate, and rotovoped to provide crude 2-(2-(2-tosylethoxy)ethoxy)ethanol (9.684 grams, 93% yield).

Compound F15-2. 2-(2-(2-Tosylethoxy)ethoxy)ethanol (9.684 g, 31.8 mmol) was dissolved in 25 mL of DMF. Sodium azide (10.34 g, 159.1 mmol) was added to the reaction solution. The reaction was left for 3 h at 80° C. The reaction mixture was worked up with EtOAc/water. The organic layer was collected and dried over magnesium sulfate and purified by silica gel column (Hexane:EtOAc=2:1-0:1) to produce compound F15-2 (4.96 g, 89% yield).

Azidotriethylene Glycol-Boc. Compound F15-2 (2.334, 13.3 mmol) was dissolved in 40 mL of DMF and cooled in ice bath. Sodium hydride 50% immersed in mineral oil (959 mg, 19.9 mmol) was added slowly. The reaction was allowed to sit for 20 minutes followed by addition of t-butyl bromoacetate (3.93 mL, 39.9 mmol). The reaction was left for four hours and extracted with ethylacetate and water. The organics were dried over magnesium sulfate and purified by silica gel column (Hexane:EtOAc=5:1-1:1) to afford azidotriethylene glycol-Boc (1.54 g; Yield: 40%; clear oil). NMR (600 MHz, CDCl$_3$) δ 4.01 (s, 2H), 3.71-3.65 (m, 10H), 3.38-3.36 (t, J=4.5 Hz, 1H), 1.45 (s, 9H), $^{13}$C NMR (150 MHz, CDCl$_3$) δ 169.75, 81.61, 70.83, 70.79, 70.78, 70.76, 70.13, 69.15, 50.79, 28.21.

Compound F15-3. Azidotriethylene glycol-Boc (1.19 g, 4.1 mmol) was dissolved in 15 mL of ethyl acetate and of Pd/C catalyst (240 mg) was added under hydrogen gas in a double balloon. Reaction was stirred until reaction was completed as monitored by TLC. The reaction mixture was filtered over celite and the filtrate was rotovaped to afford crude compound F15-3. Yield: quant; clear oil.

Compound F15-5. D-Biotin F15-4 (538 mg, 2.2 mmol) was dissolved in 10 mL of hot DMF. The solution was allowed to cool to room temperature and HATU (838 mg, 2.2 mmol) was added and allowed to preactivate for 15 minutes. To The reaction mixture diisopropylethylamine (0.968 mL, 2.4 mmol) and para-amino benzoic acid (335 mg, 2.4 mmol) were added. Reaction was allowed to react for 24 hr in which then 70 mL of dichloromethane was added to precipitate the product. The precipitate was collected via suction filtration and washed three times with ethyl acetate (50 mL) to attain NMR pure compound F15-5 (687 mg, Yield: 86%; white solid). $^1$H NMR (600 MHz, DMSO) δ 10.19 (s, N—H), 7.88-7.86 (d, J=8.4 Hz, 2H), 7.71-7.69 (d, J=9.0 Hz, 2H), 6.46 (s, N—H), 6.38 (s, N—H), 4.32-4.29 (m, 1H), 4.15-4.12 (m, 1H), 3.13-3.10 (m, 1H), 2.83-2.80 (dd, J=12.6 Hz, 5.4 Hz, 1H), 2.59-2.57 (d, J=12.6, 1H), 2.36-2.33 (t, J=7.5 Hz, 2H), 1.67-1.34 (m, 6H). $^{13}$C NMR (150 MHz, DMSO) δ 171.75, 166.97, 162.77, 143.35, 130.38, 124.90, 118.26, 61.07, 59.22, 55.40 39.94, 36.33, 28.23, 28.11, 24.99.

Compound F15-6. Compound F15-5 (1.116 g, 3.1 mmol) was dissolved in 15 mL of DMF. carbonyldiimidazole (547 mg, 3.4 mmol) was added to reaction mixture and allowed to preactivate for 40 minutes followed by the addition of compound F15-3 (977 mg, 3.7 mmol) in 5 mL of DMF. The reaction was left at room temperature for 40 hours and was passed through silica gel column (DCM:MeOH:NH$_4$OH=9:1:0.1-1:1:0.1) to afford F15-6 (738 mg; Yield: 40%; yellow flakes). $^1$H NMR (600 MHz, DMSO) δ 10.13 (s, N—H), 8.40 (m, N—H), 7.89-7.77 (d, J=8.4 Hz, 2H), 7.65-7.64 (d, J=9.0 Hz, 2H), 6.45 (s, N—H), 6.38 (s, N—H), 4.32-4.30 (m, 1H), 4.15-4.13 (m, 1H), 3.95 (s, 2H) 3.53-3.50 (m, 10H), 3.40-3.38 (m, 2H), 3.13-3.10 (m, 1H), 2.83-2.80 (dd, J=12.6 Hz, 4.8 Hz, 1H), 2.59-2.57 (d, J=12.6, 1H), 2.34-2.31 (t, J=7.2 Hz, 2H), 1.67-1.34 (m, 15H). $^{13}$C NMR (150 MHz, DMSO) δ 171.86, 169.57, 166.07, 163.03, 141.91, 128.64, 128.06, 118.18, 80.89 70.0, 69.85, 69.83, 69.75, 69.1, 68.26, 61.28, 59.42, 55.56, 44.00, 39.25, 36.43, 28.42, 28.25, 27.90 25.19.

Compound F15-7. Compound F15-6 (701 mg) was dissolved in 7 mL mixture of DCM/TFA (2:1) and was left for 3 hr. The crude product was passed through silica gel column (DCM:MeOH:NH$_4$OH=7:3:0.1-0:1:0.1) to afford the free acid (562 mg, 88% yield). The free acid (150 mg, 0.27 mmol) and N-hydroxy succamide (32 mg, 0.3 mmol) were dissolved in hot DMF. The reaction mixture was cooled to room temperature and N,N'-dicyclohexylcarbodiimide (67 mg, 0.35 mmol) was added and left for 18 h. the reaction mixture was filtrate over celite and the filtrate was rotovaped and the triturated with diethyl ether and collected by suction filtration to afford crude compound F15-7 (172 mg; Yield: 98%; white solid).

Glucoronic acid-β-propylamine (200 mg, 0.79 mmol) (obtained by reduction from compound F13-7) and compound F15-7 (672 mg, 1.03 mmol) were dissolved in dry methanol (15 mL) and stirred overnight. The reaction mixture was rotpavoped and purified by silica gel column (DCM:MeOH: NH$_4$OH=7:3:0.1-0:1:0.1) to provide GlcA-TEG-PABA-biotin (F15-8) (192 mg; Yield: 31%; white foam). $^1$H NMR (600 MHz, D$_2$O) δ 7.74-7.73 (d, J=7.8 Hz, 2H), 7.56-7.54 (d, J=9.0 Hz, 1H), 4.56-4.54 (m, 1H), 4.39-4.38 (d, J=7.8, 1H), 4.36-4.34 (m, 1H), 3.92 (s, 2H) 3.91-3.88 (m, 1H), 3.71-3.47 (m, 18H), 3.37-3.35 (t, J=6.3 Hz, 2H), 2.94-2.91 (dd, J=12.6 Hz, 4.8 Hz, 1H), 2.74-2.72 (d, J=12.0, 1H), 2.39-2.36 (t, J=7.5 Hz, 2H), 1.80-1.38 (m, 8H), $^{13}$C NMR (150 MHz, D$_2$O) δ 175.60, 175.21, 172.09, 169.54, 165.15, 140.69, 129.21, 128.16, 120.29, 102.43, 102.02, 75.95, 75.47, 72.90, 72.87, 71.76, 70.19, 69.36, 68.74, 67.50, 61.98, 60.15, 55.29, 39.63, 39.45 36.29, 35.79, 28.37, 28.13, 27.96, 27.67, 24.93.

Example 10

Preparation of GlcAβ1-4GlcNAc Disaccharide Derivatives

PmHS2 acceptor substrate specificities using UDP-GlcA as a donor substrate and α- and β-linked GlcNAc derivatives as acceptors were studied. Conversion to the disaccharide products was estimated by LCMS and TLC analysis as outlined in Table 9 below.

TABLE 9

Reaction conditions and yields for the formation of GlcA-GlcNAc dissacharide derivatives.

| Conditions | Acceptor | | | |
|---|---|---|---|---|
| | GlcNAcα2AA (5 mM) | GlcNAcβMU (5 mM) | GlcNAcαProN$_3$ (10 mM) | GlcNAcβProN$_3$ (10 mM) |
| MES (0.1M pH 6.5) | 100 mM | 100 mM | 100 mM | 100 mM |
| MnCl$_2$ | 10 mM | 10 mM | 10 mM | 10 mM |
| UDP-GlcA | 6 mM | 6 mM | 12 mM | 12 mM |
| PmHS2 | 0.55 μg | 0.55 μg | 0.55 μg | 0.55 μg |
| Total volume | 10 μL | 10 μL | 10 μL | 10 μL |
| Reaction time/Temp | 19 h/37° C. | 19 h/37° C. | 19 h/37° C. | 19 h/37° C. |
| Product (% yield) | 33% based on HPLC (UV) | 57% based on HPLC (UV) | 30% based on TLC | 60% based on TLC |

Figure 31:
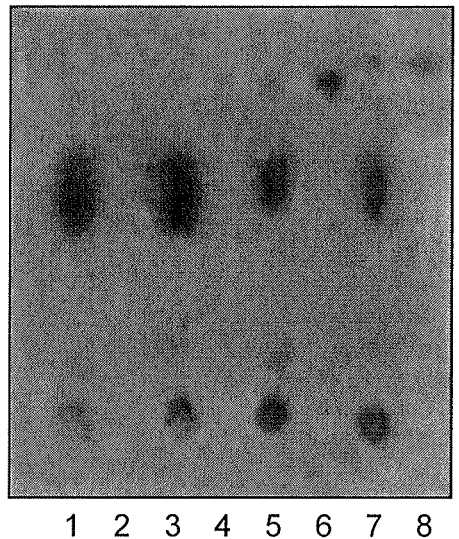
FIG. 31 shows thin-layer chromatograph analysis of PmHS2-catalyzed reaction for the formation of GlcA-GlcNAc disaccharide derivatives.

As shown in FIG. 31 and FIG. 32, TLC and LC-MS data indicated that both α- and β-linked GlcNAc with different aglycons are suitable acceptor substrates for PmHS2. Therefore, both GlcA and GlcNAc can be used as the first sugar for oligosaccharide synthesis by the methods described in this invention.

Example 11

Inhibition Assays of Monosaccharides, Disaccharides, Trisaccharides, and Tetrasaccharides Materials. Recombinant human fibroblast growth factors FGF-1, FGF-2, FGF-4, and anti-human FGF-1, FGF-2, FGF-4 were purchased from PeproTech Inc (Rocky Hill, N.J.). Heparin-biotin was from Sigma (St. Louis, Mo.). Low molecular weight heparin (LMWH) was bought from AMS Biotechnology (Lake Forest, Calif.). Alexa Fluor® 488 goat anti-rabbit IgG (H+L) was from Invitrogen (Carlsbad, Calif.). 384-Well NeutrAvidin-coated plates for the sialidase assays were from Fisher Biotech.

Methods. All assays were carried out in duplicate in 384-well NeutrAvidin coated plates. Heparin-biotin (20 μL, 2 μM) was added to each well and the plate was incubated at 4° C. for overnight. The plate was washed with 3 rounds of 1×PBS buffer containing 0.05% Tween-20 and blocked with 1% BSA (50 μL for each well) and incubated at r.t. for 30 min. After the plate was washed three times with 1×PBS buffer containing 0.05% Tween-20, each set of duplicate wells were added 20 μL of human FGF-1, FGF-2, or FGF-4 (1 μM) with or without premixing with LMWH (~22 nM or 0.1 μM), monosaccharide, or oligosaccharides (100 μM or 1 mM) and the plate was incubate at r.t. for 1 hr. After washing three times with 1×PBS buffer containing 0.05% Tween-20, anti-human FGF-1, FGF-2 or FGF-4 (20 μL) was added and the plate was incubated at r.t. for 1 hr. After the plate was washed three times with 1×PBS buffer containing 0.05% Tween-20, Alexa Fluor® 488 goat anti-rabbit IgG (H+L) (20 μL) was added and the plate was incubated at r.t. for 1 hr. After washed three times with 1×PBS buffer containing 0.05% Tween-20 and once with water, the fluorescent signals of wells in the plate were measured using a microtiter plate reader.

Figure 23:
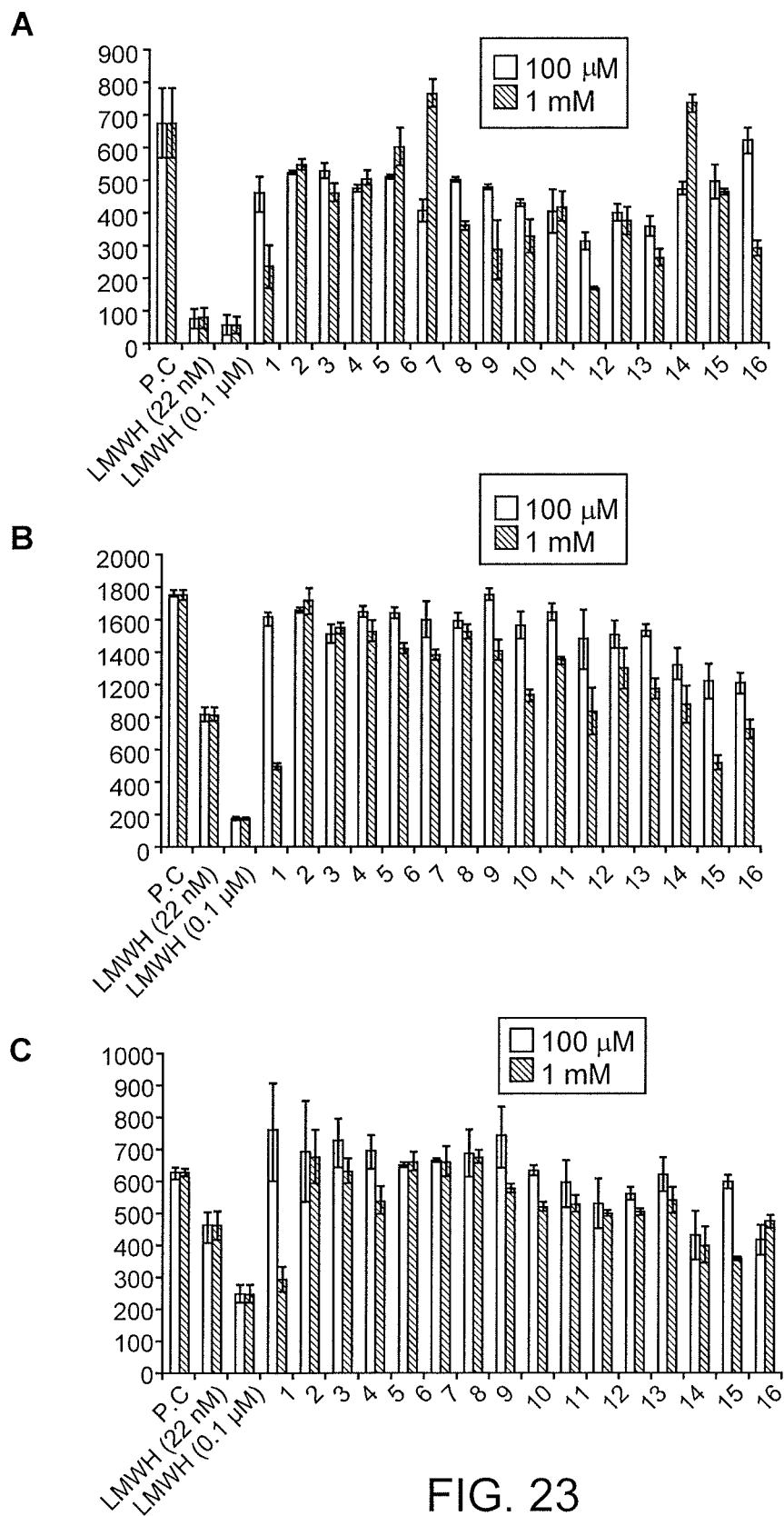
FIG. 23 shows the inhibitory activities of LMWH or compounds F24-1-F24-16 (see FIG. 24 for structures) against the binding of human fibroblast growth factors FGF-1 (FIG. 23A), FGF-2 (FIG. 23B), or FGF-4 (FIG. 23C) to the heparin-biotin immobilized on NeutrAvidin-coated 384-well plates. Samples without LMWH or monosaccharide/tetrasaccharide inhibitors were used as positive controls (P.C.).
Figure 24:
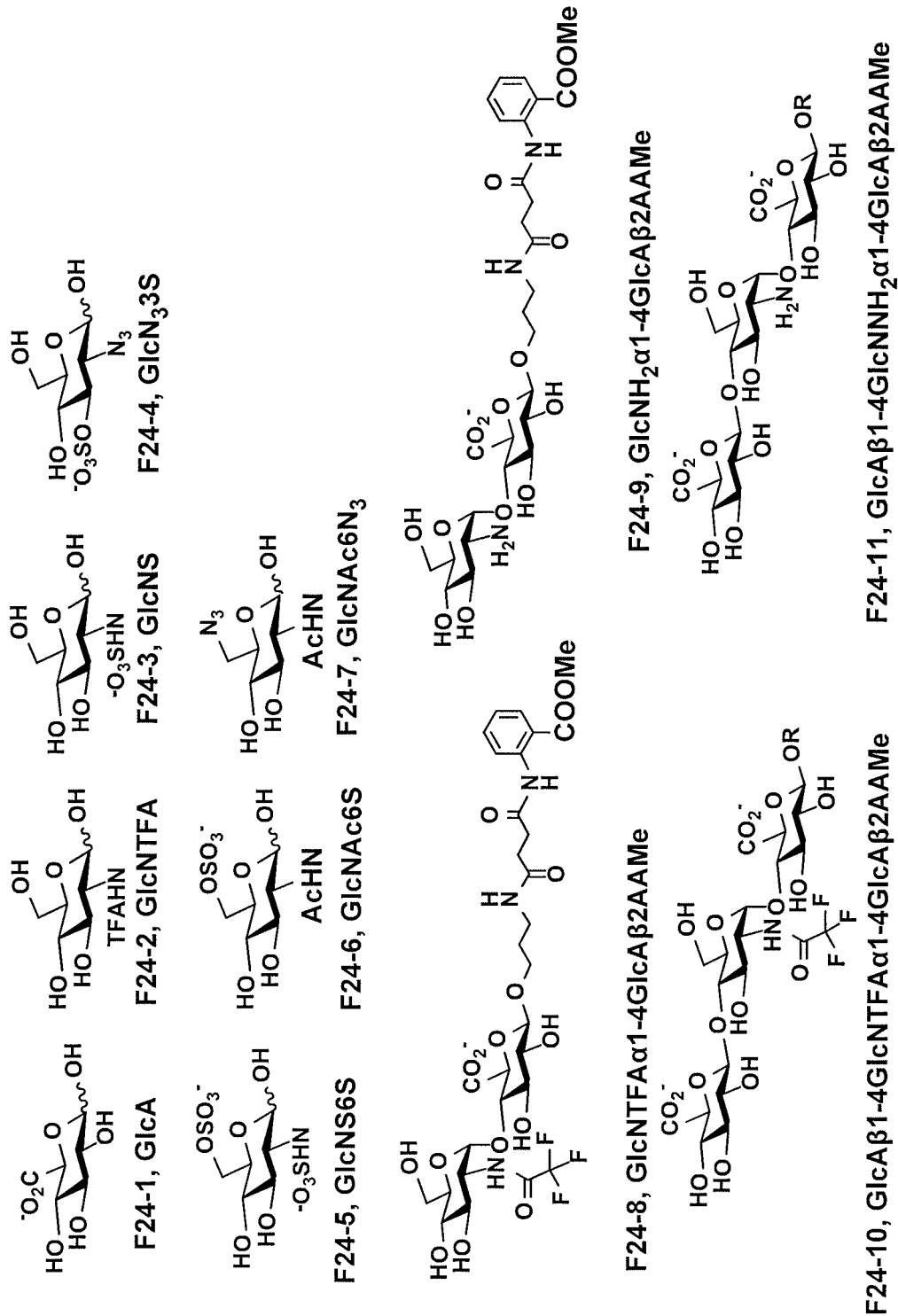
FIG. 24 shows structures of compounds F24-1-F24-16 used in FIG. 23 for inhibition studies of the binding of human fibroblast growth factors FGF-1, FGF-2, and FGF-4 to the heparin-biotin immobilized on NeutrAvidin-coated 384-well plates.
Figure 24:
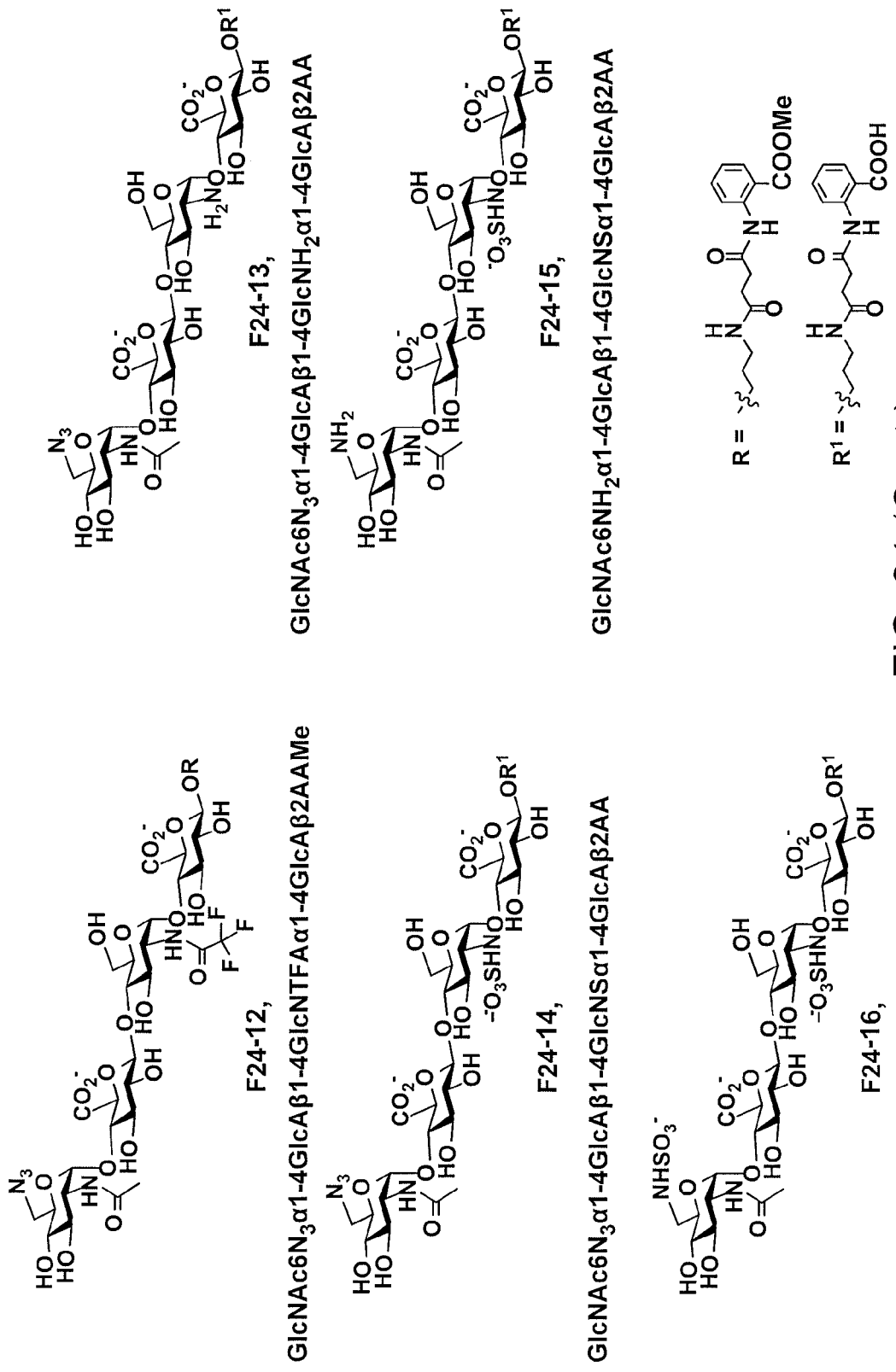

Results. LMWH was used as a control sample for testing the inhibitory activities of sixteen compounds including seven monosaccharides, two disaccharides, two trisaccharides, and five tetrasaccharides (see FIG. 24 for compound structures) against the binding of fibroblast growth factors FGF-1, FGF-2, and FGF-4 to heparin-biotin immobilized on NeutrAvidin-coated plates. See Table 10 and FIG. 23.

TABLE 10

Percentage inhibition of compounds F24-1-F24-16 (1 mM) against the binding of human FGF-1, FGF-2, and FGF-4 to heparin-biotin immobilized on NeutrAvidin-coated plates.

| Compounds | Structures | FGF-1 (% inhibition) | FGF-2 (% inhibition) | FGF-4 (% inhibition) |
|---|---|---|---|---|
| F24-1 | GlcA | 65 | 68 | 54 |
| F24-11 | GlcAβ1-4GlcNH$_2$α1-4GlcAβ2AA | 76 | — | — |
| F24-13 | GlcNAc6N$_3$α1-4GlcAβ1-4GlcNH$_2$α1-4GlcAβ2AA | 62 | — | — |
| F24-15 | GlcNAc6NH$_2$α1-4GlcAβ1-4GlcNSα1-4GlcAβ2AA | — | 68 | 43 |
| F24-16 | GlcNAc6NSα1-4GlcAβ1-4GlcNSα1-4GlcAβ2AA | 58 | 55 | — |

Example 12

Substrate Specificity of KfiA and PmHS2

Materials and Methods

PmHS2, KfiA, and related fusion proteins were expressed, purified, and characterized as described in Example 1. Reactions with UDP-sugars were carried out in duplicate at 37° C. in MES (100 mM, pH 6.5) containing UDP-GlcNAc or one of its derivatives (1 mM), GlcAβ2AA (1 mM), MnCl$_2$ (10 mM) and KfiA. (2.8 µg µl$^{-1}$) or PmHS2 (1.1 µg µl$^{-1}$) for 24 h. The reaction mixtures were stopped by adding ice-cold 10% (v/v) acetonitrile to make 100-fold dilutions and the mixtures were analyzed by HPLC as described for the pH profile.

Results

Figure 33:
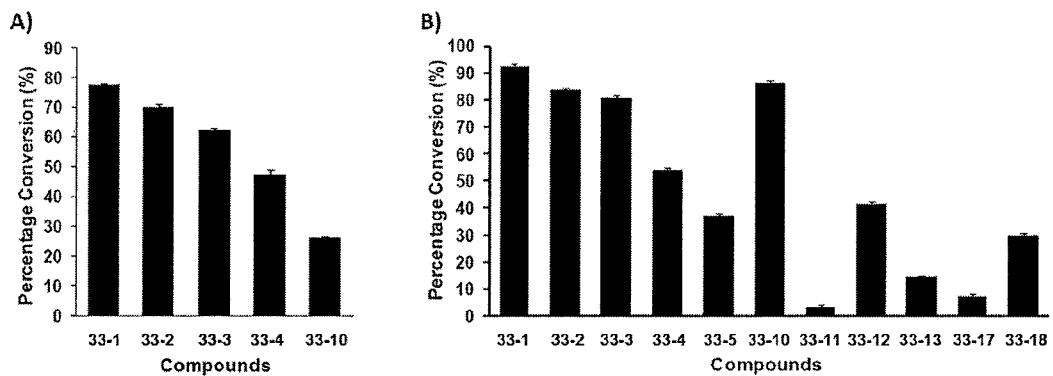
FIG. 33 shows examples of substrate specificity for the GlcNAcT activities of MBP-KfiA-His$_6$ (A) and His$_6$-PmHS2 (B). Each reaction was performed at 37° C. in MES buffer (100 mM, pH 6.5) for 24 h. Enzyme used: MBP-KfiA-His$_6$ (2.8 μg μl$^{-1}$), His$_6$-PmHS2 (1.1 μg μl$^{-1}$).

Substrate Specificity of the GlcNAcT Activities of MBP-KfiA-His$_6$ and His$_6$-PmHS2. As shown in FIG. 33, the donor substrate specificities of the α1-4-N acetylglucosaminyltransferase (α1-4GlcNAcT) activities of the recombinant MBP-KfiA-His$_6$ and His$_6$-PmHS2 were investigated using GlcAβ2AA as an acceptor and a library of twenty three UDP-sugars including UDP-GlcNAc (33-1) and its C2'- (33-2-33-9) or C6'-modified (33-10-33-16) derivatives, UDP-glucose (UDP-Glc, 33-17), UDP-N-acetylgalactosamine (UDP-GalNAc, 33-18), UDP-galactose (UDP-Gal, 33-19), UDP-N-acetylmannosamine (UDP-ManNAc, 33-20) and its derivative with a C2'-N3 modification (33-22), UDP-mannose (33-22) and its derivatives with a CT-fluorine modification (33-23). The reactions were easily analyzed by high performance liquid chromatography (HPLC) equipped with a fluorescence detector using an excitation wavelength of 315 nm and an emission wavelength of 400 nm to determine the ratio of the fluorescent disaccharide product formed and the fluorescent GlcAβ2AA acceptor. The presence of each disaccharide product was confirmed by high resolution mass spectrometry (HRMS). The catalytic efficiency of the α1-4GlcNAcT activity of His$_6$-PmHS2 was higher than that of MBP-KfiA-His$_6$ as a less molar amount of His$_6$-PmHS2 was needed to achieve the same yield under the same assay conditions. For the UDP-sugars and derivatives tested (33-1-33-23), the α1-4GlcNAcT activity of His$_6$-PmHS2 exhibited a much better tolerance towards substrate modifications than MBP-KfiA-His$_6$. For example, UDP-GlcNAc (33-1) and its C2'- (33-2-33-4) and C6'- (33-10) derivatives that can be used by MBP-KfiA-His$_6$ were also suitable donor substrates for His$_6$-PmHS2. Noticeably, UDP-GlcNAc6N3 (33-10) is a much better substrate for His$_6$-PmHS2 than MBP-KfiA-His$_6$. Some UDP-sugars including UDP-GlcNAcPh (33-5, a C2'-derivative of UDP-GlcNAc), several C6'-derivatives of UDP-GlcNAc such as UDPGlcNAc6NH$_2$ (33-11), UDP-GlcNAc6NGc (33-12), and UDP-GlcNAc6NAcN$_3$ (33-13), as well as UDP-Glc (33-17) and UDP-GalNAc (33-18) are tolerable donor substrates for His$_6$-PmHS2 but not for MBP-KfiA-His$_6$.

UDP-GlcNAc derivatives with a bulky N-diphenylacetyl group at C2' (33-6) or C6' (33-15) or with a C6'-N-phenyl acetyl substitution (33-14) were not suitable donor substrates for either MBP-KfiAHis$_6$ or the α1-4GlcNAcT activity of His$_6$-PmHS2. It seems that the N-acyl groups at CT of UDP-GlcNAc derivatives are quite important for recognition by His$_6$-PmHS2 as donor substrates. For example, UDP-GlcN$_3$ (33-7) with a C2'-azido group substitution and UDP-GlcNH$_2$ (33-8) with a C2'-amino group substitution were not acceptable donor substrates by MBP-KfiA-His$_6$ or the al-4GlcNAcT activity of His$_6$-PmHS2. In addition, N-sulfation at C2' (33-9) or O-sulfation at C6' (33-16) also block the activities of both MBP-KfiA-His$_6$ and His$_6$-PmHS2. UDP-Gal (33-19), UDPManNAc (33-20), UDP-mannose (33-22) and their derivatives (33-21 and 33-23) were not tolerable substrate for either enzymes.

Example 13

Preparation of UDP-Uronic Acid Compounds Using a One-Pot Multi-Enzyme System

Materials. The cDNA library of *Arabidopsis thaliana* was purchased from AMS Biotechnology (Lake Forest, Calif., USA). Restriction enzymes including NdeI and BamHI were purchased from New England BioLabs (Beverly, Mass., USA). Vector pET22b+ was purchased from Novagen (EMD Biosciences Inc., Madison, Wis., USA). Herculase-enhanced DNA polymerase was purchased from Stratagene (La Jolla, Calif., USA). T4 DNA ligase and 1 kb DNA ladder were from Promega (Madison, Wis., USA). Ni$^{2+}$-nitrilotriacetic acid (NTA) agarose, QIAprep spin miniprep kit and QIAquick gel extraction kit were purchased from Qiagen (Valencia, Calif., USA). Bicinchoninic acid (BCA) protein assay kit was from Pierce Biotechnology, Inc. (Rockford, Ill., USA). *Escherichia coli* DH5 (electrocompetent cells and BL21 (DE3) chemically competent cells were purchased from Invitrogen (Carlsbad, Calif., USA).

Galactose (Gal), N-Acetylgalactosamine (GalNAc), N-Acetylglucosamine (GlcNAc), Mannose (Man), N-Acetylmannosamine (ManNAc), Xylose (Xyl) were purchased from Sigma Aldrich (Saint Louis, Mo., USA). GalNAcα/βProN$_3$ were chemically synthesized in the group.

Cloning. To clone full length *Arabidopsis thaliana* glucuronokinase (EC 2.7.1.43) (AtG1 cAK) (encoded by gene GLCAK1, DNA GenBank accession number: NM_111030, locus tag: AT3G01640; protein GenBank accession number: NP_566144) into pET22b+, forward primer used was 5' ACGCGTCGACATGGATCCGAATTCCACGG 3' (SalI restriction site is bold and underlined) and reverse primer was 5' CCG<u>CTCGAG</u>TAAGGTCTGAATGTCAGAATCATTC 3' (XhoI restriction site is bold and underlined). Polymerase chain reaction (PCR) were performed in 50 μL total volume containing 200 ng of cDNA library, 0.2 μM of forward and reverse primers, 5μL of 5 X Herculase II buffer, dNTP mixture (0.2 mM), and 5 U of Herculase II DNA polymerase. The reaction was performed at an annealing temperature of 58 ° C. for 32 cycles. The PCR products were digested with SalI and XhoI, purified, and ligated at 16 ° C. overnight with pET22b+ vector predigested with SalI and XhoI. The ligated product was transformed into electrocompetent *E. coli* DH5α cells. Selected clones were grown for minipreps and positive clones were verified by restriction mapping and DNA sequencing performed by Davis Sequencing Facility.

Protein expression and purification. The plasmid containing GLCAK1 was transformed into *E. coli* BL21 (DE3) chemically competent cells for protein expression. *E. coli* cells harboring the pET22b-AtGlcAK plasmid were cultured in LB medium (10 g/L tryptone, 5 g/L yeast extract, and 10 g/L NaCl) with ampicillin (100μg /mL) at 37 ° C. with rigorous shaking at 250 rpm in a C25KC incubator shaker (New Brunswick Scientific, Edison, N.J.) until the $OD_{600\ nm}$ of the culture reached 0.8-1.0. Overexpression of the targeted proteins was achieved by adding 0.15 mM of isopropyl-1-thio-β-D-galactopyranoside (IPTG) followed by incubation at 18 ° C. for 20 h with rigorous shaking at 250 rpm.

$His_6$-tagged (SEQ ID NO:22) protein was purified from cell lysate using $Ni^{2-}$-NTA affinity column. To obtain cell lysate, cells were harvested by centrifugation at 4,000 rpm (Sorvall) at 4 ° C. for 2 h. The cell pellet was resuspended in lysis buffer (pH 8.0, 100 mM Tris-HCl containing 0.1% Triton X-100). Lysozyme (100μg/mL) and DNase I (5 μg/mL) were added to the cell suspension. The mixture was incubated at 37 ° C. for 1 h with vigorous shaking (200rpm). Cell lysate was obtained as the supernatant by centrifugation at 12,000 rpm (Sorvall) at 4° C. for 20 min. Purification was performed by loading the supernatant onto a $Ni^{2+}$-NTA column pre-equilibrated with 10 column volumes of binding buffer (40 mM imidazole, 0.5 M NaCl, 50 mM Tris-HCl, pH 7.5). The column was washed with 10 column volumes of binding buffer and 10 column volumes of washing buffer (40 mM imidazole, 0.5 M NaCl, 50 mM Tris-HCl, pH 7.5). Protein of interest was eluted with Tris-HCl (pH 7.5, 50 mM) containing imidazole (200 mM) and NaCl (0.5 M). The fractions containing the purified enzyme were collected and dialyzed against Tris-HCl buffer (pH 7.5, 25 mM) containing 10% glycerol and 0.25 M NaCl. Dialyzed proteins were stored at 4 ° C. Alternatively, fractions containing purified enzyme were dialyzed against Tris-HCl buffer (pH 7.5, 25 mM) and freeze dried.

pH Profile. Typical enzymatic assays for pH profile studies were performed in a total volume of 20 μL containing GlcA (10 mM), ATP (10 mM), $MgCl_2$ (20 mM) and AtGlcAK (412 ng) in various buffers (200 mM) with pH varying from 5.0 to 10.0. All reactions were allowed to proceed for 15 min at 37° C. The reaction mixture was quenched by boiling water bath for 1 min followed by adding 20 μL of ice cold 95% (v/v) ethanol. The samples were then centrifuged at 13,000 rpm for 2 min, and kept on ice until analyzed by a Beckman Coulter P/ACE MDQ Capillary Electrophoresis (CE) system equipped with a UV detector. A 50 cm capillary tubing (75 μm I.D., Beckman Coulter) was used. Assays were run at 25 kV with 25 mM sodium borate buffer (pH 9.8) for 22 min. Percent conversions were calculated from the ratios of ATP and ADP, which were determined by UV absorbance at 254 nm. All assays were carried out in duplicate, and standard deviations were used to represent errors.

Effects of Metal Ions and EDTA. EDTA (5 mM), 20 mM of various divalent metal salts ($CaCl_2$, $CoCl_2$, $CuSO_4$, $MnCl_2$, $ZnCl_2$) were mixed in a MOPS buffer (pH 7.5, 100 mM) to analyze their effects on the kinase activity of AtGlcAK (412 ng) in 20 μL total volume containing 10 mM of ATP and GlcA. Reaction without EDTA or metal ions was used as a control. Reactions were quenched and assayed using the same method as those for pH profile. All reactions were performed in duplicate, and standard deviations were used to represent errors.

Substrate Specificity Assays. Substrate specificity assays were performed under two conditions: low enzyme concentration assays are performed in 20 μL reaction mixture containing 10 mM ATP, 10 mM sugar substrate, 20 mM $MgCl_2$, 100 mM MOPS pH 7.5 and 412 ng AtGlcAK at 37° C. for 15 min, while high enzyme concentration assays are performed in 20 μL reaction mixture containing 10 mM ATP, 10 mM sugar substrate, 20 mM $MgCl_2$, 100 mM MOPS pH 7.5 and 2.1 μg AtGlcAK at 37 t for 60 min. The reactions were quenched and assayed with the same method as those for pH profile. All reactions were performed in duplicates.

Kinetics Assays. Kinetic parameters of GlcA were assayed in duplicate in reaction mixture of 20 μL, containing 100 mM MES buffer (pH 7.5), 20 mM of $MgCl_2$, 10 mM of ATP, different concentration of GlcA (0.5, 1.0, 2.0, and 5.0 mM, 10 mM and 20 mM), and AtGlcAK (206 ng). All reactions were allowed to proceed at 37° C. for 15 min. Reaction with no GlcA was used as negative control. The apparent kinetic parameters were obtained by fitting the experimental data (average values of duplicate assays) into the Michaelis-Menten equation using Grafit 5.0.

Kinetic parameters of ATP were assayed in duplicate in reaction mixture of 20 μL containing 100 mM MES buffer (pH 7.5), 20 mM of $MgCl_2$, 10 mM of GlcA, different concentration of ATP (0.5, 1.0, 2.0, and 5.0 mM, 10 mM and 20 mM), and AtGlcAK (206 ng). All reactions were allowed to proceed at 37° C. for 15 min. Reaction with no GlcA was used as negative control. The apparent kinetic parameters were obtained by fitting the experimental data (average values of duplicate assays) into the Michaelis-Menten equation using Grafit 5.0.

All assays were performed in a Beckman Coulter P/ACE MDQ Capillary Electrophoresis System (Fullerton, Calif., USA) equipped with a UV detector. Reactions were stopped by adding 25 μL of ice-cold ethanol, centrifuged at 13,000 rpm for 2 min, and kept on ice until aliquots of 154 were transferred into micro sample vials and subjected to CE analysis. ATP samples with higher concentrations are further diluted before injection. An eCAP Capillary Tubing (50 cm effective length, 75 μm I.D., 375 μm O.D.) from Beckman Coulter was used to separate ATP and ADP in a 25 mM sodium borate buffer (pH 9.8) under 25 kV voltages. Sample injections were achieved by pressurizing sample vial to 0.5 psi for 6 sec. Separations were achieved within 22 min and percent conversions were calculated from the ratios of sugar nucleotides and nucleotide triphosphates, which were determined by UV absorbance at 254 nm.

LC-MS Analysis of AtGlcAK Activity. The product formation was monitored by LC-MS using a LC-2010AXL High Performance Liquid Chromatography (HPLC) system linked with a LCMS-2020 mass spectrometer (Shimadzu Scientific instrument Inc., Columbia, Md.). Liquid nitrogen was used as nitrogen gas source. A Shimadzu C18 column (5 μm particle size, 4.6 mm×50 mm) was used to clean up the reaction. Mobile phase consists of 30% acetonitrile (ACN) in water.

The flow rate was set at 0.8 ml/min. Each run was set for 6 minutes and mass spectrometer was set to scan the range from 190 to 600 Da per second.

Results

Cloning, expression and purification of AtG1cAK. Full length *Arabidopsis thaliana* glucuronokinase (EC 2.7.1.43) (AtG1cAK) was amplified from the cDNA library of *Arabidopsis thaliana*, cloned in pET15b vector, and expressed as an N-His$_6$-tagged (SEQ ID NO:22) fusion protein. Positive clones were verified by restriction mapping and DNA sequencing performed by Davis Sequencing Facility. The DNA sequence of the insert matched to the reported G1cAK1gene.

Figure 34:
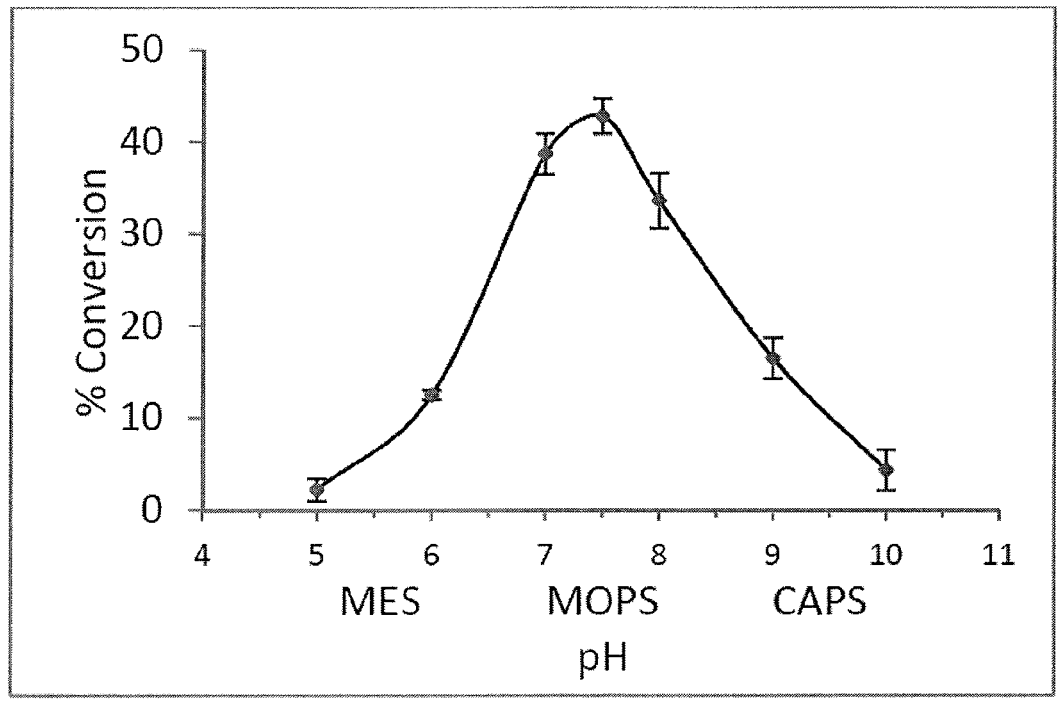
FIG. 34 shows the pH profile for AtGlcAK.

N-terminal His$_6$-tagged (SEQ ID NO:22) protein was overexpressed in *E. coli* BL21(DE3) using Luria-Bertani (LB) media. The recombinant protein was then purified from cell lysate using Ni$^{2+}$-NTA affinity column. According to SDS-PAGE analysis, the recombinant protein of around 42 kDa (calculated molecular mass 42.2 kDa) can be obtained effectively in high purity. The fractions containing the purified enzyme were collected and dialyzed against Tris-HCl buffer (pH 7.5, 20 mM) containing 30% glycerol. Dialyzed proteins were stored at −20° C. Alternatively, fractions containing purified enzyme were dialyzed against Tris-HC1 buffer (pH 7.5, 20mM) and lyophilized. On average, 65 mg of purified protein was obtained from 1 liter of cell culture.

pH Profile. A pH profile study of AtGlcAK was performed on a capillary electrophoresis (CE) system using Glucuronic acid (GlcA) and ATP as substrate. The reaction mixture also contains MgCl$_2$ (20 mM). UV absorbance at 254 nm was used for quantification. Percentage conversions of ATP to ADP were used to represent the progress of the reaction. AtGlcAK has a relatively narrow pH range (FIG. 34), with an optimal pH of 7.5. The activity dropped fast below 7.0 or above 8.0. No activity detectable below pH 5.0 or above 10.0.

Figure 35:
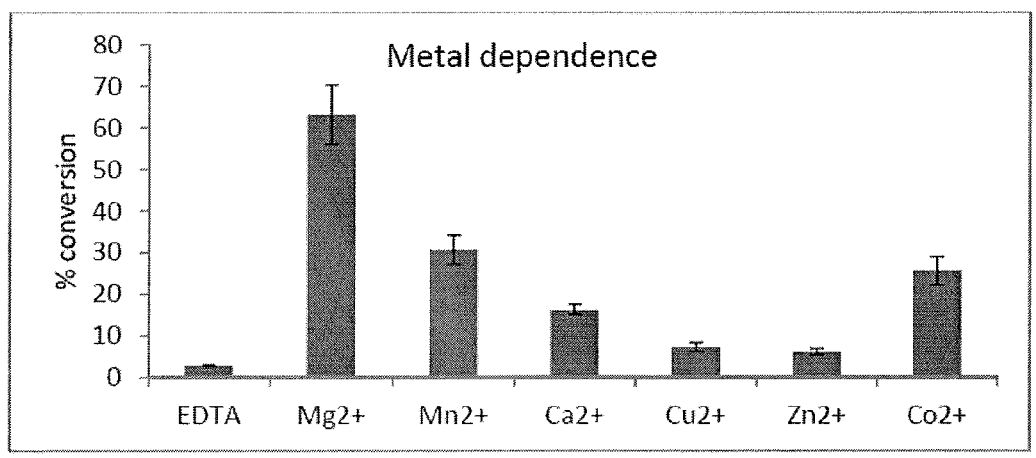
FIG. 35 shows the metal dependence of AtGlcAK-catalyzed glucuronic acid phosphorylation.

EDTA and Metal Effects. Metal dependence of AtGlcAK was assayed following a similar assay method (FIG. 35). With the presence of EDTA, AtGlcAK shows no kinase activity towards GlcA. Divalent metal (Mg$^{2+}$, Mn$^{2+}$, Ca$^{2+}$ or Co$^{2+}$) is required for its activity. However, Cu$^{2+}$ and Zn$^{2+}$ do not fit in the catalytic site very well.

Substrate Specificity of AtGlcAK.

Substrate specificity of AtGlcAK was assayed using a capillary electrophoresis (CE) system, using ATP and a variety of monosaccharides (Table 11). It is very obvious that the carboxylic acid at C6 of the sugar substrate is critical for binding to the AtGlcAK. Only those acidic monosaccharides can be phosphorylated by AtGlcAK with detectable yields.

TABLE 11

Substrate specificity of AtGlcAK

| | Percentage conversion of ATP (%) | |
|---|---|---|
| Substrate | Low enzyme Conc. (412 ng in 20 µL, 15 min, 37° C.) | High enzyme Conc. (2.1 µg in 20 µL, 60 min, 37° C.) |
| GlcA | 61.5 | N.A. |
| GalA | 6.2 | 15.3 |
| IdoA | N.D. | N.D. |
| Glc | N.D. | <5 |
| Gal | N.D. | N.D. |
| Man | N.D. | N.D. |
| Xyl | N.D. | <5 |
| Ara | N.D. | N.D. |

N.A.: Not Assayed;
N.D. Not Detected.

Figure 36:
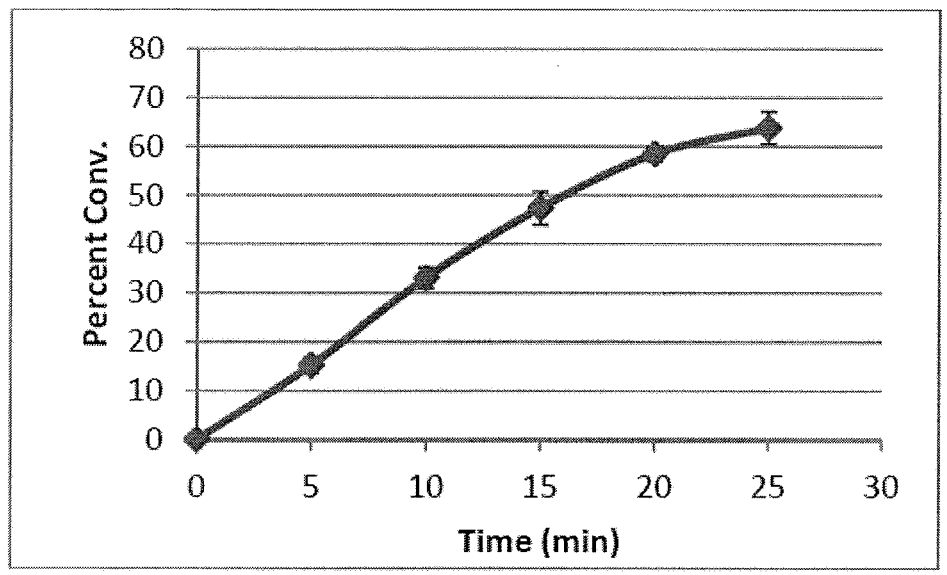
FIG. 36 shows the time-course profile for an AtGlcAK-catalyzed glucuronic acid phosphorylation reaction.

Kinetics Assays of AtGlcAK. Kinetic studies for the glucuronokinase activity of AtGlcAK with GlcA have been performed (Table 12). The enzyme amount was adjusted so that with 10 mM of ATP and GlcA, at 15 min the reaction rate was still in its linear range and the ATP conversion was relatively high. The reaction rate started to slow down after 20 min (FIG. 36).

TABLE 12

Kinetic parameters of AtGlcAK

| | $k_{cat}$ (s$^{-1}$) | $K_m$ (mM) | $k_{cat}/K_m$ (mM$^{-1}$s$^{-1}$) |
|---|---|---|---|
| ATP | 26.8 | 1.1 | 24.4 |
| GlcA | 25.4 | 1.3 | 19.5 |

LC-MS Analysis of AtGlcAK Activity. The AtGlcAK kinase activity was confirmed by LC-MS under negative mode. The peak of 273.05 represents [M−H]−, whereas the peak of 295.05 represents [M+Na−2H]− of the product. The reaction did not go to completion with a 1:1 ratio of ATP: GlcA. Complete conversion can be achieved with an excess amount of ATP.

Preparative Synthesis of Oligosaccharides Using AtGlcAK. The GlcA-1-P generated from AtGlcAK was used by a UDP-sugar pyrophosphorylase (BLUSP) in a one-pot multiple-enzyme to form UDP-GlcA, which is then used as substrate by a chondroitin synthase from *Pasteurella multocida* (PmCS), a hyaluronan synthase from *Pasteurella multocida* (PmHAS), or a heparosan synthase from *Pasteurella multocida* (PmHS2). PmCS is a polymerase which catalyzes the alternating addition of GlcAβ1-3 and GalNAcβ1-4 onto an oligosaccharide chain. GlcAβ1-3GalNAcβProN$_3$, a disaccharide derivative, was generated by *Pasteurella multocida* chondroitin sulfate (PmCS)-catalyzed reaction using GalNAcβProN$_3$ as an acceptor using a one-pot four-enzyme system containing AtGlcAK, BLUSP, *Pasteurella multocida* inorganic phosphatase (PmPpA), and PmCS. PmHAS is a polymerase which catalyzes the alternating addition of GlcAβ1-3 and GlcNAcβ1-4 onto an oligosaccharide chain. Similar to that described for the PmCS-catalyzed reaction, GlcAβ1-3GlcNAcβProN$_3$, a disaccharide derivative, was generated by *Pasteurella multocida* hyaluronan synthase (PmHAS)-catalyzed reaction using GlcNAcβProN$_3$ as an acceptor using a one-pot four-enzyme system containing AtGlcAK, BLUSP, *Pasteurella multocida* inorganic phosphatase (PmPpA), and PmHAS. Similarly, GlcAβ1-4GlcNAcα1-4GlcAβProN$_3$ trisaccharide was produced by a one-pot four-enzyme system containing AtGlcAK, BLUSP, PmPpA, and the β1-4-glucuronyltransferase (β1-4-GlcAT) activity of *Pasteurella multocida* heparosan synthase 2 (PmHS2)-catalyzed reaction using GlcNAcα1-4GlcAβ-ProN$_3$ as an acceptor. These demonstrated the important application of AtGlcAK in one-pot multienzyme chemoenzymatic synthetic schemes for synthesizing GlcA-containing compounds and possibly for other uronic acid-containing structures.

Example 14

Synthesis and Biological Activity of Novel Disialyl Hexasaccharides

As discussed above, HMOs have the potential for important therapeutic uses. Most of the HMO-related studies reported so far, however, used mixtures of HMOs and thus the key active components of HMOs are not clear. Also except for a few, the functions of individual HMOs are not well understood. This is mainly due to the lack of access to pure oligosaccharides in amount large enough for research, preclinical, and clinical studies. The present invention provides efficient enzymatic methods for obtaining biologically important HMOs and derivatives.

DSLNT contains two sialic acid residues: one is linked to the terminal galactose (Gal) residue via an α2-3-sialyl linkage; the other is linked to the internal N-acetylglucosamine (GlcNAc) residue via an α2-6-sialyl linkage. Despite recent advances in the development of chemical methods for synthesizing sialic acid-containing structures, sialosides remain to be challenging targets for chemical synthesis due to the intrinsic structural feature of sialic acids (e.g. steric hindered anomeric carbon with an electron-withdrawing carboxyl group in the sialic acid which lowers the glycosylation efficiency and the lack of a neighbouring participating group that disallow the control of the stereospecificity in the formation of sialyl bonds). Therefore, chemical synthesis of DSLNT in a free oligosaccharide oligosaccharide form has so far not been reported although a glycosyl ceramide containing the same glycan portion was reported by the Kiso group. Furthermore, despite the identification of the activity of an α2-6-sialyltransferase that catalyzes the formation of the α2-6-linked sialic acid on the internal GlcNAc residue in DSLNT (e.g. in the livers of various animals and human as well as in human placenta, bovine mammary gland, human milk, and human mammary tumor although at a lower level), the gene for the enzyme has yet to be determined. Therefore, it is currently unfeasible to obtain the desired α2-6-sialyltransferase in large amount via cloning to allow enzymatic synthesis of DSLNT in large scale.

One feasible strategy is to identify compounds that have similar or better effects than DSLNT in treating NEC but can be easily obtained synthetically. Here, we report a novel synthetic α2-6-linked disialyllacto-N-neotetraose (DSLNnT) obtained by sequential one-pot multienzyme (OPME) reactions which shows potent effect in preventing NEC in neonatal rats. The compound is readily available and can be produced in large amount for potential therapeutic application in treating NEC in preterm infants.

Materials and Methods

General Methods. Chemicals were purchased and used without further purification. $^1$H NMR (800 MHz) and $^{13}$C NMR (200 MHz) spectra were recorded on a Bruker Avance-800 NMR spectrometer. High resolution electrospray ionization (ESI) mass spectra were obtained using Thermo Electron LTQ-Orbitrap Hybrid MS at the Mass Spectrometry Facility in the University of California, Davis. Silica gel 60 Å (200-425 mesh, Fisher Chemical) was used for flash column chromatography. Thin-layer chromatography (TLC) was performed on silica gel plates using anisaldehyde sugar stain or 5% sulfuric acid in ethanol stain for detection. Gel filtration chromatography was performed with a column (100 cm×2.5 cm) packed with Bio-Gel P-2 Fine resins.

One-Pot Four-Enzyme Preparative-Scale Synthesis of Lc$_3$ Trisaccharide GlcNAcβ1-3Galβ1-4Glc. To prepare the trisaccharide, a reaction mixture in Tris-HCl buffer (100 mM, pH 8.0) in a total volume of 65 mL containing lactose (0.90 g, 2.63 mmol), N-acetylglucosamine (GlcNAc, 0.756 g, 3.42 mmol), adenosine 5'-triphosphate (ATP, 1.88 g, 3.42 mmol), uridine 5'-triphosphate (UTP, 1.99 g, 3.42 mmol), MgCl$_2$ (20 mM). NahK (19.0 mg), PmGlmU (8.0 mg), NmLgtA (6.0 mg), and PmPpA (4.0 mg) was incubated in a shaker at 37° C. for 48 hrs. The product formation was monitored by TLC (EtOAc:MeOH:H$_2$O:HOAc=4:2:1:0.2 by volume and detected by p-anisaldehyde sugar stain) and mass spectrometry. To stop the reaction, the reaction mixture was added with same volume (65 mL) of ethanol and incubated at 4° C. for 30 min. After centrifugation, the supernatant was concentrated and passed through a Bio Gel P-2 gel filtration column (water was used as an eluent). The fractions containing the product were collected, concentrated, and further purified by silica gel column (EtOAc:MeOH:H$_2$O=5:2:1 by volume) to provide Lc$_3$ trisaccharide GlcNAcβ1-3Galβ1-4Glc (1.36 g, 95%). $^1$H NMR (800 MHz, D$_2$O) δ 5.19 (d, J=4.0 Hz, 0.4H), 4.66 (d, J=8.0 Hz, 0.4H), 4.65 (d, J=8.0 Hz, 0.6H), 4.64 (d, J=8.0 Hz, 0.6H), 4.41 (d, J=8.0 Hz, 1H), 4.12 (d, J=3.2 Hz, 1H), 3.93-3.24 (m, 17H), 2.01 (s, 3H). $^{13}$C NMR (200 MHz, D$_2$O) β-isomer: δ 174.87, 102.84, 102.75, 95.66, 81.87, 78.21, 75.57, 74.80, 74.71, 74.20, 73.71, 73.49, 70.03, 69.92, 68.26, 60.88, 60.41, 60.01, 56.58, 22.09. HRMS (ESI) m/z calculated for C$_{20}$H$_{36}$NO$_{16}$ (M+H) 546.2034, found 546.2026.

One-Pot Four-Enzyme Preparative-Scale Synthesis of LNnT Galβ1-4GlcNAcβ1-3Galβ1-4Glc. To prepare LNnT, a reaction mixture in Tris-HCl buffer (100 mM, pH 8.0) in a total volume of 80 mL containing Lc$_3$ trisaccharide (1.0 g, 1.83 mmol), galactose (0.43 g, 2.38 mmol), ATP (1.40 g, 2.38 mmol), UTP (1.58 g, 2.38 mmol), MgCl$_2$ (20 mM), EcGalK (20.0 mg), BLUSP (20.0 mg), NmLgtB (15.0 mg), and PmPpA (20 mg) was incubated in a shaker at 37° C. for 30 hrs. The product formation was monitored by TLC (n-PrOH:H$_2$O:NH$_4$OH=5:2:1 by volume and detected by p-anisaldehyde sugar stain) and mass spectrometry. When an optimal yield was achieved, the reaction mixture was added with the same volume (80 mL) of ethanol and incubated at 4° C. for 30 min. The precipitates were removed by centrifugation and the supernatant was concentrated and purified by a Bio-Gel P-2 gel column (water was used as an eluent). Further purification was achieved by silica gel chromatography (EtOAc:MeOH:H$_2$O=5:3:1.5 by volume) to produce LNnT Galβ1-4GlcNAcβ1-3Galβ1-4Glc (1.19 g, 92%). $^1$H NMR (800 MHz, D$_2$O) δ 5.17 (d, J=4.0 Hz, 0.4H), 4.66 (d, J=8.0 Hz, 0.4H), 4.65 (d, J=8.0 Hz, 0.6H), 4.61 (d, J=8.0 Hz, 0.6H), 4.43 (d, J=7.2 Hz, 1H), 4.38 (d, J=8.0 Hz, 1H), 4.11 (d, J=3.2 Hz, 1H), 3.91-3.87 (m, 2H), 3.84-3.22 (m, 21H), 1.98 (s, 3H). $^{13}$C NMR (200 MHz, D$_2$O) β-isomer: δ 174.83, 102.79, 102.76, 102.73, 95.61, 81.82, 78.21, 78.11, 75.52 (2C), 74.76, 74.66, 74.22, 73.65, 73.42 (2C), 70.99, 69.88, 68.24, 68.22, 60.85, 60.84, 60.34, 59.93, 56.52, 22.03. HRMS (ESI) m/z calculated for C$_{26}$H$_{45}$NO$_{21}$Na (M+Na) 730.2382, found 730.2379.

One-Pot Two-Enzyme Preparative-Scale Synthesis of Hexasaccharide DSLNnT Neu5Acα2-6Galβ1-4GlcNAcβ1-3(Neu5Acα2-6)Galβ1-4Glc. To prepare DSLNnT, a reaction mixture in Tris-HCl buffer (100 mM, pH 8.5) in a total volume of 10 mL containing LNnT (131 mg, 0.19 mmol), Neu5Ac (143 mg, 0.46 mmol), CTP (260 mg, 0.46 mmol), MgCl$_2$ (20 mM), NmCSS (3.0 mg), and Pda-2,6ST (2.0 mg) was incubated in a shaker at 37° C. for 36 hrs. The reaction was monitored by TLC (n-PrOH:H$_2$O:NH$_4$OH=4:2:1 by volume and detected by p-anisaldehyde sugar stain) and mass spectrometry. When an optimal yield was achieved, the reaction mixture was added with the same volume (10 mL) of ethanol and incubated at 4° C. for 30 min. The precipitates were removed by centrifugation and the supernatant was concentrated and purified by a Bio Gel P-2 gel column (water was used as an eluent). Further purification was achieved by silica gel chromatography (EtOAc:MeOH:H$_2$O=4:3:2 by volume) to produce Neu5Acα2-6Galβ1-4GlcNAcβ1-3(Neu5Acα2-6)Galβ1-4Glc hexasaccharide (236 mg, 99%). $^1$H NMR (800 MHz, D$_2$O) δ 5.20 (d, J=4.0 Hz, 0.5H), 4.69 (d, J=8.0 Hz, 1H), 4.65 (d, J=8.0 Hz, 0.5H), 4.42 (d, J=8.0 Hz, 1H), 4.41 (d, J=8.0 Hz, 1H), 4.17 (d, J=2.4 Hz, 1H), 3.99-3.28 (m, 37H), 2.68 (dd, J=4.8 and 12.8 Hz, 1H), 2.64 (dd, J=4.8 and 12.8 Hz, 1H), 2.03 (s, 3H), 2.01 (s, 6H), 1.73-1.69 (m, 2H). $^{13}$C NMR (200 MHz, D$_2$O) β-isomer: δ 175.01 (3C), 173.66, 173.59, 103.65, 103.35, 102.74, 100.38, 100.23, 95.70, 82.29, 80.69, 79.76, 74.76, 74.72, 74.36, 73.80, 73.77, 73.37, 72.64 (2C), 72.62, 72.50, 71.86, 71.81, 70.83, 69.76, 68.50 (2C), 68.47 (3C), 68.32, 63.37, 63.23, 62.53 (2C), 60.23, 60.05, 54.83 (2C), 51.79, 51.69, 40.17 (2C), 22.38, 21.15, 21.12. HRMS (ESI) m/z calculated for C$_{48}$H$_{78}$N$_3$O$_{37}$ (M-H) 1288.4314, found 1288.4305.

One-Pot Two-Enzyme Preparative-Scale Synthesis of Pentasaccharide 3'''-sLNnT Neu5Acα2-3Galβ1-4GlcNAcβ1-3Galβ1-4Glc. To prepare the pentasaccharide, a reaction mixture in Tris-HCl buffer (100 mM, pH 8.5) in a total volume of 8 mL containing LNnT (100 mg, 0.14 mmol), Neu5Ac (65 mg, 0.21 mmol), CTP (119 mg, 0.21 mmol), MgCl$_2$ (20 mM), NmCSS (2.0 mg), and PmST1 M144D (1.5 mg) was incubated in a shaker at 37° C. for 48 hrs. The reaction was monitored by TLC (n-PrOH:H$_2$O:NH$_4$OH=4:2:1 by volume and detected by p-anisaldehyde sugar stain) and mass spectrometry. When an optimal yield was achieved, the reaction mixture was added with the same volume (8 mL) of ethanol and incubated at 4° C. for 30 min. The precipitates were removed by centrifugation and the supernatant was concentrated and purified by a Bio-Gel P-2 gel column (water was used as an eluent). Further purification was achieved by silica gel chromatography (EtOAc:MeOH:H$_2$O=5:3:2 by volume) to produce Neu5Acα2-3Galβ1-4GlcNAcβ1-3Galβ1-4Glc (138 mg, 98%). $^1$H NMR (800 MHz, D$_2$O) δ 5.16 (d, J=3.2 Hz, 0.4H), 4.65 (d, J=8.0 Hz, 0.4H), 4.64 (d, J=8.0 Hz, 0.6H), 4.60 (d, J=8.0 Hz, 0.6H), 4.50 (d, J=8.0 Hz, 1H), 4.38 (d, J=8.0 Hz, 1H), 4.10 (d, J=3.2 Hz, 1H), 4.06 (dd, J=3.2 and 9.6 Hz, 1H), 3.91-3.21 (m, 29H), 2.70 (dd, J=4.8 and 12.8 Hz, 1H), 1.97 (s, 6H), 1.74 (t, J=12.0 Hz, 1H). $^{13}$C NMR (200 MHz, D$_2$O) β-isomer: δ 174.86, 174.77, 173.76, 102.78, 102.69, 102.38, 99.65, 95, 59, 81.90, 78.08, 77.77, 75.29, 75.00, 74.73, 74.37, 74.17, 73.59, 72.70, 71.96, 71.60, 71.22, 70.93, 69.81, 69.21, 68.20, 67.88, 67.28, 62.37, 60.87, 59.85, 59.72, 59.61, 56.03, 51.58, 39.92, 22.02, 21.89. HRMS (ESI) m/z calculated for C$_{37}$H$_{61}$N$_2$O$_{29}$ (M-H) 997.3360, found 997.3364.

Human Milk Oligosaccharides (HMOs) and Galactooligosaccharides (GOS).

Human milk was obtained from 36 healthy volunteers recruited at the UCSD Medical Center, San Diego, Calif., after approval by the University's Institute Review Board. Human milk oligosaccharides (HMOs) were isolated from human milk as previously described. GOS syrup (Vivinal, dry matter 75%) was kindly provided by Friesland Campina Domo, The Netherlands.

Rat Studies. The efficacy of the synthesized glycans against necrotizing enterocolitis was tested in the same neonatal rat model as previously described for DSLNT. Briefly, pregnant time-dated Sprague-Dawley rats were induced at term and immediately randomized into one of the different study groups. Animals in the dam-fed group (DF) remained with the dam. All other animals were separated from the dam, housed in a temperature- and humidity-controlled incubator and orally gavaged with a special rodent formula (0.2 mL) twice daily. All animals, dam-fed and gavaged, were exposed to 10 min of hypoxia (5% O$_2$, 95% N$_2$) thrice daily in a modular chamber. All animals were sacrificed 96 hours postpartum, and 0.5 cm of the terminal ileum prepared for H&E staining per standard protocols and scored blindly based on morphological changes that included epithelial sloughing, villus edema, infiltration of neutrophils, apoptosis of villus enterocytes, crypt hyperplasia and misaligned nuclei in the epithelium. If at least one pathology sign was observed, a score of 0.5-1.5 was assigned depending on severity. Two or three signs together resulted in a score of 2-3. The maximum score of 4 was given in case of complete obliteration of the epithelium with or without intestinal perforation. Pathology scores were plotted for each animal and the mean calculated per group. Differences between the groups were calculated by Tway ANOVA with Kruskal-Wallis test and Dunn's Multiple Comparison test. Significance was defined as a P value of less than 0.05.

Results

Figure 37:
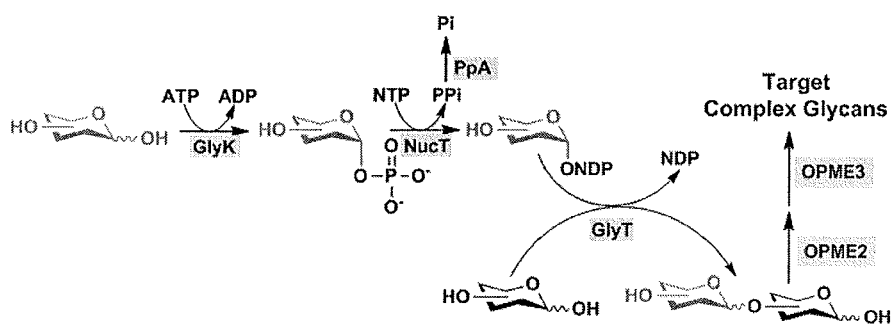
FIG. 37 shows a one-pot multi-enzyme reaction scheme for preparation of complex oligosaccharide products.

A general process for sequential one-pot multi-enzyme (OPME) reactions is shown in FIG. 37. In nature, the key enzymes that catalyze the glycosidic bond formation are glycosyltransferases (GlyT). GlyT-catalyzed transfer of mammalian monosaccharides other than sialic acids can be achieved most efficiently via three steps in a salvage pathway: activation of a monosaccharide by a glycokinase (GlyK) to form a sugar-1-phosphate (monosaccharide-1-P), which can be used by a nucleotidyltransferase (NucT) for the synthesis of a sugar nucleotide (or nucleotide diphosphate monosaccharide), the sugar nucleotide donor substrate of a suitable glycosyltransferase (GlyT) for the formation of desired glycosidic bond in the carbohydrate product. An inorganic pyrophosphorylase (PpA) can also be added to push the reaction towards completion in the direction of product formation. In comparison, more enzymes are usually involved in longer processes for de novo pathways for glycoside formation. Therefore, identifying suitable glycosyltransferases and the corresponding sugar nucleotide biosynthetic enzymes in the salvage pathways is important for developing efficient OPME systems. The availability, expression level, solubility, stability for storage, and substrate promiscuity of enzymes are commonly evaluated for their application in large scale synthesis of carbohydrates and their structurally modified derivatives. Each OPME reaction can usually be used to add one monosaccharide to a glycosyltransferase acceptor. Carrying out the OPME reactions sequentially allows the formation of complex carbohydrates and glycoconjugates. The stereo- and regio-specificities of the glycosidic bond formed, the nucleotide triphosphate required, and the selection of related sugar nucleotide biosynthetic enzymes are defined by the glycosyltransferases chosen based on the structures of the desired carbohydrate products.

Figure 38:
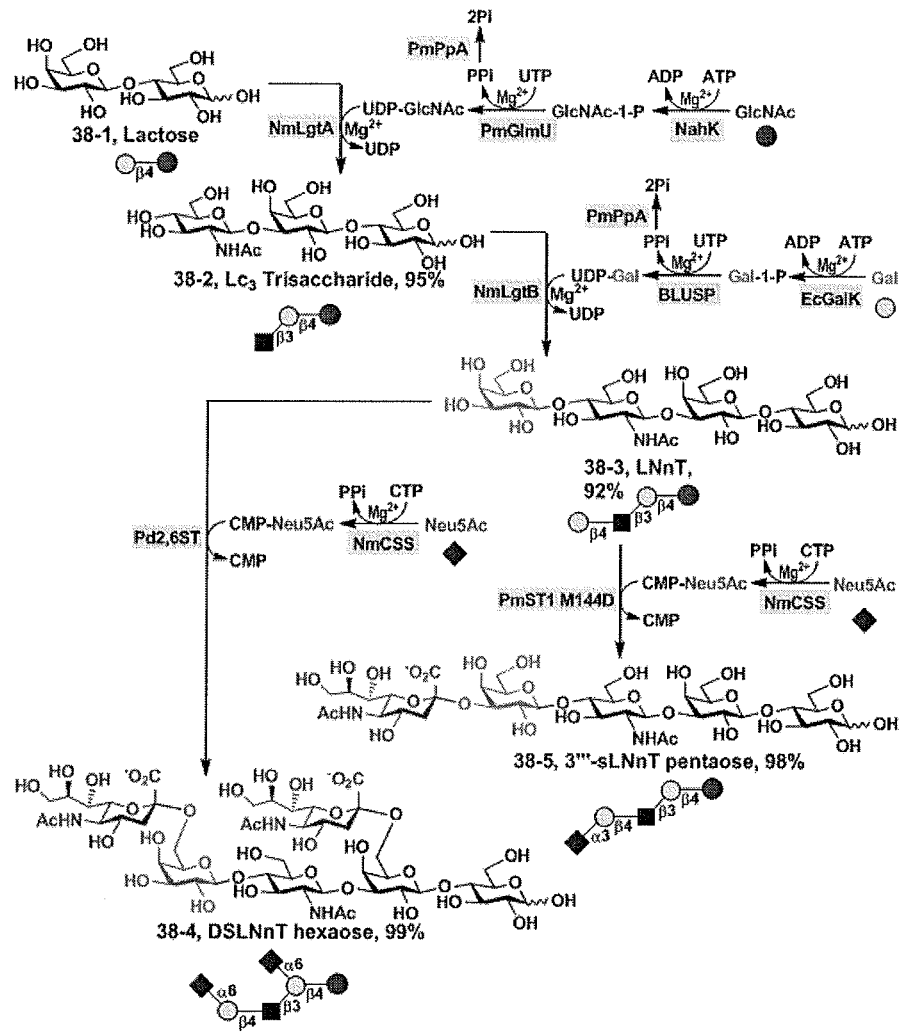
FIG. 38 shows a synthetic route for preparation of a novel disialylated oligosaccharide, DSLNnT.

To obtain lacto-N-neotetraose (LNnT), a common human milk tetrasaccharide (38-3), Lc$_3$ trisaccharide GlcNAcβ1-3Galβ1-4Glc (38-2) (FIG. 38) was synthesized from simple and inexpensive disaccharide lactose (38-1) and monosaccharide N-acetylglucosamine (GlcNAc) using a one-pot four-enzyme GlcNAc activation and transfer system containing *Bifidobacterium longum* strain ATCC55813 N-acetylhexosamine-1-kinase (NahK), *Pasteurella multocida* N-acetylglucosamine uridyltransferase (PmGlmU), *Pasteurella multocida* inorganic pyrophosphatase (PmPpA), and *Neisseria meningitidis* acetylglucosaminyltransferase (NmLgtA). In this system, adenosine 5'-triphosphate (ATP) and GlcNAc were used by NahK-catalyzed reaction to form GlcNAc-1-P, which was used with uridine 5'-triphosphate (UTP) by PmGlmU to form UDP-GlcNAc, the sugar nucleotide donor for NmLgtA for the production of Lc$_3$ trisaccharide from lactose. All of the four enzymes were quite active in Tris-HCl buffer at pH 8.0 and Lc$_3$ trisaccharide was obtained in an excellent yield (95%) by incubation at 37° C. for 2 days.

Taking advantage of a promiscuous *Bifidobacterium longum* UDP-sugar pyrophosphorylase (BLUSP) which can produce uridine 5'-diphosphate galactose (UDP-Gal) directly from UTP and galactose-1-phosphate (Gal-1-P), LNnT Galβ1-4GlcNAcβ1-3Galβ1-4Glc (38-3) was synthesized from Lc$_3$ trisaccharide (38-2) and a simple galactose (Gal) in an excellent yield (92%) using a one-pot four-enzyme Gal activation and transfer reaction containing *Escherichia coli* galactokinase (EcGalK), BLUSP, PmPpA, and *Neisseria meningitidis* β1-4-galactosyltransferase (NmLgtB). This is an improved and a more direct and effective system compared to our previously reported OPME β1-4-galactosylation process which involved the formation of UDP-glucose (UDP-Glc) from glucose-1-phosphate (Glc-1-P) followed by C4-epimerization to produce UDP-Gal indirectly.

Sialylation of LNnT can be achieved by sialyltransferase (SiaT)-catalyzed reaction with in situ generation of sugar nucleotide donor CMP-sialic acid catalyzed by a CMP-sialic acid synthetase (CSS). For the synthesis of sialosides containing the most common sialic acid form, N-acetyl-neuraminic acid (Neu5Ac), the one-pot two-enzyme sialylation system is sufficient and the application of a sialic acid aldolase to generate Neu5Ac from its six-carbon precursor N-acetylmannosamine (ManNAc) is not necessary as the commercial prices for Neu5Ac and ManNAc are similar.

Initial sialylation of LNnT using Neu5Ac in a one-pot two-enzyme sialic acid activation and transfer system containing *Neisseria meningitidis* CMP-sialic acid synthetase (NmCSS) and *Photobacterium damselae* α2-6-sialyltransferase (Pd2,6ST) with an Neu5Ac to LNnT ratio of 1.5 to 1 produced an unexpected mixture of mono-sialylated and disialyl LNnT (DSLNnT) which were difficult to separate. Increasing the Neu5Ac to LNnT ratio to 2.4 to 1 led to the complete formation of DSLNnT hexasaccharide Neu5Acα2-6Galβ1-4GlcNAcβ1-3(Neu5Acα2-6)Galβ1-4Glc (38-4) with an excellent yield (99%). Nuclear magnetic resonance (NMR) data confirmed that Pd2,6ST does not only add a Neu5Ac α2-6-linked to the terminal Gal, it also adds an α2-6-linked Neu5Ac to the internal Gal residue in LNnT. As shown in Table 1, the attachment of Neu5Ac to the C-6 of the internal Gal (Gal$^{II}$) and the terminal Gal (Gal$^{IV}$) in LNnT results in significant downfield shifts of the substituted carbons (a downfield shift of 2.39 ppm for the C-6 of Gal$^{II}$ and a downfield shift of 2.52 ppm for the C-6 of Gal$^{IV}$ in DSLNnT. There are obvious interactions of the Neu5Ac residues and GlcNAc$^{III}$ and Glc$^{I}$ which result in a significant downfield shift of 2.58 ppm for the C-4 of GlcNAc$^{III}$ and a downfield shift of 1.55 ppm for the C-4 of Glc$^{I}$. These unusual chemical shift changes seen in Neu5Acα2-6Gal sialosides are in accordance with those observed for the glycans with same or similar structural element. To our knowledge, this property of adding multiple Neu5Ac residues to both terminal and internal Gal by Pd2,6ST has never been discovered before and the obtained DSLNnT is a new structure that has never been synthesized.

TABLE 13

$^{13}$C NMR chemical shifts for compound Galβ1-4Glc (Lac), GlcNAcβ1-3Galβ1-4Glc (Lc$_3$ glycan), Galβ1-4GlcNAcβ1-3Galβ1-4Glc (LNnT; 38-3), and Neu5Acα2-6Galβ1-4GlcNAcβ1-3(Neu5Acα2-6)Galβ1-4Glc (DSLNnT; 38-4).

| | VI | | IV | III | V | II | I |
|---|---|---|---|---|---|---|---|
| | Neu5Acα2-6Galβ1-4GlcNAcβ1-3(Neu5Acα2-6)Galβ1-4Glc | | | | | | |
| Sugar Unit | Carbon atoms | | Lac | Lc$_3$ glycan | LNnT | | DSLNnT |
| β-D-Glc$^{I}$ | 1 | | 95.64 | 95.66 | 95.61 | | 95.70 |
| | 2 | | 73.70 | 73.71 | 73.65 | | 73.37 |
| | 3 | | 74.26 | 74.20 | 74.22 | | 74.36 |
| | 4 | | 78.19 | 78.21 | 78.21 | | 79.76 |
| | 5 | | 74.69 | 74.71 | 74.76 | | 74.76 |
| | 6 | | 59.78 | 60.01 | 60.34 | | 60.23 |
| β-D-Gal$^{II}$(1-4) | 1 | | 102.79 | 102.84 | 102.76 | | 103.35 |
| | 2 | | 70.86 | 70.03 | 69.88 | | 69.76 |
| | 3 | | 72.42 | 81.87 | 81.82 | | 82.29 |
| | 4 | | 68.46 | 68.26 | 68.22 | | 68.32 |
| | 5 | | 75.25 | 74.80 | 75.52 | | 73.77 |
| | 6 | | 60.94 | 60.88 | 60.84 | | 63.23 |
| β-D-GlcNAc$^{III}$(1-3) | 1 | | | 102.75 | 102.73 | | 102.74 |
| | 2 | | | 56.58 | 56.52 | | 54.83 |
| | 3 | | | 73.49 | 73.42 | | 72.50 |
| | 4 | | | 69.92 | 78.11 | | 80.69 |
| | 5 | | | 75.57 | 74.66 | | 74.72 |
| | 6 | | | 60.41 | 59.93 | | 60.05 |
| | C=O | | | 174.87 | 174.83 | | 175.01 |
| | CH$_3$ | | | 22.09 | 22.03 | | 22.38 |
| β-D-Gal$^{IV}$(1-4) | 1 | | | | 102.79 | | 103.65 |
| | 2 | | | | 70.99 | | 70.83 |
| | 3 | | | | 73.42 | | 72.62 |
| | 4 | | | | 68.24 | | 68.47 |
| | 5 | | | | 75.52 | | 73.80 |
| | 6 | | | | 60.85 | | 63.37 |
| α-D-Neu5Ac$^{V}$(2-6) | 1 | | | | | | 173.59 |
| | 2 | | | | | | 100.38 |
| | 3 | | | | | | 40.17 |
| | 4 | | | | | | 68.47 |
| | 5 | | | | | | 51.69 |
| | 6 | | | | | | 72.64 |
| | 7 | | | | | | 68.50 |
| | 8 | | | | | | 71.86 |
| | 9 | | | | | | 62.53 |
| | C=O | | | | | | 175.01 |
| | CH$_3$ | | | | | | 22.12 |
| α-D-Neu5Ac$^{VI}$(2-6) | 1 | | | | | | 173.66 |
| | 2 | | | | | | 100.23 |
| | 3 | | | | | | 40.17 |
| | 4 | | | | | | 68.47 |
| | 5 | | | | | | 51.79 |
| | 6 | | | | | | 72.64 |
| | 7 | | | | | | 68.50 |
| | 8 | | | | | | 71.81 |
| | 9 | | | | | | 62.53 |
| | C=O | | | | | | 175.01 |
| | CH$_3$ | | | | | | 22.15 |

As DSLNnT resembles some structural features of DSLNT, we hypothesized that the newly obtained DSLNnT may also have NEC preventing activity. As a control, mono-sialyl pentasaccharide 3'''-sialyl LNnT (3'''-sLNnT) was synthesized from LNnT using a one-pot two-enzyme sialic acid activation and transfer system similar to that described above for DSLNnT except that a different sialyltransferase was used. A single-site mutant of *Pasteurella multocida* multi-functional α2-3-sialyltransferase (Pm STI M144D) was used to form an α2-3-sialyl linkage instead of the α2-6-sialyl linkages in DSLNnT described above. In addition, unlike Pd2,6ST-catalyzed sialylation reaction which could add either one or two α2-6-linked sialic acid residues to LNnT, PmST1 M144D-catalyzed sialylation reaction only added one α2-3-linked sialic acid residue to the terminal Gal in LNnT. The application of the PmST1 M144D mutant instead of wild-type PmST1 avoids the product hydrolysis by the α2-3-sialidase activity of the wild-type enzyme, thus improves the yield of the one-pot two-enzyme α2-3-sialylation reaction. Indeed, an excellent yield (98%) was achieved without the need of close monitor of the reaction process or to stop the reaction promptly.

Figure 39:
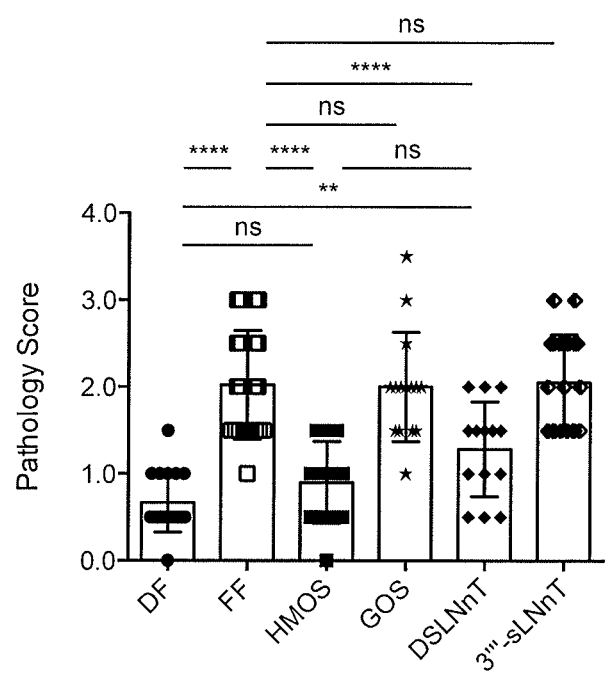
FIG. 39 shows that DSLNnT protects neonatal rats from necrotizing enterocolitis. Ileum pathology scores (0: healthy; 4: complete destruction) are plotted for each animal in the different intervention groups. DF: dam fed (number of rats n=18); FF: fed formula without additional glycans (n=22); HMOs: fed formula that contains oligosaccharides isolated from pooled human milk (2 mg/mL, n=15); GOS: fed formula that contains galacto-oligosaccharides (2 mg/mL, n=15); DSLNnT: formula containing synthesized disialyl LNnT (300 μg/mL, n=14); 3'''-sLNnT: formula containing synthesized 3'''-sialyl LNnT (300 μg/mL, n=19). Bars represent mean±standard deviation. ns: not significant; P<0.01; **P<0.0001.

The efficacy of DSLNnT or 3'''-sLNnT in protecting against NEC was tested in the same neonatal rat model that had been used previously to show the NEC protection effect of DSLNT. Since DSLNT was not available, a mixture of human milk oligosaccharides (HMOs) isolated from pooled human milk was used as a positive intervention control instead. A galactooligosaccharides (GOS) sample, shown to be ineffective in preventing NEC, was used as negative intervention control. As shown in FIG. 39, dam-fed (DF) animals hardly developed any signs of NEC (mean pathology score 0.67±0.34). Pathology scores were significantly higher in animals that were orally gavaged with rodent formula (FF) without the addition of glycans (2.02±0.63, p<0.0001 compared to DF). Adding HMOs to the formula led to significantly lower pathology scores (0.90±0.47, p<0.0001 compared to FF), which were not significantly different from the DF control (p=0.122). Adding GOS had no effect on lowering pathology scores (2.00±0.64, p=0.915 compared to FF). All these results are in accordance with the previously reported data. Adding the synthesized DSLNnT to the formula led to significantly lower pathology scores (1.29±0.54, p=0.0008 compared to FF), which was not significantly different from the effects seen in animals that received HMOs (p=0.052), but still different from the DF control (p=0.0013). Adding the synthesized 3'''-sLNnT to the formula did not lower pathology scores (2.05±0.55, p=0.872 compared to FF).

These results show that similar to DSLNT, DSLNnT reduces pathology scores in an NEC neonatal rat model. Both DSLNT and DSLNnT are disialyl hexasaccharides but with noticeable structural differences. First of all, DSLNT is a disialyl type I glycan whose core tetrasaccharide has a Gal residue β1-3-linked to Lc₃ trisaccharide, while DSLNnT is a disialyl type II glycan whose core tetrasaccharide has a Gal residue β1-4-linked to the Lc₃ trisaccharide. Secondly, although both have a Neu5Ac α2-6-linked to an internal monosaccharide, the internal monosaccharide is GlcNAc in DSLNT while a Gal in DSLNnT. Thirdly, the outermost Neu5Ac is linked to the penultimate Gal in an α2-3-linkage in DSLNT but an α2-6-linkage in DSLNnT. These structural differences of DSLNT and DSLNnT and their similarity in protecting neonatal rats from NEC indicate that the negatively charged disialyl component is important for the NEC preventing effect while the tetrasaccharide scaffold (type I or type II) does not seem to be important. The importance of disialyl component is further supported by the lacking of NEC preventing effect by monosialyl pentasaccharides such as LSTb shown previously and 3'''-sLNnT shown here.

As DSLNnT is synthetically readily available, it has the potential to be used for treating NEC in preterm infants. The sequential OPME systems described here allow the use of inexpensive and simple disaccharide and monosaccharides to synthesize desired complex oligosaccharides with high efficiency and selectivity. These are efficient approaches that can be used to obtain DSLNnT in amounts large enough for pre-clinical and clinical applications.

The novel synthetic disialyllacto-N-neotetraose (DSLNnT) can protect neonatal rats from NEC. Unlike the NEC-preventing DSLNT previously identified from human milk which is not easily obtainable by either purification or synthesis, the newly identified DSLNnT is readily available by enzymatic synthesis. Highly efficient one-pot multienzyme GlcNAcylation, galactosylation, and sialylation systems for the high-yield synthesis of DSLNnT have been established. The readily available DSLNnT is a good therapeutic candidate for treating NEC in preterm infants.

Example 15

Synthesis of Other Novel Disialyl Oligosaccharides

Compound 15.2a:
Neu5Acα2-3(Neu5Acα2-6)Galβ1-4Glc

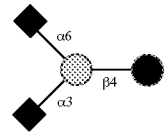

Neu5Acα2-3Galβ1-4Glc (GM3, 83 mg, 0.13 mmol), Neu5Ac (61 mg, 0.20 mmol), and CTP (113 mg, 0.20 mmol) were dissolved in Tris-HCl buffer (5 mL, pH 8.5) containing MgCl₂ (20 mM), *N. meningitidis* CMP-sialic acid synthetase (NmCSS, 1.7 mg), and *Photobacterium damselae* α2-6-sialyltransferase (Pd2,6ST, 2.1 mg). The reaction was carried out by incubating the reaction mixture in an incubator shaker at 37° C. for 24 hrs. The reaction was monitored by TLC (n-PrOH:H₂O:NH₄OH=4:2:1 by volume and detected by p-anisaldehyde sugar stain) and mass spectrometry. When an optimal yield was achieved, to the reaction mixture was added the same volume (5 mL) of EtOH, and the mixture was incubated at 4° C. for 30 min. The precipitates were removed by centrifugation and the supernatant was concentrated and purified by a Bio-Gel P-2 gel column (water was used as eluent). Further purification was achieved by silica gel chromatography (EtOAc:MeOH:H₂O=4:2:1 by volume) and finally by Bio-Gel P-2 column (eluted with H₂O) to provide Neu5Acα2-3(Neu5Acα2-6)Galβ1-4Glc tetrasaccharide (112 mg, 93%). ¹H NMR (600 MHz, D₂O) δ 5.24 (d, J=3.6 Hz, 0.4H), 4.69 (d, J=7.8 Hz, 0.6H), 4.53 (d, J=7.8 Hz, 1H), 4.15-4.13 (m, 1H), 4.00-3.96 (m, 3H), 3.91-3.62 (m, 9H) 3.72-3.32 (m, 13H), 2.77 (dd, J=4.2 and 12.0 Hz, 1H), 2.72 (dd, J=4.2 and 12.0 Hz, 1H), 2.05 (s, 6H), 1.82 (t, J=12.0 Hz, 1H), 1.76 (t, J=12.0 Hz, 1H). ¹³C NMR (150 MHz, D₂O) β-isomer: δ 174.90, 174.79, 173.73, 173.38, 102.87, 100.19, 99.90, 95.59, 79.67, 79.56, 75.18, 74.57, 74.52, 73.63, 73.42, 72.78, 72.41, 71.65, 71.62, 69.16, 68.33, 68.32, 68.02, 67.52, 63.45, 62.57, 62.50, 60.20, 51.69, 51.58, 39.98, 39.40, 21.98, 21.96. HRMS (ESI) m/z calculated for C₃₄H₅₆N₂O₂₇ (M–H) 924.3070, found 924.3060.

Compound 15.2b: Neu5Acα2-8Neu5Acα2-3 Galβ1-4Glc

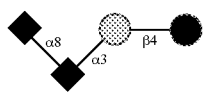

Neu5Acα2-3Galβ1-4Glc (GM3, 200 mg, 0.32 mmol), Neu5Ac (107 mg, 0.35 mmol), and CTP (197 mg, 0.35 mmol) were dissolved in Tris-HCl buffer (15 mL, pH 8.5) containing MgCl₂ (20 mM), NmCSS (3.8 mg), and *Campylobacter jejuni* α2-8-sialyltransferase (CstII, 3.0 mg). The reaction was carried out by incubating the reaction mixture in an incubator shaker at 37° C. for 20 hrs. The reaction was monitored by TLC (n-PrOH:H$_2$O:NH$_4$OH=4:2:1 by volume and detected by p-anisaldehyde sugar stain) and mass spectrometry. When an optimal yield was achieved, to the reaction mixture was added the same volume (15 mL) of EtOH, and the mixture was incubated at 4° C. for 30 min. The precipitates were removed by the centrifuge and the supernatant was concentrated and purified by a Bio-Gel P-2 gel column (water was used as eluent). Further purification was achieved by silica gel chromatography (EtOAc:MeOH:H$_2$O=5:3:2 by volume) and finally Bio-Gel P-2 column (eluted with H$_2$O) to provide Neu5Acα2-8Neu5Acα2-3Galβ1-4Glc tetrasaccharide (239 mg, 82%). $^1$H NMR (800 MHz, D$_2$O) δ 5.22 (d, J=3.2 Hz, 0.3H), 4.66 (d, J=8.0 Hz, 0.7H), 4.52 (d, J=7.2 Hz, 1H), 4.18-4.08 (m, 3H), 3.98-3.95 (m, 2H), 3.91-3.29 (m, 21H), 2.77 (dd, J=4.8 and 12.8 Hz, 1H), 2.67 (dd, J=4.8 and 12.8 Hz, 1H), 2.07 (s, 3H), 2.03 (s, 3H), 1.74 (t, J=12.0 Hz, 2H). $^{13}$C NMR (200 MHz, D$_2$O) β-isomer: δ 174.89, 174.88, 173.40, 173.26, 102.58, 100.42, 100.09, 95.71, 78.09, 77.98, 77.83, 75.34, 75.11, 74.72, 74.17, 73.90, 72.54, 71.69, 71.08, 69.17, 68.37, 68.00, 67.81, 67.39, 62.49, 61.46, 61.99, 59.89, 51.18, 51.66, 40.38, 39.61, 22.23, 21.96. HRMS (ESI) m/z calculated for C$_{34}$H$_{56}$N$_2$O$_{27}$ (M−H) 924.3070, found 924.3071.

Compound 15.11: Neu5Acα2-6Galβ1-4GlcNAcβ1-3 (Neu5Acα2-6)Galβ1-4Glc (DSLNnT)

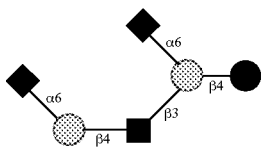

To prepare DSLNnT, a reaction mixture in a total volume of 10 mL in Tris-HCl buffer (100 mM, pH 8.5) containing LNnT (131 mg, 0.19 mmol), Neu5Ac (143 mg, 0.46 mmol), CTP (260 mg, 0.46 mmol), MgCl$_2$ (20 mM), NmCSS (3.0 mg), and Pdα-2,6ST (2.0 mg) was incubated in a shaker at 37° C. for 36 hrs. The reaction was monitored by TLC (n-PrOH:H$_2$O:NH$_4$OH=4:2:1 by volume and detected by p-anisaldehyde sugar stain) and mass spectrometry. When an optimal yield was achieved, the reaction mixture was added with the same volume (10 mL) of ethanol and incubated at 4° C. for 30 min. The precipitates were removed by centrifugation and the supernatant was concentrated and purified by a Bio Gel P-2 gel column (water was used as an eluent). Further purification was achieved by silica gel chromatography (EtOAc:MeOH:H$_2$O=4:3:2 by volume) and finally Bio-Gel P-2 column (eluted with H$_2$O) to produce Neu5Acα2-6Galβ1-4GlcNAcβ1-3(Neu5Acα2-6)Galβ1-4Glc hexasaccharide (236 mg, 99%). $^1$H NMR (800 MHz, D$_2$O) δ 5.20 (d, J=4.0 Hz, 0.5H), 4.69 (d, J=8.0 Hz, 1H), 4.65 (d, J=8.0 Hz, 0.5H), 4.42 (d, J=8.0 Hz, 1H), 4.41 (d, J=8.0 Hz, 1H), 4.17 (d, J=2.4 Hz, 1H), 3.99-3.28 (m, 37H), 2.68 (dd, J=4.8 and 12.8 Hz, 1H), 2.64 (dd, J=4.8 and 12.8 Hz, 1H), 2.03 (s, 3H), 2.01 (s, 6H), 1.73-1.69 (m, 2H). $^{13}$C NMR (200 MHz, D$_2$O) β-isomer: δ 175.01 (3C), 173.66, 173.59, 103.65, 103.35, 102.74, 100.38, 100.23, 95.70, 82.29, 80.69, 79.76, 74.76, 74.72, 74.36, 73.80, 73.77, 73.37, 72.64 (2C), 72.62, 72.50, 71.86, 71.81, 70.83, 69.76, 68.50 (2C), 68.47 (3C), 68.32, 63.37, 63.23, 62.53 (2C), 60.23, 60.05, 54.83 (2C), 51.79, 51.69, 40.17 (2C), 22.38, 21.15, 21.12. HRMS (ESI) m/z calculated for C$_{48}$H$_{78}$N$_3$O$_{37}$ (M−H) 1288.4314, found 1288.4305.

Compound 15.12: Neu5Acα2-6Galβ1-3GlcNAcβ1-3 (Neu5Acα2-6)Galβ1-4Glc (DSLNT')

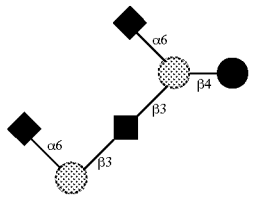

Galβ1-3GlcNAcβ1-3Galβ1-4Glc (LNT, 150 mg, 0.21 mmol), Neu5Ac (169 mg, 0.55 mmol), and CTP (307 mg, 0.55 mmol) were dissolved in Tris-HCl buffer (10 mL, pH 8.5) containing MgCl$_2$ (20 mM), NmCSS (4.0 mg), and Pd2,6ST (3.0 mg). The reaction was carried out by incubating the reaction mixture in an incubator shaker at 37° C. for 36 hrs. The reaction was monitored by TLC (n-PrOH:H$_2$O:NH$_4$OH=4:2:1 by volume and detected by p-anisaldehyde sugar stain) and mass spectrometry. When an optimal yield was achieved, to the reaction mixture was added the same volume (10 mL) of EtOH and the mixture was incubated at 4° C. for 30 min. The precipitates were removed by centrifugation and the supernatant was concentrated and purified by a Bio-Gel P-2 gel column (water was used as eluent). Further purification was achieved by silica gel chromatography (EtOAc:MeOH:H$_2$O=4:3:2 by volume) and finally Bio-Gel P-2 column (eluted with H$_2$O) to provide Neu5Acα2-6Galβ1-3GlcNAcβ1-3(Neu5Acα2-6)Galβ1-4Glc hexasaccharide (268 mg, 98%). $^1$H NMR (600 MHz, D$_2$O) δ 5.24 (d, J=3.6 Hz, 0.4H), 4.74 (d, J=8.4 Hz, 1H), 4.68 (d, J=8.4 Hz, 0.6H), 4.44 (d, J=7.8 Hz, 1H), 4.40 (d, J=7.8 Hz, 1H), 4.19 (d, J=3.8 Hz, 1H), 4.00-3.31 (m, 371-1), 2.73-2.70 (m, 2H), 2.04 (s, 6H), 2.03 (s, 3H), 1.75 (t, J=12.0 Hz, 1H), 1.71 (t, J=12.0 Hz, 1H). $^{13}$C NMR (200 MHz, D$_2$O) β-isomer: δ 174.86, 174.83 (2C), 173.42 (2C), 103.80, 103.14, 102.51, 100.19, 100.07, 95.56, 83.58, 81.98, 79.57, 75.19, 74.58, 74.54, 73.62, 73.49, 73.21, 72.43, 72.38, 72.29, 71.74, 71.68, 70.45, 69.88, 69.66, 68.61, 68.38, 68.31, 68.29, 68.20, 68.08, 63.41, 63.39, 62.56 (2C), 60.58, 60.17, 54.37, 51.74, 51.70, 40.07, 40.02, 22.15, 21.98 (2C). HRMS (ESI) m/z calculated for C$_{48}$H$_{78}$N$_3$O$_{37}$ (M−H) 1288.4314, found 1288.4290.

Compound 15.18: Neu5Acα2-3(Neu5Acα2-6)Galβ1-9Kdn

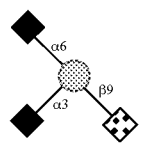

Neu5Acα2-3Galβ1-9Kdn was prepared first by following the general one-pot two-enzyme α2-3-sialylation system described above from Galβ1-9Kdn (101 mg, 0.22 mmol) in Tris-HCl buffer (100 mM, pH 8.5) containing Neu5Ac (109 mg, 0.33 mmol), CTP (188 mg, 0.33 mmol), MgCl$_2$ (20 mM), NmCSS (0.8 mg), and PmST1 (0.04 mg). The reaction was incubated at 37° C. for 3 h with shaking (120 rpm). The crude product was purified by Bio-Gel P-2 gel filtration to afford the sialoside product Neu5Acα2-3Galβ1-9Kdn (148 mg, 89%). $^1$H NMR (600 MHz, D$_2$O): δ 4.33 (d, 1H, J=7.8 Hz, H'-1), 4.00 (dd, 1H, J=1.8 and 10.8 Hz), 3.93 (dd, 1H, J=3.6 and 11.2 Hz), 3.82-3.65 (m, 9H), 3.60-3.39 (m, 9H), 2.58 (dd, 1H, J=4.2 and 12.6 Hz, H-3 eq"), 2.01 (dd, 1H, J=4.8 and 13.2 Hz, H-3 eq), 1.85 (s, 3H, CH$_3$), 1.62 (t, 1H, J=12.0 Hz, H-3ax), 1.60 (t, 1H, J=12.0 Hz, H-3ax"). $^{13}$C NMR (75 MHz, D$_2$O): δ 176.29, 175.17, 173.95, 103.28, 99.93, 96.35, 75.87, 75.07, 73.02, 71.93, 71.90, 71.86, 71.61, 70.44, 69.64, 69.50, 69.15, 68.48, 68.25, 67.97, 67.67, 62.75, 61.13, 59.50, 51.84, 39.82, 39.14, 22.22. HRMS (ESI) calcd. for C$_{26}$H$_{41}$NNaO$_{22}$ (MNa), 742.2018, found 742.2001.

Neu5Acα2-3(Neu5Acα2-6)Galβ1-9Kdn was then prepared from Neu5Acα2-3Galβ1-9Kdn (130 mg, 0.17 mmol) in Tris-HCl buffer (100 mM, pH 8.5) containing Neu5Ac (84 mg, 0.25 mmol), CTP (143 mg, 0.25 mmol), MgCl$_2$ (20 mM), NmCSS (0.8 mg), and Pd2,6ST (0.2 mg). The reaction was incubated at 37° C. for 12 hrs with shaking (120 rpm). The crude product was purified by Bio-Gel P-2 gel filtration to afford the sialoside product (159 mg, 87%). $^1$H NMR (600 MHz, D$_2$O): δ 4.33 (d, 1H, J=7.8 Hz, H'-1), 3.99 (m, 1H), 3.94 (dd, 1H, J=3.0 and 9.6 Hz), 3.83-3.59 (m, 13H), 3.56-3.38 (m, 12H), 2.59-2.53 (m, 2H, H-3 eq", H-3 eq'''), 2.00 (dd, 1H, J=4.8 and 13.2 Hz, H-3 eq), 1.85 (s, 6H, 2CH$_3$), 1.64-1.57 (m, 2H, H-3ax, H-3ax"), 1.52 (t, 1H, J=12.0 Hz, H-3ax'''). $^{13}$C NMR (75 MHz, D$_2$O): δ 177.12, 175.16 (2C), 173.94, 173.60, 103.26, 100.64, 100.13, 96.62, 75.66, 73.40, 73.02, 72.78, 71.96, 71.90, 71.87, 71.55, 70.59, 69.49, 69.44, 69.27, 68.56, 68.49, 68.47, 68.28, 67.79, 63.57, 62.85, 62.78, 61.03, 52.04, 51.84, 40.31, 39.73, 39.32, 22.27 (2C). HRMS (ESI) calcd. for C$_{37}$H$_{57}$N$_2$Na$_2$O$_{30}$ (M-Na) 1055.2792, found 1055.2853.

---

DNA AND PROTEIN SEQUENCES FOR GENES AND ENZYMES

```
DNA sequence of NahK_ATCC15697 (SEQ ID NO: 1)
(Note: The sequences for His6-tag are underlined)
ATGAACAACACCAATGAAGCCCTGTTCGACGTCGCTTCGCACTTCGCGCTGGAAGGCACCGT

CGACAGCATCGAACCATACGGAGACGGCCATATCAACACCACCTATCTGGTGACCACGGACG

GCCCCCGCTACATCCTCCAACGGATGAACACCGGCATCTTCCCCGATACGGTGAATCTGATG

CGCAATGTCGAGCTGGTCACCTCCACTCTCAAGGCTCAGGGCAAAGAGACGCTGGACATCGT

GCGCACCACCTCCGGCGACACCTGGGCCGAGATCGACGGCGGCCATGGCGCGTCTACAAGT

TCATCGAACACACCATGTCATACAACCTCGTGCCGAACCCGGACGTGTTCCGCGAAGCCGGC

AGGGCGTTCGGTGATTTCCAGAACTTCCTGTCCGGGTTCGACGCCAACCAGCTGACCGAGAC

CATCGCCCACTTCCACGACACCCCGCACCGCTTCGAGGACTTCAAGAAGGCGCTCGCCGCGG

ACGAGCTCGGGCGTGCCGCCGGGTGCGGCCCGGAGATCGAGTTCTATCTGAGTCACGCCGAC

CAGTACGCCGTCGTGATGGATGGGCTCAGGGATGGTTCGATCCCGCTGCGCGTGACCCACAA

CGACACCAAACTCAACAACATCCTCATGGATGCCACCACCGGCAAGGCCCGTGCGATCATCG

ATCTAGACACCATCATGCCGGGGTCCATGCTCTTCGACTTCGGCGATTCCATCCGTTTCGGC

GCGTCCACGGCCTTGGAGGATGAGCGGGATCTGGACAAGGTGCATTTCAGCACCGAGCTGTT

CCGCGCCTACACGGAAGGCTTCGTGGGCGAACTACGCGACAGCATCACCGCGCGCGAGGCCG

AACTGCTGCCGTTCAGCGGCAACCTGCTCACCATGGAATGCGGCATGCGCTTTCTCGCCGAC

TACCTGGAAGGCGACGTCTACTTCGCCACCAAGTACCCCGAGCATAACCTGGTGCGCTCCCG

CACCCAGATCAAGCTCGTGAGGGAGATGGAGCAGCGAGCCGATGAGACCCGCGCCATCGTGG

CCGACGTCATGGAGTCGACCAAGCTCGAGCACCACCACCACCACCACTGA

Protein sequence of NahK_ATCC15697 (SEQ ID NO: 2)
(Note: The sequences for His6-tag are underlined)
MNNTNEALFDVASHFALEGTVDSIEPYGDGHINTTYLVTTDGPRYILQRMNTGIFPDTVNLM

RNVELVTSTLKAQGKETLDIVRTTSGDTWAEIDGGAWRVYKFIEHTMSYNLVPNPDVFREAG

RAFGDFQNFLSGFDANQLTETIAHFHDTPHRFEDFKKALAADELGRAAGCGPEIEFYLSHAD

QYAVVMDGLRDGSIPLRVTHNDTKLNNILMDATTGKARAIIDLDTIMPGSMLFDFGDSIREG

ASTALEDERDLDKVHFSTELFRAYTEGFVGELRDSITAREAELLPFSGNLLTMECGMRFLAD

YLEGDVYFATKYPEHNLVRSRTQIKLVREMEQRADETRAIVADVMESTKLEHHHHHH
```

| DNA AND PROTEIN SEQUENCES FOR GENES AND ENZYMES |
|---|

DNA sequence of NahK_ATCC55813 (SEQ ID NO: 3)
(Note: The sequences for His$_6$-tag are underlined)

ATGACCGAAAGCAATGAAGTTTTATTCGGCATCGCCTCGCATTTTGCGCTGGAAGGTGCCGT

GACCGGTATCGAACCTTACGGAGACGGCCACATCAACACCACCTATCTGGTGACCACGGACG

GCCCCCGCTACATCCTCCAGCAGATGAACACCAGCATCTTCCCCGATACGGTGAATCTGATG

CGCAATGTCGAACTGGTCACCTCCACTCTCAAGGCTCAGGGCAAAGAGACGCTGGACATTGT

GCCCACCACCTCAGGCGCCACCTGGGCCGAGATCGATGGCGGCGCATGGCGCGTCTACAAGT

TCATCGAACACACCGTGTCCTACAACCTCGTGCCGAACCCGGACGTGTTCCGCGAAGCCGGC

AGCGCATTCGGCGACTTCCAGAACTTCCTGTCCGAATTCGACGCCAGCCAGCTGACCGAAAC

CATCGCCCACTTCCACGACACCCCGCATCGTTTCGAGGACTTCAAGGCCGCCCTCGCCGCGG

ACAAGCTCGGCCGCGCCGCCGCATGCCAGCCGGAAATCGACTTCTATCTGAGTCACGCCGAC

CAGTATGCCGTCGTGATGGATGGGCTCAGGGACGGTTCGATTCCGCTGCGCGTGACCCACAA

TGACACCAAGCTCAACAACATCCTCATGGACGCCACCACCGGCAAGGCGCGTGCGATCATCG

ATCTCGACACCATCATGCCCGGCTCCATGCTGTTCGACTTCGGCGATTCCATACGCTTTGGT

GCGTCCACTGCTCTGGAAGACGAAAAGGACCTCAGCAAGGTGCATTTCAGCACCGAGCTGTT

CCGCGCCTACACGGAAGGCTTCGTGGGCGAACTACGCGGCAGCATCACCGCGCGCGAGGCCG

AACTGCTGCCGTTCAGCGGCAACCTGCTCACCATGGAATGCGGCATGCGCTTTCTCGCCGAC

TACTTGGAAGGCGATATCTACTTTGCCACCAAGTACCCCGAGCATAATCTGGTGCGCACCCG

CACCCAGATCAAACTCGTGCAGGAGATGGAGCAGAAGGCCAGTGAAACCCACGCCATCGTAG

CCGACATCATGGAGGCTGCCAGGCTCGAG<u>CACCACCACCACCACCAC</u>TGA

Protein sequence of NahK_ATCC55813 (SEQ ID NO: 4)
(Note: The sequences for His$_6$-tag are underlined)

MTESNEVLFGIASHFALEGAVTGIEPYGDGHINTTYLVTTDGPRYILQQMNTSIFPDTVNLM

RNVELVTSTLKAQGKETLDIVPTTSGATWAEIDGGAWRVYKFIEHTVSYNLVPNPDVFREAG

SAFGDFQNFLSEFDASQLTETIAHFHDTPHRFEDFKAALAADKLGRAAACQPEIDFYLSHAD

QYAVVMDGLRDGSIPLRVTHNDTKLNNILMDATTGKARAIIDLDTIMPGSMLFDFGDSIRFG

ASTALEDEKDLSKVHFSTELFRAYTEGFVGELRGSITAREAELLPFSGNLLTMECGMRFLAD

YLEGDIYFATKYPEHNLVRTRTQIKLVQEMEQKASETHAIVADIMEAARLE<u>HHHHHH</u>

DNA sequence of AtGlcAK (SEQ ID NO: 5)
(Note: Italic sections of the sequences are from pET15b vector and primer).

*ATGGGCAGCAGCCATCATCATCATCATCACAGCAGCGGCCTGGTGCCGCGCGGCAGCCATAT*

GGATCCGAATTCCACGGTTTCCGGCGATGGTCAGGCGACGGCGGCGATAGAGCATCGGTCCT

TCGCTCGGATCGGATTTCTCGGAAACCCGAGCGATGTATACTTCGGGCGAACCATATCATTG

ACCATCGGAAACTTCTGGGCATCCGTGAAGCTGGAGCCATCGGAGCATCTCGTAATCAAGCC

TCATCCATTCCATGATCTCGTCCAGTTCACCTCTCTCGACCATCTCCTGAATCGTTTGCAAA

ATGAAGGATACTACGGTGGGGTAAGGTTGCTAATGGCGATATGTAAAGTATTCCGTAACTAT

TGCAAAGAGAATGACATTCAACTTCACCAAGCCAACTTCTCTCTTTCTTATGATACCAATAT

CCCTAGGCAGACAGGGCTTTCGGGTTCTAGTGCCATCGTATCCGCTGCCCTTAACTGCCTTC

TCGACTTCTACAATGTCAGGCATTTGATCAAAGTACAAGTCCGCCCTAACATTGTTCTCAGT

GCTGAGAAAGAACTTGGCATTGTTGCTGGTCTTCAGGACAGGGTTGCTCAGGTCTATGGTGG

TCTTGTTCACATGGATTTTAGCAAGGAGCACATGGATAAATTGGGGCATGGGATTTACACTC

| DNA AND PROTEIN SEQUENCES FOR GENES AND ENZYMES |
| --- |
| CTATGGATATCAGTCTCCTCCCTCCTCTGCATCTCATCTATGCTGAGAATCCGAGCGACTCA |
| GGGAAGGTACATAGTATGGTTCGGCAAAGATGGTTAGACGGTGATGAGTTTATAATCTCATC |
| AATGAAAGAAGTCGGAAGTCTAGCAGAAGAAGGTCGAACTGCATTACTCAACAAGGACCATT |
| CCAAACTTGTGGAACTCATGAACCTTAATTTCGACATTCGGAGGCGGATGTTTGGGGATGAA |
| TGCTTAGGAGCAATGAACATGGAGATGGTGGAAGTAGCAAGGAGGGTTGGTGCAGCCTCAAA |
| GTTCACTGGAAGTGGAGGAGCAGTGGTGGTTTTCTGCCCTGAAGGTCCATCTCAGGTGAAAC |
| TTCTGGAAGAAGAATGCAGGAAAGCGGGATTTACGCTTCAGCCGGTAAAAATTGCGCCTTCA |
| TGTTTGAATGATTCTGACATTCAGACCTTATGA |
| Protein sequence of AtGlcAK (SEQ ID NO: 6)(Note: Italic sections of the sequences are from pET15b vector and primer. N-terminal His$_6$-tag (SEQ ID NO: 22) is underlined in the protein sequence) *MGSS*<u>*HHHHHH*</u>*SSGLVPRGSH*MDPNSTVSGDGQATAAIEHRSFARIGFLGNPSDVYFGRTISL |
| TIGNFWASVKLEPSEHLVIKPHPFHDLVQFTSLDHLLNRLQNEGYYGGVRLLMAICKVFRNY |
| CKENDIQLHQANFSLSYDTNIPRQTGLSGSSAIVSAALNCLLDFYNVRHLIKVQVRPNIVLS |
| AEKELGIVAGLQDRVAQVYGGLVHMDFSKEHMDKLGHGIYTPMDISLLPPLHLIYAENPSDS |
| GKVHSMVRQRWLDGDEFIISSMKEVGSLAEEGRTALLNKDHSKLVELMNLNFDIRRRMFGDE |
| CLGAMNMEMVEVARRVGAASKFTGSGGAVVVFCPEGPSQVKLLEEECRKAGFTLQPVKIAPS |
| CLNDSDIQTL |
| DNA sequence of His$_6$-PmGlmU (SEQ ID NO: 7) (Note: Italic sections of the sequences are from pET15b vector and primer) *ATGGGCAGCAGCCATCATCATCATCATCACAGCAGCGGCCTGGTGCCGCGCGGCAGCCAT*AT |
| GAAAGAGAAAGCATTAAGTATCGTGATTTTAGCGGC<u>A</u>GGTAAAGGGACGCGGATGTATTCTG |
| ATTTACCAAAAGTGCTACATAAAATTGCCGGAAAACCGATGGTAAAACATGTGATCGATACG |
| GTGAAATCCATTCATGCAAAAAATATCCATTTAGTGTATGGACATGGTGGGGAAGTGATGCA |
| AACTCG<u>C</u>TTGCAAGATGAACCTGTGAATTGGGTCTTACAAGCCGAGCAATTAGGTACGGGGC |
| ATGCTATGCAGCAAGCAGCCCCGTTTTTTGCAGATGATGAAAATATTTTGATGCTTTATGGT |
| GATGGACCATTAATTACTGC<u>GA</u>AAAC<u>C</u>TTACAAACATTAATTGCGGCAAAACCTGAACATGG |
| TATTGCATTATTGACCGTCGTATTAGATGACCCAACTGGTTATGGGCGTATTGTGCGTGAAA |
| ATGGCAATGTGGTGGCGATTGTGGAACAAAAAGATGCCAATGCAGAGCAATTAAAAATCCAA |
| GAAATTAACACAGGCTTGTTAGTGGCAGACGGTAAAAGTTTGAAAAAATGGTTATCACAGTT |
| AACCAACAACAATGCACAGGGAGAATATTATATTACGGATGTGATCGCCTTAGCGAATCAAG |
| ACGGTTGCCA<u>A</u>GTAGTGGCGGTACAAGCCAGT<u>A</u>ACTTTATGGAAGTAGAGGGCGTGAATAAC |
| CGTCAGCAATTAGCGCGTTTAGAGCGTTATTATCAGCGCAAACAAGCAGACAATTTATTATT |
| GGCTGGGGTGGCATTAGCGGATCCTGAGCGTTTTGATTTACGCGGGGAACTAAGCCATGGGA |
| AAGACGTG<u>C</u>AAATTGATGTGAACGTGATTATCGAGGGCAAAGTCAGCTTAGGTCACCGAGTT |
| AAAATTGGAGC<u>A</u>GGTTGTGTGTTAAAAAATTGCCAGATTGGTGATGATGTAGAAATTAAACC |
| TTATTCTGTGTTGGAAGAGGCGATTGTTGGACAAGCTGCGCAAATTGGACCCTTCTCTCGTT |
| TGCGTCCGGGG<u>GCT</u>GCATTAGCCGACAACACTCATATTGGTAATTTCGTTGAAATTAAGAAA |
| GCGCATATTGGGAC<u>A</u>GGCTCGAAAGTAAACCATTTAAGTTATGTGGGAGATGCCGAAGTCGG |
| GATGCAATGTAATATTGGTGCCGGCGTGATCACTTGTAACTATGATGGCGCAAATAAATTTA |
| AGACCATTATTGGTGATAATGTGTTTGTAGGGTCTGATGTACAACTCGTGGCACCGGTTACC |

DNA AND PROTEIN SEQUENCES FOR GENES AND ENZYMES

ATCGAAACGGGTGCAACCATTGG*T*GCGGGGACTACGGTGACCAAAGATGTGGCTTGTGATGA

GTTAGTGATTTCACGTGTTCCTCAACGTCATATTCAAGGTTGGCAACGCCCTACTAAACAAA

CGAAAAAGTAA

Protein sequence of His₆-PmGlmU (SEQ ID NO: 8) (Note: Italic sections of the sequences are from pET15b vector and primer. N-terminal His₆-tag (SEQ ID NO: 22) is underlined in the protein sequence)

*MGSS<u>HHHHHH</u>SSGLVPRGSH*MKEKALSIVILAAGKGTRMYSDLPKVLHKIAGKPMVKHVIDT

VKSIHAKNIHLVYGHGGEVMQTRLQDEPVNWVLQAEQLGTGHAMQQAAPFFADDENILMLYG

DGPLITA<u>K</u>TLQTLIAAKPEHGIALLTVVLDDPTGYGRIVRENGNVVAIVEQKDANAEQLKIQ

EINTGLLVADGKSLKKWLSQLTNNNAQGEYYITDVIALANQDGCQVVAVQAS<u>N</u>FMEVEGVNN

RQQLARLERYYQRKQADNLLLAGVALADPERFDLRGELSHGKDV<u>Q</u>IDVNVIIEGKVSLGHRV

KIGAGCVLKNCQIGDDVEIKPYSVLEEAIVGQAAQIGPFSRLRPG<u>A</u>ALADNTHIGNFVEIKK

AHIGTGSKVNHLSYVGDAEVGMQCNIGAGVITCNYDGANKFKTIIGDNVFVGSDVQLVAPVT

IETGATIGAGTTVTKDVACDELVISRVPQRHIQGWQRPTKQTKK

DNA sequence of BLUSP (SEQ ID NO: 9)
(Note: The sequences for His₆-tag are underlined)
ATGGGCAGCAGC<u>CATCATCATCATCATCAC</u>AGCAGCGGCCTGGTGCCGCGCGGCAGCCATAT

GACAGAAATAAACGATAAGGCCCAACTGGATATCGCCGCCGCCGGCGACACCGACGCCGTTA

CCTCGGACACCCCCGAAGAAACCGTAAACACCCCCGAAGTGGATGAGACTTTCGAGCTTTCG

GCCGCCAAGATGCGCGAGCATGGCATGAGCGAAACCGCCATCAACCAGTTCCACCATTTGTA

TGACGTATGGCGCCATGAAGAAGCCTCCAGCTGGATTCGTGAGGACGACATCGAGCCGCTTG

GCCACGTGCCCAGCTTCCACGACGTCTATGAGACCATCAACCACGACAAGGCCGTGGACGCC

TTCGCCAAGACCGCATTCCTCAAGCTCAATGGCGGTCTGGGCACCTCCATGGGATTAGACAA

GGCCAAGTCGCTGTTGCCGGTGCGTAGGCACAAGGCCAAGCAGATGCGCTTCATCGACATCA

TCATCGGTCAGGTGCTTACCGCTCGCACCCGCCTGAACGTCGAACTGCCGCTGACGTTCATG

AACTCCTTCCACACTTCGGCGGACACGATGAAGGTGCTCAAGCATCATCGCAAGTTCAGTCA

GCATGACGTGCCGATGGAAATCATCCAGCATCAGGAACCCAAGCTCGTGGCCGCCACCGGCG

AACCTGTGAGCTACCCTGCGAACCCGGAGCTGGAATGGTGCCCGCCCGGCCACGGCGACCTG

TTCTCCACCATCTGGGAGTCTGGTCTGCTTGACGTATTGGAGGAGCGCGGCTTCAAGTATCT

GTTCATCTCCAATTCCGACAATCTCGGTGCGCGCGCCTCGCGTACGTTGGCCCAGCACTTCG

AAAACACAGGTGCCCCGTTTATGGCTGAAGTGGCCATCCGCACCAAGGCCGATCGCAAGGGC

GGCCATATTGTACGAGACAAGGCCACTGGTCGCCTAATACTGCGTGAAATGAGCCAGGTCCA

TCCGGACGATAAGGAAGCGGCCCAAGACATCACCAAGCATCCTTACTTCAACACCAACTCAA

TCTGGGTTCGCATCGACGCTTTGAAAGACAAGCTCGCCGAATGCGATGGTGTGTTGCCGTTG

CCGGTGATTCGTAACAAAAAGACCGTGAATCCCACGGACCCGGATTCCGAACAGGTGATTCA

GCTGGAAACCGCCATGGGCGCCGCAATCGGTCTGTTCAACGGTTCTATCTGCGTCCAAGTGG

ATCGTATGCGCTTCCTTCCGGTGAAAACCACCAATGATTTGTTCATTATGCGTTCCGATCGA

TTCCACCTGACGGACACGTATGAGATGGAAGACGGCAATTACATCTTCCCGAACGTCGAACT

TGATCCGCGATACTACAAGAACATCCACGATTTCGACGAACGGTTCCCCTACGCCGTGCCAT

CTTTGGCCGCAGCCAACTCGGTTTCCATTCAGGGCGACTGGACATTCGGACGTGACGTCATG

| DNA AND PROTEIN SEQUENCES FOR GENES AND ENZYMES |
|---|
| ATGTTCGCCGACGCCAAACTGGAAGATAAAGGCGAGCCAAGCTATGTGCCGAACGGCGAATA |
| CGTTGGTCCGCAAGGCATCGAACCGGACGATTGGGTGTGA |
| Protein sequence of BLUSP (SEQ ID NO: 10) (Note: The sequences for His<sub>6</sub>-tag are underlined)<br>MGSS<u>HHHHHH</u>SSGLVPRGSHMTEINDKAQLDIAAAGDTDAVTSDTPEETVNTPEVDETFELS |
| AAKMREHGMSETAINQFHHLYDVWRHEEASSWIREDDIEPLGHVPSFHDVYETINHDKAVDA |
| FAKTAFLKLNGGLGTSMGLDKAKSLLPVRRHKAKQMRFIDIIIGQVLTARTRLNVELPLTFM |
| NSFHTSADTMKVLKHHRKFSQHDVPMEIIQHQEPKLVAATGEPVSYPANPELEWCPPGHGDL |
| FSTIWESGLLDVLEERGFKYLFISNSDNLGARASRTLAQHFENTGAPFMAEVAIRTKADRKG |
| GHIVRDKATGRLILREMSQVHPDDKEAAQDITKHPYFNTNSIWVRIDALKDKLAECDGVLPL |
| PVIRNKKTVNPTDPDSEQVIQLETAMGAAIGLFNGSICVQVDRMRFLPVKTTNDLFIMRSDR |
| FHLTDTYEMEDGNYIFPNVELDPRYYKNIHDFDERFPYAVPSLAAANSVSIQGDWTFGRDVM |
| MFADAKLEDKGEPSYVPNGEYVGPQGIEPDDWV |
| DNA sequence of PmUgd-His<sub>6</sub> (SEQ ID NO: 11) (Note: The sequences for His6-tag are underlined)<br>ATGAAGAAAATTACAATTGCTGGGGCTGGCTATGTTGGTTTATCCAATGCAGTATTATTAGC |
| TCAACACCACAATGTGATCTTATTAGATATTGATCAAAATAAAGTTGATTTAATTAATAATA |
| AAAAATCGCCCATCACAGATAAAGAAATCGAAGATTTCTTACAAAATAAATCACTGACAATG |
| ATGGCAACAACAGATAAAGAAGTGGCATTAAAAAACGCAGACTTTGTCATCATCGCAACGCC |
| AACAGACTATAATACCGAAACAGGTTATTTTAATACATCCACTGTTGAAGCTGTCATTGAAC |
| AAACCCTTTCAATCAATCCACAAGCAACGATTATTATAAAATCAACGATTCCCGTTGGTTTT |
| ACCGAAAAAATGCGTGAGAAATTTCATACCAAGAACATTATTTTTTCTCCTGAGTTTTTAAG |
| AGAAGGAAAAGCACTTCATGACAATTTGTTTCCAAGCAGAATTATTGTTGGCAGTACTTCTT |
| ATCAAGCAAAAGTATTTGCCGATATGTTGACACAGTGTGCCAGAAAAAAGATGTAACTGTT |
| TTATTTACACACAATACTGAGGCTGAAGCTGTTAAATTATTTGCAAATACGTATCTCGCAAT |
| GCGAGTTGCCTTTTTTAATGAATTAGATACTTATGCGAGTCTTCACCATTTAAATACAAAG |
| ACATTATCAATGGTATTTCTACTGATCCTCGCATTGGTACACACTACAATAACCCAAGTTTC |
| GGCTATGGCGGTTATTGTTTACCCAAAGACACTAAACAGTTACTGGCTAACTATGCTGACGT |
| ACCTCAAAATCTCATTGAAGCCATTGTCAAATCTAATGAAACCAGAAAACGTTTCATTACTC |
| ATGATGTATTAAATAAGAAACCTAAAACTGTTGGTATTTATCGTTTAATCATGAAGTCAGGT |
| TCTGATAACTTCAGAGCTTCTGCTATTCTCGATATTATGCCGCATCTCAAAGAAAACGGTGT |
| TGAGATTGTGATTTATGAGCCAACCTTAAATCAACAGGCATTTGAGGACTACCCCGTTATTA |
| ATCAACTCTCTGAATTTATTAATCGCTCTGATGTCATTCTCGCTAATCGTTCTGAGCCAGAT |
| TTAAATCAATGTTCCCATAAAATCTATACAAGAGATATTTTTGGCGGTGATGCTCTCGAG<u>CA</u> |
| <u>CCACCACCACCACCAC</u>TGA |
| Protein sequence of PmUgd-His<sub>6</sub> (SEQ ID NO: 12) (Note: The sequences for His<sub>6</sub>-tag are underlined)<br>MKKITIAGAGYVGLSNAVLLAQHHNVILLDIDQNKVDLINNKKSPITDKEIEDFLQNKSLTM |
| MATTDKEVALKNADFVIIATPTDYNTETGYFNTSTVEAVIEQTLSINPQATIIIKSTIPVGF |
| TEKMREKFHTKNIIFSPEFLREGKALHDNLFPSRIIVGSTSYQAKVFADMLTQCARKKDVTV |
| LFTHNTEAEAVKLFANTYLAMRVAFFNELDTYASLHHLNTKDIINGISTDPRIGTHYNNPSF |
| GYGGYCLPKDTKQLLANYADVPQNLIEAIVKSNETRKRFITHDVLNKKPKTVGIYRLIMKSG |

DNA AND PROTEIN SEQUENCES FOR GENES AND ENZYMES

SDNFRASAILDIMPHLKENGVEIVIYEPTLNQQAFEDYPVINQLSEFINRSDVILANRSEPD

LNQCSHKIYTRDIFGGDALE<u>HHHHHH</u>

DNA sequence of MBP-PmHS1-His$_6$ (SEQ ID NO: 13) (Note: Italic sections of the sequences are from pMAL-c4X vector and primer. The sequences for His$_6$-tag are underlined)

*CTCGGGATCGAGGGAAGGATTTCAGAATTCGGATCC*ATGAGCTTATTTAAACGTGCTACTGA

GCTATTTAAGTCAGGAAACTATAAAGATGCACTAACTCTATATGAAAATATAGCTAAAATTT

ATGGTTCAGAAAGCCTTGTTAAATATAATATTGATATATGTAAAAAAAATATAACACAATCA

AAAAGTAATAAAATAGAAGAAGATAATATTTCTGGAGAAAACAAATTTTCAGTATCAATAAA

AGATCTATATAACGAAATAAGCAATAGTGAATTAGGGATTACAAAAGAAAGACTAGGAGCCC

CCCCTCTAGTCAGTATTATAATGACTTCTCATAATACAGAAAAATTCATTGAAGCCTCAATT

AATTCACTATTATTGCAAACATACAATAACTTAGAAGTTATCGTTGTAGATGATTATAGCAC

AGATAAAACATTTCAGATCGCATCCAGAATAGCAAACTCTACAAGTAAAGTAAAAACATTCC

GATTAAACTCAAATCTAGGGACATACTTTGCGAAAAATACAGGAATTTTAAAGTCTAAAGGA

GATATTATTTTCTTTCAGGATAGCGATGATGTATGTCACCATGAAAGAATCGAAAGATGTGT

TAATGCATTATTATCGAATAAAGATAATATAGCTGTTAGATGTGCATATTCTAGAATAAATC

TAGAAACACAAAATATAATAAAAGTTAATGATAATAAATACAAATTAGGATTAATAACTTTA

GGCGTTTATAGAAAAGTATTTAATGAAATTGGTTTTTTTAACTGCACAACCAAAGCATCGGA

TGATGAATTTTATCATAGAATAATTAAATACTATGGTAAAAATAGGATAAATAACTTATTTC

TACCACTGTATTATAACACAATGCGTGAAGATTCATTATTTTCTGATATGGTTGAGTGGGTA

GATGAAAATAATATAAAGCAAAAAACCTCTGATGCTAGACAAAATTATCTCCATGAATTCCA

AAAAATACACAATGAAAGGAAATTAAATGAATTAAAAGAGATTTTTAGCTTTCCTAGAATTC

ATGACGCCTTACCTATATCAAAAGAAATGAGTAAGCTCAGCAACCCTAAAATTCCTGTTTAT

ATAAATATATGCTCAATACCTTCAAGAATAAAACAACTTCAATACACTATTGGAGTACTAAA

AAACCAATGCGATCATTTTCATATTTATCTTGATGGATATCCAGAAGTACCTGATTTTATAA

AAAAACTAGGGAATAAAGCGACCGTTATTAATTGTCAAAACAAAATGAGTCTATTAGAGAT

AATGGAAAGTTTATTCTATTAGAAAAACTTATAAAGGAAAATAAAGATGGATATTATATAAC

TTGTGATGATGATATCCGGTATCCTGCTGACTACATAAACACTATGATAAAAAAAATTAATA

AATACAATGATAAAGCAGCAATTGGATTACATGGTGTTATATTCCCAAGTAGAGTCAACAAG

TATTTTTCATCAGACAGAATTGTCTATAATTTTCAAAAACCTTTAGAAAATGATACTGCTGT

AAATATATTAGGAACTGGAACTGTTGCCTTTAGAGTATCTATTTTTAATAAATTTTCTCTAT

CTGATTTTGAGCATCCTGGCATGGTAGATATCTATTTTTCTATACTATGTAAGAAAAACAAT

ATACTCCAAGTTTGTATATCACGACCATCGAATTGGCTAACAGAAGATAACAAAAACACTGA

GACCTTATTTCATGAATTCCAAAATAGAGATGAAATACAAAGTAAACTCATTATTTCAAACA

ACCCTTGGGGATACTCAAGTATATATCCATTATTAAATAATAATGCTAATTATTCTGAACTT

ATTCCGTGTTTATCTTTTTATAACGAG<u>CATCATCATCATCATCAC</u>TAA

DNA AND PROTEIN SEQUENCES FOR GENES AND ENZYMES

Protein sequence of MBP-PmHS1-His$_6$ (SEQ ID NO: 14) (Note: Italic sections of the sequences are from pMAL-c4X vector and primer. The sequences for His$_6$-tag (SEQ ID NO: 22) are underlined)

*LGIEGRISEFGS*MSLFKRATELFKSGNYKDALTLYENIAKIYGSESLVKYNIDICKKNITQS

KSNKIEEDNISGENKFSVSIKDLYNEISNSELGITKERLGAPPLVSIIMTSHNTEKFIEASI

NSLLLQTYNNLEVIVVDDYSTDKTFQIASRIANSTSKVKTFRLNSNLGTYFAKNTGILKSKG

DIIFFQDSDDVCHHERIERCVNALLSNKDNIAVRCAYSRINLETQNIIKVNDNKYKLGLITL

GVYRKVFNEIGFFNCTTKASDDEFYHRIIKYYGKNRINNLFLPLYYNTMREDSLFSDMVEWV

DENNIKQKTSDARQNYLHEFQKIHNERKLNELKEIFSFPRIHDALPISKEMSKLSNPKIPVY

INICSIPSRIKQLQYTIGVLKNQCDHFHIYLDGYPEVPDFIKKLGNKATVINCQNKNESIRD

NGKFILLEKLIKENKDGYYITCDDDIRYPADYINTMIKKINKYNDKAAIGLHGVIFPSRVNK

YESSDRIVYNFQKPLENDTAVNILGTGTVAFRVSIFNKFSLSDFEHPGMVDIYFSILCKKNN

ILQVCISRPSNWLTEDNKNTETLFHEFQNRDEIQSKLIISNNPWGYSSIYPLLNNNANYSEL

IPCLSFYNE<u>HHHHHH</u>

DNA sequence of His$_6$-PmHS2 (SEQ ID NO: 15) (Note: Italic sections of the sequences are from pET15b vector and primer. The sequences for His$_6$-tag are underlined)

*ATGGGCAGCAGC<u>CATCATCATCATCATCAC</u>AGCAGCGGCCTGGTGCCGCGCGGCAGCCATAT*

GAAGGGAAAAAAAGAGATGACTCAAAAACAAATGACTAAAAATCCACCCCAACATGAAAAG

AAAATGAACTCAACACCTTTCAAAATAAAATTGATAGTCTAAAAACAACTTTAAACAAAGAC

ATTATTTCTCAACAAACTTTATTGGCAAAACAGGACAGTAAACATCCGCTATCCGAATCCCT

TGAAAACGAAAATAAACTTTTATTAAAACAACTCCAATTGGTTCTACAAGAATTTGAAAAAA

TATATACCTATAATCAAGCATTAGAAGCAAAGCTAGAAAAAGATAAGCAAACAACATCAATA

ACAGATTTATATAATGAAGTCGCTAAAAGTGATTTAGGGTTAGTCAAAGAAACCAACAGCGC

AAATCCATTAGTCAGTATTATCATGACATCTCACAATACAGCGCAATTTATCGAAGCTTCTA

TTAATTCATTATTGTTACAAACATATAAAAACATAGAAATTATTATTGTAGATGATGATAGC

TCGGATAATACATTTGAAATTGCCTCGAGAATAGCGAATACAACAAGCAAAGTCAGAGTATT

TAGATTAAATTCAAACCTAGGAACTTACTTTGCGAAAAATACAGGCATATTAAAATCTAAAG

GTGACATTATTTTCTTTCAAGATAGTGATGATGTATGTCATCATGAAAGAATAGAAAGATGT

GTAAATATATTATTAGCTAATAAAGAAACTATTGCTGTTCGTTGTGCATACTCAAGACTAGC

ACCAGAAACACAACATATCATTAAAGTCAATAATATGGATTATAGATTAGGTTTTATAACCT

TGGGTATGCACAGAAAAGTATTTCAAGAAATTGGTTTCTTCAATTGTACGACTAAAGGCTCA

GATGATGAGTTTTTTCATAGAATTGCGAAATATTATGGAAAAGAAAAAATAAAAAATTTACT

CTTGCCGTTATACTACAACACAATGAGAGAAAACTCTTTATTTACTGATATGGTTGAATGGA

TAGACAATCATAACATAATACAGAAAATGTCTGATACCAGACAACATTATGCAACCCTGTTT

CAAGCGATGCATAACGAAACAGCCTCACATGATTTCAAAAATCTTTTTCAATTCCCTCGTAT

TTACGATGCCTTACCAGTACCACAAGAAATGAGTAAGTTGTCCAATCCTAAGATTCCTGTTT

ATATCAATATTTGTTCTATTCCCTCAAGAATAGCGCAATTACAACGTATTATCGGCATACTA

AAAAATCAATGTGATCATTTTCATATTTATCTTGATGGCTATGTAGAAATCCCTGACTTCAT

AAAAAATTTAGGTAATAAAGCAACCGTTGTTCATTGCAAAGATAAAGATAACTCCATTAGAG

ATAATGGCAAATTCATTTTACTGGAAGAGTTGATTGAAAAAAATCAAGATGGATATTATATA

ACCTGTGATGATGACATTATCTATCCAAGCGATTACATCAATACGATGATCAAAAAGCTGAA

DNA AND PROTEIN SEQUENCES FOR GENES AND ENZYMES

TGAATACGATGATAAAGCGGTTATTGGTTTACACGGCATTCTCTTTCCAAGTAGAATGACCA

AATATTTTTCGGCGGATAGACTGGTATATAGCTTCTATAAACCTCTGGAAAAAGACAAAGCG

GTCAATGTATTAGGTACAGGAACTGTTAGCTTTAGAGTCAGTCTCTTTAATCAATTTTCTCT

TTCTGACTTTACCCATTCAGGCATGGCTGATATCTATTTCTCTCTCTTGTGTAAGAAAAATA

ATATTCTTCAGATTTGTATTTCAAGACCAGCAAACTGGCTAACGGAAGATAATAGAGACAGC

GAAACACTCTATCATCAATATCGAGACAATGATGAGCAACAAACTCAGCTGATCATGGAAAA

CGGTCCATGGGATATTCAAGTATTTATCCATTAGTCAAAAATCATCCTAAATTTACTGACC

TTATCCCCTGTTTACCTTTTTATTTTTTATAA

Protein sequence of His$_6$-PmHS2 (SEQ ID NO: 16) (Note: Italic sections of the sequences are from pET15b vector and primer. The sequences for His$_6$-tag (SEQ ID NO: 22) are underlined)
*MGSS*<u>*HHHHHH*</u>*SSGLVPRGSH*MKGKKEMTQKQMTKNPPQHEKENELNTFQNKIDSLKTTLNKD

IISQQTLLAKQDSKHPLSESLENENKLLLKQLQLVLQEFEKIYTYNQALEAKLEKDKQTTSI

TDLYNEVAKSDLGLVKETNSANPLVSIIMTSHNTAQFIEASINSLLLQTYKNIEIIIVDDDS

SDNTFEIASRIANTTSKVRVFRLNSNLGTYFAKNTGILKSKGDIIFFQDSDDVCHHERIERC

VNILLANKETIAVRCAYSRLAPETQHIIKVNNMDYRLGFITLGMHRKVFQEIGFFNCTTKGS

DDEFFHRIAKYYGKEKIKNLLLPLYYNTMRENSLFTDMVEWIDNHNIIQKMSDTRQHYATLF

QAMHNETASHDFKNLFQFPRIYDALPVPQEMSKLSNPKIPVYINICSIPSRIAQLQRIIGIL

KNQCDHFHIYLDGYVEIPDFIKNLGNKATVVHCKDKDNSIRDNGKFILLEELIEKNQDGYYI

TCDDDIIYPSDYINTMIKKLNEYDDKAVIGLHGILFPSRMTKYFSADRLVYSFYKPLEKDKA

VNVLGTGTVSFRVSLENQFSLSDFTHSGMADIYESLLCKKNNILQICISRPANWLTEDNRDS

ETLYHQYRDNDEQQTQLIMENGPWGYSSIYPLVKNHPKFTDLIPCLPFYFL

DNA sequence of MBP-KfiA-His$_6$ (SEQ ID NO: 17) (Note: Italic sections of the sequences are from pMAL-c4X vector and primer. The sequences for His$_6$-tag are underlined)
*AACCTCGGGATCGAGGGAAGGATTTCAGAATTC*ATGATTGTTGCAAATATGAGCAGCTATCC

TCCGCGTAAAAAAGAACTGGTTCATAGCATTCAGAGCCTGCATGCACAGGTGGATAAAATTA

ATCTGTGCCTGAATGAATTTGAAGAAATTCCGGAAGAACTGGATGGCTTTAGCAAACTGAAT

CCGGTTATTCCGGATAAAGATTATAAAGATGTGGGCAAATTTATTTTTCCGTGCGCCAAAAA

TGATATGATTGTTCTGACCGATGATGATATTATTTATCCGCCAGATTATGTGGAAAAAATGC

TGAATTTTTATAATAGCTTTGCCATTTTTAATTGCATTGTGGGTATTCATGGCTGCATTTAT

ATTGATGCCTTTGATGGTGATCAGAGCAAACGTAAAGTGTTTAGCTTTACCCAGGGTCTGCT

GCGTCCGCGTGTTGTTAATCAGCTGGGCACCGGCACCGTTTTTCTGAAAGCAGATCAGCTGC

CGAGCCTGAAATATATGGATGGTAGCCAGCGTTTTGTGGATGTTCGTTTTAGCCGTTATATG

CTGGAAAATGAAATTGGCATGATTTGTGTTCCGCGTGAAAAAAATTGGCTGCGTGAAGTTAG

CAGCGGTAGCATGGAAGGTCTGTGGAATACCTTTACCAAAAAATGGCCTCTGGATATCATTA

AGAAACCCAGGCAATTGCCGGTTATAGTAAACTGAATCTGGAACTGGTGTATAATGTGGAA

GGT<u>CACCACCACCACCACCAC</u>TAA

DNA AND PROTEIN SEQUENCES FOR GENES AND ENZYMES

Protein sequence of MBP-KfiA-His₆ (SEQ ID NO: 18) (Note: Italic sections of the sequences are from pMAL-c4X vector and primer. The sequences for His₆-tag (SEQ ID NO: 22) are underlined)

*NLGIEGRISEF*MIVANMSSYPPRKKELVHSIQSLHAQVDKINLCLNEFEEIPEELDGFSKLN

PVIPDKDYKDVGKFIFPCAKNDMIVLTDDDIIYPPDYVEKMLNFYNSFATFNCIVGIHGCIY

IDAFDGDQSKRKVESFTQGLLRPRVVNQLGTGTVFLKADQLPSLKYMDGSQRFVDVRFSRYM

LENEIGMICVPREKNWLREVSSGSMEGLWNTFTKKWPLDIIKETQAIAGYSKLNLELVYNVE

<u>GHHHHHH</u>

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A sialylated oligosaccharide selected from the group consisting of:

Neu5Acα2-3(Neu5Acα2-6)Galβ1-4Glc;
Neu5Acα2-3(Neu5Acα2-6)Galβ1-3GalNAc;
Neu5Acα2-3(Neu5Acα2-6)Galβ1-3GlcNAc;
and
Neu5Acα2-6Galβ1-3GlcNAcβ1-3(Neu5Acα2-6)Galβ1-4Glc.

2. A sialylated oligosaccharide which is Neu5Acα2-6Galβ1-4GlcNAcβ1-3(Neu5Acα2-6)Galβ1-4Glc.

3. A method for treating necrotizing enterocolitis (NEC), the method comprising administering to a subject in need thereof a sialylated oligosaccharide according to claim 1.

4. A method for treating necrotizing enterocolitis (NEC), the method comprising administering to a subject in need thereof the sialylated oligosaccharide according to claim 2.

* * * * *

```
                          SEQUENCE LISTING

<160> NUMBER OF SEQ ID NOS: 45

<210> SEQ ID NO 1
<211> LENGTH: 1104
<212> TYPE: DNA
<213> ORGANISM: Artificial Sequence
<220> FEATURE:
<223> OTHER INFORMATION: synthetic Bifidobacterium longum subsp.
      infantis strain ATCC #15697 N-acetylhexosamine 1-kinase
      (NahK_ATCC15697) with His-6-tag

<400> SEQUENCE: 1
atgaacaaca ccaatgaagc cctgttcgac gtcgcttcgc acttcgcgct ggaaggcacc        60
gtcgacagca tcgaaccata cggagacggc catatcaaca ccacctatct ggtgaccacg       120
gacggccccc gctacatcct ccaacggatg aacaccggca tcttccccga tacggtgaat       180
ctgatgcgca atgtcgagct ggtcacctcc actctcaagg ctcagggcaa agagacgctg       240
gacatcgtgc gcaccacctc cggcgacacc tgggccgaga tcgacggcgg cgcatggcgc       300
gtctacaagt tcatcgaaca caccatgtca tacaacctcg tgccgaaccc ggacgtgttc       360
cgcgaagccg gcagggcgtt cggtgatttc cagaacttcc tgtccgggtt cgacgccaac       420
cagctgaccg agaccatcgc ccacttccac gacacccgc accgcttcga ggacttcaag       480
aaggcgctcg ccgcggacga gctcgggcgt gccgccgggt gcggcccgga gatcgagttc       540
tatctgagtc acgccgacca gtacgccgtc gtgatggatg ggctcaggga tggttcgatc       600
ccgctgcgcg tgacccacaa cgacaccaaa ctcaacaaca tcctcatgga tgccaccacc       660
ggcaaggccc gtgcgatcat cgatctagac accatcatgc cggggtccat gctcttcgac       720
ttcggcgatt ccatccgttt cggcgcgtcc acggccttgg aggatgagcg ggatctggac       780
aaggtgcatt tcagcaccga gctgttccgc gcctacacgg aaggcttcgt gggcgaacta       840
cgcgacagca tcaccgcgcg cgaggccgaa ctgctgccgt tcagcggcaa cctgctcacc       900
atggaatgcg gcatgcgctt tctcgccgac tacctggaag gcgacgtcta cttcgccacc       960
aagtaccccg agcataacct ggtgcgctcc cgcacccaga tcaagctcgt gagggagatg      1020
gagcagcgag ccgatgagac ccgcgccatc gtggccgacg tcatggagtc gaccaagctc      1080
gagcaccacc accaccacca ctga                                             1104

<210> SEQ ID NO 2
```

<211> LENGTH: 367
<212> TYPE: PRT
<213> ORGANISM: Artificial Sequence
<220> FEATURE:
<223> OTHER INFORMATION: synthetic Bifidobacterium longum subsp.
    infantis strain ATCC #15697 N-acetylhexosamine 1-kinase
    (NahK_ATCC15697) with His-6-tag

<400> SEQUENCE: 2

Met Asn Asn Thr Asn Glu Ala Leu Phe Asp Val Ala Ser His Phe Ala
1               5                   10                  15

Leu Glu Gly Thr Val Asp Ser Ile Glu Pro Tyr Gly Asp Gly His Ile
            20                  25                  30

Asn Thr Thr Tyr Leu Val Thr Thr Asp Gly Pro Arg Tyr Ile Leu Gln
        35                  40                  45

Arg Met Asn Thr Gly Ile Phe Pro Asp Thr Val Asn Leu Met Arg Asn
    50                  55                  60

Val Glu Leu Val Thr Ser Thr Leu Lys Ala Gln Gly Lys Glu Thr Leu
65                  70                  75                  80

Asp Ile Val Arg Thr Thr Ser Gly Asp Thr Trp Ala Glu Ile Asp Gly
                85                  90                  95

Gly Ala Trp Arg Val Tyr Lys Phe Ile Glu His Thr Met Ser Tyr Asn
            100                 105                 110

Leu Val Pro Asn Pro Asp Val Phe Arg Glu Ala Gly Arg Ala Phe Gly
        115                 120                 125

Asp Phe Gln Asn Phe Leu Ser Gly Phe Asp Ala Asn Gln Leu Thr Glu
    130                 135                 140

Thr Ile Ala His Phe His Asp Thr Pro His Arg Phe Glu Asp Phe Lys
145                 150                 155                 160

Lys Ala Leu Ala Ala Asp Glu Leu Gly Arg Ala Ala Gly Cys Gly Pro
                165                 170                 175

Glu Ile Glu Phe Tyr Leu Ser His Ala Asp Gln Tyr Ala Val Val Met
            180                 185                 190

Asp Gly Leu Arg Asp Gly Ser Ile Pro Leu Arg Val Thr His Asn Asp
        195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255

Arg Asp Leu Asp Lys Val His Phe Ser Thr Glu Leu Phe Arg Ala Tyr
            260                 265                 270

Thr Glu Gly Phe Val Gly Glu Leu Arg Asp Ser Ile Thr Ala Arg Glu
        275                 280                 285

Ala Glu Leu Leu Pro Phe Ser Gly Asn Leu Leu Thr Met Glu Cys Gly
    290                 295                 300

Met Arg Phe Leu Ala Asp Tyr Leu Glu Gly Asp Val Tyr Phe Ala Thr
305                 310                 315                 320

Lys Tyr Pro Glu His Asn Leu Val Arg Ser Arg Thr Gln Ile Lys Leu
                325                 330                 335

Val Arg Glu Met Glu Gln Arg Ala Asp Glu Thr Arg Ala Ile Val Ala
            340                 345                 350

Asp Val Met Glu Ser Thr Lys Leu Glu His His His His His
        355                 360                 365

<210> SEQ ID NO 3
<211> LENGTH: 1104
<212> TYPE: DNA
<213> ORGANISM: Artificial Sequence
<220> FEATURE:
<223> OTHER INFORMATION: synthetic Bifidobacterium longum Reuter strain
      ATCC #55813 N-acetylhexosamine 1-kinase
      (NahK_ATCC55813) with His-6-tag

<400> SEQUENCE: 3

```
atgaccgaaa gcaatgaagt tttattcggc atcgcctcgc attttgcgct ggaaggtgcc      60
gtgaccggta tcgaacctta cggagacggc cacatcaaca ccacctatct ggtgaccacg     120
gacggccccc gctacatcct ccagcagatg aacaccagca tcttccccga tacggtgaat     180
ctgatgcgca atgtcgaact ggtcacctcc actctcaagg ctcagggcaa agagacgctg     240
gacattgtgc ccaccacctc aggcgccacc tgggccgaga tcgatggcgg cgcatggcgc     300
gtctacaagt tcatcgaaca caccgtgtcc tacaacctcg tgccgaaccc ggacgtgttc     360
cgcgaagccg gcagcgcatt cggcgacttc agaacttcc tgtccgaatt cgacgccagc      420
cagctgaccg aaaccatcgc ccacttccac gacaccccgc atcgtttcga ggacttcaag     480
gccgccctcg ccgcggacaa gctcggccgc gccgccgcat gccagccgga aatcgacttc     540
tatctgagtc acgccgacca gtatgccgtc gtgatggatg ggctcaggga cggttcgatt     600
ccgctgcgcg tgacccacaa tgacaccaag ctcaacaaca tcctcatgga cgccaccacc     660
ggcaaggcgc gtgcgatcat cgatctcgac accatcatgc ccggctccat gctgttcgac     720
ttcggcgatt ccatacgctt tggtgcgtcc actgctctgg aagacgaaaa ggacctcagc     780
aaggtgcatt tcagcaccga gctgttccgc gcctacacgg aaggcttcgt gggcgaacta     840
cgcggcagca tcaccgcgcg cgaggccgaa ctgctgccgt tcagcggcaa cctgctcacc     900
atggaatgcg gcatgcgctt tctcgccgac tacttggaag gcgatatcta ctttgccacc     960
aagtaccccg agcataatct ggtgcgcacc cgcacccaga tcaaactcgt gcaggagatg    1020
gagcagaagg ccagtgaaac ccacgccatc gtagccgaca tcatggaggc tgccaggctc    1080
gagcaccacc accaccacca ctga                                          1104
```

<210> SEQ ID NO 4
<211> LENGTH: 367
<212> TYPE: PRT
<213> ORGANISM: Artificial Sequence
<220> FEATURE:
<223> OTHER INFORMATION: synthetic Bifidobacterium longum Reuter strain
      ATCC #55813 N-acetylhexosamine 1-kinase
      (NahK_ATCC55813) with His-6-tag

<400> SEQUENCE: 4

```
Met Thr Glu Ser Asn Glu Val Leu Phe Gly Ile Ala Ser His Phe Ala
  1               5                  10                  15

Leu Glu Gly Ala Val Thr Gly Ile Glu Pro Tyr Gly Asp Gly His Ile
             20                  25                  30

Asn Thr Thr Tyr Leu Val Thr Thr Asp Gly Pro Arg Tyr Ile Leu Gln
         35                  40                  45

Gln Met Asn Thr Ser Ile Phe Pro Asp Thr Val Asn Leu Met Arg Asn
     50                  55                  60

Val Glu Leu Val Thr Ser Thr Leu Lys Ala Gln Gly Lys Glu Thr Leu
 65                  70                  75                  80

Asp Ile Val Pro Thr Thr Ser Gly Ala Thr Trp Ala Glu Ile Asp Gly
                 85                  90                  95
```

Gly Ala Trp Arg Val Tyr Lys Phe Ile Glu His Thr Val Ser Tyr Asn
            100                 105                 110

Leu Val Pro Asn Pro Asp Val Phe Arg Glu Ala Gly Ser Ala Phe Gly
        115                 120                 125

Asp Phe Gln Asn Phe Leu Ser Glu Phe Asp Ala Ser Gln Leu Thr Glu
    130                 135                 140

Thr Ile Ala His Phe His Asp Thr Pro His Arg Phe Glu Asp Phe Lys
145                 150                 155                 160

Ala Ala Leu Ala Ala Asp Lys Leu Gly Arg Ala Ala Ala Cys Gln Pro
                165                 170                 175

Glu Ile Asp Phe Tyr Leu Ser His Ala Asp Gln Tyr Ala Val Val Met
            180                 185                 190

Asp Gly Leu Arg Asp Gly Ser Ile Pro Leu Arg Val Thr His Asn Asp
        195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255

Lys Asp Leu Ser Lys Val His Phe Ser Thr Glu Leu Phe Arg Ala Tyr
            260                 265                 270

Thr Glu Gly Phe Val Gly Glu Leu Arg Gly Ser Ile Thr Ala Arg Glu
        275                 280                 285

Ala Glu Leu Leu Pro Phe Ser Gly Asn Leu Leu Thr Met Glu Cys Gly
    290                 295                 300

Met Arg Phe Leu Ala Asp Tyr Leu Glu Gly Asp Ile Tyr Phe Ala Thr
305                 310                 315                 320

Lys Tyr Pro Glu His Asn Leu Val Arg Thr Arg Thr Gln Ile Lys Leu
                325                 330                 335

Val Gln Glu Met Glu Gln Lys Ala Ser Glu Thr His Ala Ile Val Ala
            340                 345                 350

Asp Ile Met Glu Ala Ala Arg Leu Glu His His His His His
        355                 360                 365

<210> SEQ ID NO 5
<211> LENGTH: 1149
<212> TYPE: DNA
<213> ORGANISM: Artificial Sequence
<220> FEATURE:
<223> OTHER INFORMATION: synthetic Arabidopsis thaliana ecotype Columbia
      glucuronokinase G (AtGlcAK, GlcAK1, ATGLCAK,
      GLCAK), locus tag At3g01640, F4P13.18, with
      His-6-tag

<400> SEQUENCE: 5
atgggcagca gccatcatca tcatcatcac agcagcggcc tggtgccgcg cggcagccat      60
atggatccga attccacggt tccggcgat ggtcaggcga cggcggcgat agagcatcgg     120
tccttcgctc ggatcggatt tctcggaaac ccgagcgatg tatacttcgg gcgaaccata     180
tcattgacca tcggaaactt ctgggcatcc gtgaagctgg agccatcgga gcatctcgta     240
atcaagcctc atccattcca tgatctcgtc cagttcacct ctctcgacca tctcctgaat     300
cgtttgcaaa atgaaggata ctacggtggg gtaaggttgc taatggcgat atgtaaagta     360
ttccgtaact attgcaaaga gaatgacatt caacttcacc aagccaactt ctctctttct     420

```
tatgatacca atatccctag gcagacaggg ctttcgggtt ctagtgccat cgtatccgct    480
gcccttaact gccttctcga cttctacaat gtcaggcatt tgatcaaagt acaagtccgc    540
cctaacattg ttctcagtgc tgagaaagaa cttggcattg ttgctggtct tcaggacagg    600
gttgctcagg tctatggtgg tcttgttcac atggatttta gcaaggagca catggataaa    660
ttggggcatg ggatttacac tcctatggat atcagtctcc tccctcctct gcatctcatc    720
tatgctgaga atccgagcga ctcagggaag gtacatagta tggttcggca agatggtta    780
gacggtgatg agtttataat ctcatcaatg aaagaagtcg gaagtctagc agaagaaggt    840
cgaactgcat tactcaacaa ggaccattcc aaacttgtgg aactcatgaa ccttaatttc    900
gacattcgga ggcggatgtt tggggatgaa tgcttaggag caatgaacat ggagatggtg    960
gaagtagcaa ggagggttgg tgcagcctca aagttcactg aagtggagg agcagtggtg   1020
gttttctgcc ctgaaggtcc atctcaggtg aaacttctgg aagaagaatg caggaaagcg   1080
ggatttacgc ttcagccggt aaaaattgcg ccttcatgtt tgaatgattc tgacattcag   1140
accttatga                                                          1149

<210> SEQ ID NO 6
<211> LENGTH: 382
<212> TYPE: PRT
<213> ORGANISM: Artificial Sequence
<220> FEATURE:
<223> OTHER INFORMATION: synthetic Arabidopsis thaliana ecotype Columbia
      glucuronokinase G (AtGlcAK, GlcAK1, ATGLCAK,
      GLCAK), locus tag At3g01640, F4P13.18, with
      His-6-tag

<400> SEQUENCE: 6
```

Met Gly Ser Ser His His His His His His Ser Ser Gly Leu Val Pro
1               5                   10                  15

Arg Gly Ser His Met Asp Pro Asn Ser Thr Val Ser Gly Asp Gly Gln
            20                  25                  30

Ala Thr Ala Ala Ile Glu His Arg Ser Phe Ala Arg Ile Gly Phe Leu
        35                  40                  45

Gly Asn Pro Ser Asp Val Tyr Phe Gly Arg Thr Ile Ser Leu Thr Ile
    50                  55                  60

Gly Asn Phe Trp Ala Ser Val Lys Leu Glu Pro Ser Glu His Leu Val
65                  70                  75                  80

Ile Lys Pro His Pro Phe His Asp Leu Val Gln Phe Thr Ser Leu Asp
                85                  90                  95

His Leu Leu Asn Arg Leu Gln Asn Glu Gly Tyr Tyr Gly Gly Val Arg
            100                 105                 110

Leu Leu Met Ala Ile Cys Lys Val Phe Arg Asn Tyr Cys Lys Glu Asn
        115                 120                 125

Asp Ile Gln Leu His Gln Ala Asn Phe Ser Leu Ser Tyr Asp Thr Asn
    130                 135                 140

Ile Pro Arg Gln Thr Gly Leu Ser Gly Ser Ser Ala Ile Val Ser Ala
145                 150                 155                 160

Ala Leu Asn Cys Leu Leu Asp Phe Tyr Asn Val Arg His Leu Ile Lys
                165                 170                 175

Val Gln Val Arg Pro Asn Ile Val Leu Ser Ala Glu Lys Glu Leu Gly
            180                 185                 190

Ile Val Ala Gly Leu Gln Asp Arg Val Ala Gln Val Tyr Gly Gly Leu
        195                 200                 205

Val His Met Asp Phe Ser Lys Glu His Met Asp Lys Leu Gly His Gly

```
    210                 215                 220

Ile Tyr Thr Pro Met Asp Ile Ser Leu Leu Pro Pro Leu His Leu Ile
225                 230                 235                 240

Tyr Ala Glu Asn Pro Ser Asp Ser Gly Lys Val His Ser Met Val Arg
                245                 250                 255

Gln Arg Trp Leu Asp Gly Asp Glu Phe Ile Ile Ser Ser Met Lys Glu
            260                 265                 270

Val Gly Ser Leu Ala Glu Glu Gly Arg Thr Ala Leu Leu Asn Lys Asp
        275                 280                 285

His Ser Lys Leu Val Glu Leu Met Asn Leu Asn Phe Asp Ile Arg Arg
    290                 295                 300

Arg Met Phe Gly Asp Glu Cys Leu Gly Ala Met Asn Met Glu Met Val
305                 310                 315                 320

Glu Val Ala Arg Arg Val Gly Ala Ala Ser Lys Phe Thr Gly Ser Gly
                325                 330                 335

Gly Ala Val Val Val Phe Cys Pro Glu Gly Pro Ser Gln Val Lys Leu
            340                 345                 350

Leu Glu Glu Glu Cys Arg Lys Ala Gly Phe Thr Leu Gln Pro Val Lys
        355                 360                 365

Ile Ala Pro Ser Cys Leu Asn Asp Ser Asp Ile Gln Thr Leu
    370                 375                 380

<210> SEQ ID NO 7
<211> LENGTH: 1437
<212> TYPE: DNA
<213> ORGANISM: Artificial Sequence
<220> FEATURE:
<223> OTHER INFORMATION: synthetic Pasteurella multocida strain P-1059
      (ATCC 15742) N-acetylglucosamine-1-phosphate
      uridylyltransferase (PmGlmU) with His-6-tag

<400> SEQUENCE: 7
atgggcagca gccatcatca tcatcatcac agcagcggcc tggtgccgcg cggcagccat      60
atgaaagaga aagcattaag tatcgtgatt ttagcggcag gtaaagggac gcggatgtat     120
tctgatttac caaaagtgct acataaaatt gccggaaaac cgatggtaaa acatgtgatc     180
gatacggtga aatccattca tgcaaaaaat atccatttag tgtatggaca tggtggggaa     240
gtgatgcaaa ctcgcttgca agatgaacct gtgaattggg tcttacaagc cgagcaatta     300
ggtacggggc atgctatgca gcaagcagcc ccgtttttttg cagatgatga aaatattttg     360
atgctttatg gtgatggacc attaattact gcgaaaacct tacaaacatt aattgcggca     420
aaacctgaac atggtattgc attattgacc gtcgtattag atgacccaac tggttatggg     480
cgtattgtgc gtgaaaatgg caatgtggtg gcgattgtgg aacaaaaaga tgccaatgca     540
gagcaattaa aaatccaaga aattaacaca ggcttgttag tggcagacgg taaaagtttg     600
aaaaaatggt tatcacagtt aaccaacaac aatgcacagg gagaatatta tattacggat     660
gtgatcgcct tagcgaatca agacggttgc caagtagtgg cggtacaagc cagtaacttt     720
atggaagtag agggcgtgaa taaccgtcag caattagcgc gtttagagcg ttattatcag     780
cgcaaacaag cagacaattt attattggct ggggtggcat tagcggatcc tgagcgtttt     840
gatttacgcg gggaactaag ccatgggaaa gacgtgcaaa ttgatgtgaa cgtgattatc     900
gagggcaaag tcagcttagg tcaccgagtt aaaattggag caggttgtgt gttaaaaaat     960
tgccagattg gtgatgatgt agaaattaaa ccttattctg tgttggaaga ggcgattgtt    1020
ggacaagctg cgcaaattgg accctctct cgtttgcgtc cgggggctgc attagccgac    1080
```

```
aacactcata ttggtaattt cgttgaaatt aagaaagcgc atattgggac aggctcgaaa   1140
gtaaaccatt taagttatgt gggagatgcc gaagtcggga tgcaatgtaa tattggtgcc   1200
ggcgtgatca cttgtaacta tgatggcgca aataaattta agaccattat tggtgataat   1260
gtgtttgtag ggctctgatgt acaactcgtg gcaccggtta ccatcgaaac gggtgcaacc   1320
attggtgcgg ggactacggt gaccaaagat gtggcttgtg atgagttagt gatttcacgt   1380
gttcctcaac gtcatattca aggttggcaa cgccctacta acaaacgaa aaagtaa      1437
```

<210> SEQ ID NO 8
<211> LENGTH: 478
<212> TYPE: PRT
<213> ORGANISM: Artificial Sequence
<220> FEATURE:
<223> OTHER INFORMATION: synthetic Pasteurella multocida strain P-1059
      (ATCC 15742) N-acetylglucosamine-1-phosphate
      uridylyltransferase (PmGlmU) with His-6-tag

<400> SEQUENCE: 8

```
Met Gly Ser Ser His His His His His His Ser Ser Gly Leu Val Pro
1               5                   10                  15

Arg Gly Ser His Met Lys Glu Lys Ala Leu Ser Ile Val Ile Leu Ala
            20                  25                  30

Ala Gly Lys Gly Thr Arg Met Tyr Ser Asp Leu Pro Lys Val Leu His
        35                  40                  45

Lys Ile Ala Gly Lys Pro Met Val Lys His Val Ile Asp Thr Val Lys
    50                  55                  60

Ser Ile His Ala Lys Asn Ile His Leu Val Tyr Gly His Gly Gly Glu
65                  70                  75                  80

Val Met Gln Thr Arg Leu Gln Asp Glu Pro Val Asn Trp Val Leu Gln
                85                  90                  95

Ala Glu Gln Leu Gly Thr Gly His Ala Met Gln Gln Ala Ala Pro Phe
            100                 105                 110

Phe Ala Asp Asp Glu Asn Ile Leu Met Leu Tyr Gly Asp Gly Pro Leu
        115                 120                 125

Ile Thr Ala Lys Thr Leu Gln Thr Leu Ile Ala Ala Lys Pro Glu His
    130                 135                 140

Gly Ile Ala Leu Leu Thr Val Val Leu Asp Asp Pro Thr Gly Tyr Gly
145                 150                 155                 160

Arg Ile Val Arg Glu Asn Gly Asn Val Val Ala Ile Val Glu Gln Lys
                165                 170                 175

Asp Ala Asn Ala Glu Gln Leu Lys Ile Gln Glu Ile Asn Thr Gly Leu
            180                 185                 190

Leu Val Ala Asp Gly Lys Ser Leu Lys Lys Trp Leu Ser Gln Leu Thr
        195                 200                 205

Asn Asn Asn Ala Gln Gly Glu Tyr Tyr Ile Thr Asp Val Ile Ala Leu
    210                 215                 220

Ala Asn Gln Asp Gly Cys Gln Val Val Ala Val Gln Ala Ser Asn Phe
225                 230                 235                 240

Met Glu Val Glu Gly Val Asn Asn Arg Gln Gln Leu Ala Arg Leu Glu
                245                 250                 255

Arg Tyr Tyr Gln Arg Lys Gln Ala Asp Asn Leu Leu Leu Ala Gly Val
            260                 265                 270

Ala Leu Ala Asp Pro Glu Arg Phe Asp Leu Arg Gly Glu Leu Ser His
        275                 280                 285
```

```
Gly Lys Asp Val Gln Ile Asp Val Asn Val Ile Ile Glu Gly Lys Val
        290                 295                 300
Ser Leu Gly His Arg Val Lys Ile Gly Ala Gly Cys Val Leu Lys Asn
305                 310                 315                 320
Cys Gln Ile Gly Asp Asp Val Glu Ile Lys Pro Tyr Ser Val Leu Glu
                325                 330                 335
Glu Ala Ile Val Gly Gln Ala Ala Gln Ile Gly Pro Phe Ser Arg Leu
            340                 345                 350
Arg Pro Gly Ala Ala Leu Ala Asp Asn Thr His Ile Gly Asn Phe Val
        355                 360                 365
Glu Ile Lys Lys Ala His Ile Gly Thr Gly Ser Lys Val Asn His Leu
370                 375                 380
Ser Tyr Val Gly Asp Ala Glu Val Gly Met Gln Cys Asn Ile Gly Ala
385                 390                 395                 400
Gly Val Ile Thr Cys Asn Tyr Asp Gly Ala Asn Lys Phe Lys Thr Ile
                405                 410                 415
Ile Gly Asp Asn Val Phe Val Gly Ser Asp Val Gln Leu Val Ala Pro
            420                 425                 430
Val Thr Ile Glu Thr Gly Ala Thr Ile Gly Ala Gly Thr Thr Val Thr
        435                 440                 445
Lys Asp Val Ala Cys Asp Glu Leu Val Ile Ser Arg Val Pro Gln Arg
450                 455                 460
His Ile Gln Gly Trp Gln Arg Pro Thr Lys Gln Thr Lys Lys
465                 470                 475
```

<210> SEQ ID NO 9
<211> LENGTH: 1590
<212> TYPE: DNA
<213> ORGANISM: Artificial Sequence
<220> FEATURE:
<223> OTHER INFORMATION: synthetic Bifidobacterium longum Reuter strain
      ATCC#55813, ugpA, locus tag HMPREF0175_1671
      UDP-sugar pyrophosphorylase (BLUSP) with His-6-tag

<400> SEQUENCE: 9

```
atgggcagca gccatcatca tcatcatcac agcagcggcc tggtgccgcg cggcagccat    60
atgacagaaa taaacgataa ggcccaactg gatatcgccg ccgccggcga caccgacgcc   120
gttacctcgg acacccccga agaaaccgta aacacccccg aagtggatga cttttcgag    180
cttttcggccg ccaagatgcg cgagcatggc atgagcgaaa ccgccatcaa ccagttccac   240
catttgtatg acgtatggcg ccatgaagaa gcctccagct ggattcgtga ggacgacatc   300
gagccgcttg ccacgtgcc cagcttccac gacgtctatg agaccatcaa ccacgacaag   360
gccgtggacg ccttcgccaa gaccgcattc ctcaagctca atggcggtct ggcaccctcc   420
atgggattag acaaggccaa gtcgctgttg ccggtgcgta ggcacaaggc caagcagatg   480
cgcttcatcg acatcatcat cggtcaggtg cttaccgctc gcacccgcct gaacgtcgaa   540
ctgccgctga cgttcatgaa ctccttccac acttcggcgg acacgatgaa ggtgctcaag   600
catcatcgca gttcagtca gcatgacgtg ccgatggaaa tcatccagca tcaggaaccc   660
aagctcgtgg ccgccaccgg cgaacctgtg agctacctg cgaacccgga gctggaatgg   720
tgcccgcccg ccacggcga cctgttctcc accatctggg agtctggtct gcttgacgta   780
ttggaggagc gcggcttcaa gtatctgttc atctccaatt ccgacaatct cggtgcgcgc   840
gcctcgcgta cgttggccca gcacttcgaa aacacaggtg ccccgtttat ggctgaagtg   900
gccatccgca ccaaggccga tcgcaagggc ggccatattg tacgagacaa ggccactggt   960
```

```
cgcctaatac tgcgtgaaat gagccaggtc catccggacg ataaggaagc ggcccaagac   1020
atcaccaagc atccttactt caacaccaac tcaatctggg ttcgcatcga cgctttgaaa   1080
gacaagctcg ccgaatgcga tggtgtgttg ccgttgccgg tgattcgtaa caaaaagacc   1140
gtgaatccca cggaccccga ttccgaacag gtgattcagc tggaaaccgc catgggcgcc   1200
gcaatcggtc tgttcaacgg ttctatctgc gtccaagtgg atcgtatgcg cttccttccg   1260
gtgaaaacca ccaatgattt gttcattatg cgttccgatc gattccacct gacggacacg   1320
tatgagatgg aagacggcaa ttacatcttc ccgaacgtcg aacttgatcc gcgatactac   1380
aagaacatcc acgatttcga cgaacggttc ccctacgccg tgccatcttt ggccgcagcc   1440
aactcggttt ccattcaggg cgactggaca ttcggacgtg acgtcatgat gttcgccgac   1500
gccaaactgg aagataaagg cgagccaagc tatgtgccga acggcgaata cgttggtccg   1560
caaggcatcg aaccggacga ttgggtgtga                                    1590
```

<210> SEQ ID NO 10
<211> LENGTH: 529
<212> TYPE: PRT
<213> ORGANISM: Artificial Sequence
<220> FEATURE:
<223> OTHER INFORMATION: synthetic Bifidobacterium longum Reuter strain
    ATCC#55813, ugpA, locus tag HMPREF0175_1671
    UDP-sugar pyrophosphorylase (BLUSP) with His-6-tag

<400> SEQUENCE: 10

```
Met Gly Ser Ser His His His His His His Ser Ser Gly Leu Val Pro
 1               5                  10                  15

Arg Gly Ser His Met Thr Glu Ile Asn Asp Lys Ala Gln Leu Asp Ile
            20                  25                  30

Ala Ala Ala Gly Asp Thr Asp Ala Val Thr Ser Asp Thr Pro Glu Glu
        35                  40                  45

Thr Val Asn Thr Pro Glu Val Asp Glu Thr Phe Glu Leu Ser Ala Ala
    50                  55                  60

Lys Met Arg Glu His Gly Met Ser Glu Thr Ala Ile Asn Gln Phe His
65                  70                  75                  80

His Leu Tyr Asp Val Trp Arg His Glu Glu Ala Ser Ser Trp Ile Arg
                85                  90                  95

Glu Asp Asp Ile Glu Pro Leu Gly His Val Pro Ser Phe His Asp Val
           100                 105                 110

Tyr Glu Thr Ile Asn His Asp Lys Ala Val Asp Ala Phe Ala Lys Thr
       115                 120                 125

Ala Phe Leu Lys Leu Asn Gly Gly Leu Gly Thr Ser Met Gly Leu Asp
   130                 135                 140

Lys Ala Lys Ser Leu Leu Pro Val Arg Arg His Lys Ala Lys Gln Met
145                 150                 155                 160

Arg Phe Ile Asp Ile Ile Ile Gly Gln Val Leu Thr Ala Arg Thr Arg
                165                 170                 175

Leu Asn Val Glu Leu Pro Leu Thr Phe Met Asn Ser Phe His Thr Ser
           180                 185                 190

Ala Asp Thr Met Lys Val Leu Lys His Arg Lys Phe Ser Gln His
       195                 200                 205

Asp Val Pro Met Glu Ile Ile Gln His Gln Glu Pro Lys Leu Val Ala
   210                 215                 220

Ala Thr Gly Glu Pro Val Ser Tyr Pro Ala Asn Pro Glu Leu Glu Trp
225                 230                 235                 240
```

-continued

```
Cys Pro Pro Gly His Gly Asp Leu Phe Ser Thr Ile Trp Glu Ser Gly
                245                 250                 255
Leu Leu Asp Val Leu Glu Glu Arg Gly Phe Lys Tyr Leu Phe Ile Ser
            260                 265                 270
Asn Ser Asp Asn Leu Gly Ala Arg Ala Ser Arg Thr Leu Ala Gln His
        275                 280                 285
Phe Glu Asn Thr Gly Ala Pro Phe Met Ala Glu Val Ala Ile Arg Thr
    290                 295                 300
Lys Ala Asp Arg Lys Gly Gly His Ile Val Arg Asp Lys Ala Thr Gly
305                 310                 315                 320

Arg Leu Ile Leu Arg Glu Met Ser Gln Val His Pro Asp Asp Lys Glu
                325                 330                 335
Ala Ala Gln Asp Ile Thr Lys His Pro Tyr Phe Asn Thr Asn Ser Ile
            340                 345                 350
Trp Val Arg Ile Asp Ala Leu Lys Asp Lys Leu Ala Glu Cys Asp Gly
        355                 360                 365
Val Leu Pro Leu Pro Val Ile Arg Asn Lys Lys Thr Val Asn Pro Thr
    370                 375                 380
Asp Pro Asp Ser Glu Gln Val Ile Gln Leu Glu Thr Ala Met Gly Ala
385                 390                 395                 400
Ala Ile Gly Leu Phe Asn Gly Ser Ile Cys Val Gln Val Asp Arg Met
                405                 410                 415
Arg Phe Leu Pro Val Lys Thr Thr Asn Asp Leu Phe Ile Met Arg Ser
            420                 425                 430
Asp Arg Phe His Leu Thr Asp Thr Tyr Glu Met Glu Asp Gly Asn Tyr
        435                 440                 445
Ile Phe Pro Asn Val Glu Leu Asp Pro Arg Tyr Tyr Lys Asn Ile His
    450                 455                 460
Asp Phe Asp Glu Arg Phe Pro Tyr Ala Val Pro Ser Leu Ala Ala Ala
465                 470                 475                 480
Asn Ser Val Ser Ile Gln Gly Asp Trp Thr Phe Gly Arg Asp Val Met
                485                 490                 495
Met Phe Ala Asp Ala Lys Leu Glu Asp Lys Gly Glu Pro Ser Tyr Val
            500                 505                 510

Pro Asn Gly Glu Tyr Val Gly Pro Gln Gly Ile Glu Pro Asp Asp Trp
        515                 520                 525
Val

<210> SEQ ID NO 11
<211> LENGTH: 1197
<212> TYPE: DNA
<213> ORGANISM: Artificial Sequence
<220> FEATURE:
<223> OTHER INFORMATION: synthetic Pasteurella multocida strain P-1059
      (ATCC#15742) UDP-glucose dehydrogenase (PmUgd)
      with His-6-tag
<400> SEQUENCE: 11
atgaagaaaa ttacaattgc tggggctggc tatgttggtt tatccaatgc agtattatta      60
gctcaacacc acaatgtgat cttattagat attgatcaaa ataaagttga tttaattaat     120
aataaaaaat cgcccatcac agataaagaa atcgaagatt tcttacaaaa taaatcactg     180
acaatgatgg caacaacaga taaagaagtg gcattaaaaa acgcagactt tgtcatcatc     240
gcaacgccaa cagactataa taccgaaaca ggttatttta atacatccac tgttgaagct     300
```

-continued

```
gtcattgaac aaacccttc aatcaatcca caagcaacga ttattataaa atcaacgatt    360
cccgttggtt ttaccgaaaa aatgcgtgag aaatttcata ccaagaacat tatttttct    420
cctgagtttt taagagaagg aaaagcactt catgacaatt tgtttccaag cagaattatt    480
gttggcagta cttcttatca agcaaaagta tttgccgata tgttgacaca gtgtgccaga    540
aaaaagatg taactgtttt atttacacac aatactgagg ctgaagctgt taaattattt    600
gcaaatacgt atctcgcaat gcgagttgcc ttttttaatg aattagatac ttatgcgagt    660
cttcaccatt taaatacaaa agacattatc aatggtattt ctactgatcc tcgcattggt    720
acacactaca ataacccaag tttcggctat ggcggttatt gtttacccaa agacactaaa    780
cagttactgg ctaactatgc tgacgtacct caaaatctca ttgaagccat tgtcaaatct    840
aatgaaacca gaaacgtttt cattactcat gatgtattaa ataagaaacc taaaactgtt    900
ggtatttatc gtttaatcat gaagtcaggt tctgataact tcagagcttc tgctattctc    960
gatattatgc cgcatctcaa agaaaacggt gttgagattg tgatttatga gccaaccta   1020
aatcaacagg catttgagga ctaccccgtt attaatcaac tctctgaatt tattaatcgc   1080
tctgatgtca ttctcgctaa tcgttctgag ccagatttaa atcaatgttc ccataaaatc   1140
tatacaagag atattttgg cggtgatgct ctcgagcacc accaccacca ccactga      1197
```

<210> SEQ ID NO 12
<211> LENGTH: 398
<212> TYPE: PRT
<213> ORGANISM: Artificial Sequence
<220> FEATURE:
<223> OTHER INFORMATION: synthetic Pasteurella multocida strain P-1059
(ATCC#15742) UDP-glucose dehydrogenase (PmUgd)
with His-6-tag

<400> SEQUENCE: 12

```
Met Lys Lys Ile Thr Ile Ala Gly Ala Gly Tyr Val Gly Leu Ser Asn
 1               5                  10                  15

Ala Val Leu Leu Ala Gln His His Asn Val Ile Leu Leu Asp Ile Asp
            20                  25                  30

Gln Asn Lys Val Asp Leu Ile Asn Asn Lys Lys Ser Pro Ile Thr Asp
        35                  40                  45

Lys Glu Ile Glu Asp Phe Leu Gln Asn Lys Ser Leu Thr Met Met Ala
    50                  55                  60

Thr Thr Asp Lys Glu Val Ala Leu Lys Asn Ala Asp Phe Val Ile Ile
65                  70                  75                  80

Ala Thr Pro Thr Asp Tyr Asn Thr Glu Thr Gly Tyr Phe Asn Thr Ser
                85                  90                  95

Thr Val Glu Ala Val Ile Glu Gln Thr Leu Ser Ile Asn Pro Gln Ala
            100                 105                 110

Thr Ile Ile Ile Lys Ser Thr Ile Pro Val Gly Phe Thr Glu Lys Met
        115                 120                 125

Arg Glu Lys Phe His Thr Lys Asn Ile Ile Phe Ser Pro Glu Phe Leu
    130                 135                 140

Arg Glu Gly Lys Ala Leu His Asp Asn Leu Phe Pro Ser Arg Ile Ile
145                 150                 155                 160

Val Gly Ser Thr Ser Tyr Gln Ala Lys Val Phe Ala Asp Met Leu Thr
                165                 170                 175

Gln Cys Ala Arg Lys Lys Asp Val Thr Val Leu Phe Thr His Asn Thr
            180                 185                 190

Glu Ala Glu Ala Val Lys Leu Phe Ala Asn Thr Tyr Leu Ala Met Arg
```

```
              195                 200                 205
Val Ala Phe Phe Asn Glu Leu Asp Thr Tyr Ala Ser Leu His His Leu
210                 215                 220

Asn Thr Lys Asp Ile Ile Asn Gly Ile Ser Thr Asp Pro Arg Ile Gly
225                 230                 235                 240

Thr His Tyr Asn Asn Pro Ser Phe Gly Tyr Gly Gly Tyr Cys Leu Pro
                245                 250                 255

Lys Asp Thr Lys Gln Leu Leu Ala Asn Tyr Ala Asp Val Pro Gln Asn
                260                 265                 270

Leu Ile Glu Ala Ile Val Lys Ser Asn Glu Thr Arg Lys Arg Phe Ile
            275                 280                 285

Thr His Asp Val Leu Asn Lys Lys Pro Lys Thr Val Gly Ile Tyr Arg
        290                 295                 300

Leu Ile Met Lys Ser Gly Ser Asp Asn Phe Arg Ala Ser Ala Ile Leu
305                 310                 315                 320

Asp Ile Met Pro His Leu Lys Glu Asn Gly Val Glu Ile Val Ile Tyr
                325                 330                 335

Glu Pro Thr Leu Asn Gln Gln Ala Phe Glu Asp Tyr Pro Val Ile Asn
                340                 345                 350

Gln Leu Ser Glu Phe Ile Asn Arg Ser Asp Val Ile Leu Ala Asn Arg
            355                 360                 365

Ser Glu Pro Asp Leu Asn Gln Cys Ser His Lys Ile Tyr Thr Arg Asp
        370                 375                 380

Ile Phe Gly Gly Asp Ala Leu Glu His His His His His His
385                 390                 395
```

<210> SEQ ID NO 13
<211> LENGTH: 1908
<212> TYPE: DNA
<213> ORGANISM: Artificial Sequence
<220> FEATURE:
<223> OTHER INFORMATION: synthetic fusion protein of N-terminal maltose-
      binding protein (MBP) with Pasteurella multocida strain P-934
      (ATCC#12948) heparosan synthase 1 (HS1), glycosyltransferase, with
      His-6-tag (MBP-PmHS1-His-6)

<400> SEQUENCE: 13

```
ctcgggatcg agggaaggat ttcagaattc ggatccatga gcttatttaa acgtgctact    60 gagctatttta agtcaggaaa ctataaagat gcactaactc tatatgaaaa tatagctaaa   120
atttatggtt cagaaagcct tgttaaatat aatattgata tatgtaaaaa aaatataaca   180
caatcaaaaa gtaataaaat agaagaagat aatatttctg gagaaaacaa attttcagta   240
tcaataaaag atctatataa cgaaataagc aatagtgaat tagggattac aaaagaaaga   300
ctaggagccc ccctctagt cagtattata atgacttctc ataatacaga aaaattcatt   360
gaagcctcaa ttaattcact attattgcaa acatacaata acttagaagt tatcgttgta   420
gatgattata gcacagataa acatttcag atcgcatcca gaatagcaaa ctctacaagt   480
aaagtaaaaa cattccgatt aaactcaaat ctagggacat actttgcgaa aaatacagga   540
attttaaagt ctaaggaga tattattttc tttcaggata gcgatgatgt atgtcaccat   600
gaaagaatcg aaagatgtgt taatgcatta ttatcgaata agataatat agctgttaga   660 tgtgcatatt ctagaataaa tctagaaaca caaaatataa taaagttaa tgataataaa   720 tacaaattag gattaataac tttaggcgtt tatagaaaag tatttaatga aattggtttt   780
tttaactgca caaccaaagc atcggatgat gaattttatc atagaataat taaatactat    840
```

-continued

```
ggtaaaaata ggataaataa cttatttcta ccactgtatt ataacacaat gcgtgaagat    900
tcattatttt ctgatatggt tgagtgggta gatgaaaata atataaagca aaaaacctct    960
gatgctagac aaaattatct ccatgaattc caaaaaatac acaatgaaag gaaattaaat   1020
gaattaaaag agatttttag ctttcctaga attcatgacg ccttacctat atcaaaagaa   1080
atgagtaagc tcagcaaccc taaaattcct gtttatataa atatatgctc aatatccttca   1140 agaataaaac aacttcaata cactattgga gtactaaaaa accaatgcga tcattttcat   1200
atttatcttg atggatatcc agaagtacct gattttataa aaaaactagg gaataaagcg   1260
accgttatta attgtcaaaa caaaaatgag tctattagag ataatggaaa gtttattcta   1320
ttagaaaaac ttataaagga aaataaagat ggatattata taacttgtga tgatgatatc   1380
cggtatcctg ctgactacat aaacactatg ataaaaaaaa ttaataaata caatgataaa   1440
gcagcaattg gattacatgg tgttatattc ccaagtagag tcaacaagta tttttcatca   1500
gacagaattg tctataattt tcaaaaacct ttagaaaatg atactgctgt aaatatatta   1560
ggaactggaa ctgttgcctt tagagtatct atttttaata aattttctct atctgatttt   1620
gagcatcctg gcatggtaga tatctatttt tctatactat gtaagaaaaa caatatactc   1680
caagtttgta tatcacgacc atcgaattgg ctaacagaag ataacaaaaa cactgagacc   1740
ttatttcatg aattccaaaa tagagatgaa atacaaagta aactcattat ttcaaacaac   1800
ccttggggat actcaagtat atatccatta ttaaataata atgctaatta ttctgaactt   1860
attccgtgtt tatcttttta taacgagcat catcatcatc atcactaa                1908
```

```

<210> SEQ ID NO 14
<211> LENGTH: 635
<212> TYPE: PRT
<213> ORGANISM: Artificial Sequence
<220> FEATURE:
<223> OTHER INFORMATION: synthetic fusion protein of N-terminal maltose-
      binding protein (MBP) with Pasteurella multocida strain P-934
      (ATCC#12948) heparosan synthase 1 (HS1), glycosyltransferase, with
      His-6-tag (MBP-PmHS1-His-6)

<400> SEQUENCE: 14

Leu Gly Ile Glu Gly Arg Ile Ser Glu Phe Gly Ser Met Ser Leu Phe
 1               5                  10                  15

Lys Arg Ala Thr Glu Leu Phe Lys Ser Gly Asn Tyr Lys Asp Ala Leu
            20                  25                  30

Thr Leu Tyr Glu Asn Ile Ala Lys Ile Tyr Gly Ser Glu Ser Leu Val
        35                  40                  45

Lys Tyr Asn Ile Asp Ile Cys Lys Lys Asn Ile Thr Gln Ser Lys Ser
    50                  55                  60

Asn Lys Ile Glu Glu Asp Asn Ile Ser Gly Glu Asn Lys Phe Ser Val
65                  70                  75                  80

Ser Ile Lys Asp Leu Tyr Asn Glu Ile Ser Asn Ser Glu Leu Gly Ile
                85                  90                  95

Thr Lys Glu Arg Leu Gly Ala Pro Pro Leu Val Ser Ile Ile Met Thr
            100                 105                 110

Ser His Asn Thr Glu Lys Phe Ile Glu Ala Ser Ile Asn Ser Leu Leu
        115                 120                 125

Leu Gln Thr Tyr Asn Asn Leu Glu Val Ile Val Val Asp Asp Tyr Ser
    130                 135                 140

Thr Asp Lys Thr Phe Gln Ile Ala Ser Arg Ile Ala Asn Ser Thr Ser
145                 150                 155                 160
```

```
Lys Val Lys Thr Phe Arg Leu Asn Ser Asn Leu Gly Thr Tyr Phe Ala
            165                 170                 175
Lys Asn Thr Gly Ile Leu Lys Ser Lys Gly Asp Ile Ile Phe Phe Gln
        180                 185                 190
Asp Ser Asp Val Cys His His Glu Arg Ile Glu Arg Cys Val Asn
    195                 200                 205
Ala Leu Leu Ser Asn Lys Asp Asn Ile Ala Val Arg Cys Ala Tyr Ser
    210                 215                 220
Arg Ile Asn Leu Glu Thr Gln Asn Ile Ile Lys Val Asn Asp Asn Lys
225                 230                 235                 240
Tyr Lys Leu Gly Leu Ile Thr Leu Gly Val Tyr Arg Lys Val Phe Asn
            245                 250                 255
Glu Ile Gly Phe Phe Asn Cys Thr Thr Lys Ala Ser Asp Asp Glu Phe
            260                 265                 270
Tyr His Arg Ile Ile Lys Tyr Gly Lys Asn Arg Ile Asn Asn Leu
    275                 280                 285
Phe Leu Pro Leu Tyr Tyr Asn Thr Met Arg Glu Asp Ser Leu Phe Ser
    290                 295                 300
Asp Met Val Glu Trp Val Asp Glu Asn Asn Ile Lys Gln Lys Thr Ser
305                 310                 315                 320
Asp Ala Arg Gln Asn Tyr Leu His Glu Phe Gln Lys Ile His Asn Glu
                325                 330                 335
Arg Lys Leu Asn Glu Leu Lys Glu Ile Phe Ser Phe Pro Arg Ile His
            340                 345                 350
Asp Ala Leu Pro Ile Ser Lys Glu Met Ser Lys Leu Ser Asn Pro Lys
            355                 360                 365
Ile Pro Val Tyr Ile Asn Ile Cys Ser Ile Pro Ser Arg Ile Lys Gln
    370                 375                 380
Leu Gln Tyr Thr Ile Gly Val Leu Lys Asn Gln Cys Asp His Phe His
385                 390                 395                 400
Ile Tyr Leu Asp Gly Tyr Pro Glu Val Pro Asp Phe Ile Lys Lys Leu
                405                 410                 415
Gly Asn Lys Ala Thr Val Ile Asn Cys Gln Asn Lys Asn Glu Ser Ile
            420                 425                 430
Arg Asp Asn Gly Lys Phe Ile Leu Leu Glu Lys Leu Ile Lys Glu Asn
    435                 440                 445
Lys Asp Gly Tyr Tyr Ile Thr Cys Asp Asp Asp Ile Arg Tyr Pro Ala
    450                 455                 460
Asp Tyr Ile Asn Thr Met Ile Lys Lys Ile Asn Lys Tyr Asn Asp Lys
465                 470                 475                 480
Ala Ala Ile Gly Leu His Gly Val Ile Phe Pro Ser Arg Val Asn Lys
            485                 490                 495
Tyr Phe Ser Ser Asp Arg Ile Val Tyr Asn Phe Gln Lys Pro Leu Glu
                500                 505                 510
Asn Asp Thr Ala Val Asn Ile Leu Gly Thr Gly Thr Val Ala Phe Arg
            515                 520                 525
Val Ser Ile Phe Asn Lys Phe Ser Leu Ser Asp Phe Glu His Pro Gly
    530                 535                 540
Met Val Asp Ile Tyr Phe Ser Ile Leu Cys Lys Lys Asn Asn Ile Leu
545                 550                 555                 560
Gln Val Cys Ile Ser Arg Pro Ser Asn Trp Leu Thr Glu Asp Asn Lys
                565                 570                 575
Asn Thr Glu Thr Leu Phe His Glu Phe Gln Asn Arg Asp Glu Ile Gln
```

Ser Lys Leu Ile Ile Ser Asn Asn Pro Trp Gly Tyr Ser Ser Ile Tyr
    580                 585                 590

Pro Leu Leu Asn Asn Asn Ala Asn Tyr Ser Glu Leu Ile Pro Cys Leu
        595                 600                 605

Ser Phe Tyr Asn Glu His His His His His His
625                 630                 635

<210> SEQ ID NO 15
<211> LENGTH: 2016
<212> TYPE: DNA
<213> ORGANISM: Artificial Sequence
<220> FEATURE:
<223> OTHER INFORMATION: synthetic Pasteurella multocida strain P-1059
      (ATCC#15742) heparosan synthase 2 (HS2),
      glycosyltransferase, with His-6-tag (His-6-PmHS2)

<400> SEQUENCE: 15

```
atgggcagca gccatcatca tcatcatcac agcagcggcc tggtgccgcg cggcagccat      60
atgaagggaa aaaagagat gactcaaaaa caaatgacta aaaatccacc ccaacatgaa     120
aaagaaaatg aactcaacac cttttcaaaat aaaattgata gtctaaaaac aactttaaac     180
aaagacatta tttctcaaca aactttattg gcaaacagg acagtaaaca tccgctatcc     240
gaatcccttg aaaacgaaaa taaactttta ttaaaacaac tccaattggt tctacaagaa     300
tttgaaaaaa tatataccta taatcaagca ttagaagcaa agctagaaaa agataagcaa     360
acaacatcaa taacagattt atataatgaa gtcgctaaaa gtgatttagg gttagtcaaa     420
gaaaccaaca gcgcaaatcc attagtcagt attatcatga catctcacaa tacagcgcaa     480
tttatcgaag cttctattaa ttcattattg ttacaaacat ataaaaacat agaaattatt     540
attgtagatg atgatagctc ggataataca tttgaaattg cctcgagaat agcgaataca     600
acaagcaaag tcagagtatt tagattaaat tcaaacctag gaacttactt tgcgaaaaat     660
acaggcatat taaaatctaa aggtgacatt attttctttc aagatagtga tgatgtatgt     720
catcatgaaa gaatagaaag atgtgtaaat atattattag ctaataaaga aactattgct     780
gttcgttgtg catactcaag actagcacca gaaacacaac atatcattaa agtcaataat     840
atggattata gattaggttt tataaccttg ggtatgcaca gaaaagtatt tcaagaaatt     900
ggttctttca attgtacgac taaaggctca gatgatgagt ttttcatag aattgcgaaa     960
tattatggaa agaaaaaat aaaaaattta ctcttgccgt tatactacaa cacaatgaga    1020
gaaaactctt tatttactga tatggttgaa tggatagaca atcataacat aatacagaaa    1080
atgtctgata ccagacaaca ttatgcaacc tgtttcaag cgatgcataa cgaaacagcc    1140
tcacatgatt tcaaaaatct ttttcaattc cctcgtattt acgatgcctt accagtacca    1200
caagaaatga gtaagttgtc caatcctaag attcctgttt atatcaatat tgttctatt     1260
ccctcaagaa tagcgcaatt acaacgtatt atcggcatac taaaaaatca atgtgatcat    1320
tttcatatt atcttgatgg ctatgtagaa atccctgact catataaaaaa tttaggtaat     1380
aaagcaaccg ttgttcattg caaagataaa gataactcca ttagataaa tggcaaattc     1440
attttactgg aagagttgat tgaaaaaaat caagatggga ttatataac ctgtgatgat    1500
gacattatct atccaagcga ttacatcaat acgatgatca aaagctgaa tgaatacgat    1560
gataaagcgg ttattggttt acacggcatt ctctttccaa gtagaatgac caaatatttt    1620
tcggcggata gactggtata tagcttctat aaacctctgg aaaaagacaa agcggtcaat    1680
```

```
gtattaggta caggaactgt tagctttaga gtcagtctct ttaatcaatt ttctctttct    1740
gactttaccc attcaggcat ggctgatatc tatttctctc tcttgtgtaa gaaaaataat    1800
attcttcaga tttgtatttc aagaccagca aactggctaa cggaagataa tagagacagc    1860
gaaacactct atcatcaata tcgagacaat gatgagcaac aaactcagct gatcatggaa    1920
aacggtccat ggggatattc aagtatttat ccattagtca aaaatcatcc taaatttact    1980
gaccttatcc cctgtttacc tttttatttt ttataa                              2016
```

<210> SEQ ID NO 16
<211> LENGTH: 671
<212> TYPE: PRT
<213> ORGANISM: Artificial Sequence
<220> FEATURE:
<223> OTHER INFORMATION: synthetic Pasteurella multocida strain P-1059
      (ATCC#15742) heparosan synthase 2 (HS2),
      glycosyltransferase, with His-6-tag (His-6-PmHS2)

<400> SEQUENCE: 16

```
Met Gly Ser Ser His His His His His Ser Ser Gly Leu Val Pro
 1               5                  10                  15

Arg Gly Ser His Met Lys Gly Lys Lys Glu Met Thr Gln Lys Gln Met
            20                  25                  30

Thr Lys Asn Pro Pro Gln His Glu Lys Glu Asn Glu Leu Asn Thr Phe
        35                  40                  45

Gln Asn Lys Ile Asp Ser Leu Lys Thr Thr Leu Asn Lys Asp Ile Ile
    50                  55                  60

Ser Gln Gln Thr Leu Leu Ala Lys Gln Asp Ser Lys His Pro Leu Ser
65                  70                  75                  80

Glu Ser Leu Glu Asn Glu Asn Lys Leu Leu Leu Lys Gln Leu Gln Leu
                85                  90                  95

Val Leu Gln Glu Phe Glu Lys Ile Tyr Thr Tyr Asn Gln Ala Leu Glu
            100                 105                 110

Ala Lys Leu Glu Lys Asp Lys Gln Thr Thr Ser Ile Thr Asp Leu Tyr
        115                 120                 125

Asn Glu Val Ala Lys Ser Asp Leu Gly Leu Val Lys Glu Thr Asn Ser
    130                 135                 140

Ala Asn Pro Leu Val Ser Ile Ile Met Thr Ser His Asn Thr Ala Gln
145                 150                 155                 160

Phe Ile Glu Ala Ser Ile Asn Ser Leu Leu Leu Gln Thr Tyr Lys Asn
                165                 170                 175

Ile Glu Ile Ile Ile Val Asp Asp Asp Ser Ser Asp Asn Thr Phe Glu
            180                 185                 190

Ile Ala Ser Arg Ile Ala Asn Thr Thr Ser Lys Val Arg Val Phe Arg
        195                 200                 205

Leu Asn Ser Asn Leu Gly Thr Tyr Phe Ala Lys Asn Thr Gly Ile Leu
    210                 215                 220

Lys Ser Lys Gly Asp Ile Ile Phe Phe Gln Asp Ser Asp Asp Val Cys
225                 230                 235                 240

His His Glu Arg Ile Glu Arg Cys Val Asn Ile Leu Leu Ala Asn Lys
                245                 250                 255

Glu Thr Ile Ala Val Arg Cys Ala Tyr Ser Arg Leu Ala Pro Glu Thr
            260                 265                 270

Gln His Ile Ile Lys Val Asn Asn Met Asp Tyr Arg Leu Gly Phe Ile
        275                 280                 285

Thr Leu Gly Met His Arg Lys Val Phe Gln Glu Ile Gly Phe Phe Asn
```

```
                290             295             300
Cys Thr Thr Lys Gly Ser Asp Asp Glu Phe Phe His Arg Ile Ala Lys
305             310             315             320

Tyr Tyr Gly Lys Glu Lys Ile Lys Asn Leu Leu Pro Leu Tyr Tyr
                325             330             335

Asn Thr Met Arg Glu Asn Ser Leu Phe Thr Asp Met Val Glu Trp Ile
                340             345             350

Asp Asn His Asn Ile Ile Gln Lys Met Ser Asp Thr Arg Gln His Tyr
                355             360             365

Ala Thr Leu Phe Gln Ala Met His Asn Glu Thr Ala Ser His Asp Phe
                370             375             380

Lys Asn Leu Phe Gln Phe Pro Arg Ile Tyr Asp Ala Leu Pro Val Pro
385             390             395             400

Gln Glu Met Ser Lys Leu Ser Asn Pro Lys Ile Pro Val Tyr Ile Asn
                405             410             415

Ile Cys Ser Ile Pro Ser Arg Ile Ala Gln Leu Gln Arg Ile Ile Gly
                420             425             430

Ile Leu Lys Asn Gln Cys Asp His Phe His Ile Tyr Leu Asp Gly Tyr
                435             440             445

Val Glu Ile Pro Asp Phe Ile Lys Asn Leu Gly Asn Lys Ala Thr Val
450             455             460

Val His Cys Lys Asp Lys Asp Asn Ser Ile Arg Asp Asn Gly Lys Phe
465             470             475             480

Ile Leu Leu Glu Glu Leu Ile Glu Lys Asn Gln Asp Gly Tyr Tyr Ile
                485             490             495

Thr Cys Asp Asp Asp Ile Ile Tyr Pro Ser Asp Tyr Ile Asn Thr Met
                500             505             510

Ile Lys Lys Leu Asn Glu Tyr Asp Asp Lys Ala Val Ile Gly Leu His
                515             520             525

Gly Ile Leu Phe Pro Ser Arg Met Thr Lys Tyr Phe Ser Ala Asp Arg
530             535             540

Leu Val Tyr Ser Phe Tyr Lys Pro Leu Glu Lys Asp Lys Ala Val Asn
545             550             555             560

Val Leu Gly Thr Gly Thr Val Ser Phe Arg Val Ser Leu Phe Asn Gln
                565             570             575

Phe Ser Leu Ser Asp Phe Thr His Ser Gly Met Ala Asp Ile Tyr Phe
                580             585             590

Ser Leu Leu Cys Lys Lys Asn Asn Ile Leu Gln Ile Cys Ile Ser Arg
                595             600             605

Pro Ala Asn Trp Leu Thr Glu Asp Asn Arg Asp Ser Glu Thr Leu Tyr
610             615             620

His Gln Tyr Arg Asp Asn Asp Glu Gln Gln Thr Gln Leu Ile Met Glu
625             630             635             640

Asn Gly Pro Trp Gly Tyr Ser Ser Ile Tyr Pro Leu Val Lys Asn His
                645             650             655

Pro Lys Phe Thr Asp Leu Ile Pro Cys Leu Pro Phe Tyr Phe Leu
                660             665             670

<210> SEQ ID NO 17
<211> LENGTH: 768
<212> TYPE: DNA
<213> ORGANISM: Artificial Sequence
<220> FEATURE:
<223> OTHER INFORMATION: synthetic fusion protein of N-terminal maltose-
      binding protein (MBP) with Escherichia coli strain Nissle 1917
``` serovar O6:K5:H1 ORF79 KfiA with codons optimized for E. coli
expression with His-6-tag (MBP-KfiA-His-6)

<400> SEQUENCE: 17

```
aacctcggga tcgagggaag gatttcagaa ttcatgattg ttgcaaatat gagcagctat    60
cctccgcgta aaaagaact ggttcatagc attcagagcc tgcatgcaca ggtggataaa   120
attaatctgt gcctgaatga atttgaagaa attccggaag aactggatgg ctttagcaaa   180
ctgaatccgg ttattccgga taagattat aaagatgtgg gcaaatttat ttttccgtgc   240
gccaaaaatg atatgattgt tctgaccgat gatgatatta tttatccgcc agattatgtg   300
gaaaaaatgc tgaatttta taatagcttt gccattttta attgcattgt gggtattcat   360
ggctgcattt atattgatgc ctttgatggt gatcagagca acgtaaagt gtttagcttt   420
acccagggtc tgctgcgtcc gcgtgttgtt aatcagctgg gcaccggcac cgttttctg   480
aaagcagatc agctgccgag cctgaaatat atggatggta ccagcgttt tgtggatgtt   540
cgttttagcc gttatatgct ggaaaatgaa attggcatga tttgtgttcc gcgtgaaaaa   600
aattggctgc gtgaagttag cagcggtagc atggaaggtc tgtggaatac ctttaccaaa   660
aaatggcctc tggatatcat taaagaaacc caggcaattg ccggttatag taaactgaat   720
ctggaactgg tgtataatgt ggaaggtcac caccaccacc accactaa                768
```

<210> SEQ ID NO 18
<211> LENGTH: 255
<212> TYPE: PRT
<213> ORGANISM: Artificial Sequence
<220> FEATURE:
<223> OTHER INFORMATION: synthetic fusion protein of N-terminal maltose-
    binding protein (MBP) with Escherichia coli strain Nissle 1917
    serovar O6:K5:H1 ORF79 KfiA with codons optimized for E. coli
    expression with His-6-tag (MBP-KfiA-His-6)

<400> SEQUENCE: 18

```
Asn Leu Gly Ile Glu Gly Arg Ile Ser Glu Phe Met Ile Val Ala Asn
 1               5                  10                  15

Met Ser Ser Tyr Pro Pro Arg Lys Lys Glu Leu Val His Ser Ile Gln
            20                  25                  30

Ser Leu His Ala Gln Val Asp Lys Ile Asn Leu Cys Leu Asn Glu Phe
        35                  40                  45

Glu Glu Ile Pro Glu Glu Leu Asp Gly Phe Ser Lys Leu Asn Pro Val
    50                  55                  60

Ile Pro Asp Lys Asp Tyr Lys Asp Val Gly Lys Phe Ile Phe Pro Cys
65                  70                  75                  80

Ala Lys Asn Asp Met Ile Val Leu Thr Asp Asp Asp Ile Ile Tyr Pro
                85                  90                  95

Pro Asp Tyr Val Glu Lys Met Leu Asn Phe Tyr Asn Ser Phe Ala Ile
           100                 105                 110

Phe Asn Cys Ile Val Gly Ile His Gly Cys Ile Tyr Ile Asp Ala Phe
       115                 120                 125

Asp Gly Asp Gln Ser Lys Arg Lys Val Phe Ser Phe Thr Gln Gly Leu
   130                 135                 140

Leu Arg Pro Arg Val Val Asn Gln Leu Gly Thr Gly Thr Val Phe Leu
145                 150                 155                 160

Lys Ala Asp Gln Leu Pro Ser Leu Lys Tyr Met Asp Gly Ser Gln Arg
                165                 170                 175

Phe Val Asp Val Arg Phe Ser Arg Tyr Met Leu Glu Asn Glu Ile Gly
           180                 185                 190
```

Met Ile Cys Val Pro Arg Glu Lys Asn Trp Leu Arg Glu Val Ser Ser
            195                 200                 205

Gly Ser Met Glu Gly Leu Trp Asn Thr Phe Thr Lys Lys Trp Pro Leu
    210                 215                 220

Asp Ile Ile Lys Glu Thr Gln Ala Ile Ala Gly Tyr Ser Lys Leu Asn
225                 230                 235                 240

Leu Glu Leu Val Tyr Asn Val Glu Gly His His His His His His
                245                 250                 255

<210> SEQ ID NO 19
<211> LENGTH: 359
<212> TYPE: PRT
<213> ORGANISM: Bifidobacterium longum
<220> FEATURE:
<223> OTHER INFORMATION: Bifidobacterium longum subsp. longum strain
    JCM 1217 N-acetylhexosamine kinase (NahK_JCM1217)

<400> SEQUENCE: 19

Met Thr Glu Ser Asn Glu Val Leu Phe Gly Ile Ala Ser His Phe Ala
 1               5                  10                  15

Leu Glu Gly Ala Val Thr Gly Ile Glu Pro Tyr Gly Asp Gly His Ile
            20                  25                  30

Asn Thr Thr Tyr Leu Val Thr Thr Asp Gly Pro Arg Tyr Ile Leu Gln
        35                  40                  45

Gln Met Asn Thr Ser Ile Phe Pro Asp Thr Val Asn Leu Met Arg Asn
    50                  55                  60

Val Glu Leu Val Thr Ser Thr Leu Lys Ala Gln Gly Lys Glu Thr Leu
65                  70                  75                  80

Asp Ile Val Pro Thr Thr Ser Gly Ala Thr Trp Ala Glu Ile Asp Gly
                85                  90                  95

Gly Ala Trp Arg Val Tyr Lys Phe Ile Glu His Thr Met Ser Tyr Asn
            100                 105                 110

Leu Val Pro Asn Pro Asp Val Phe Arg Glu Ala Gly Ser Ala Phe Gly
        115                 120                 125

Asp Phe Gln Asn Phe Leu Ser Glu Phe Asp Ala Ser Gln Leu Thr Glu
130                 135                 140

Thr Ile Ala His Phe His Asp Thr Pro His Arg Phe Glu Asp Phe Lys
145                 150                 155                 160

Ala Ala Leu Ala Ala Asp Lys Leu Gly Arg Ala Ala Cys Cys Pro
            165                 170                 175

Glu Ile Asp Phe Tyr Leu Ser His Ala Asp Gln Tyr Ala Val Val Met
        180                 185                 190

Asp Gly Leu Arg Asp Gly Ser Ile Pro Leu Arg Val Thr His Asn Asp
    195                 200                 205

Thr Lys Leu Asn Asn Ile Leu Met Asp Ala Thr Thr Gly Lys Ala Arg
210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
            245                 250                 255

Arg Asp Leu Ser Lys Val His Phe Ser Thr Glu Leu Phe Arg Ala Tyr
        260                 265                 270

Thr Glu Gly Phe Val Gly Glu Leu Arg Gly Ser Ile Thr Ala Arg Glu
    275                 280                 285

Ala Glu Leu Leu Pro Phe Ser Gly Asn Leu Leu Thr Met Glu Cys Gly

```
                290                 295                 300
Met Arg Phe Leu Ala Asp Tyr Leu Glu Gly Asp Ile Tyr Phe Ala Thr
305                 310                 315                 320

Lys Tyr Pro Glu His Asn Leu Val Arg Thr Arg Thr Gln Ile Lys Leu
                325                 330                 335

Val Gln Glu Met Glu Gln Lys Ala Ser Glu Thr Arg Ala Ile Val Ala
                340                 345                 350

Asp Ile Met Glu Ala Ala Arg
            355

<210> SEQ ID NO 20
<211> LENGTH: 359
<212> TYPE: PRT
<213> ORGANISM: Bifidobacterium longum
<220> FEATURE:
<223> OTHER INFORMATION: Bifidobacterium longum Reuter strain ATCC
      #155813 N-acetylhexosamine 1-kinase (NahK_ATCC55813)

<400> SEQUENCE: 20

Met Thr Glu Ser Asn Glu Val Leu Phe Gly Ile Ala Ser His Phe Ala
1               5                   10                  15

Leu Glu Gly Ala Val Thr Gly Ile Glu Pro Tyr Gly Asp Gly His Ile
                20                  25                  30

Asn Thr Thr Tyr Leu Val Thr Thr Asp Gly Pro Arg Tyr Ile Leu Gln
            35                  40                  45

Gln Met Asn Thr Ser Ile Phe Pro Asp Thr Val Asn Leu Met Arg Asn
50                  55                  60

Val Glu Leu Val Thr Ser Thr Leu Lys Ala Gln Gly Lys Glu Thr Leu
65                  70                  75                  80

Asp Ile Val Pro Thr Thr Ser Gly Ala Thr Trp Ala Glu Ile Asp Gly
                85                  90                  95

Gly Ala Trp Arg Val Tyr Lys Phe Ile Glu His Thr Met Ser Tyr Asn
                100                 105                 110

Leu Val Pro Asn Pro Asp Val Phe Arg Glu Ala Gly Ser Ala Phe Gly
            115                 120                 125

Asp Phe Gln Asn Phe Leu Ser Glu Phe Asp Ala Ser Gln Leu Thr Glu
    130                 135                 140

Thr Ile Ala His Phe His Asp Thr Pro His Arg Phe Glu Asp Phe Lys
145                 150                 155                 160

Ala Ala Leu Ala Ala Asp Lys Leu Gly Arg Ala Ala Cys Cys Pro
                165                 170                 175

Glu Ile Asp Phe Tyr Leu Ser His Ala Asp Gln Tyr Ala Val Val Met
                180                 185                 190

Asp Gly Leu Arg Asp Gly Ser Ile Pro Leu Arg Val Thr His Asn Asp
            195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255

Arg Asp Leu Ser Lys Val His Phe Ser Thr Glu Leu Phe Arg Ala Tyr
                260                 265                 270

Thr Glu Gly Phe Val Gly Glu Leu Arg Gly Ser Ile Thr Ala Arg Glu
            275                 280                 285
```

```
Ala Glu Leu Leu Pro Phe Ser Gly Asn Leu Leu Thr Met Glu Cys Gly
    290                 295                 300

Met Arg Phe Leu Ala Asp Tyr Leu Glu Gly Asp Ile Tyr Phe Ala Thr
305                 310                 315                 320

Lys Tyr Pro Glu His Asn Leu Val Arg Thr Arg Thr Gln Ile Lys Leu
                325                 330                 335

Val Gln Glu Met Glu Gln Lys Ala Ser Glu Thr His Ala Ile Val Ala
            340                 345                 350

Asp Ile Met Glu Ala Ala Arg
        355

<210> SEQ ID NO 21
<211> LENGTH: 359
<212> TYPE: PRT
<213> ORGANISM: Bifidobacterium longum
<220> FEATURE:
<223> OTHER INFORMATION: Bifidobacterium longum subsp. infantis strain
      ATCC #15697 N-acetylhexosamine 1-kinase (NahK_ATCC15697)

<400> SEQUENCE: 21

Met Asn Thr Asn Glu Ala Leu Phe Asp Val Ala Ser His Phe Ala
1               5                   10                  15

Leu Glu Gly Thr Val Asp Ser Ile Glu Pro Tyr Gly Asp Gly His Ile
            20                  25                  30

Asn Thr Thr Tyr Leu Val Thr Thr Asp Gly Pro Arg Tyr Ile Leu Gln
        35                  40                  45

Arg Met Asn Thr Gly Ile Phe Pro Asp Thr Val Asn Leu Met Arg Asn
    50                  55                  60

Val Glu Leu Val Thr Ser Thr Leu Lys Ala Gln Gly Lys Glu Thr Leu
65                  70                  75                  80

Asp Ile Val Arg Thr Thr Ser Gly Asp Thr Trp Ala Glu Ile Asp Gly
                85                  90                  95

Gly Ala Trp Arg Val Tyr Lys Phe Ile Glu His Thr Met Ser Tyr Asn
            100                 105                 110

Leu Val Pro Asn Pro Asp Val Phe Arg Glu Ala Gly Arg Ala Phe Gly
        115                 120                 125

Asp Phe Gln Asn Phe Leu Ser Gly Phe Asp Ala Asn Gln Leu Thr Glu
    130                 135                 140

Thr Ile Ala His Phe His Asp Thr Pro His Arg Phe Glu Asp Phe Lys
145                 150                 155                 160

Lys Ala Leu Ala Ala Asp Glu Leu Gly Arg Ala Ala Gly Cys Gly Pro
                165                 170                 175

Glu Ile Glu Phe Tyr Leu Ser His Ala Asp Gln Tyr Ala Val Val Met
            180                 185                 190

Asp Gly Leu Arg Asp Gly Ser Ile Pro Leu Arg Val Thr His Asn Asp
        195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255

Arg Asp Leu Asp Lys Val His Phe Ser Thr Glu Leu Phe Arg Ala Tyr
            260                 265                 270

Thr Glu Gly Phe Val Gly Glu Leu Arg Asp Ser Ile Thr Ala Arg Glu
        275                 280                 285
```

Ala Glu Leu Leu Pro Phe Ser Gly Asn Leu Leu Thr Met Glu Cys Gly
        290                 295                 300

Met Arg Phe Leu Ala Asp Tyr Leu Glu Gly Asp Val Tyr Phe Ala Thr
305                 310                 315                 320

Lys Tyr Pro Glu His Asn Leu Val Arg Ser Arg Thr Gln Ile Lys Leu
                325                 330                 335

Val Arg Glu Met Glu Gln Arg Ala Asp Glu Thr Arg Ala Ile Val Ala
            340                 345                 350

Asp Val Met Glu Thr Thr Lys
        355

<210> SEQ ID NO 22
<211> LENGTH: 6
<212> TYPE: PRT
<213> ORGANISM: Artificial Sequence
<220> FEATURE:
<223> OTHER INFORMATION: synthetic His-6-tag, C-terminal or N-terminal

<400> SEQUENCE: 22

His His His His His His
 1               5

<210> SEQ ID NO 23
<211> LENGTH: 31
<212> TYPE: DNA
<213> ORGANISM: Artificial Sequence
<220> FEATURE:
<223> OTHER INFORMATION: synthetic PCR amplification forward primer for
      cloning NahK_ATCC15697

<400> SEQUENCE: 23
accccatatg aacaacacca atgaagccct g                                    31

<210> SEQ ID NO 24
<211> LENGTH: 32
<212> TYPE: DNA
<213> ORGANISM: Artificial Sequence
<220> FEATURE:
<223> OTHER INFORMATION: synthetic PCR amplification reverse primer for
      cloning NahK_ATCC15697

<400> SEQUENCE: 24
tgacctcgag cttggtcgtc tccatgacgt cg                                   32

<210> SEQ ID NO 25
<211> LENGTH: 34
<212> TYPE: DNA
<213> ORGANISM: Artificial Sequence
<220> FEATURE:
<223> OTHER INFORMATION: synthetic PCR amplification forward primer for
      cloning NahK_ATCC55813

<400> SEQUENCE: 25
accccatatg accgaaagca atgaagtttt attc                                 34

<210> SEQ ID NO 26
<211> LENGTH: 29
<212> TYPE: DNA
<213> ORGANISM: Artificial Sequence
<220> FEATURE:
<223> OTHER INFORMATION: synthetic PCR amplification reverse primer for
      cloning NahK_ATCC55813

<400> SEQUENCE: 26
tgacctcgag cctggcagcc tccatgatg                                          29

<210> SEQ ID NO 27
<211> LENGTH: 29
<212> TYPE: DNA
<213> ORGANISM: Artificial Sequence
<220> FEATURE:
<223> OTHER INFORMATION: synthetic PCR forward primer for cloning
      AtGlcAK

<400> SEQUENCE: 27
ggaattccat atggatccga attccacgg                                          29

<210> SEQ ID NO 28
<211> LENGTH: 37
<212> TYPE: DNA
<213> ORGANISM: Artificial Sequence
<220> FEATURE:
<223> OTHER INFORMATION: synthetic PCR reverse primer for cloning
      AtGlcAK

<400> SEQUENCE: 28
ccgctcgagt cataaggtct gaatgtcaga atcattc                                 37

<210> SEQ ID NO 29
<211> LENGTH: 34
<212> TYPE: DNA
<213> ORGANISM: Artificial Sequence
<220> FEATURE:
<223> OTHER INFORMATION: synthetic PCR forward primer for cloning PmGlmU
      N-His-6-tagged fusion protein

<400> SEQUENCE: 29
gatccatatg aaagagaaag cattaagtat cgtg                                    34

<210> SEQ ID NO 30
<211> LENGTH: 36
<212> TYPE: DNA
<213> ORGANISM: Artificial Sequence
<220> FEATURE:
<223> OTHER INFORMATION: synthetic PCR reverse primer for cloning PmGlmU
      N-His-6-tagged fusion protein

<400> SEQUENCE: 30
ccgctcgagt tactttttcg tttgtttagt agggcg                                  36

<210> SEQ ID NO 31
<211> LENGTH: 34
<212> TYPE: DNA
<213> ORGANISM: Artificial Sequence
<220> FEATURE:
<223> OTHER INFORMATION: synthetic PCR forward primer for cloning PmGlmU
      C-His-6-tagged fusion protein

<400> SEQUENCE: 31
gatccatatg aaagagaaag cattaagtat cgtg                                    34

<210> SEQ ID NO 32
<211> LENGTH: 37
<212> TYPE: DNA
<213> ORGANISM: Artificial Sequence
<220> FEATURE:
<223> OTHER INFORMATION: synthetic PCR reverse primer for cloning PmGlmU
      C-His-6-tagged fusion protein

<400> SEQUENCE: 32
ccgctcgagc tttttcgttt gtttagtagg gcgttgc                                 37

<210> SEQ ID NO 33
<211> LENGTH: 34
<212> TYPE: DNA
<213> ORGANISM: Artificial Sequence
<220> FEATURE:
<223> OTHER INFORMATION: synthetic PCR forward primer for cloning BLUSP

<400> SEQUENCE: 33
ggaattccat atgacagaaa taaacgataa ggcc        34

<210> SEQ ID NO 34
<211> LENGTH: 26
<212> TYPE: DNA
<213> ORGANISM: Artificial Sequence
<220> FEATURE:
<223> OTHER INFORMATION: synthetic PCR reverse primer for cloning BLUSP

<400> SEQUENCE: 34
cgcggatcct cacacccaat cgtccg        26

<210> SEQ ID NO 35
<211> LENGTH: 33
<212> TYPE: DNA
<213> ORGANISM: Artificial Sequence
<220> FEATURE:
<223> OTHER INFORMATION: synthetic PCR amplification forward primer for
      cloning PmUgd

<400> SEQUENCE: 35
gatccatatg aagaaaatta caattgctgg ggc        33

<210> SEQ ID NO 36
<211> LENGTH: 35
<212> TYPE: DNA
<213> ORGANISM: Artificial Sequence
<220> FEATURE:
<223> OTHER INFORMATION: synthetic PCR amplification reverse primer for
      cloning PmUgd

<400> SEQUENCE: 36
ccgctcgaga gcatcaccgc caaaaatatc tcttg        35

<210> SEQ ID NO 37
<211> LENGTH: 31
<212> TYPE: DNA
<213> ORGANISM: Artificial Sequence
<220> FEATURE:
<223> OTHER INFORMATION: synthetic PCR amplification primer
      KfiA_pMAL-c4X_F_EcoRI for cloning KfiA

<400> SEQUENCE: 37
gaccgaattc atgattgttg caaatatgag c        31

<210> SEQ ID NO 38
<211> LENGTH: 47
<212> TYPE: DNA
<213> ORGANISM: Artificial Sequence
<220> FEATURE:
<223> OTHER INFORMATION: synthetic PCR amplification primer
      KfiA_pMAL-c4X_R_HindIII for cloning KfiA

<400> SEQUENCE: 38
gtcgaagctt ttagtggtgg tggtggtggt gaccttccac attatac        47

<210> SEQ ID NO 39

```
<211> LENGTH: 32
<212> TYPE: DNA
<213> ORGANISM: Artificial Sequence
<220> FEATURE:
<223> OTHER INFORMATION: synthetic PCR amplification primer
      PmHS1_pMAL-c4X_F_BamHI for cloning PmHS1

<400> SEQUENCE: 39
cgcggatcca tgagcttatt taaacgtgct ac                                    32

<210> SEQ ID NO 40
<211> LENGTH: 55
<212> TYPE: DNA
<213> ORGANISM: Artificial Sequence
<220> FEATURE:
<223> OTHER INFORMATION: synthetic PCR amplification primer
      PmHS1_pMAL-c4X_R_HindIII for cloning PmHS1

<400> SEQUENCE: 40
gatcaagctt ttagtgatga tgatgatgat gctcgttata aaagataaa cacgg            55

<210> SEQ ID NO 41
<211> LENGTH: 30
<212> TYPE: DNA
<213> ORGANISM: Artificial Sequence
<220> FEATURE:
<223> OTHER INFORMATION: synthetic PCR amplification primer
      PmHS2_pET15b/22b+_F_NdeI for cloning PmHS2

<400> SEQUENCE: 41
gatccatatg aagggaaaaa aagagatgac                                       30

<210> SEQ ID NO 42
<211> LENGTH: 35
<212> TYPE: DNA
<213> ORGANISM: Artificial Sequence
<220> FEATURE:
<223> OTHER INFORMATION: synthetic PCR amplification primer
      PmHS2_pET15b_R_BamHI for cloning PmHS2

<400> SEQUENCE: 42
aagggatcct tataaaaaat aaaaaggtaa acagg                                 35

<210> SEQ ID NO 43
<211> LENGTH: 53
<212> TYPE: DNA
<213> ORGANISM: Artificial Sequence
<220> FEATURE:
<223> OTHER INFORMATION: synthetic PCR amplification primer
      PmHS2_pET22b+_R_BamHI for cloning PmHS2

<400> SEQUENCE: 43
aagggatcct tagtggtggt ggtggtggtg taaaaaataa aaaggtaaac agg             53

<210> SEQ ID NO 44
<211> LENGTH: 29
<212> TYPE: DNA
<213> ORGANISM: Artificial Sequence
<220> FEATURE:
<223> OTHER INFORMATION: synthetic PCR forward primer for cloning
      AtGlcAK

<400> SEQUENCE: 44
acgcgtcgac atggatccga attccacgg                                        29

<210> SEQ ID NO 45
<211> LENGTH: 34
```

-continued

```
<212> TYPE: DNA
<213> ORGANISM: Artificial Sequence
<220> FEATURE:
<223> OTHER INFORMATION: synthetic PCR reverse primer for cloning
      AtGlcAK

<400> SEQUENCE: 45
ccgctcgagt aaggtctgaa tgtcagaatc attc                              34
```